(12) United States Patent
Beatty et al.

(10) Patent No.: US 8,895,277 B2
(45) Date of Patent: Nov. 25, 2014

(54) LEGUME ISOPRENE SYNTHASE FOR PRODUCTION OF ISOPRENE

(71) Applicants: Danisco US Inc., Palo Alto, CA (US); The Goodyear Tire & Rubber Company, Akron, OH (US)

(72) Inventors: Mary K. Beatty, Earlham, IA (US); Kevin Hayes, Urbandale, IA (US); Zhenglin Hou, Ankeny, IA (US); David J. Meyer, Urbandale, IA (US); Kishore Nannapaneni, Johnston, IA (US); Christopher L. Rife, Redwood City, CA (US); Derek H. Wells, Palo Alto, CA (US); Gina M. Zastrow-Hayes, Urbandale, IA (US)

(73) Assignees: Danisco US Inc., Palo Alto, CA (US); The Goodyear Tire & Rubber Company, Akron, OH (US)

( * ) Notice: Subject to any disclaimer, the term of this patent is extended or adjusted under 35 U.S.C. 154(b) by 0 days.

(21) Appl. No.: 13/802,360

(22) Filed: Mar. 13, 2013

(65) Prior Publication Data
US 2013/0330709 A1    Dec. 12, 2013

Related U.S. Application Data

(60) Provisional application No. 61/641,861, filed on May 2, 2012.

(51) Int. Cl.
| | | |
|---|---|---|
| *C12P 5/02* | (2006.01) | |
| *C07H 21/02* | (2006.01) | |
| *C12N 15/00* | (2006.01) | |
| *C12Q 1/527* | (2006.01) | |
| *C07K 14/415* | (2006.01) | |
| *C12P 5/00* | (2006.01) | |
| *C12N 9/88* | (2006.01) | |

(52) U.S. Cl.
CPC .......... *C12P 5/007* (2013.01); *C12Y 402/03027* (2013.01); *C12Q 1/527* (2013.01); *C07K 14/415* (2013.01); *C12N 9/88* (2013.01)
USPC ..................... 435/167; 435/320.1; 536/23.2

(58) Field of Classification Search
USPC ............................... 435/167, 320.1; 536/23.2
See application file for complete search history.

(56) References Cited

U.S. PATENT DOCUMENTS

| 4,570,029 | A | 2/1986 | Kulprathipanja et al. |
| 4,703,007 | A | 10/1987 | Mulholland et al. |
| 7,659,097 | B2 | 2/2010 | Renninger et al. |
| 7,785,858 | B2 | 8/2010 | Kozlov et al. |
| 7,947,478 | B2 * | 5/2011 | Melis ............................ 435/167 |
| 2005/0287655 | A1 | 12/2005 | Tabata et al. |
| 2008/0038805 | A1 | 2/2008 | Melis |
| 2009/0203102 | A1 | 8/2009 | Cervin et al. |
| 2009/0282545 | A1 | 11/2009 | Eichelberger et al. |
| 2010/0003716 | A1 | 1/2010 | Cervin et al. |
| 2010/0048964 | A1 | 2/2010 | Calabria et al. |
| 2010/0086978 | A1 | 4/2010 | Beck et al. |
| 2010/0196977 | A1 | 8/2010 | Chotani et al. |
| 2010/0285549 | A1 | 11/2010 | Muramatsu et al. |
| 2010/0297749 | A1 | 11/2010 | Aravanis et al. |
| 2011/0045563 | A1 | 2/2011 | Melis |
| 2011/0159557 | A1 | 6/2011 | Beck et al. |
| 2011/0178261 | A1 | 7/2011 | Feher et al. |
| 2013/0045891 | A1 * | 2/2013 | Beck et al. ...................... 506/10 |

FOREIGN PATENT DOCUMENTS

| JP | 2008/61506 A | 3/2008 |
| WO | WO-98/02550 A2 | 1/1998 |
| WO | WO-98/02550 A3 | 1/1998 |
| WO | WO-2004/033646 A2 | 4/2004 |
| WO | WO-2004/033646 A3 | 4/2004 |
| WO | WO-2009/076676 A2 | 6/2009 |
| WO | WO-2009/076676 A3 | 6/2009 |
| WO | WO-2009/132220 A2 | 10/2009 |
| WO | WO-2009/132220 A3 | 10/2009 |
| WO | WO-2009/132220 A9 | 10/2009 |
| WO | WO-2010/003007 A2 | 1/2010 |
| WO | WO-2010/003007 A3 | 1/2010 |
| WO | WO-2010/013077 A1 | 2/2010 |
| WO | 03001079 * | 3/2010 |
| WO | WO-2010/031062 A1 | 3/2010 |
| WO | WO-2010/031068 A1 | 3/2010 |
| WO | WO-2010/031076 A2 | 3/2010 |
| WO | WO-2010/031076 A3 | 3/2010 |
| WO | WO-2010/031077 A1 | 3/2010 |
| WO | WO-2010/078457 A2 | 7/2010 |
| WO | WO-2010/078457 A3 | 7/2010 |
| WO | 2010124146 * | 10/2010 |
| WO | WO-2010/148150 A1 | 12/2010 |
| WO | WO-2010/148256 A1 | 12/2010 |
| WO | WO-2011/034863 A1 | 3/2011 |
| WO | WO-2011/159853 A1 | 12/2011 |

OTHER PUBLICATIONS

Altschul, S.F. et al. (1990). "Basic Local Alignment Search Tool," *J. Mol. Biol.* 215:403-410.
Altschul, S.F. et al. (1996). "Local Alignment Statistics," Chapter 27 in *Multiple Alignment and Phylogenetic Trees*, American Press, Inc. 266:460-480.
Altschul, S.F. et al. (1997). "Gapped BLAST and PSI-BLAST: A New Generation of Protein Database Search Programs," *Nucleic Acids Research* 25(17):3389-3402.
Baldwin, S.A. et. al. (1978). "Novel Kinetic and Structural Properties of the Class-I D-Fructose 1,6-Bisphosphate Aldolase from *Escherichia coli* (Crookes' Strain)," *Biochem. J.* 169(3):643-652.
Berka, R.M. et al. (1989). "The Development of Gene Expression Systems for Filamentous Fungi," *Biotechnology Advances* 7(2):127-154.

(Continued)

*Primary Examiner* — Maryam Monshipouri
(74) *Attorney, Agent, or Firm* — Morrison & Foerster LLP

(57) ABSTRACT

The present invention provides methods and compositions of polypeptides having isoprene synthase activity with improved performance characteristics. In particular, the present invention provides legume isoprene synthases for increased isoprene production in recombinant host cells.

18 Claims, 24 Drawing Sheets

(56) References Cited

OTHER PUBLICATIONS

Bhayana, V. et al. (1984). "Amino Acid Sequence of *Escherichia coli* Citrate Synthase," *Biochemistry* 23:2900-2905 (Figure 5).
Bologna, F.P. et al. (Aug. 2007). "*Escherichia coli* Malic Enzymes: Two Isoforms with Substantial Differences in Kinetic Properties, Metabolic Regulation, and Structure," *Journal of Bacteriology* 189(16):5937-5946.
Bologna, F.P. et al. (2010). "Characterization of *Escherichia coli* EutD: a Phosphotransacetylase of the Ethanolamine Operon," *The Journal of Microbiology* 48(5):629-636.
Branlant, G. et al. (1985). "Nucleotide Sequence of the *Escherichia coli* Gap Gene. Different evolutionary behavior of the $NAD^+$-binding domain and of the catalytic domain of D-glyceraldehyde-3-phosphate dehydrogenase," *Eur. J. Biochem.* 150:61-66.
Bunch, P.K. et al. (1997). "The *ldhA* Gene Encoding the Fermentative Lactate Dehydrogenase of *Escherichia coli*," *Microbiology* 143:187-195.
Campbell, E.I. et al. (1989). "Improved Transformation Efficiency of *Aspergillus niger* Using the Homologous *niaD* Gene for Nitrate Reductase," *Current Genetics* 16:53-56.
Dawes, E.A. et al. (1966). "The Route to Ethanol Formation in *Zymomonas mobilis*," *Biochem. J.* 98:795-803.
Devereux, J. et al. (1984). "A Comprehensive Set of Sequence Analysis Programs for the VAX," *Nucleic Acids Research* 12(1):387-395.
Duckworth, H.W. et al. (1987). "Structural Basis for Regulation in Gram-Negative Bacterial Citrate Synthases," *Biochem. Soc. Symp.* 54:83-92.
Egan, S.E. et al. (Jul. 1992). "Molecular Characterization of the Entner-Doudoroff Pathway in *Escherichia coli*: Sequence Analysis and Localization of Promoters for the *edd-eda* Operon," *Journal of Bacteriology* 174(14):4638-4646.
Feng, D-F. et al. (1987). "Progressive Sequence Alignment as a Prerequisite to Correct Phylogenetic Trees," *Journal of Molecular Evolution* 25:351-360.
Fowler, Z.L. et. al. (Sep. 2009). "Increased Malonyl Coenzyme A Biosynthesis by Tuning the *Escherichia coli* Metabolic Network and Its Application to Flavanone Production," *Applied and Environmental Microbiology* 75(18):5831-5839.
GenBank Accession No. AB266390, last updated on Aug. 11, 2006, located at <http://www.ebi.ac.uk/ena/data/view/AB266390&display=text>, last visited on May 13, 2014, 2 pages.
GenBank Accession No. AB540131.1, last updated on Oct. 9, 2013, located at <http://www.ncbi.nlm.nih.gov/nuccore/299758081>, last visited on May 13, 2014, 2 pages.
GenBank Accession No. AY279379, last updated on Mar. 11, 2005, located at <http://www.ncbi.nlm.nih.gov/nuccore/AY279379>, last visited on May 13, 2014, 2 pages.
GenBank Accession No. CAC35696, last updated on Apr. 15, 2005, located at <http://www.ncbi.nlm.nih.gov/protein/CAC35696>, last visited on May 13, 2014, 2 pages.
GenBank Accession No. JN173037, created Jan. 19, 2012, last updated on Apr. 17, 2013, located at http://www.ebi.ac.uk/ena/data/view/JN173037&display=text, last visited on May 13, 2014, 2 pages.
GenBank Accession No. JN173038, created Jan. 19, 2012, last updated on Apr. 17, 2013, located at http://www.ebi.ac.uk/ena/data/view/JN173038&display=text, last visited on May 13, 2014, 2 pages.
GenBank Accession No. JN173039, created Jan. 19, 2012, last updated on Apr. 17, 2013, located at http://www.ebi.ac.uk/ena/data/view/JN173039&display=text, last visited on May 13, 2014, 2 pages.
GenBank Accession No. JN173040, created Jan. 19, 2012, last updated on Apr. 17, 2013, located at http://www.ebi.ac.uk/ena/data/view/JN173040&display=text, last visited on May 13, 2014, 2 pages.
GenBank Accession No. JN173041, created Jan. 19, 2012, last updated on Apr. 17, 2013, located at http://www.ebi.ac.uk/ena/data/view/JN173041&display=text, last visited on May 13, 2014, 2 pages.
GenBank Accession No. JN173042, created Jan. 19, 2012, last updated on Apr. 17, 2013, located at http://www.ebi.ac.uk/ena/data/view/JN173042&display=text, last visited on May 13, 2014, 2 pages.
GenBank Accession No. JN173043, created Jan. 19, 2012, last updated on Apr. 17, 2013, located at http://www.ebi.ac.uk/ena/data/view/JN173043&display=text, last visited on May 13, 2014, 2 pages.
GenBank Accession No. NC_001416, last updated on Mar. 11, 2011, located at http://www.ncbi.nlm.nih.gov/nuccore/9626243?report=genbank, last visited on May 13, 2014, 42 pages.
Greenberg, J.P. et al. (1993). "Sub-Parts Per Billion Detection of Isoprene Using a Reduction Gas Detector with a Portable Gas Chromatograph," *Atmospheric Environment* 27A(16):2689-2692.
Hedl, M. et al. (Apr. 2002). "*Enterococcus faecalis* Acetoacetyl-Coenzyme a Thiolase/3-Hydroxy-3-Methyglutaryl-Coenzyme A Reductase, a Dual-Function Protein of Isopentenyl Diphosphate Biosynthesis," *Journal of Bacteriology* 184(8):2116-2122.
Henikoff, S. et al. (Nov. 1992). "Amino Acid Substitution Matrices from Protein Blocks," *Proc. Natl. Acad. Sci. USA* 89:10915:10919.
Higgins, D.G. et al. (1989). "Fast and Sensitive Multiple Sequence Alignments on a Microcomputer," *Cabios Communications* 5(2):151-153.
Iwakura, M. et al. (1979). "Studies on Regulatory Functions of Malic Enzymes," *J. Biochem.* 85:1355-1365.
JGI Accession No. Glyma06g45780.1, (Online) Retrieved from: http://www.phytozome.net/cgi-bin/gbrowse_details/soybean?class=mRNA;name=Glyma06g45780.1, last visited on May 13, 2014, 2 pages.
JGI Accession No. Glyma09g21900.1, (Online) Retrieved from: http://www.phytozome.net/cgi-bin/gbrowse_details/soybean?class=mRNA;name=Glyma09g21900.1, last visited on May 9, 2014, 2 pages.
JGI Accession No. Glyma12g10990.1, (Online) Retrieved from: http://www.phytozome.net/cgi-bin/gbrowse_details/soybean?class=mRNA;name=Glyma12g10990.1, last visited on May 13, 2014, 3 pages.
JGI Accession No. Glyma20g18280.1, (Online) Retrived from: http://www.phytozome.net/cgi-bin/gbrowse_details/soybean?class=mRNA;name=Glyma20g18280.1, last visited on May 13, 2014, 2 pages.
Kakuda, H. et al. (1994). "Identification and Characterization of the *ack*A (Acetate Kinase A)-*pta* (Phosphotransacetylase) Operon and Complementation Analysis of Acetate Utilization by an *ackA-pta* Deletion Mutant of *Escherichia coli*," *J. Biochem.* 116:916-922.
Karlin, S. et al. (Jun. 1993). "Applications and Statistics for Multiple High-scoring Segments in Molecular Sequences," *Proc. Natl. Acad. Sci. USA* 90:5873-5877.
Kotlarz, D. et al. (1975). "Regulation of the Amount and of the Activity of Phosphofructokinases and Pyruvate Kinases in *Escherichia coli*," *Biochimica et Biophysica Acta* 381:257-268.
Lindberg, P. et al. (2010). "Engineering a Platform for Photosynthetic Isoprene Production in Cyanobacteria, Using *Synechocystis* as the Model Organism," *Metabolic Engineering* 12(1):70-79.
Maurus, R. et al. (2003). "Insights into the Evolution of Allosteric Properties. The NADH Binding Site of Hexameric Type II Citrate Synthases," *Biochemistry* 42:5555-5565.
Meile, L. et al. (May 2001). "Characterization of the D-Xylulose 5-Phosphate/D-Fructose 6-Phosphate Phosphoketolase Gene (*xfp*) from *Bifidobacterium lactis*," *Journal of Bacteriology* 183(9):2929-2936.
Miller, B. et al. (2001, e-pub. May 10, 2001). "First Isolation of an Isoprene Synthase Gene from Poplar and Successful Expression of the Gene in *Escherichia Coli*," *Planta* 213(3):483-487.
Needleman, S.B. et al. (1970). "A General Method Applicable to the Search for Similarities in the Amino Acid Sequence of Two Proteins," *J. Mol. Biol.* 48:443-453.
Ner, S.S. et al. (Nov. 8, 1983). "Complete Sequence of the *glt* A Gene Encoding Citrate Synthase in *Escherichia coli*," *Biochemistry* 22(23):5243-5249.
Ogasawara, H. et al. (2007). "PdhR (Pyruvate Dehydrogenase Complex Regulator) Controls the Respiratory Electron Transport System in *Escherichia coli*," *Journal of Bacteriology* 189(15):5534-5541.
Oh, M-K. et al. (Apr. 12, 2002). "Global Expression Profiling of Acetate-grown *Escherichia coli*," *The Journal of Biological Chemistry* 277(15):13175-13183.

(56) References Cited

OTHER PUBLICATIONS

Okamura, E. et al. (Jun. 22, 2010). "Unprecedented Acetoacetyl-coenzyme a Synthesizing Enzyme of the Thiolase Superfamily Involved in the Mevalonate Pathway," *PNAS* 107(25):11265-11270.

Pearson, W.R. et al. (Apr. 1988). "Improved Tools for Biological Sequence Comparison," *Proc. Natl. Acad. Sci. USA* 85:2444-2448.

Peekhaus, N. et al. (Jul. 1998). "What's for Dinner?: Entner-Doudoroff Metabolism in *Escherichia coli*," *Journal of Bacteriology* 180(14):3495-3502.

Quant, P.A. et al. (1989). "Treatment of Rats With Glucagon or Mannoheptulose Increases Mitochondrial 3-Hydroxy-3-Methylglutaryl-CoA Synthase Activity and Decreases Succinyl-CoA Content in Liver," *Biochem. J.* 262:159-164.

Romanos, M.A. et al. (1992). "Foreign Gene Expression in Yeast: a Review," *Yeast* 8(6):423-488.

Sánchez, A.M. et al. (2005). "Novel Pathway Engineering Design of the Anaerobic Central Metabolic Pathway in *Escherichia coli* to Increase Succinate Yield and Productivity," *Metabolic Engineering* 7:229-239.

Sharkey, T.D. et al. (Feb. 2005). "Evolution of the Isoprene Biosynthetic Pathway in Kudzu," *Plant Physiology* 137:700-712.

Sharkey, T.D. et al. (Apr. 2013, e-pub. Dec. 20, 2012). "Isoprene Synthase Genes Form a Monophyletic Clade of Acyclic Terpene Synthases in the TPS-B Terpene Synthase Family," *Evolution* 67(4):1026-1040 (available on line at doi: 10.1111/evo.12013).

Shimizu, M. et al. (1969). "Phosphotransacetylase of *Escherichia coli* B, Purification and Properties," *Biochimica et Biophysica Acta* 191:550-558.

Silver, G.M. et al. (1991). "Enzymatic Synthesis of Isoprene from Dimethylallyl Diphosphate in Aspen Leaf Extracts," *Plant Physiol.* 97:1588-1591.

Silver, G.M. et al. (Jun. 2, 1995). "Characterization of Aspen Isoprene Synthase, an Enzyme Responsible for Leaf Isoprene Emission to the Atmosphere," *The Journal of Biological Chemistry* 270(22):13010-13016.

Smith, T.F. et al. (1981). "Comparison of Biosequences," *Advances in Applied Mathematics* 2:482-489.

Sprenger, G.A. (1995). "Genetics of Pentose-Phosphate Pathway Enzymes of *Escherichia coli* K-12," *Arch. Microbiol.* 164:324-330.

Stokell, D.J. et al. (Sep. 12, 2003). "Probing the Roles of Key Residues in the Unique Regulatory NADH Binding Site of Type II Citrate Synthase of *Escherichia coli*," *The Journal of Biological Chemistry* 278(37):35435-35443.

Stülke, J. et al. (2000). "Regulation of Carbon Catabolism in *Bacillus* Species," *Annu. Rev. Microbiol.* 54:849-880.

Tabata, K. et al. (2004). "Production of Mevalonate by a Metabolically-engineered *Escherichia coli*," *Biotechnology Letters* 26:1487-1491.

Underwood, S.A. et al. (2002). "Flux through Citrate Synthase Limits the Growth of Ethanologenic *Escherichia coli* KO11 During Xylose Fermentation," *Applied and Environmental Microbiology* 68(3):1071-1081.

UniProt Database Accession No. H2CSU6, Mar. 21, 2012, located at http://www.uniprot.org/uniprot/H2CSU6.txt, last visited on May 13, 2014, 1 page.

UniProt Database Accession No. H2CSU7, Mar. 21, 2012, located at http://www.uniprot.org/uniprot/H2CSU7.txt, last visited on May 13, 2014, 1 page.

Weissermel, K. et al. (2003). "Isoprene," in *Industrial Organic Chemistry*, 4th Completely Revised Edition, translated by Lindley, C.R. et al., Wiley-VCH GmbH & Co. KGaA, Weinheim, Germany, pp. 117-122.

Wiegand, G. et al. (1986). "Citrate Synthase: Structure, Control, and Mechanism," *Ann. Rev. Biophys. Biophys. Chem.* 15:97-117.

Wolfe, A.J. (2005). "The Acetate Switch," *Microbiol. Mol. Biol. Rev.* 69(1):12-50.

Yang, J. et al. (2012, e-pub. Oct. 20, 2011). "Bio-Isoprene Production Using Exogenous MVA Pathway and Isoprene Synthase in *Escherichia coli*" *Bioresource Technology* 104:642-647.

International Search Report mailed on Jul. 29, 2013 for PCT Patent Application No. PCT/US2013/039315, filed on May 2, 2013, 5 pages.

\* cited by examiner

Figure 1 peanut_fom_1n24. TRRSANYQPNLWDFEFLQSVENDLQVERLEERARKLEEEVRGLMKKVEIEPLSLLELMDN
Palba_from_1n24. ARRSANYEPNSWDYDYLLSSDTDESIEVYKDKAKKLEAEVRREINNEKAEFLTLLELIDN peanut_fom_1n24. VERLGLTYKFEEDIKSALNNRIVPLLHHHTINKYG----LHATALSFRFLRQHAFHVSPD
Palba_from_1n24. VQRLGLGYRFESDIRGALDR----FVSSGGFDAVTKTSLHGTALSFRLLRQHGFEVSQE peanut_fom_1n24. VFESFKEEGK-FKKEISGDVLGLLNLYETSYLGFEGETILDEARAFSATHLKNLLQTNQV
Palba_from_1n24. AFSGFKDQNGNFLENLKEDIKAILSLYEASFLALEGENILDEAKVFAISHLKELSE-EKI peanut_fom_1n24. QNKVMAEKVRHALELPYHRRVHRLEARWFIERYEQKEAHDGALLELAKLDFNMVQSVMKK
Palba_from_1n24. GKELAEQ-VNHALELPLHRRTQRLEAVWSIEAYRKKEDANQVLLELAILDYNMIQSVYQR peanut_fom_1n24. ELQELSRWWREIGLTSKLDFVRDRLMEVYFWALGMAPHPQLTECRKAVTKMFGLVTIIDD
Palba_from_1n24. DLRETSRWWRRVGLATKLHFARDRLIESFYWAVGVAFEPQYSDCRNSVAKMFSFVTIIDD peanut_fom_1n24. VYDVYGTLDELQLFTDAVDRWDVNAVETLPDYMKLCYLALYNSVNDTAYSTLREKGDNSL
Palba_from_1n24. IYDVYGTLDELELFTDAVERWDVNAINDLPDYMKLCFLALYNTINEIAYDNLKDKGENIL peanut_fom_1n24. PHLAKSWRDLCKAFLQEAKWSNNKIIPPFDAYIRNASVSSSGGALLAPCYFSVTQDSTSQ
Palba_from_1n24. PYLTKAWADLCNAFLQEAKWLYNKSTPTFDDYFGNAWKSSSGPLQLVFAYFAVV-QNIKK peanut_fom_1n24. -AIDSITNYHGIVRSSCAIFRLCNDLATSAAELERGETTNSITSYMTENGTTEEEARESL
Palba_from_1n24. EEIENLQKYHDTISRPSHIFRLCNDLASASAEIARGETANSVSCYMRTKGISEELATESV peanut_fom_1n24. GKLIDQEWKKMNRDVVLESAYPNVFKEIAINMARVSHCTYQYGDGLGRPDDTAENRIKLS
Palba_from_1n24. MNLIDETWKKMNKEKLGGSLFAKPFVETAINLARQSHCTYHNGDAHTSPDELTRKRVLSV peanut_fom_1n24. LIEPIP
Palba_from_1n24. ITEPIL

SEQUENCE LISTING

<160> NUMBER OF SEQ ID NOS: 59

<210> SEQ ID NO 1
<211> LENGTH: 544
<212> TYPE: PRT
<213> ORGANISM: Artificial Sequence
<220> FEATURE:
<223> OTHER INFORMATION: Synthetic Construct

<400> SEQUENCE: 1

Met Glu Ala Arg Arg Ser Ala Asn Tyr Glu Pro Asn Ser Trp Asp Tyr
1               5                   10                  15

Asp Tyr Leu Leu Ser Ser Asp Thr Asp Glu Ser Ile Glu Val Tyr Lys
            20                  25                  30

Asp Lys Ala Lys Lys Leu Glu Ala Glu Val Arg Arg Glu Ile Asn Asn
        35                  40                  45

Glu Lys Ala Glu Phe Leu Thr Leu Leu Glu Leu Ile Asp Asn Val Gln
    50                  55                  60

Arg Leu Gly Leu Gly Tyr Arg Phe Glu Ser Asp Ile Arg Gly Ala Leu
65                  70                  75                  80

Asp Arg Phe Val Ser Ser Gly Gly Phe Asp Ala Val Thr Lys Thr Ser
                85                  90                  95

```
Leu His Gly Thr Ala Leu Ser Phe Arg Leu Arg Gln His Gly Phe
            100                 105                 110
Glu Val Ser Gln Glu Ala Phe Ser Gly Phe Lys Asp Gln Asn Gly Asn
        115                 120                 125
Phe Leu Glu Asn Leu Lys Glu Asp Ile Lys Ala Ile Leu Ser Leu Tyr
    130                 135                 140
Glu Ala Ser Phe Leu Ala Leu Glu Gly Glu Asn Ile Leu Asp Glu Ala
145                 150                 155                 160
Lys Val Phe Ala Ile Ser His Leu Lys Glu Leu Ser Glu Glu Lys Ile
                165                 170                 175
Gly Lys Glu Leu Ala Glu Gln Val Asn His Ala Leu Glu Leu Pro Leu
            180                 185                 190
His Arg Arg Thr Gln Arg Leu Glu Ala Val Trp Ser Ile Glu Ala Tyr
        195                 200                 205
Arg Lys Lys Glu Asp Ala Asn Gln Val Leu Leu Glu Leu Ala Ile Leu
    210                 215                 220
Asp Tyr Asn Met Ile Gln Ser Val Tyr Gln Arg Asp Leu Arg Glu Thr
225                 230                 235                 240
Ser Arg Trp Trp Arg Arg Val Gly Leu Ala Thr Lys Leu His Phe Ala
                245                 250                 255
Arg Asp Arg Leu Ile Glu Ser Phe Tyr Trp Ala Val Gly Val Ala Phe
            260                 265                 270
Glu Pro Gln Tyr Ser Asp Cys Arg Asn Ser Val Ala Lys Met Phe Ser
        275                 280                 285
Phe Val Thr Ile Ile Asp Asp Ile Tyr Asp Val Tyr Gly Thr Leu Asp
    290                 295                 300
Glu Leu Glu Leu Phe Thr Asp Ala Val Glu Arg Trp Asp Val Asn Ala
305                 310                 315                 320
Ile Asn Asp Leu Pro Asp Tyr Met Lys Leu Cys Phe Leu Ala Leu Tyr
                325                 330                 335
Asn Thr Ile Asn Glu Ile Ala Tyr Asp Asn Leu Lys Asp Lys Gly Glu
            340                 345                 350
Asn Ile Leu Pro Tyr Leu Thr Lys Ala Trp Ala Asp Leu Cys Asn Ala
        355                 360                 365
Phe Leu Gln Glu Ala Lys Trp Leu Tyr Asn Lys Ser Thr Pro Thr Phe
    370                 375                 380
Asp Asp Tyr Phe Gly Asn Ala Trp Lys Ser Ser Ser Gly Pro Leu Gln
385                 390                 395                 400
Leu Val Phe Ala Tyr Phe Ala Val Val Gln Asn Ile Lys Lys Glu Glu
                405                 410                 415
Ile Glu Asn Leu Gln Lys Tyr His Asp Thr Ile Ser Arg Pro Ser His
            420                 425                 430
Ile Phe Arg Leu Cys Asn Asp Leu Ala Ser Ala Ser Ala Glu Ile Ala
        435                 440                 445
Arg Gly Glu Thr Ala Asn Ser Val Ser Cys Tyr Met Arg Thr Lys Gly
    450                 455                 460
Ile Ser Glu Glu Leu Ala Thr Glu Ser Val Met Asn Leu Ile Asp Glu
465                 470                 475                 480
Thr Trp Lys Lys Met Asn Lys Glu Lys Leu Gly Gly Ser Leu Phe Ala
                485                 490                 495
Lys Pro Phe Val Glu Thr Ala Ile Asn Leu Ala Arg Gln Ser His Cys
            500                 505                 510
```

| | | | | | | | | | | | | |
|---|---|---|---|---|---|---|---|---|---|---|---|---|
|Thr|Tyr|His|Asn|Gly|Asp|Ala|His|Thr|Ser|Pro|Asp|Glu|Leu|Thr|Arg|
| | |515| | | |520| | | |525| | | | | |

| | | | | | | | | | | | |
|---|---|---|---|---|---|---|---|---|---|---|---|
|Lys|Arg|Val|Leu|Ser|Val|Ile|Thr|Glu|Pro|Ile|Leu|Pro|Phe|Glu|Arg|
| |530| | | | |535| | | |540| | | | | |

<210> SEQ ID NO 2
<211> LENGTH: 1635
<212> TYPE: DNA
<213> ORGANISM: Artificial Sequence
<220> FEATURE:
<223> OTHER INFORMATION: Synthetic Construct

<400> SEQUENCE: 2

```
atggaagcac gtcgctctgc gaactacgaa cctaacagct gggactatga ttacctgctg      60
tcctccgaca cggacgagtc catcgaagta tacaaagaca aagcgaaaaa gctggaagcc     120
gaagttcgtc gcgagattaa taacgaaaaa gcagaatttc tgaccctgct ggaactgatt     180
gacaacgtcc agcgcctggg cctgggttac cgtttcgagt ctgatatccg tggtgcgctg     240
gatcgcttcg tttcctccgg cggcttcgat gcggtaacca agacttccct gcacggtacg     300
gcactgtctt ccgtctgct gcgtcaacac ggttttgagg tttctcagga agcgttcagc     360
ggcttcaaag accaaaacgg caacttcctg agaaacctga aggaagatat caaagctatc     420
ctgagcctgt acgaggccag cttcctggct ctggaaggcg aaaacatcct ggacgaggcg     480
aaggttttcg caatctctca tctgaaagaa ctgtctgaag aaagatcgg taagagctg     540
gcagaacagg tgaaccatgc actggaactg ccactgcatc gccgtactca gcgtctggaa     600
gcagtatggt ctatcgaggc ctaccgtaaa aaggaggacg cgaatcaggt tctgctggag     660
ctggcaattc tggattacaa catgatccag tctgtatacc agcgtgatct gcgtgaaacg     720
tcccgttggg ggcgtcgtgt gggtctggcg accaaactgc actttgctcg tgaccgcctg     780
attgagagct tctactgggc cgtgggtgta gcattcgaac cgcaatactc cgactgccgt     840
aactccgtcg caaaaatgtt ttctttcgta accattatcg acgatatcta cgatgtatac     900
ggcaccctgg acgaactgga gctgtttact gatgcagttg agcgttggga cgtaaacgcc     960
atcaacgacc tgccggatta catgaaactg tgctttctgg ctctgtataa cactattaac    1020
gaaatcgcct acgacaacct gaaagataaa ggtgagaaca tcctgccgta tctgaccaaa    1080
gcctgggctg acctgtgcaa cgcttttcctg caagaagcca agtggctgta caacaaatct    1140
actccgacct tgacgacta cttcggcaac gcatggaaat cctcttctgg cccgctgcaa    1200
ctggtgttcg cttacttcgc tgtcgtgcag aacattaaaa aggaagagat cgaaaacctg    1260
caaaaatacc atgacaccat ctctcgtcct tcccatatct tccgtctgtg caatgacctg    1320
gctagcgcgt ctgcggaaat tgcgcgtggt gaaccgcaa atagcgtttc ttgttacatg    1380
cgcactaaag gtatctccga agaactggct accgaaagcg tgatgaatct gatcgatgaa    1440
acctggaaaa agatgaacaa ggaaaaactg ggtggtagcc tgttcgcgaa accgttcgtg    1500
gaaaccgcga tcaacctggc acgtcaatct cactgcactt atcataacgg cgacgcgcat    1560
acctctccgg atgagctgac ccgcaaacgc gttctgtctg taatcactga accgattctg    1620
ccgtttgaac gctaa                                                    1635
```

<210> SEQ ID NO 3
<211> LENGTH: 544
<212> TYPE: PRT
<213> ORGANISM: Artificial Sequence
<220> FEATURE:
<223> OTHER INFORMATION: Synthetic Construct

<400> SEQUENCE: 3

Met Asn Thr Arg Arg Ser Ala Asn Tyr Gln Pro Asn Leu Trp Asp Phe
1               5                   10                  15

Glu Phe Leu Gln Ser Val Glu Asn Asp Leu Gln Val Glu Arg Leu Glu
            20                  25                  30

Glu Arg Ala Arg Lys Leu Glu Glu Val Arg Gly Leu Met Lys Lys
                35                  40                  45

Val Glu Ile Glu Pro Leu Ser Leu Leu Glu Leu Met Asp Asn Val Glu
    50                  55                  60

Arg Leu Gly Leu Thr Tyr Lys Phe Glu Asp Ile Lys Ser Ala Leu
65                  70                  75                  80

Asn Asn Arg Ile Val Pro Leu Leu His His His Thr Ile Asn Lys Tyr
                85                  90                  95

Gly Leu His Ala Thr Ala Leu Ser Phe Arg Phe Leu Arg Gln His Ala
                100                 105                 110

Phe His Val Ser Pro Asp Val Phe Glu Ser Phe Lys Glu Glu Gly Lys
            115                 120                 125

Phe Lys Lys Glu Ile Ser Gly Asp Val Leu Gly Leu Leu Asn Leu Tyr
130                 135                 140

Glu Thr Ser Tyr Leu Gly Phe Glu Gly Glu Thr Ile Leu Asp Glu Ala
145                 150                 155                 160

Arg Ala Phe Ser Ala Thr His Leu Lys Asn Leu Leu Gln Thr Asn Gln
                165                 170                 175

Val Gln Asn Lys Val Met Ala Glu Lys Val Arg His Ala Leu Glu Leu
            180                 185                 190

Pro Tyr His Arg Arg Val His Arg Leu Glu Ala Arg Trp Phe Ile Glu
            195                 200                 205

Arg Tyr Glu Gln Lys Glu Ala His Asp Gly Ala Leu Leu Glu Leu Ala
            210                 215                 220

Lys Leu Asp Phe Asn Met Val Gln Ser Val Met Lys Lys Glu Leu Gln
225                 230                 235                 240

Glu Leu Ser Arg Trp Trp Arg Glu Ile Gly Leu Thr Ser Lys Leu Asp
                245                 250                 255

Phe Val Arg Asp Arg Leu Met Glu Val Tyr Phe Trp Ala Leu Gly Met
            260                 265                 270

Ala Pro His Pro Gln Leu Thr Glu Cys Arg Lys Ala Val Thr Lys Met
            275                 280                 285

Phe Gly Leu Val Thr Ile Ile Asp Asp Val Tyr Asp Val Tyr Gly Thr
290                 295                 300

Leu Asp Glu Leu Gln Leu Phe Thr Asp Ala Val Asp Arg Trp Asp Val
305                 310                 315                 320

Asn Ala Val Glu Thr Leu Pro Asp Tyr Met Lys Leu Cys Tyr Leu Ala
                325                 330                 335

Leu Tyr Asn Ser Val Asn Asp Thr Ala Tyr Ser Thr Leu Arg Glu Lys
            340                 345                 350

Gly Asp Asn Ser Leu Pro His Leu Ala Lys Ser Trp Arg Asp Leu Cys
            355                 360                 365

Lys Ala Phe Leu Gln Glu Ala Lys Trp Ser Asn Asn Lys Ile Ile Pro
370                 375                 380

Pro Phe Asp Ala Tyr Ile Arg Asn Ala Ser Val Ser Ser Ser Gly Gly
385                 390                 395                 400

Ala Leu Leu Ala Pro Cys Tyr Phe Ser Val Thr Gln Asp Ser Thr Ser

|       |       |       | 405   |       |       |       | 410   |       |       |       | 415   |       |       |
|-------|-------|-------|-------|-------|-------|-------|-------|-------|-------|-------|-------|-------|-------|

Gln Ala Ile Asp Ser Ile Thr Asn Tyr His Gly Ile Val Arg Ser Ser
            420                 425                 430

Cys Ala Ile Phe Arg Leu Cys Asn Asp Leu Ala Thr Ser Ala Ala Glu
            435                 440                 445

Leu Glu Arg Gly Glu Thr Thr Asn Ser Ile Thr Ser Tyr Met Thr Glu
    450                 455                 460

Asn Gly Thr Thr Glu Glu Ala Arg Glu Ser Leu Gly Lys Leu Ile
465                 470                 475                 480

Asp Gln Glu Trp Lys Lys Met Asn Arg Asp Val Val Leu Glu Ser Ala
                485                 490                 495

Tyr Pro Asn Val Phe Lys Glu Ile Ala Ile Asn Met Ala Arg Val Ser
            500                 505                 510

His Cys Thr Tyr Gln Tyr Gly Asp Gly Leu Gly Arg Pro Asp Asp Thr
        515                 520                 525

Ala Glu Asn Arg Ile Lys Leu Ser Leu Ile Glu Pro Ile Pro Ile Asn
        530                 535                 540

<210> SEQ ID NO 4
<211> LENGTH: 1635
<212> TYPE: DNA
<213> ORGANISM: Artificial Sequence
<220> FEATURE:
<223> OTHER INFORMATION: Synthetic Construct

<400> SEQUENCE: 4

| | | | | | |
|---|---|---|---|---|---|
| atgaacaccc | gtcgcagcgc | caattaccag | ccgaacctgt | gggatttcga | gtttttgcaa | 60 |
| agcgtcgaaa | acgacttgca | ggtggaacgc | ctggaagagc | gtgcacgtaa | gctggaagaa | 120 |
| gaagtgcgtg | gtctgatgaa | aaaggtcgag | attgagccgt | tgagcctgct | ggaactgatg | 180 |
| gacaacgttg | agcgcctggg | tctgacctac | aaattcgaag | aggacatcaa | agcgcgttg | 240 |
| aataaccgca | ttgtcccact | gttgcatcac | catactatca | ataagtacgg | tctgcacgcc | 300 |
| acggctctga | gcttccgttt | cctgcgtcaa | cacgcctttc | acgtcagccc | ggatgttttt | 360 |
| gaaagcttca | agaagaagg | taagttcaag | aaagagatta | gcggcgacgt | gctgggtctg | 420 |
| ctgaacctgt | acgagactag | ctacctgggc | tttgaaggtg | aaaccattct | ggacgaggca | 480 |
| cgcgccttca | gcgctaccca | tctgaaaaat | ctgttgcaaa | ccaaccaggt | gcagaataaa | 540 |
| gttatggcgg | agaaggtccg | ccatgcgttg | gagctgccgt | atcaccgtcg | tgttcaccgt | 600 |
| ttggaagccc | gctggtttat | tgagcgctat | gagcagaaag | aggcgcatga | tggtgccttg | 660 |
| ctggagctgg | cgaaactgga | tttcaacatg | gttcagtctg | tgatgaagaa | agagctgcaa | 720 |
| gagctgagcc | gctggtggcg | tgagatcggt | ctgaccagca | agctggactt | cgtgcgtgat | 780 |
| cgtctgatgg | aagtgtactt | tgggcgctg | ggtatggctc | cgcacccgca | gctgacggag | 840 |
| tgccgtaaag | cagtgaccaa | gatgtttggc | ctggttacca | tcattgacga | tgtttacgat | 900 |
| gtgtatggca | ccctggacga | gctgcaactg | tttacggatg | cggttgaccg | ttgggacgtt | 960 |
| aacgcagtcg | aaacgctgcc | ggactacatg | aaactgtgtt | acctggcgct | gtataactcc | 1020 |
| gttaatgaca | cggcatatag | cactctgcgt | gagaagggtg | acaatagcct | gcctcacttg | 1080 |
| gcaaagtcgt | ggcgtgatct | gtgtaaggcg | tttctgcaag | aggcgaagtg | gagcaataac | 1140 |
| aagatcattc | cgccgttcga | tgcgtacatc | cgcaacgcat | ctgtcagcag | cagcggcggt | 1200 |
| gctctgttgg | cgccatgtta | cttctccgtt | acgcaagaca | gcacgagcca | ggccatcgat | 1260 |
| tctattacga | actaccacgg | catcgtccgt | tcgagctgcg | caatcttccg | cctgtgcaat | 1320 |

```
gacctggcga cctctgctgc ggagctggag cgtggcgaaa ccaccaattc catcacgtcc   1380
tatatgaccg aaaatggcac caccgaagaa gaggcgcgtg aaagcctggg taaactgatt   1440
gaccaagagt ggaagaaaat gaatcgtgat gtggtcctgg aaagcgcgta tccgaacgtg   1500
tttaaagaaa ttgcgattaa catggcacgc gttagccatt gcacctatca gtatggcgat   1560
ggtctgggtc gtccggatga tactgcggag aatcgtatca agctgtctct gatcgaaccg   1620
attccgatca actaa                                                    1635
```

<210> SEQ ID NO 5
<211> LENGTH: 545
<212> TYPE: PRT
<213> ORGANISM: Artificial Sequence
<220> FEATURE:
<223> OTHER INFORMATION: Synthetic Construct

<400> SEQUENCE: 5

```
Met Glu Thr Arg Arg Ser Ala Asn Tyr Gln Pro Asn Leu Trp Asn Phe
  1               5                  10                  15

Glu Phe Leu Pro Pro Ser Leu Glu Asn Asp His Lys Val Glu Lys Leu
             20                  25                  30

Glu Glu Arg Ala Arg Lys Val Glu Glu Val Arg Arg Met Ile Asn
         35                  40                  45

Gly Ala Asp Thr Glu Ala Leu Arg Leu Leu Glu Leu Ile Asp Glu Ile
     50                  55                  60

Gln Arg Leu Gly Leu Thr Tyr Lys Phe Glu Lys Asp Ile Phe Lys Ala
 65                  70                  75                  80

Leu Glu Lys Thr Ile Ser Leu Asp Glu Asn Glu Lys His Ile Ser Gly
                 85                  90                  95

Leu His Ala Thr Ala Leu Ser Phe Arg Leu Leu Arg Gln His Gly Phe
            100                 105                 110

Glu Val Ser Gln Asp Val Phe Lys Arg Phe Lys Asp Lys Glu Gly Gly
        115                 120                 125

Phe Ile Asn Glu Leu Lys Gly Asp Met Gln Gly Leu Leu Ser Leu Tyr
    130                 135                 140

Glu Ala Ser Tyr Leu Gly Phe Glu Gly Glu Thr Leu Leu Asp Glu Ala
145                 150                 155                 160

Arg Ala Tyr Ser Ile Thr His Leu Lys Asn Asn Leu Lys Val Gly Val
                165                 170                 175

Asn Thr Glu Val Lys Glu Gln Val Ser His Ala Leu Glu Leu Pro Tyr
            180                 185                 190

His Arg Gly Leu Asn Arg Leu Glu Ala Arg Trp Phe Leu Glu Lys Tyr
        195                 200                 205

Glu Pro Asn Glu Ser His His His Val Leu Leu Glu Leu Ala Lys Ile
    210                 215                 220

Asp Phe Asn Leu Val Gln Val Met Tyr Gln Lys Glu Leu Arg Glu Leu
225                 230                 235                 240

Ser Arg Trp Trp Ser Glu Met Gly Leu Thr Ser Lys Leu Lys Phe Val
                245                 250                 255

Arg Asp Arg Leu Met Glu Val Tyr Phe Trp Val Leu Gly Met Ala Pro
            260                 265                 270

Arg Pro Gln Phe Ser Glu Cys Arg Lys Ala Val Thr Lys Thr Phe Ala
        275                 280                 285

Leu Ile Gly Ile Ile Asp Asp Val Tyr Asp Val Tyr Gly Thr Leu Asp
    290                 295                 300
```

```
Glu Leu Gln Leu Phe Thr Asp Ala Ile Glu Arg Trp Asp Val Asn Ala
305                 310                 315                 320

Met Asn Thr Leu Pro Asp Tyr Met Lys Leu Cys Tyr Leu Ala Val Tyr
                325                 330                 335

Asn Thr Val Asn Asp Thr Cys Tyr Ser Thr Leu Lys Ala Lys Gly His
            340                 345                 350

Asn Asn Met Ser Tyr Leu Thr Lys Ser Trp Cys Glu Leu Cys Lys Ala
        355                 360                 365

Phe Leu Gln Glu Ala Lys Trp Ser Asn Asn Lys Ile Val Pro Thr Phe
370                 375                 380

Ser Lys Tyr Leu Glu Asn Ala Ser Val Ser Ser Gly Met Ala Leu
385                 390                 395                 400

Leu Thr Ala Ser Tyr Phe Ser Val Cys Gln Gln Asp Ile Ser Asn
                405                 410                 415

Gln Gln Ala Leu Cys Ser Leu Thr Asn Phe Gln Gly Leu Val Arg Ser
            420                 425                 430

Ser Ser Asn Ile Phe Arg Leu Cys Asn Asp Leu Ala Thr Ser Ala Ala
        435                 440                 445

Glu Leu Glu Thr Gly Glu Thr Ala Asn Ser Ile Thr Cys Tyr Met His
450                 455                 460

Glu Lys Asp Thr Ser Glu Glu Gln Ala Arg Glu Glu Leu Thr Asn Leu
465                 470                 475                 480

Ile Asp Ala Glu Trp Lys Lys Met Asn Arg Glu Phe Val Ser Asn Ser
                485                 490                 495

Thr Leu Pro Lys Ala Phe Lys Glu Ile Ala Ile Asn Met Ala Arg Val
            500                 505                 510

Ser His Cys Met Tyr Gln Tyr Gly Asp Gly Leu Gly Arg Pro Gly Tyr
        515                 520                 525

Thr Thr Glu Asn Lys Ile Lys Leu Leu Leu Ile Asp Pro Val Pro Ile
530                 535                 540

Asn
545

<210> SEQ ID NO 6
<211> LENGTH: 1638
<212> TYPE: DNA
<213> ORGANISM: Artificial Sequence
<220> FEATURE:
<223> OTHER INFORMATION: Synthetic Construct

<400> SEQUENCE: 6
atggaaactc gtcgctctgc caattaccaa ccgaacctgt ggaactttga attttgccg      60 ccgtccctgg agaatgacca caaggttgag aaattggaag aacgtgcacg caaggttgaa    120
gaagaagtcc gtcgcatgat caacggcgca gataccgagg ctctgcgcct gctggaactg    180
attgatgaga ttcaacgttt gggtctgacc tacaagtttg agaaggacat cttcaaggct    240
ctggagaaaa ccattagcct ggacgagaac gagaaacaca ttagcggtct gcacgcgacg    300
gcgctgtcct ttcgcctgct cgccagcac ggcttcgagg taagccagga cgtgttcaaa    360
cgctttaagg acaagaagg cggttttatc aatgagctga aggtgatat gcagggtctg    420 ctgagcctgt acgaagcgtc gtatttgggc tttgaaggtg aaacgctgct ggatgaagcc    480
cgtgcgtata gcatcaccca cctgaaaaac aacttgaaag tgggtgttaa taccgaggtg    540
aaagagcagg tgtcccacgc actggaactg ccgtaccatc gcggcctgaa tcgtttggaa    600
```

```
gctcgttggt tcctggagaa gtatgagccg aacgagagcc atcatcatgt gctgctggag    660
ctggcgaaga tcgactttaa cctggttcag gtcatgtacc agaaagaact gcgtgagttg    720
agccgttggt ggagcgaaat gggcctgacc agcaagctga agtttgtccg tgatcgcctg    780
atggaagtct acttttgggt cttgggtatg gcaccgcgtc cgcagttcag cgagtgccgt    840
aaggcggtga ccaaaacctt cgccctgatt ggtatcatcg acgatgtgta tgacgtctat    900
ggcacccctg gatgagctgca attgttcacc gatgcgatcg agcgttggga cgttaatgca    960
atgaatacgc tgccggacta tatgaagctg tgttacttgg cagtttacaa taccgtgaat   1020
gatacctgtt actctaccct gaaggcaaaa ggccacaata acatgtccta tctgaccaag   1080
agctggtgtg agctgtgcaa agccttcctg caagaggcga gtggagcaa caacaaaatt   1140
gttccgacct tcagcaaata cttggagaac gcgagcgtca gcagctcggg tatggccctg   1200
ctgaccgcga gctatttctc cgtgtgtcag caacaggaca tttctaatca gcaagcactg   1260
tgcagcctga cgaattttca aggtctggtt cgttctagca gcaacatttt ccgtctgtgc   1320
aatgatctgg cgacgtctgc ggcggaactg gaaactggtg agactgccaa cagcatcacc   1380
tgctatatgc acgagaaaga cacgagcgaa gagcaagcgc gtgaagaatt gacgaacctg   1440
atcgacgccg agtggaagaa aatgaaccgc gagttcgtga gcaattcgac cctgccaaaa   1500
gctttcaaag agattgcgat caatatggcg cgtgttagcc attgcatgta ccaatacgag   1560
gatggcctgg tcgtccgggg ttacacgacg gagaacaaga ttaagctgct gctgattgat   1620
ccggtcccta tcaattaa                                                  1638
```

<210> SEQ ID NO 7
<211> LENGTH: 545
<212> TYPE: PRT
<213> ORGANISM: Artificial Sequence
<220> FEATURE:
<223> OTHER INFORMATION: Synthetic Construct

<400> SEQUENCE: 7

```
Met Glu Thr Arg Arg Ser Ala Asn Tyr Gln Pro Asn Leu Trp Asn Phe
1               5                   10                  15

Glu Phe Leu Pro Pro Ser Leu Glu Asn Asp His Lys Val Glu Lys Leu
            20                  25                  30

Glu Glu Arg Ala Lys Lys Val Glu Glu Val Arg Lys Val Ile Asn
        35                  40                  45

Gly Ile Asp Thr Lys Pro Leu Leu Glu Leu Ile Asp Asp Val Gln
    50                  55                  60

His Leu Gly Leu Thr Tyr Lys Phe Glu Lys Asp Ile Ile Lys Ala Leu
65                  70                  75                  80

Glu Lys Ile Val Ser Leu Asp Glu Asn Glu His Lys Ser Glu Leu
                85                  90                  95

Tyr Tyr Thr Ala Leu Ser Phe Arg Leu Leu Arg Gln His Gly Phe Glu
            100                 105                 110

Val Ser Gln Asp Val Phe Lys Arg Phe Lys Asp Lys Glu Gly Gly Phe
        115                 120                 125

Ser Gly Glu Leu Lys Gly Asp Val Gln Gly Leu Leu Ser Leu Tyr Glu
    130                 135                 140

Ala Ser Tyr Leu Gly Phe Glu Gly Asp Asn Leu Leu Asp Glu Ala Arg
145                 150                 155                 160

Ala Phe Ser Thr Thr His Leu Lys Asn Asn Leu Lys Gln Gly Ile Asn
                165                 170                 175
```

Thr Lys Glu Ala Glu Gln Val Asn His Ala Leu Glu Leu Pro Tyr His
            180                 185                 190

Arg Arg Leu Gln Arg Leu Glu Ala Arg Trp Tyr Leu Glu Lys Tyr Glu
        195                 200                 205

Pro Lys Glu Pro His His Gln Leu Leu Glu Leu Ala Lys Leu Asp
    210                 215                 220

Phe Asn Met Val Gln Leu Leu His Gln Lys Glu Leu Gln Glu Leu Ser
225                 230                 235                 240

Arg Trp Trp Ser Glu Met Gly Leu Ala Ser Lys Leu Glu Phe Ala Arg
                245                 250                 255

Asp Arg Leu Met Glu Val Tyr Phe Trp Ala Leu Gly Met Ala Pro Asp
            260                 265                 270

Pro Gln Phe Arg Glu Cys Arg Lys Ala Val Thr Lys Met Phe Gly Leu
        275                 280                 285

Val Thr Ile Ile Asp Asp Val Tyr Asp Ile Tyr Gly Thr Leu Asp Glu
290                 295                 300

Leu Gln Leu Phe Thr Asp Ala Val Glu Arg Trp Asp Val Asn Val Val
305                 310                 315                 320

Asn Thr Leu Pro Asp Tyr Met Lys Leu Cys Tyr Leu Ala Leu Tyr Asn
                325                 330                 335

Thr Val Asn Asp Thr Ala Tyr Ser Ile Leu Lys Glu Lys Gly Arg Asn
            340                 345                 350

Asn Leu Ser Tyr Leu Lys Lys Ser Trp Cys Glu Leu Cys Lys Ala Phe
        355                 360                 365

Leu Gln Glu Ala Lys Trp Ser Asn Asn Lys Ile Val Pro Ala Phe Ser
    370                 375                 380

Lys Tyr Leu Glu Asn Ala Ser Val Ser Ser Ser Gly Val Ala Leu Leu
385                 390                 395                 400

Ala Pro Ser Tyr Phe Ser Val Cys Gln Glu Gln Asp Ile Ser Phe Ser
                405                 410                 415

Asp Lys Thr Leu His Tyr Leu Thr Asn Phe Gly Gly Leu Val Arg Ser
            420                 425                 430

Ser Cys Thr Ile Phe Arg Leu Cys Asn Asp Leu Thr Thr Ser Ala Ala
        435                 440                 445

Glu Leu Glu Arg Gly Glu Thr Thr Asn Ser Ile Met Ser Tyr Met His
    450                 455                 460

Glu Asn Gly Thr Ser Glu Glu His Ala Cys Glu Leu Arg Asn Leu
465                 470                 475                 480

Ile Asp Ile Glu Trp Lys Lys Met Asn Arg Gln Arg Val Ser Asp Ser
                485                 490                 495

Thr Leu Pro Lys Ala Phe Arg Glu Ile Ala Met Asn Met Ala Arg Val
            500                 505                 510

Ser His Asn Thr Tyr Gln Tyr Gly Asp Gly Leu Gly Arg Pro Asp Tyr
        515                 520                 525

Asn Ile Glu Asn Arg Ile Lys Phe Leu Leu Ile Asp Pro Val Pro Ile
    530                 535                 540

Asn
545

<210> SEQ ID NO 8
<211> LENGTH: 1635
<212> TYPE: DNA
<213> ORGANISM: Artificial Sequence
<220> FEATURE:
<223> OTHER INFORMATION: Synthetic Construct

<400> SEQUENCE: 8

```
atggaaaccc gtcgtagcgc caattatcaa cctaacctgt ggaattttga gttttttgccg    60
ccgtccctgg agaatgatca aggtggaaa aaactggaag agcgcgcgaa gaaggtcgaa    120
gaagaggtcc gcaaggtcat caatggcatt gataccaaac cgctgttgct ggagttgatc    180
gacgatgtgc aacatctggg tctgacctat aagtttgaga ggacatcat taaggcgctg    240
gagaagattg ttagcctgga tgagaacgaa gagcacaaaa gcgaattgta ttacaccgcg    300
ctgagctttc gcctgctgcg tcagcatggc tttgaagtgt cccaggacgt tttcaaacgt    360
ttcaaggata agagggtgg tttcagcggt gaactgaaag cgacgtcca aggcttgctg    420
tcgctgtatg aagcgtcgta cctgggtttc gagggcgata acctgctgga cgaggcacgt    480
gcatttttcta cgacgcacct gaagaacaat ttgaagcagg gtattaacac caaagaggcg    540
gagcaagtta ccacgcact ggaactgccg tatcaccgtc gtctgcaacg tctggaagcg    600
cgctggtatc tggagaaata cgaaccaaaa gagccgcacc accaactgct gttggaactg    660
gctaaattgg acttcaacat ggtgcagctg ctgcatcaga agaattgca ggagctgtct    720
cgttggtgga gcgagatggg tctggcaagc aagctggagt ttgcgcgcga tcgcctgatg    780
gaagtgtact tttgggcact gggtatggcg cctgacccgc agttccgtga gtgtcgtaag    840
gcggttacca aatgttcgg tctggtcacc atcattgacg atgtttacga catttacggt    900
acgctggacg aactgcaact gtttacggac gccgtggagc gttgggacgt caatgttgtg    960
aacacgctgc cggactatat gaactgtgc tacttggcct tgtacaacac ggttaatgat   1020
actgcgtact ctattctgaa agagaaaggc cgcaacaatc tgagctattt gaagaaaagc   1080
tggtgcgaac tgtgcaaagc ctttctgcaa gaggctaagt ggtccaacaa taagattgtg   1140
ccggcattca gcaaatacct ggaaaatgca agcgtcagca gcagcggcgt cgctctgctg   1200
gcgccgagct acttcagcgt gtgtcaggag caggatatta gcttcagcga caagaccctg   1260
cactatctga cgaatttcgg tggtctggtg cgctctagct gtaccatttt ccgtctgtgc   1320
aatgacctga cgaccagcgc agcggagctg aacgcggtg aaaccactaa tagcattatg   1380
tcctatatgc acgagaacgg taccagcgaa gagcatgcct gcgaagagtt gcgtaacctg   1440
atcgacatcg agtggaagaa gatgaaccgc aacgtgtttt cggatagcac cctgccgaag   1500
gctttccgtg agatcgcgat gaacatggcc cgtgtttctc ataacaccta ccagtacggc   1560
gatggcctgg tcgtccggga ttacaacatc gagaatcgca tcaaatttct gctgatcgat   1620
ccagttccga tcaat                                                     1635
```

<210> SEQ ID NO 9
<211> LENGTH: 600
<212> TYPE: PRT
<213> ORGANISM: Artificial Sequence
<220> FEATURE:
<223> OTHER INFORMATION: Synthetic Construct

<400> SEQUENCE: 9

```
Met Ala Thr Lys Val Leu Cys Leu Ser Asn Gln Phe Leu Tyr Pro Thr
 1               5                  10                  15
Pro Thr Leu Thr Ser Thr Arg Phe Leu Gln Thr Glu Asn Phe Thr Gln
             20                  25                  30
Lys Thr Ser Leu Ile Asn Pro Lys Pro Tyr Pro Leu Phe Cys Val Val
         35                  40                  45
Thr Ser Gln Phe Ser Gln Ile Thr Glu Asp Asn Thr Arg Arg Ser Ala
```

```
            50                  55                  60
Asn Tyr His Pro Asn Leu Trp Asn Phe Glu Phe Leu Gln Ser Leu Glu
 65                  70                  75                  80

Asn Asp Pro Lys Ile Glu Lys Leu Glu Glu Lys Ala Thr Lys Leu Val
                 85                  90                  95

Glu Glu Val Arg His Met Met Asn Lys Ala Thr Glu Pro Leu Ser
                100                 105                 110

Leu Leu Glu Leu Ile Asp Asp Val Gln Arg Leu Gly Leu Thr Tyr Lys
                115                 120                 125

Phe Glu Lys Asp Ile Ile Asn Ala Leu Glu Lys Thr Ile Ser Leu Asp
            130                 135                 140

Glu Asn Gln Lys His Ile Ser Gly Leu His Ala Thr Ser Leu Ser Phe
145                 150                 155                 160

Arg Leu Leu Arg Gln His Gly Phe Glu Val Ser Gln Asp Val Phe Lys
                165                 170                 175

Lys Phe Lys Asp Glu Asp Gly Gly Phe Ser Ala Glu Leu Lys Gly Asp
                180                 185                 190

Val Gln Gly Leu Leu Ser Leu Tyr Glu Ala Ser Tyr Leu Gly Phe Glu
                195                 200                 205

Gly Glu Asn Leu Leu Asp Glu Ala Arg Glu Phe Ser Ile Glu His Leu
                210                 215                 220

Lys Asn Asn Leu Asn Lys Gly Ile Thr Thr Lys Val Ala Glu Gln Val
225                 230                 235                 240

Ser His Ala Leu Glu Leu Pro Tyr His Arg Arg Ile His Arg Leu Glu
                245                 250                 255

Ala Arg Trp Phe Leu Asp Lys Tyr Glu Pro Lys Glu Ser Gln His Lys
                260                 265                 270

Leu Leu Leu Glu Leu Ala Lys Leu Asp Phe Asn Met Val Gln Ser Leu
                275                 280                 285

His Gln Lys Glu Leu Arg Glu Leu Ser Met Trp Trp Arg Glu Ile Gly
                290                 295                 300

Leu Thr Ser Lys Leu Asp Phe Val Arg Asp Arg Leu Met Glu Val Tyr
305                 310                 315                 320

Phe Trp Ala Leu Gly Met Ala Pro Asp Pro Gln Phe Ser Glu Cys Arg
                325                 330                 335

Lys Ala Val Thr Lys Met Phe Gly Leu Val Thr Ile Ile Asp Asp Val
                340                 345                 350

Tyr Asp Val Tyr Gly Thr Leu Asp Glu Leu Gln Leu Phe Thr Asp Ala
                355                 360                 365

Val Glu Arg Trp Asp Val Asn Ala Ile Asn Thr Leu Pro Asp Tyr Met
                370                 375                 380

Lys Leu Cys Phe Leu Ala Leu Tyr Asn Thr Val Asn Asp Thr Thr Tyr
385                 390                 395                 400

Ser Ile Leu Lys Glu Lys Gly His Asn Ile Ser Tyr Leu Thr Lys
                405                 410                 415

Ser Trp Cys Glu Leu Cys Lys Ala Phe Leu Gln Glu Ala Lys Trp Ser
                420                 425                 430

Asn Asn Lys Ile Ile Pro Thr Phe Asn Lys Tyr Leu Arg Asn Ala Ser
                435                 440                 445

Val Ser Ser Ser Gly Val Ala Leu Leu Ala Pro Ser Phe Phe Leu Val
                450                 455                 460

Cys Gln Glu Gln Asp Ile Ser Glu Gln Ala Leu His Ser Leu Ile Asn
465                 470                 475                 480
```

```
Phe His Gly Leu Val Arg Ser Ser Cys Val Ile Phe Arg Leu Cys Asn
                485                 490                 495

Asp Leu Ala Thr Ser Ala Ala Glu Leu Glu Arg Gly Glu Thr Thr Asn
            500                 505                 510

Ser Ile Thr Ser Tyr Met His Glu Asn Gly Thr Ser Glu Gln Ala
        515                 520                 525

Arg Gln Glu Leu Arg Ile Leu Ile Asp Ala Glu Trp Lys Asn Met Asn
    530                 535                 540

Gln Glu Arg Tyr Leu Asp Ser Thr Leu Pro Asp Ala Phe Met Glu Ile
545                 550                 555                 560

Thr Ile Asn Leu Ala Arg Val Ser His Cys Thr Tyr Gln Tyr Gly Asp
                565                 570                 575

Gly Leu Gly Arg Pro Asp Tyr Thr Thr Lys Asn Arg Ile Lys Leu Leu
            580                 585                 590

Leu Ile Asp Pro Leu Pro Ile Asn
            595                 600

<210> SEQ ID NO 10
<211> LENGTH: 1632
<212> TYPE: DNA
<213> ORGANISM: Artificial Sequence
<220> FEATURE:
<223> OTHER INFORMATION: Synthetic Construct

<400> SEQUENCE: 10
atgaacacgc gtcgctcggc caactatcac ccaaacctgt ggaacttcga attcttgcaa      60
agcctggaga tgatccgaa gatcgaaaag ctggaagaga aggcgacgaa gctggtcgaa     120
gaggttcgtc acatgatgaa taaggcggaa accgagccgc tgagcctgct ggaactgatc     180
gacgacgtgc agcgcctggg tttgacctac aagtttgaaa aagacatcat taatgcactg     240
gagaaaacga ttagcctgga tgagaaccaa aagcacatta gcggcttgca tgccacgagc     300 ctgtctttc gtctgctgcg ccaacacggt tttgaggtgt ctcaagatgt gttcaaaaag     360
tttaaagatg aggacggtgg tttcagcgcg gaactgaagg cgacgttca gggtctgctg     420 agcttgtacg aggcgagcta tctgggcttt gagggtgaga tctgctgga tgaagcgcgc     480 gaatttccca tcgaacacct gaaaaacaat ctgaacaagg tattacgac caaagtggcg     540 gaacaagtga gccacgccct ggagctgccg tatcaccgcc gcatccatcg cctggaagcg     600
cgttggttcc tggacaaata cgaaccgaaa gagtcccagc ataagctgct gttggagctg     660
gcgaaactgg atttcaacat ggtgcagagc ctgcatcaaa aagagctgcg cgagctgagc     720
atgtggtggc gtgagattgg cctgacctct aagctggact tcgtccgtga tcgtttgatg     780
gaagtttact tttgggcact gggcatggca ccggacccgc aatttctga atgtcgtaaa     840 gcagtgacta aaatgttcgg tttggtgacc atcattgatg acgtctacga tgtttatggt     900
acgctggatg agctgcaact gttcactgac gcggtcgagc gttgggacgt caatgctatc     960 aatacctgc cggactatat gaagctgtgc ttttggctc tgtacaacac ggtcaacgac    1020
actacctaca gcatcctgaa agaaaagggt cacaataaca tcagctactt gaccaaatcc    1080
tggtgcgagc tgtgcaaagc ttttctgcaa gaagcgaagt ggagcaataa caaaatcatt    1140
ccaaccttca taagtatct gcgtaatgcg agcgtaagca gcagcggcgt tgccctgctg    1200
gcacttcttt tcttcctggt ctgccaggag caggatattt ccgagcaggc gttgcattcc    1260
ctgattaact ttcacggtct ggttcgcagc agctgtgtta tcttccgttt gtgcaatgat    1320
```

```
ctggctacga gcgcagcgga gctggagcgt ggtgaaacga ccaacagcat taccagctat    1380
atgcacgaga atggcaccag cgaagagcag gcacgtcagg aactgcgtat tttgatcgac    1440
gcggagtgga aaaacatgaa tcaggaacgt tatctggata gcacgctgcc ggatgccttc    1500
atggagatta ccatcaacct ggcccgtgtt tcgcattgta cctaccagta cggcgacggt    1560
ctgggccgtc cggactacac caccaagaac cgcattaaac tgctgctgat cgacccgctg    1620
ccgatcaatt aa                                                        1632
```

<210> SEQ ID NO 11
<211> LENGTH: 598
<212> TYPE: PRT
<213> ORGANISM: Artificial Sequence
<220> FEATURE:
<223> OTHER INFORMATION: Synthetic Construct

<400> SEQUENCE: 11

```
Met Ala Thr His His Leu Leu Cys Leu Ser Asn Pro Phe Ser Pro
 1               5                  10                  15

Ser Pro Thr Leu Ser Thr Ala Thr Arg Ser Phe Pro Leu Thr Asn Asn
                20                  25                  30

Phe Asn His Lys Thr Ser Leu Ala Asn Ser Lys Pro Cys Pro Phe Ile
            35                  40                  45

Cys Ser Gln Ile Thr His His His Thr Arg Arg Ser Ala Asn Tyr
     50                  55                  60

Gln Pro Asn Leu Trp Asn Phe Glu Phe Leu Gln Ser Leu Gln Asn His
65                  70                  75                  80

His Gln Val Phe Thr Met Phe Arg Arg Lys Leu Glu Lys Glu Val Arg
                85                  90                  95

Cys Met Met Asn Lys Ala Asp Ala Glu Ala Leu Ser Leu Leu Glu Leu
            100                 105                 110

Ile Asp Asp Val Gln Arg Leu Gly Leu Thr Tyr Arg Phe Glu Lys Asp
        115                 120                 125

Ile Ile Lys Val Leu Glu Lys Ile Val Ser Leu Asp Glu Ile Glu Lys
    130                 135                 140

His Gln Ser Gly Leu His Ala Thr Ala Leu Thr Phe Arg Leu Leu Arg
145                 150                 155                 160

Gln His Gly Phe His Gln Val Ser Gln Asp Met Phe Lys Arg Phe Lys
                165                 170                 175

Asp Lys Glu Gly Gly Phe Asn Asp Glu Leu Lys Gly Asp Val Gln Gly
            180                 185                 190

Leu Leu Ser Leu Tyr Glu Ala Ser Tyr Leu Gly Phe Glu Gly Glu Tyr
        195                 200                 205

Leu Leu Asp Glu Ala Arg Ala Phe Ser Ile Thr His Leu Asn Asn Ser
    210                 215                 220

Leu Lys Gln Gly Ile Asn Thr Lys Leu Ala Glu Gln Val Ser His Ala
225                 230                 235                 240

Leu Gln Leu Pro His His Arg Arg Leu His Arg Leu Glu Ala Arg Trp
                245                 250                 255

Gln Leu Asp Lys Tyr Glu Pro Lys Glu Pro His His His Leu Leu Leu
            260                 265                 270

His Leu Ala Lys Leu Asp Phe Asn Ile Leu Gln Ser Leu Tyr Gln Asn
        275                 280                 285

Glu Leu Arg Glu Leu Ser Arg Trp Trp Arg Glu Met Gly Leu Thr Ser
    290                 295                 300
```

```
Lys Leu Glu Phe Val Arg Asp Arg Leu Met Glu Val Tyr Phe Trp Ala
305                 310                 315                 320
Leu Gly Met Ala Pro His Pro Glu Phe Ser Glu Cys Arg Lys Ala Ile
            325                 330                 335
Thr Lys Met Phe Gly Leu Val Thr Ile Ile Asp Asp Val Tyr Asp Val
        340                 345                 350
Tyr Gly Thr Leu Asp Glu Leu Gln Leu Phe Thr Asp Ala Val Glu Arg
    355                 360                 365
Trp Asp Val Asn Val Val Asn Thr Leu Pro Tyr Tyr Met Lys Leu Cys
    370                 375                 380
Tyr Leu Ala Leu Tyr Asn Thr Val Asn Glu Thr Ser Tyr Ser Ile Leu
385                 390                 395                 400
Lys Glu Asn Gly His Asn Ser Leu Ser Tyr Leu Ala Lys Ser Trp Cys
            405                 410                 415
Glu Leu Cys Lys Ala Phe Leu Glu Glu Ala Lys Trp Ser Lys Lys Lys
        420                 425                 430
Val Ile Pro Ala Leu Asn Arg Tyr Leu Glu Asn Ala Trp Val Ser Ser
    435                 440                 445
Ser Gly Val Ala Leu Leu Ala Pro Cys Tyr Phe Ser Val Cys Lys Glu
    450                 455                 460
Glu Asp Lys Ile Ser Asp Glu Ala Leu His Ser Leu Thr Asn Phe His
465                 470                 475                 480
Gly Leu Val Arg Ser Ser Cys Ala Ile Phe Arg Leu Tyr Asn Asp Leu
            485                 490                 495
Ala Thr Ser Ala Ala Glu Leu Glu Arg Asp Glu Thr Thr Asn Ser Met
        500                 505                 510
Thr Cys Tyr Met His Glu Asn Gly Ser Cys Glu Glu Gln Ala Arg Glu
    515                 520                 525
Glu Leu Arg Lys Met Ile Glu Val Glu Trp Lys Lys Met Asn Gln Glu
    530                 535                 540
Gly Val Leu Asp Cys Thr Leu Pro Thr Ala Phe Lys Glu Ile Ala Met
545                 550                 555                 560
Asn Met Ala Arg Val Ser His Cys Thr Tyr Gln His Gly Asp Gly Leu
            565                 570                 575
Gly Arg Pro Asp Tyr Thr Thr Gln Asn Arg Ile Lys Leu Leu Leu Ile
        580                 585                 590
Asp Pro Leu Pro Ile Asn
    595

<210> SEQ ID NO 12
<211> LENGTH: 1632
<212> TYPE: DNA
<213> ORGANISM: Artificial Sequence
<220> FEATURE:
<223> OTHER INFORMATION: Synthetic Construct

<400> SEQUENCE: 12
atgcacactc gccgctcggc caactaccaa ccaaacctgt ggaacttcga attcttgcaa      60
tccctgcaaa atcaccatca ggtgtttacg atgtttcgtc gtaaactgga gaaagaagtg     120
cgttgcatga tgaataaagc ggatgcggaa gcgctgtctc tgctggagtt gattgatgac     180
gtgcagcgcc tgggtctgac ctaccgtttt gagaaagata tcattaaggt cctggagaag     240
atcgttagcc tggatgagat cgagaaacac cagagcggtc tgcacgccac ggcattgacc     300
ttccgcctgt tgcgccaaca tggctttcac caggttagcc aggatatgtt caacgtttc      360
```

```
aaagacaaag agggtggttt caatgatgaa ctgaagggcg atgttcaggg tctgctgtcc    420
ctgtacgaag caagctatct gggcttcgag ggcgaatacc tgctggacga ggcacgcgcg    480
ttcagcatta cccacctgaa caacagcctg aaacagggca tcaacaccaa gctggcagag    540
caggtgagcc atgctctgca actgccgcat caccgccgtc tgcaccgtct ggaagctcgt    600
tggcagctgg ataagtatga gccgaaagaa ccgcaccatc atctgctgct gcatctggcg    660
aagctggact ttaacattct gcaaagcctg tatcaaaacg agctgcgtga gttgagccgt    720
tggtggcgtg agatgggcct gaccagcaag ctggagtttg ttcgtgatcg cctgatggaa    780
gtctactttt gggctctggg tatggctccg catccagagt tcagcgaatg ccgcaaagca    840
attaccaaaa tgtttggttt ggtcaccatt atcgacgacg tgtatgacgt ctacggtacc    900
ctggacgagc tgcaactgtt tacgacgcg gttgagcgtt gggacgttaa tgttgttaat    960
accctgcctt actatatgaa gctgtgctat ctggcattgt acaacaccgt gaatgaaacg    1020
agctactcta ttctgaaaga aaatggtcac aatagcctga gctacttggc gaagagctgg    1080
tgtgaactgt gcaaggcgtt cctggaagag gccaagtgga gcaagaagaa agtcatcccg    1140
gcgttgaacc gttatttgga gaacgcgtgg gttagctcgt ccggcgtggc gctgctggcc    1200
ccgtgctatt tctccgtgtg taagaagag acaaaatct ccgacgaggc tctgcatagc    1260
ctgaccaact tcacggcct ggtgcgtagc agctgcgcca tcttccgtct gtacaacgat    1320
ttggcgacga gcgcagcgga gctggagcgc gacgaaacg cgaatagcat gacttgttac    1380
atgcacgaaa atggttcttg tgaagagcag gcgcgtgaag agctgcgcaa gatgatcgag    1440
gtcgaatgga aaaagatgaa tcaggaaggt gtcctggatt gcaccctgcc gacggccttc    1500
aaagagattg cgatgaacat ggcacgtgtg agccactgta cctatcaaca cggtgatggt    1560
ctgggccgtc cggactacac cacgcaaaat cgtattaagc tgctgttgat cgatccgctg    1620
ccgattaatt aa                                                       1632
```

<210> SEQ ID NO 13
<211> LENGTH: 553
<212> TYPE: PRT
<213> ORGANISM: Artificial Sequence
<220> FEATURE:
<223> OTHER INFORMATION: Synthetic Construct

<400> SEQUENCE: 13

```
Met Thr Glu Arg Gln Ser Ala Asn Phe Gln Pro Ser Leu Trp Ser Tyr
1               5                   10                  15

Glu Tyr Ile Gln Ser Leu Lys Asn Gly Tyr Glu Ala Asp Leu Tyr Glu
            20                  25                  30

Asp Arg Ala Lys Lys Leu Gly Glu Glu Val Arg Arg Met Ile Asn Asn
        35                  40                  45

Lys Asp Thr Lys Leu Leu Thr Thr Leu Glu Leu Ile Asp Asp Ile Glu
    50                  55                  60

Arg Leu Gly Leu Gly Tyr Arg Phe Lys Glu Glu Ile Met Arg Ala Leu
65                  70                  75                  80

Asp Arg Phe Val Thr Leu Lys Gly Cys Glu Glu Phe Thr Asn Gly Ser
                85                  90                  95

Ile His Asp Thr Ala Leu Ser Phe Arg Leu Leu Arg Gln His Gly Phe
            100                 105                 110

Gly Val Ser Gln Asp Met Phe Asn Cys Phe Lys Asp Gln Lys Gly Asn
        115                 120                 125

Phe Lys Glu Cys Leu Ser Lys Asp Ile Lys Gly Leu Leu Ser Leu Tyr
```

```
            130                 135                 140
Glu Ala Ser Tyr Leu Gly Phe Glu Gly Glu Asn Leu Leu Asp Glu Ala
145                 150                 155                 160

Arg Glu Phe Thr Thr Met His Leu Lys Asp Leu Lys Gly Asp Val Ser
                165                 170                 175

Arg Thr Leu Lys Glu Glu Val Arg His Ser Leu Glu Met Pro Leu His
                180                 185                 190

Arg Arg Met Arg Arg Leu Glu Gln Arg Trp Tyr Ile Asp Ala Tyr Asn
                195                 200                 205

Met Lys Glu Ala His Asp Arg Lys Leu Leu Glu Leu Ala Lys Leu Asp
            210                 215                 220

Phe Asn Ile Val Gln Ser Val His Gln Arg Asp Leu Lys Asp Met Ser
225                 230                 235                 240

Arg Trp Trp Gln Glu Met Gly Leu Gly Asn Lys Leu Ser Phe Ala Arg
                245                 250                 255

Asp Arg Leu Met Glu Cys Phe Phe Ser Val Gly Met Ala Phe Glu
                260                 265                 270

Pro Gln Phe Ser Asn Ser Arg Lys Ala Val Thr Lys Met Phe Ser Phe
                275                 280                 285

Ile Thr Val Ile Asp Asp Ile Tyr Asp Val Tyr Ala Thr Leu Glu Glu
                290                 295                 300

Leu Glu Met Phe Thr Asp Ile Val Gln Arg Trp Asp Val Lys Ala Val
305                 310                 315                 320

Lys Asp Leu Pro Glu Tyr Met Lys Leu Cys Phe Leu Ala Leu Phe Asn
                325                 330                 335

Thr Val Asn Glu Met Val Tyr Asp Thr Leu Lys Glu Gln Gly Val Asp
                340                 345                 350

Ile Leu Pro Tyr Leu Thr Lys Ala Trp Gly Asp Ile Cys Lys Ala Phe
                355                 360                 365

Leu Gln Glu Thr Lys Trp Arg Tyr Tyr Lys Arg Thr Pro Ser Ser Glu
                370                 375                 380

Asp Tyr Leu Asp Asn Ala Trp Ile Ser Val Ser Gly Ala Leu Leu Leu
385                 390                 395                 400

Ile His Ala Tyr Phe Leu Met Ser Pro Ser Ile Thr Asp Arg Ala Leu
                405                 410                 415

Lys Gly Leu Glu Asp Tyr His Asn Ile Leu Arg Trp Pro Ser Ile Ile
                420                 425                 430

Phe Arg Leu Thr Asn Asp Leu Gly Thr Ser Thr Ala Glu Leu Glu Arg
                435                 440                 445

Gly Glu Thr Ala Asn Ser Ile Leu Cys Tyr Met Arg Glu Thr Ser Arg
            450                 455                 460

Ser Glu Asp Phe Ala Arg Glu His Ile Ser Asn Leu Ile Asp Lys Thr
465                 470                 475                 480

Trp Lys Lys Met Asn Lys Asp Arg Phe Ser Asp Ser Pro Phe Glu Glu
                485                 490                 495

Pro Phe Leu Glu Thr Ala Ile Asn Leu Ala Arg Ile Ser His Cys Ile
                500                 505                 510

Tyr Gln His Gly Asp Gly His Gly Ala Pro Asp Thr Arg Thr Lys Asp
                515                 520                 525

Arg Val Leu Ser Leu Ile Ile Glu Pro Ile Pro Cys Tyr Asp Pro Ser
            530                 535                 540

Thr Asn Phe His Ser Gln Ile His Leu
545                 550
```

<210> SEQ ID NO 14
<211> LENGTH: 1662
<212> TYPE: DNA
<213> ORGANISM: Artificial Sequence
<220> FEATURE:
<223> OTHER INFORMATION: Synthetic Construct

<400> SEQUENCE: 14

```
atgaccgaac gtcaaagcgc gaactttcaa ccgtccctgt ggagctacga atacattcag      60
agcctgaaga tggctatga ggcggacctg tatgaagatc gtgcgaagaa gctgggtgaa     120
gaggtgcgcc gtatgattaa caataaggac accaagttgc tgaccacgct ggaactgatc     180
gacgatattg agcgtctggg tctgggttac cgcttcaaag aagagatcat gcgcgcgttg     240
gaccgtttcg ttacgctgaa gggttgtgaa gagttcacga acggttccat ccatgatacg     300
gcgttgagct tccgtttgct gcgtcagcac ggttttggcg tgagccagga catgtttaac     360
tgtttcaaag accagaaagg caatttcaaa gagtgtctgt ctaaagacat caagggtctg     420
ctgagcctgt atgaggcgag ctatctgggt tttgagggtg agaatctgct ggatgaagca     480
cgtgagttca ctaccatgca cctgaaagac ctgaaaggcg acgtttcgcg taccctgaaa     540
gaagaggtcc gtcacagcct ggagatgccg ctgcatcgtc gcatgcgtcg tctggagcag     600
cgttggtata tcgatgctta caacatgaaa gaagcccatg atcgtaagct gctggagctg     660
gcaaaattgg acttcaacat tgttcagagc gtgcaccagc gcgacttgaa ggacatgagc     720
cgttggtggc aagaaatggg cctgggcaac aagctgtcgt tcgcacgcga ccgcctgatg     780
gagtgcttct ttttctccgt cggtatggcg tttgagccgc aatttagcaa tagccgcaaa     840
gcggtcacca agatgtttag ctttatcacc gtgatcgatg acatctacga tgtttacgcg     900
accctggaag agctggaaat tgttcacgga tcgtgcaac gctgggacgt gaaagcagtc     960
aaagacttgc cggagtatat gaagttgtgc tttctggcct tgtttaacac cgtcaatgag    1020
atggtttacg acacgctgaa agagcaaggc gtcgacattc tgccgtacct gaccaaggcc    1080
tggggtgata tttgcaaagc cttcctgcaa gaaaccaagt ggcgctatta caagcgtacc    1140
ccgagcagcg aggattacct ggacaacgca tggatttccg ttagcggtgc tctgctgctg    1200
attcacgcgt acttcctgat gtctccgagc atcaccgatc gtgcgctgaa aggcctggaa    1260
gattatcata acatcctgcg ttggccgagc attatctttc gtctgaccaa cgatttgggt    1320
actagcacgg ctgagctgga gcgtggcgaa accgccaata gcattttgtg ttatatgcgc    1380
gaaaccagcc gctctgagga ttttgcgcgt gaacacatca gcaatctgat tgataaaacc    1440
tggaagaaga tgaataaaga tcgtttcagc gacagcccat cgaagaaccc gtttctggaa    1500
acggcaatta acctggcccg catcagccat tgcatctacc agcacggcga tggtcacggt    1560
gcgccagaca cgcgcaccaa ggaccgtgtt ctgtctctga tcattgagcc gattccgtgc    1620
tacgatccta gcacgaattt ccatagccag attcacctgt aa                       1662
```

<210> SEQ ID NO 15
<211> LENGTH: 551
<212> TYPE: PRT
<213> ORGANISM: Artificial Sequence
<220> FEATURE:
<223> OTHER INFORMATION: Synthetic Construct

<400> SEQUENCE: 15

```
Met Asn Ser Arg Arg Ser Ala Asn Tyr Gln Pro Asn Leu Trp Asn Phe
 1               5                  10                  15
```

```
Glu Phe Leu Gln Ser Leu Glu Asn Asp Leu Lys Val Glu Lys Leu Glu
             20                  25                  30

Glu Lys Ala Thr Lys Leu Glu Glu Val Arg Cys Met Ile Asn Arg
         35                  40                  45

Val Asp Thr Gln Pro Leu Ser Leu Leu Glu Leu Ile Asp Asp Val Gln
     50                  55                  60

Arg Leu Gly Leu Thr Tyr Lys Phe Glu Lys Asp Ile Ile Lys Ala Leu
 65                  70                  75                  80

Glu Asn Ile Val Leu Leu Asp Glu Asn Lys Lys Asn Lys Ser Asp Leu
                 85                  90                  95

His Ala Thr Ala Leu Ser Phe Arg Leu Leu Arg Gln His Gly Phe Glu
            100                 105                 110

Val Ser Gln Asp Val Phe Glu Arg Phe Lys Asp Lys Glu Gly Gly Phe
        115                 120                 125

Ser Gly Glu Leu Lys Gly Asp Val Gln Gly Leu Leu Ser Leu Tyr Glu
    130                 135                 140

Ala Ser Tyr Leu Gly Phe Glu Gly Glu Asn Leu Leu Glu Glu Ala Arg
145                 150                 155                 160

Thr Phe Ser Ile Thr His Leu Lys Asn Asn Leu Lys Glu Gly Ile Asn
                165                 170                 175

Thr Lys Val Ala Glu Gln Val Ser His Ala Leu Glu Leu Pro Tyr His
            180                 185                 190

Gln Arg Leu His Arg Leu Glu Ala Arg Trp Phe Leu Asp Lys Tyr Glu
        195                 200                 205

Pro Lys Glu Pro His His Gln Leu Leu Leu Glu Leu Ala Lys Leu Asp
    210                 215                 220

Phe Asn Met Val Gln Thr Leu His Gln Lys Glu Leu Gln Asp Leu Ser
225                 230                 235                 240

Arg Trp Trp Thr Glu Met Gly Leu Ala Ser Lys Leu Asp Phe Val Arg
                245                 250                 255

Asp Arg Leu Met Glu Val Tyr Phe Trp Ala Leu Gly Met Ala Pro Asp
            260                 265                 270

Pro Gln Phe Gly Glu Cys Arg Lys Ala Val Thr Lys Met Phe Gly Leu
        275                 280                 285

Val Thr Ile Ile Asp Asp Val Tyr Asp Val Tyr Gly Thr Leu Asp Glu
    290                 295                 300

Leu Gln Leu Phe Thr Asp Ala Val Glu Arg Trp Asp Val Asn Ala Ile
305                 310                 315                 320

Asn Thr Leu Pro Asp Tyr Met Lys Leu Cys Phe Leu Ala Leu Tyr Asn
                325                 330                 335

Thr Val Asn Asp Thr Ser Tyr Ser Ile Leu Lys Glu Lys Gly His Asn
            340                 345                 350

Asn Leu Ser Tyr Leu Thr Lys Ser Trp Arg Glu Leu Cys Lys Ala Phe
        355                 360                 365

Leu Gln Glu Ala Lys Trp Ser Asn Asn Lys Ile Ile Pro Ala Phe Ser
    370                 375                 380

Lys Tyr Leu Glu Asn Ala Ser Val Ser Ser Gly Val Ala Leu Leu
385                 390                 395                 400

Ala Pro Ser Tyr Phe Ser Val Cys Gln Gln Gln Glu Asp Ile Ser Asp
                405                 410                 415

His Ala Leu Arg Ser Leu Thr Asp Phe His Gly Leu Val Arg Ser Ser
            420                 425                 430
```

Cys Val Ile Phe Arg Leu Cys Asn Asp Leu Ala Thr Ser Ala Ala Glu
        435                 440                 445

Leu Glu Arg Gly Glu Thr Thr Asn Ser Ile Ile Ser Tyr Met His Glu
    450                 455                 460

Asn Asp Gly Thr Ser Glu Glu Gln Ala Arg Glu Glu Leu Arg Lys Leu
465                 470                 475                 480

Ile Asp Ala Glu Trp Lys Lys Met Asn Arg Glu Arg Val Ser Asp Ser
                485                 490                 495

Thr Leu Leu Pro Lys Ala Phe Met Glu Ile Ala Val Asn Met Ala Arg
            500                 505                 510

Val Ser His Cys Thr Tyr Gln Tyr Gly Asp Gly Leu Gly Arg Pro Asp
        515                 520                 525

Tyr Ala Thr Glu Asn Arg Ile Lys Leu Leu Leu Ile Asp Pro Phe Pro
530                 535                 540

Ile Asn Gln Leu Met Tyr Val
545                 550

<210> SEQ ID NO 16
<211> LENGTH: 1656
<212> TYPE: DNA
<213> ORGANISM: Artificial Sequence
<220> FEATURE:
<223> OTHER INFORMATION: Synthetic Construct

<400> SEQUENCE: 16
atgaattccc gtcgttccgc aaactatcag ccaaacctgt ggaatttcga attcctgcaa      60
tccctggaga cgacctgaa agtggaaaag ctggaggaga agcgaccaa actggaggaa       120 gaagttcgct gcatgatcaa ccgtgtagac acccagccgc tgtccctgct ggagctgatc     180
gacgatgtgc agcgcctggg tctgacctac aaatttgaaa aagacatcat taaagccctg    240
gaaaacatcg tactgctgga cgaaaacaaa agaacaaat ctgacctgca cgcaaccgct     300
ctgtctttcc gtctgctgcg tcagcacggt ttcgaggttt tcaggatgt ttttgagcgt     360 ttcaaggata agaaggtgg tttcagcggt gaactgaaag gtgacgtcca aggcctgctg     420
agcctgtatg aagcgtctta cctgggtttc gagggtgaga acctgctgga ggaggcgcgt   480 acctttttcca tcacccacct gaagaacaac ctgaagaag gcattaatac caaggttgca    540
gaacaagtga gccacgccct ggaactgcca tatcaccagc gtctgcaccg tctggaggca    600
cgttggttcc tggataaata cgaaccgaaa gaaccgcatc accagctgct gctggagctg    660
gcgaagctgg attttaacat ggtacagacc ctgcaccaga aagagctgca agatctgtcc    720
cgctggtgga ccgagatggg cctggctagc aaactggatt ttgtacgcga ccgcctgatg    780
gaagtttatt tctgggcact gggtatggcg ccagacccgc agtttggtga atgtcgcaaa    840
gctgttacta aaatgtttgg tctggtgacg atcatcgatg acgtgtatga cgtttatggc    900
actctggacg aactgcaact gttcaccgat gctgtagagc gctgggacgt taacgctatt    960
aacaccctgc cggactatat gaaactgtgt ttcctggcac tgtacaacac cgttaacgac    1020
acgtcctatt ctattctgaa agagaaaggt cataacaacc tgtcctatct gacgaaaagc    1080
tggcgtgaac tgtgcaaagc ctttctgcaa gaggcgaaat ggccaacaa caaaattatc    1140 ccggctttct ccaagtacct ggaaaacgcc agcgtttcct cctccggtgt agcgctgctg    1200
gcgccgtctt acttttccgt atgccagcag caggaagaca tctccgacca cgcgctgcgt    1260
tccctgaccg acttccatgg tctggtgcgt tctagctgcg ttatcttccg cctgtgcaac    1320
gatctggcca cctctgcggc ggagctggaa cgtggcgaga ctaccaattc tatcattagc    1380

-continued

```
tacatgcacg aaaacgatgg taccagcgag gaacaggccc gcgaagaact gcgtaaactg    1440
atcgacgccg aatggaaaaa gatgaatcgt gaacgcgtta gcgactccac cctgctgcct    1500
aaagcgttca tggaaatcgc agttaacatg gcacgtgttt cccactgcac ctaccagtat    1560
ggcgatggtc tgggtcgccc agactacgcg actgaaaacc gcatcaaact gctgctgatt    1620
gaccctttcc cgattaacca gctgatgtat gtctaa                              1656
```

<210> SEQ ID NO 17
<211> LENGTH: 557
<212> TYPE: PRT
<213> ORGANISM: Artificial Sequence
<220> FEATURE:
<223> OTHER INFORMATION: Synthetic Construct

<400> SEQUENCE: 17

```
Met Glu Thr Arg Arg Ser Ala Asn Tyr Gln Pro Ser Ile Trp Asp His
 1               5                  10                  15

Asp Phe Leu Gln Ser Leu Asn Ser Asn Tyr Thr Asp Glu Thr Tyr Arg
                20                  25                  30

Arg Arg Ala Glu Glu Leu Lys Gly Lys Val Lys Ile Ala Ile Lys Asp
            35                  40                  45

Val Thr Glu Pro Leu Asp Gln Leu Glu Leu Ile Asp Asn Leu Gln Arg
        50                  55                  60

Leu Gly Leu Ala Tyr Arg Phe Glu Thr Glu Ile Arg Asn Ile Leu His
 65                  70                  75                  80

Asn Ile Tyr Asn Asn Lys Asp Tyr Val Trp Arg Lys Glu Asn Leu
                85                  90                  95

Tyr Ala Thr Ser Leu Glu Phe Arg Leu Leu Arg Gln His Gly Tyr Pro
            100                 105                 110

Val Ser Gln Glu Val Phe Asn Gly Phe Lys Asp Asp Gln Gly Gly Phe
        115                 120                 125

Ile Phe Asp Asp Phe Lys Gly Ile Leu Ser Leu His Glu Ala Ser Tyr
    130                 135                 140

Tyr Ser Leu Glu Gly Glu Ser Ile Met Glu Glu Ala Trp Gln Phe Thr
145                 150                 155                 160

Ser Lys His Leu Lys Glu Val Met Ile Ser Lys Ser Met Glu Glu Asp
                165                 170                 175

Val Phe Val Ala Glu Gln Ala Lys Arg Ala Leu Glu Leu Pro Leu His
            180                 185                 190

Trp Lys Val Pro Met Leu Glu Ala Arg Trp Phe Ile His Val Tyr Glu
        195                 200                 205

Lys Arg Glu Asp Lys Asn His Leu Leu Leu Glu Leu Ala Lys Met Glu
    210                 215                 220

Phe Asn Thr Leu Gln Ala Ile Tyr Gln Glu Glu Leu Lys Glu Ile Ser
225                 230                 235                 240

Gly Trp Trp Lys Asp Thr Gly Leu Gly Glu Lys Leu Ser Phe Ala Arg
                245                 250                 255

Asn Arg Leu Val Ala Ser Phe Leu Trp Ser Met Gly Ile Ala Phe Glu
            260                 265                 270

Pro Gln Phe Ala Tyr Cys Arg Arg Val Leu Thr Ile Ser Ile Ala Leu
        275                 280                 285

Ile Thr Val Ile Asp Asp Ile Tyr Asp Val Tyr Gly Thr Leu Asp Glu
    290                 295                 300

Leu Glu Ile Phe Thr Asp Ala Val Ala Arg Trp Asp Ile Asn Tyr Ala
```

```
                305                 310                 315                 320
Leu Lys His Leu Pro Gly Tyr Met Lys Met Cys Phe Leu Ala Leu Tyr
                    325                 330                 335
Asn Phe Val Asn Glu Phe Ala Tyr Tyr Val Leu Lys Gln Gln Asp Phe
                    340                 345                 350
Asp Met Leu Leu Ser Ile Lys Asn Ala Trp Leu Gly Leu Ile Gln Ala
                    355                 360                 365
Tyr Leu Val Glu Ala Lys Trp Tyr His Ser Lys Tyr Thr Pro Lys Leu
    370                 375                 380
Glu Glu Tyr Leu Glu Asn Gly Leu Val Ser Ile Thr Gly Pro Leu Ile
385                 390                 395                 400
Ile Ala Ile Ser Tyr Leu Ser Gly Thr Asn Pro Ile Ile Lys Lys Glu
                    405                 410                 415
Leu Glu Phe Leu Glu Ser Asn Pro Asp Ile Val His Trp Ser Ser Lys
                    420                 425                 430
Ile Phe Arg Leu Gln Asp Asp Leu Gly Thr Ser Ser Asp Glu Ile Gln
                    435                 440                 445
Arg Gly Asp Val Pro Lys Ser Ile Gln Cys Tyr Met His Glu Thr Gly
    450                 455                 460
Ala Ser Glu Glu Val Ala Arg Glu His Ile Lys Asp Met Met Arg Gln
465                 470                 475                 480
Met Trp Lys Lys Val Asn Ala Tyr Thr Ala Asp Lys Asp Ser Pro Leu
                    485                 490                 495
Thr Arg Thr Thr Thr Glu Phe Leu Leu Asn Leu Val Arg Met Ser His
                    500                 505                 510
Phe Met Tyr Leu His Gly Asp Gly His Gly Val Gln Asn Gln Glu Thr
                    515                 520                 525
Ile Asp Val Gly Phe Thr Leu Leu Phe Gln Pro Ile Pro Leu Glu Asp
                    530                 535                 540
Lys Asp Met Ala Phe Thr Ala Ser Pro Gly Thr Lys Gly
545                 550                 555

<210> SEQ ID NO 18
<211> LENGTH: 544
<212> TYPE: PRT
<213> ORGANISM: Artificial Sequence
<220> FEATURE:
<223> OTHER INFORMATION: Synthetic Construct

<400> SEQUENCE: 18

Met Glu Thr Arg Arg Ser Ala Asn Tyr Gln Pro Asn Leu Trp Asp Phe
1               5                   10                  15
Glu Phe Leu Gln Ser Val Glu Asn Asp Leu Gln Val Glu Arg Leu Glu
                20                  25                  30
Glu Arg Ala Arg Lys Leu Glu Glu Val Arg Gly Leu Met Lys Lys
            35                  40                  45
Val Glu Ile Glu Pro Leu Ser Leu Leu Glu Leu Met Asp Asn Val Glu
    50                  55                  60
Arg Leu Gly Leu Thr Tyr Lys Phe Glu Glu Asp Ile Lys Ser Ala Leu
65                  70                  75                  80
Asn Asn Arg Ile Val Pro Leu Leu His His Thr Ile Asn Lys Tyr
                85                  90                  95
Gly Leu His Ala Thr Ala Leu Ser Phe Arg Phe Leu Arg Gln His Ala
                100                 105                 110
Phe His Val Ser Pro Asp Val Phe Glu Ser Phe Lys Glu Glu Gly Lys
```

-continued

```
            115                 120                 125
Phe Lys Lys Glu Ile Ser Gly Asp Val Leu Gly Leu Asn Leu Tyr
            130                 135                 140
Glu Thr Ser Tyr Leu Gly Phe Glu Gly Glu Thr Ile Leu Asp Glu Ala
145                 150                 155                 160
Arg Ala Phe Ser Ala Thr His Leu Lys Asn Leu Leu Gln Thr Asn Gln
                    165                 170                 175
Val Gln Asn Lys Val Met Ala Glu Lys Val Arg His Ala Leu Glu Leu
                180                 185                 190
Pro Tyr His Arg Arg Val His Arg Leu Glu Ala Arg Trp Phe Ile Glu
                    195                 200                 205
Arg Tyr Glu Gln Lys Glu Ala His Asp Gly Ala Leu Leu Glu Leu Ala
            210                 215                 220
Lys Leu Asp Phe Asn Met Val Gln Ser Val Met Lys Lys Glu Leu Gln
225                 230                 235                 240
Glu Leu Ser Arg Trp Trp Arg Glu Ile Gly Leu Thr Ser Lys Leu Asp
                    245                 250                 255
Phe Val Arg Asp Arg Leu Met Glu Val Tyr Phe Trp Ala Leu Gly Met
                260                 265                 270
Ala Pro His Pro Gln Leu Thr Glu Cys Arg Lys Ala Val Thr Lys Met
                    275                 280                 285
Phe Gly Leu Val Thr Ile Ile Asp Asp Val Tyr Asp Val Tyr Gly Thr
            290                 295                 300
Leu Asp Glu Leu Gln Leu Phe Thr Asp Ala Val Asp Arg Trp Asp Val
305                 310                 315                 320
Asn Ala Val Glu Thr Leu Pro Asp Tyr Met Lys Leu Cys Tyr Leu Ala
                    325                 330                 335
Leu Tyr Asn Ser Val Asn Asp Thr Ala Tyr Ser Thr Leu Arg Glu Lys
                340                 345                 350
Gly Asp Asn Ser Leu Pro His Leu Ala Lys Ser Trp Arg Asp Leu Cys
            355                 360                 365
Lys Ala Phe Leu Gln Glu Ala Lys Trp Ser Asn Asn Lys Ile Ile Pro
            370                 375                 380
Pro Phe Asp Ala Tyr Ile Arg Asn Ala Ser Val Ser Ser Ser Gly Gly
385                 390                 395                 400
Ala Leu Leu Ala Pro Cys Tyr Phe Ser Val Thr Gln Asp Ser Thr Ser
                    405                 410                 415
Gln Ala Ile Asp Ser Ile Thr Asn Tyr His Gly Ile Val Arg Ser Ser
                420                 425                 430
Cys Ala Ile Phe Arg Leu Cys Asn Asp Leu Ala Thr Ser Ala Ala Glu
                    435                 440                 445
Leu Glu Arg Gly Glu Thr Thr Asn Ser Ile Thr Ser Tyr Met Thr Glu
            450                 455                 460
Asn Gly Thr Thr Glu Glu Glu Ala Arg Glu Ser Leu Gly Lys Leu Ile
465                 470                 475                 480
Asp Gln Glu Trp Lys Lys Met Asn Arg Asp Val Val Leu Glu Ser Ala
                    485                 490                 495
Tyr Pro Asn Val Phe Lys Glu Ile Ala Ile Asn Met Ala Arg Val Ser
                500                 505                 510
His Cys Thr Tyr Gln Tyr Gly Asp Gly Leu Gly Arg Pro Asp Asp Thr
                    515                 520                 525
Ala Glu Asn Arg Ile Lys Leu Ser Leu Ile Glu Pro Ile Pro Ile Asn
            530                 535                 540
```

<210> SEQ ID NO 19
<211> LENGTH: 544
<212> TYPE: PRT
<213> ORGANISM: Artificial Sequence
<220> FEATURE:
<223> OTHER INFORMATION: Synthetic Construct

<400> SEQUENCE: 19

Met Glu Thr Arg Arg Ser Ala Asn Tyr Gln Pro Ser Ile Trp Asn His
 1               5                  10                  15

Asp Tyr Ile Glu Ser Leu Arg Ile Glu Tyr Val Gly Glu Thr Cys Thr
            20                  25                  30

Arg Gln Ile Asn Val Leu Lys Glu Gln Val Arg Met Met Leu His Lys
        35                  40                  45

Val Val Asn Pro Leu Glu Gln Leu Glu Leu Ile Glu Ile Leu Gln Arg
    50                  55                  60

Leu Gly Leu Ser Tyr His Phe Glu Glu Glu Ile Lys Arg Ile Leu Asp
65                  70                  75                  80

Gly Val Tyr Asn Asn Asp His Gly Gly Asp Thr Trp Lys Ala Glu Asn
                85                  90                  95

Leu Tyr Ala Thr Ala Leu Lys Phe Arg Leu Leu Arg Gln His Gly Tyr
            100                 105                 110

Ser Val Ser Gln Glu Val Phe Asn Ser Phe Lys Asp Glu Arg Gly Ser
        115                 120                 125

Phe Lys Ala Cys Leu Cys Glu Asp Thr Lys Gly Met Leu Ser Leu Tyr
    130                 135                 140

Glu Ala Ser Phe Phe Leu Ile Glu Gly Glu Asn Ile Leu Glu Glu Ala
145                 150                 155                 160

Arg Asp Phe Ser Thr Lys His Leu Glu Glu Tyr Val Lys Gln Asn Lys
                165                 170                 175

Glu Lys Asn Leu Ala Thr Leu Val Asn His Ser Leu Glu Phe Pro Leu
            180                 185                 190

His Trp Arg Met Pro Arg Leu Glu Ala Arg Trp Phe Ile Asn Ile Tyr
        195                 200                 205

Arg His Asn Gln Asp Val Asn Pro Ile Leu Leu Glu Phe Ala Glu Leu
    210                 215                 220

Asp Phe Asn Ile Val Gln Ala Ala His Gln Ala Asp Leu Lys Gln Val
225                 230                 235                 240

Ser Thr Trp Trp Lys Ser Thr Gly Leu Val Glu Asn Leu Ser Phe Ala
                245                 250                 255

Arg Asp Arg Pro Val Glu Asn Phe Phe Trp Thr Val Gly Leu Ile Phe
            260                 265                 270

Gln Pro Gln Phe Gly Tyr Cys Arg Arg Met Phe Thr Lys Val Phe Ala
        275                 280                 285

Leu Ile Thr Thr Ile Asp Asp Val Tyr Asp Val Tyr Gly Thr Leu Asp
    290                 295                 300

Glu Leu Glu Leu Phe Thr Asp Val Val Glu Arg Trp Asp Ile Asn Ala
305                 310                 315                 320

Met Asp Gln Leu Pro Asp Tyr Met Lys Ile Cys Phe Leu Thr Leu His
                325                 330                 335

Asn Ser Val Asn Glu Met Ala Leu Asp Thr Met Lys Glu Gln Arg Phe
            340                 345                 350

His Ile Ile Lys Tyr Leu Lys Lys Ala Trp Val Asp Leu Cys Arg Tyr
        355                 360                 365

```
Tyr Leu Val Glu Ala Lys Trp Tyr Ser Asn Lys Tyr Arg Pro Ser Leu
        370                 375                 380

Gln Glu Tyr Ile Glu Asn Ala Trp Ile Ser Ile Gly Ala Pro Thr Ile
385                 390                 395                 400

Leu Val His Ala Tyr Phe Phe Val Thr Asn Pro Ile Thr Lys Glu Ala
                405                 410                 415

Leu Asp Cys Leu Glu Glu Tyr Pro Asn Ile Ile Arg Trp Ser Ser Ile
            420                 425                 430

Ile Ala Arg Leu Ala Asp Asp Leu Gly Thr Ser Thr Asp Glu Leu Lys
        435                 440                 445

Arg Gly Asp Val Pro Lys Ala Ile Gln Cys Tyr Met Asn Glu Thr Gly
    450                 455                 460

Ala Ser Glu Glu Gly Ala Arg Glu Tyr Ile Lys Tyr Leu Ile Ser Ala
465                 470                 475                 480

Thr Trp Lys Lys Met Asn Lys Asp Arg Ala Ala Ser Ser Pro Phe Ser
                485                 490                 495

His Ile Phe Ile Glu Ile Ala Leu Asn Leu Ala Arg Met Ala Gln Cys
            500                 505                 510

Leu Tyr Gln His Gly Asp Gly His Gly Leu Gly Asn Arg Glu Thr Lys
        515                 520                 525

Asp Arg Ile Leu Ser Leu Leu Ile Gln Pro Ile Pro Leu Asn Lys Asp
    530                 535                 540

<210> SEQ ID NO 20
<211> LENGTH: 507
<212> TYPE: PRT
<213> ORGANISM: Artificial Sequence
<220> FEATURE:
<223> OTHER INFORMATION: Synthetic Construct

<400> SEQUENCE: 20

Arg Ala Arg Lys Val Glu Glu Val Arg Met Ile Asn Gly Ala
1               5                   10                  15

Asp Thr Glu Ala Leu Arg Leu Leu Glu Leu Ile Asp Glu Ile Gln Arg
                20                  25                  30

Leu Gly Leu Thr Tyr Lys Phe Glu Lys Asp Ile Phe Lys Ala Leu Glu
            35                  40                  45

Lys Thr Ile Ser Leu Asp Glu Asn Glu Lys His Ile Ser Gly Leu His
        50                  55                  60

Ala Thr Ala Leu Ser Phe Arg Leu Leu Arg Gln His Gly Phe Glu Val
65                  70                  75                  80

Ser Gln Asp Val Phe Lys Arg Phe Lys Asp Lys Glu Gly Gly Phe Ile
                85                  90                  95

Asn Glu Leu Lys Gly Asp Met Gln Gly Leu Leu Ser Leu Tyr Glu Ala
                100                 105                 110

Ser Tyr Leu Gly Phe Glu Gly Glu Thr Leu Leu Asp Glu Ala Arg Ala
            115                 120                 125

Tyr Ser Ile Thr His Leu Lys Asn Asn Leu Lys Val Gly Val Asn Thr
        130                 135                 140

Glu Val Lys Glu Gln Val Ser His Ala Leu Glu Leu Pro Tyr His Arg
145                 150                 155                 160

Gly Leu Asn Arg Leu Glu Ala Arg Trp Phe Leu Glu Lys Tyr Glu Pro
                165                 170                 175

Asn Glu Ser His His His Val Leu Leu Glu Leu Ala Lys Ile Asp Phe
                180                 185                 190
```

```
Asn Leu Val Gln Val Met Tyr Gln Lys Glu Leu Arg Glu Leu Ser Arg
            195                 200                 205

Trp Trp Ser Glu Met Gly Leu Thr Ser Lys Leu Lys Phe Val Arg Asp
            210                 215                 220

Arg Leu Met Glu Val Tyr Phe Trp Val Leu Gly Met Ala Pro Arg Pro
225                 230                 235                 240

Gln Phe Ser Glu Cys Arg Lys Ala Val Thr Lys Thr Phe Ala Leu Ile
            245                 250                 255

Gly Ile Ile Asp Asp Val Tyr Asp Val Tyr Gly Thr Leu Asp Glu Leu
            260                 265                 270

Gln Leu Phe Thr Asp Ala Ile Glu Arg Trp Asp Val Asn Ala Met Asn
            275                 280                 285

Thr Leu Pro Asp Tyr Met Lys Leu Cys Tyr Leu Ala Val Tyr Asn Thr
            290                 295                 300

Val Asn Asp Thr Cys Tyr Ser Thr Leu Lys Ala Lys Gly His Asn Asn
305                 310                 315                 320

Met Ser Tyr Leu Thr Lys Ser Trp Cys Glu Leu Cys Lys Ala Phe Leu
            325                 330                 335

Gln Glu Ala Lys Trp Ser Asn Asn Lys Ile Val Pro Thr Phe Ser Lys
            340                 345                 350

Tyr Leu Glu Asn Ala Ser Val Ser Ser Ser Gly Met Ala Leu Leu Thr
            355                 360                 365

Ala Ser Tyr Phe Ser Val Cys Gln Gln Gln Asp Ile Ser Asn Gln Gln
            370                 375                 380

Ala Leu Cys Ser Leu Thr Asn Phe Gln Gly Leu Val Arg Ser Ser Ser
385                 390                 395                 400

Asn Ile Phe Arg Leu Cys Asn Asp Leu Ala Thr Ser Ala Ala Glu Leu
            405                 410                 415

Glu Thr Gly Glu Thr Ala Asn Ser Ile Thr Cys Tyr Met His Glu Lys
            420                 425                 430

Asp Thr Ser Glu Glu Gln Ala Arg Glu Glu Leu Thr Asn Leu Ile Asp
            435                 440                 445

Ala Glu Trp Lys Lys Met Asn Arg Glu Phe Val Ser Asn Ser Thr Leu
            450                 455                 460

Pro Lys Ala Phe Lys Glu Ile Ala Ile Asn Met Ala Arg Val Ser His
465                 470                 475                 480

Cys Met Tyr Gln Tyr Glu Asp Gly Leu Gly Arg Pro Gly Tyr Thr Thr
            485                 490                 495

Glu Asn Lys Ile Lys Leu Leu Leu Ile Asp Pro
            500                 505

<210> SEQ ID NO 21
<211> LENGTH: 526
<212> TYPE: PRT
<213> ORGANISM: Artificial Sequence
<220> FEATURE:
<223> OTHER INFORMATION: Synthetic Construct

<400> SEQUENCE: 21

Met Glu Thr Arg Arg Thr Ala Asn Tyr His Pro Thr Ile Trp Asp Tyr
  1               5                  10                  15

Asp Tyr Val Gln Ser Leu Arg Ser Asp Tyr Val Gly Glu Thr Tyr Thr
             20                  25                  30

Arg Arg Leu Asp Lys Leu Lys Arg Asp Val Lys Pro Met Leu Gly Lys
         35                  40                  45
```

```
Val Lys Lys Pro Leu Asp Gln Leu Glu Leu Ile Asp Val Leu Gln Arg
 50                  55                  60

Leu Gly Ile Tyr Tyr His Phe Lys Asp Glu Ile Lys Arg Ile Leu Asn
 65                  70                  75                  80

Ser Ile Tyr Asn Gln Tyr Asn Arg His Glu Glu Trp Gln Lys Asp Asp
                 85                  90                  95

Leu Tyr Ala Thr Ala Leu Glu Phe Arg Leu Leu Arg Gln His Gly Tyr
                100                 105                 110

Asp Val Pro Gln Asp Val Phe Ser Arg Phe Lys Asp Thr Gly Ser
                115                 120                 125

Phe Lys Ala Cys Leu Cys Glu Asp Met Lys Gly Met Leu Cys Leu Tyr
130                 135                 140

Glu Ala Ser Tyr Leu Cys Val Gln Gly Glu Ser Thr Met Glu Gln Ala
145                 150                 155                 160

Arg Asp Phe Ala His Arg His Leu Gly Lys Gly Leu Glu Gln Asn Ile
                165                 170                 175

Asp Gln Asn Leu Ala Ile Glu Val Lys His Ala Leu Glu Leu Pro Leu
                180                 185                 190

His Trp Arg Met Pro Arg Leu Glu Ala Arg Trp Phe Ile Asp Val Tyr
                195                 200                 205

Glu Lys Arg Gln Asp Met Asn Pro Ile Leu Leu Glu Phe Ala Lys Leu
210                 215                 220

Asp Phe Asn Met Val Gln Ala Thr His Gln Glu Asp Leu Arg His Met
225                 230                 235                 240

Ser Ser Trp Trp Ser Ser Thr Arg Leu Gly Glu Lys Leu Asn Phe Ala
                245                 250                 255

Arg Asp Arg Leu Met Glu Asn Phe Leu Trp Thr Val Gly Val Ile Phe
                260                 265                 270

Glu Pro Gln Tyr Gly Tyr Cys Arg Arg Met Ser Thr Lys Val Asn Thr
                275                 280                 285

Leu Ile Thr Ile Ile Asp Asp Val Tyr Asp Val Tyr Gly Thr Met Asp
290                 295                 300

Glu Leu Glu Leu Phe Thr Asp Val Val Asp Arg Trp Asp Ile Asn Ala
305                 310                 315                 320

Met Asp Pro Leu Pro Glu Tyr Met Lys Leu Cys Phe Leu Ala Leu Tyr
                325                 330                 335

Asn Ser Thr Asn Glu Met Ala Tyr Asp Ala Leu Lys Glu His Gly Leu
                340                 345                 350

His Ile Val Ser Tyr Leu Arg Lys Ala Trp Ser Asp Leu Cys Lys Ser
                355                 360                 365

Tyr Leu Leu Glu Ala Lys Trp Tyr Tyr Ser Arg Tyr Thr Pro Ser Leu
                370                 375                 380

Gln Glu Tyr Ile Ser Asn Ser Trp Ile Ser Ile Ser Gly Pro Val Ile
385                 390                 395                 400

Leu Val His Ala Tyr Phe Leu Val Ala Asn Pro Ile Thr Lys Glu Ala
                405                 410                 415

Leu Gln Ser Leu Glu Arg Tyr His Asn Ile Ile Arg Trp Ser Ser Met
                420                 425                 430

Ile Leu Arg Leu Ser Asp Asp Leu Gly Thr Ser Leu Asp Glu Leu Lys
                435                 440                 445

Arg Gly Asp Val Pro Lys Ser Ile Gln Cys Tyr Met Tyr Glu Thr Gly
450                 455                 460
```

```
Ala Ser Glu Glu Asp Ala Arg Lys His Thr Ser Tyr Leu Ile Gly Glu
465                 470                 475                 480

Thr Trp Lys Lys Leu Asn Glu Asp Gly Ala Val Glu Ser Pro Phe Pro
                485                 490                 495

Glu Thr Phe Ile Gly Ile Ala Met Asn Leu Ala Arg Met Ala Gln Cys
            500                 505                 510

Met Tyr Gln His Gly Asp Gly His Gly Ile Glu Tyr Gly Glu
            515                 520                 525

<210> SEQ ID NO 22
<211> LENGTH: 545
<212> TYPE: PRT
<213> ORGANISM: Artificial Sequence
<220> FEATURE:
<223> OTHER INFORMATION: Synthetic Construct

<400> SEQUENCE: 22

Met Glu Thr Arg Arg Ser Ala Asn Tyr Gln Pro Asn Leu Trp Asn Phe
1               5                   10                  15

Glu Phe Leu Pro Pro Ser Leu Glu Asn Asp His Lys Val Glu Lys Leu
                20                  25                  30

Glu Glu Arg Ala Lys Lys Val Glu Glu Val Arg Lys Val Ile Asn
            35                  40                  45

Gly Ile Asp Thr Lys Pro Leu Leu Glu Leu Ile Asp Asp Val Gln
50                  55                  60

His Leu Gly Leu Thr Tyr Lys Phe Glu Lys Asp Ile Ile Lys Ala Leu
65                  70                  75                  80

Glu Lys Ile Val Ser Leu Asp Glu Asn Glu His Lys Ser Glu Leu
                85                  90                  95

Tyr Tyr Thr Ala Leu Ser Phe Arg Leu Leu Arg Gln His Gly Phe Glu
                100                 105                 110

Val Ser Gln Asp Val Phe Lys Arg Phe Lys Asp Lys Glu Gly Gly Phe
            115                 120                 125

Ser Gly Glu Leu Lys Gly Asp Val Gln Gly Leu Leu Ser Leu Tyr Glu
130                 135                 140

Ala Ser Tyr Leu Gly Phe Glu Gly Asp Asn Leu Leu Asp Glu Ala Arg
145                 150                 155                 160

Ala Phe Ser Thr Thr His Leu Lys Asn Asn Leu Lys Gln Gly Ile Asn
                165                 170                 175

Thr Lys Glu Ala Glu Gln Val Asn His Ala Leu Glu Leu Pro Tyr His
            180                 185                 190

Arg Arg Leu Gln Arg Leu Glu Ala Arg Trp Tyr Leu Glu Lys Tyr Glu
        195                 200                 205

Pro Lys Glu Pro His His Gln Leu Leu Leu Glu Leu Ala Lys Leu Asp
    210                 215                 220

Phe Asn Met Val Gln Leu Leu His Gln Lys Glu Leu Gln Glu Leu Ser
225                 230                 235                 240

Arg Trp Trp Ser Glu Met Gly Leu Ala Ser Lys Leu Glu Phe Ala Arg
                245                 250                 255

Asp Arg Leu Met Glu Val Tyr Phe Trp Ala Leu Gly Met Ala Pro Asp
            260                 265                 270

Pro Gln Phe Arg Glu Cys Arg Lys Ala Val Thr Lys Met Phe Gly Leu
        275                 280                 285

Val Thr Ile Ile Asp Asp Val Tyr Asp Ile Tyr Gly Thr Leu Asp Glu
    290                 295                 300
```

Leu Gln Leu Phe Thr Asp Ala Val Glu Arg Trp Asp Val Asn Val Val
305                 310                 315                 320

Asn Thr Leu Pro Asp Tyr Met Lys Leu Cys Tyr Leu Ala Leu Tyr Asn
                325                 330                 335

Thr Val Asn Asp Thr Ala Tyr Ser Ile Leu Lys Glu Lys Gly Arg Asn
            340                 345                 350

Asn Leu Ser Tyr Leu Lys Lys Ser Trp Cys Glu Leu Cys Lys Ala Phe
        355                 360                 365

Leu Gln Glu Ala Lys Trp Ser Asn Asn Lys Ile Val Pro Ala Phe Ser
    370                 375                 380

Lys Tyr Leu Glu Asn Ala Ser Val Ser Ser Gly Val Ala Leu Leu
385                 390                 395                 400

Ala Pro Ser Tyr Phe Ser Val Cys Gln Glu Gln Asp Ile Ser Phe Ser
                405                 410                 415

Asp Lys Thr Leu His Tyr Leu Thr Asn Phe Gly Gly Leu Val Arg Ser
            420                 425                 430

Ser Cys Thr Ile Phe Arg Leu Cys Asn Asp Leu Thr Thr Ser Ala Ala
        435                 440                 445

Glu Leu Glu Arg Gly Glu Thr Thr Asn Ser Ile Met Ser Tyr Met His
450                 455                 460

Glu Asn Gly Thr Ser Glu Glu His Ala Cys Glu Glu Leu Arg Asn Leu
465                 470                 475                 480

Ile Asp Ile Glu Trp Lys Lys Met Asn Arg Gln Arg Val Ser Asp Ser
                485                 490                 495

Thr Leu Pro Lys Ala Phe Arg Glu Ile Ala Met Asn Met Ala Arg Val
            500                 505                 510

Ser His Asn Thr Tyr Gln Tyr Gly Asp Gly Leu Gly Arg Pro Asp Tyr
        515                 520                 525

Asn Ile Glu Asn Arg Ile Lys Phe Leu Leu Ile Asp Pro Val Pro Ile
    530                 535                 540

Asn
545

<210> SEQ ID NO 23
<211> LENGTH: 556
<212> TYPE: PRT
<213> ORGANISM: Artificial Sequence
<220> FEATURE:
<223> OTHER INFORMATION: Synthetic Construct

<400> SEQUENCE: 23

Met Glu Thr Arg Arg Ser Gly Asn Tyr Lys Pro Ser Ile Trp Asp Tyr
1               5                   10                  15

Asp Phe Val Gln Ser Leu Gly Ser Gly Tyr Lys Val Glu Ala His Gly
            20                  25                  30

Thr Arg Val Lys Lys Leu Lys Glu Val Val Lys His Leu Leu Lys Glu
        35                  40                  45

Thr Asp Ser Ser Leu Ala Gln Ile Glu Leu Ile Asp Lys Leu Arg Arg
    50                  55                  60

Leu Gly Leu Arg Trp Leu Phe Lys Asn Glu Ile Lys Gln Val Leu Tyr
65                  70                  75                  80

Thr Ile Ser Ser Asp Asn Thr Ser Ile Glu Met Arg Lys Asp Leu His
                85                  90                  95

Ala Val Ser Thr Arg Phe Arg Leu Leu Arg Gln His Gly Tyr Lys Val
            100                 105                 110

```
Ser Thr Asp Val Phe Asn Asp Phe Lys Asp Glu Lys Gly Cys Phe Lys
            115                 120                 125

Pro Ser Leu Ser Met Asp Ile Lys Gly Met Leu Ser Leu Tyr Glu Ala
        130                 135                 140

Ser His Leu Ala Phe Gln Gly Glu Thr Val Leu Asp Glu Ala Arg Ala
145                 150                 155                 160

Phe Val Ser Thr His Leu Met Asp Ile Lys Glu Asn Ile Asp Pro Ile
                165                 170                 175

Leu His Lys Lys Val Glu His Ala Leu Asp Met Pro Leu His Trp Arg
            180                 185                 190

Leu Glu Lys Leu Glu Ala Arg Trp Tyr Met Asp Ile Tyr Met Arg Glu
        195                 200                 205

Glu Gly Met Asn Ser Ser Leu Leu Glu Leu Ala Met Leu His Phe Asn
    210                 215                 220

Ile Val Gln Thr Thr Phe Gln Thr Asn Leu Lys Ser Leu Ser Arg Trp
225                 230                 235                 240

Trp Lys Asp Leu Gly Leu Gly Glu Gln Leu Ser Phe Thr Arg Asp Arg
                245                 250                 255

Leu Val Glu Cys Phe Phe Trp Ala Ala Ala Met Thr Pro Glu Pro Gln
            260                 265                 270

Phe Gly Arg Cys Gln Glu Val Ala Lys Val Ala Gln Leu Ile Ile
        275                 280                 285

Ile Ile Asp Asp Ile Tyr Asp Val Tyr Gly Thr Val Asp Glu Leu Glu
290                 295                 300

Leu Phe Thr Asn Ala Ile Asp Arg Trp Asp Leu Glu Ala Met Glu Gln
305                 310                 315                 320

Leu Pro Glu Tyr Met Lys Thr Cys Phe Leu Ala Leu Tyr Asn Ser Ile
                325                 330                 335

Asn Glu Ile Gly Tyr Asp Ile Leu Lys Glu Gly Arg Asn Val Ile
            340                 345                 350

Pro Tyr Leu Arg Asn Thr Trp Thr Glu Leu Cys Lys Ala Phe Leu Val
        355                 360                 365

Glu Ala Lys Trp Tyr Ser Ser Gly Tyr Thr Pro Thr Leu Glu Glu Tyr
    370                 375                 380

Leu Gln Thr Ser Trp Ile Ser Ile Gly Ser Leu Pro Met Gln Thr Tyr
385                 390                 395                 400

Val Phe Ala Leu Leu Gly Lys Asn Leu Ala Pro Glu Ser Ser Asp Phe
                405                 410                 415

Ala Glu Lys Ile Ser Asp Ile Leu Arg Leu Gly Gly Met Met Ile Arg
            420                 425                 430

Leu Pro Asp Asp Leu Gly Thr Ser Thr Asp Glu Leu Lys Arg Gly Asp
        435                 440                 445

Val Pro Lys Ser Ile Gln Cys Tyr Met His Glu Ala Gly Val Thr Glu
    450                 455                 460

Asp Val Ala Arg Asp His Ile Met Gly Leu Phe Gln Glu Thr Trp Lys
465                 470                 475                 480

Lys Leu Asn Glu Tyr Leu Val Glu Ser Ser Leu Pro His Ala Phe Ile
                485                 490                 495

Asp His Ala Met Asn Leu Gly Arg Val Ser Tyr Cys Thr Tyr Lys His
            500                 505                 510

Gly Asp Gly Phe Ser Asp Gly Phe Gly Asp Pro Gly Ser Gln Glu Lys
        515                 520                 525

Lys Met Phe Met Ser Leu Phe Ala Glu Pro Leu Gln Val Asp Glu Ala
```

```
            530                 535                 540
Lys Gly Ile Ser Phe Tyr Val Asp Gly Gly Ser Ala
545                 550                 555

<210> SEQ ID NO 24
<211> LENGTH: 551
<212> TYPE: PRT
<213> ORGANISM: Artificial Sequence
<220> FEATURE:
<223> OTHER INFORMATION: Synthetic Construct

<400> SEQUENCE: 24

Met Glu Thr Arg Arg Ser Ala Asn Tyr Gln Pro Asn Leu Trp Asn Phe
1               5                   10                  15

Glu Phe Leu Gln Ser Leu Glu Asn Asp Leu Lys Val Glu Lys Leu Glu
            20                  25                  30

Glu Lys Ala Thr Lys Leu Glu Glu Glu Val Arg Cys Met Ile Asn Arg
        35                  40                  45

Val Asp Thr Gln Pro Leu Ser Leu Leu Glu Leu Ile Asp Asp Val Gln
    50                  55                  60

Arg Leu Gly Leu Thr Tyr Lys Phe Glu Lys Asp Ile Ile Lys Ala Leu
65                  70                  75                  80

Glu Asn Ile Val Leu Leu Asp Glu Asn Lys Lys Asn Lys Ser Asp Leu
                85                  90                  95

His Ala Thr Ala Leu Ser Phe Arg Leu Leu Arg Gln His Gly Phe Glu
            100                 105                 110

Val Ser Gln Asp Val Phe Glu Arg Phe Lys Asp Lys Glu Gly Gly Phe
        115                 120                 125

Ser Gly Glu Leu Lys Gly Asp Val Gln Gly Leu Leu Ser Leu Tyr Glu
    130                 135                 140

Ala Ser Tyr Leu Gly Phe Glu Gly Glu Asn Leu Leu Glu Glu Ala Arg
145                 150                 155                 160

Thr Phe Ser Ile Thr His Leu Lys Asn Asn Leu Lys Glu Gly Ile Asn
                165                 170                 175

Thr Lys Val Ala Glu Gln Val Ser His Ala Leu Glu Leu Pro Tyr His
            180                 185                 190

Gln Arg Leu His Arg Leu Glu Ala Arg Trp Phe Leu Asp Lys Tyr Glu
        195                 200                 205

Pro Lys Glu Pro His His Gln Leu Leu Leu Glu Leu Ala Lys Leu Asp
    210                 215                 220

Phe Asn Met Val Gln Thr Leu His Gln Lys Glu Leu Gln Asp Leu Ser
225                 230                 235                 240

Arg Trp Trp Thr Glu Met Gly Leu Ala Ser Lys Leu Asp Phe Val Arg
                245                 250                 255

Asp Arg Leu Met Glu Val Tyr Phe Trp Ala Leu Gly Met Ala Pro Asp
            260                 265                 270

Pro Gln Phe Gly Glu Cys Arg Lys Ala Val Thr Lys Met Phe Gly Leu
        275                 280                 285

Val Thr Ile Ile Asp Asp Val Tyr Asp Val Tyr Gly Thr Leu Asp Glu
    290                 295                 300

Leu Gln Leu Phe Thr Asp Ala Val Glu Arg Trp Asp Val Asn Ala Ile
305                 310                 315                 320

Asn Thr Leu Pro Asp Tyr Met Lys Leu Cys Phe Leu Ala Leu Tyr Asn
                325                 330                 335

Thr Val Asn Asp Thr Ser Tyr Ser Ile Leu Lys Glu Lys Gly His Asn
```

```
                340                 345                 350
Asn Leu Ser Tyr Leu Thr Lys Ser Trp Arg Glu Leu Cys Lys Ala Phe
            355                 360                 365

Leu Gln Glu Ala Lys Trp Ser Asn Asn Lys Ile Ile Pro Ala Phe Ser
        370                 375                 380

Lys Tyr Leu Glu Asn Ala Ser Val Ser Ser Gly Val Ala Leu Leu
385                 390                 395                 400

Ala Pro Ser Tyr Phe Ser Val Cys Gln Gln Gln Glu Asp Ile Ser Asp
                405                 410                 415

His Ala Leu Arg Ser Leu Thr Asp Phe His Gly Leu Val Arg Ser Ser
            420                 425                 430

Cys Val Ile Phe Arg Leu Cys Asn Asp Leu Ala Thr Ser Ala Ala Glu
        435                 440                 445

Leu Glu Arg Gly Glu Thr Thr Asn Ser Ile Ile Ser Tyr Met His Glu
    450                 455                 460

Asn Asp Gly Thr Ser Glu Glu Gln Ala Arg Glu Glu Leu Arg Lys Leu
465                 470                 475                 480

Ile Asp Ala Glu Trp Lys Lys Met Asn Arg Glu Arg Val Ser Asp Ser
                485                 490                 495

Thr Leu Leu Pro Lys Ala Phe Met Glu Ile Ala Val Asn Met Ala Arg
            500                 505                 510

Val Ser His Cys Thr Tyr Gln Tyr Gly Asp Gly Leu Gly Arg Pro Asp
        515                 520                 525

Tyr Ala Thr Glu Asn Arg Ile Lys Leu Leu Leu Ile Asp Pro Phe Pro
    530                 535                 540

Ile Asn Gln Leu Met Tyr Val
545                 550

<210> SEQ ID NO 25
<211> LENGTH: 548
<212> TYPE: PRT
<213> ORGANISM: Artificial Sequence
<220> FEATURE:
<223> OTHER INFORMATION: Synthetic Construct

<400> SEQUENCE: 25

Met Glu Gly Arg Arg Ser Ala Asn Tyr Gln Pro Ser Val Trp Thr Tyr
1               5                   10                  15

Asn Tyr Leu Gln Ser Ile Val Ala Gly Glu Gly Arg Gln Ser Arg Arg
            20                  25                  30

Glu Val Glu Gln Gln Lys Glu Lys Val Gln Ile Leu Glu Gly Glu Val
        35                  40                  45

Arg Gly Ala Leu Asn Asp Glu Lys Ala Glu Thr Phe Thr Ile Phe Ala
    50                  55                  60

Thr Val Asp Asp Ile Gln Arg Leu Gly Leu Gly Asp His Phe Glu Glu
65                  70                  75                  80

Asp Ile Ser Asn Ala Leu Arg Arg Cys Val Ser Lys Gly Ala Val Phe
                85                  90                  95

Met Ser Leu Gln Lys Ser Leu His Gly Thr Ala Leu Gly Phe Arg Leu
            100                 105                 110

Leu Arg Gln His Gly Tyr Glu Val Ser Gln Asp Val Phe Lys Ile Phe
        115                 120                 125

Leu Asp Glu Ser Gly Ser Phe Val Lys Thr Leu Gly Gly Asp Val Gln
    130                 135                 140

Gly Val Leu Ser Leu Tyr Glu Ala Ser His Leu Ala Phe Glu Glu Glu
```

```
            145                 150                 155                 160
        Asp Ile Leu His Lys Ala Arg Ser Phe Ala Ile Lys His Leu Glu Asn
                        165                 170                 175
        Leu Asn Ser Asp Val Asp Lys Asp Leu Gln Asp Gln Val Lys His Glu
                        180                 185                 190
        Leu Glu Leu Pro Leu His Arg Arg Met Pro Leu Leu Glu Ala Arg Arg
                        195                 200                 205
        Ser Ile Glu Ala Tyr Ser Arg Arg Glu Tyr Thr Asn Pro Gln Ile Leu
                210                 215                 220
        Glu Leu Ala Leu Thr Asp Phe Asn Val Ser Gln Ser Thr Leu Gln Arg
        225                 230                 235                 240
        Asp Leu Gln Glu Met Leu Gly Trp Trp Asn Asn Thr Gly Leu Ala Lys
                        245                 250                 255
        Arg Leu Ser Phe Ala Arg Asp Arg Leu Ile Glu Cys Phe Phe Trp Ala
                        260                 265                 270
        Val Gly Ile Ala His Glu Pro Ser Leu Ser Ile Cys Arg Lys Ala Val
                        275                 280                 285
        Thr Lys Ala Phe Ala Leu Ile Leu Val Leu Asp Asp Val Tyr Asp Val
                        290                 295                 300
        Phe Gly Thr Leu Glu Glu Leu Glu Leu Phe Thr Glu Ala Val Arg Arg
        305                 310                 315                 320
        Trp Asp Leu Asn Ala Val Glu Asp Leu Pro Val Tyr Met Lys Leu Cys
                        325                 330                 335
        Tyr Leu Ala Leu Tyr Asn Ser Val Asn Glu Met Ala Tyr Glu Thr Leu
                        340                 345                 350
        Lys Glu Lys Gly Glu Asn Val Ile Pro Tyr Leu Ala Lys Ala Trp Tyr
                        355                 360                 365
        Asp Leu Cys Lys Ala Phe Leu Gln Glu Ala Lys Trp Ser Asn Ser Arg
                        370                 375                 380
        Ile Ile Pro Gly Val Glu Glu Tyr Leu Asn Asn Gly Trp Val Ser Ser
        385                 390                 395                 400
        Ser Gly Ser Val Met Leu Ile His Ala Tyr Phe Leu Ala Ser Pro Ser
                        405                 410                 415
        Ile Arg Lys Glu Glu Leu Glu Ser Leu Glu His Tyr His Asp Leu Leu
                        420                 425                 430
        Arg Leu Pro Ser Leu Ile Phe Arg Leu Thr Asn Asp Ile Ala Ser Ser
                        435                 440                 445
        Ser Ala Glu Leu Glu Arg Gly Glu Thr Thr Asn Ser Ile Arg Cys Phe
        450                 455                 460
        Met Gln Glu Lys Gly Ile Ser Glu Leu Glu Ala Arg Glu Cys Val Lys
        465                 470                 475                 480
        Glu Glu Ile Asp Thr Ala Trp Lys Lys Met Asn Lys Tyr Met Val Asp
                        485                 490                 495
        Arg Ser Thr Phe Asn Gln Ser Phe Val Arg Met Thr Tyr Asn Leu Ala
                        500                 505                 510
        Arg Met Ala His Cys Val Tyr Gln Asp Gly Asp Ala Ile Gly Ser Pro
                        515                 520                 525
        Asp Asp Leu Ser Trp Asn Arg Val His Ser Leu Ile Ile Lys Pro Ile
                        530                 535                 540
        Ser Pro Ala Ala
        545

<210> SEQ ID NO 26
```

<211> LENGTH: 553
<212> TYPE: PRT
<213> ORGANISM: Artificial Sequence
<220> FEATURE:
<223> OTHER INFORMATION: Synthetic Construct

<400> SEQUENCE: 26

```
Met Glu Thr Arg Gln Ser Ala Asn Phe Gln Pro Ser Leu Trp Ser Tyr
 1               5                  10                  15
Glu Tyr Ile Gln Ser Leu Lys Asn Gly Tyr Glu Ala Asp Leu Tyr Glu
            20                  25                  30
Asp Arg Ala Lys Lys Leu Gly Glu Glu Val Arg Arg Met Ile Asn Asn
        35                  40                  45
Lys Asp Thr Lys Leu Leu Thr Thr Leu Glu Leu Ile Asp Asp Ile Glu
50                  55                  60
Arg Leu Gly Leu Gly Tyr Arg Phe Lys Glu Glu Ile Met Arg Ala Leu
65                  70                  75                  80
Asp Arg Phe Val Thr Leu Lys Gly Cys Glu Glu Phe Thr Asn Gly Ser
                85                  90                  95
Ile His Asp Thr Ala Leu Ser Phe Arg Leu Leu Arg Gln His Gly Phe
            100                 105                 110
Gly Val Ser Gln Asp Met Phe Asn Cys Phe Lys Asp Gln Lys Gly Asn
        115                 120                 125
Phe Lys Glu Cys Leu Ser Lys Asp Ile Lys Gly Leu Leu Ser Leu Tyr
130                 135                 140
Glu Ala Ser Tyr Leu Gly Phe Glu Gly Glu Asn Leu Leu Asp Glu Ala
145                 150                 155                 160
Arg Glu Phe Thr Thr Met His Leu Lys Asp Leu Lys Gly Asp Val Ser
                165                 170                 175
Arg Thr Leu Lys Glu Glu Val Arg His Ser Leu Glu Met Pro Leu His
            180                 185                 190
Arg Arg Met Arg Arg Leu Glu Gln Arg Trp Tyr Ile Asp Ala Tyr Asn
        195                 200                 205
Met Lys Glu Ala His Asp Arg Lys Leu Leu Glu Leu Ala Lys Leu Asp
210                 215                 220
Phe Asn Ile Val Gln Ser Val His Gln Arg Asp Leu Lys Asp Met Ser
225                 230                 235                 240
Arg Trp Trp Gln Glu Met Gly Leu Gly Asn Lys Leu Ser Phe Ala Arg
                245                 250                 255
Asp Arg Leu Met Glu Cys Phe Phe Ser Val Gly Met Ala Phe Glu
            260                 265                 270
Pro Gln Phe Ser Asn Ser Arg Lys Ala Val Thr Lys Met Phe Ser Phe
        275                 280                 285
Ile Thr Val Ile Asp Asp Ile Tyr Asp Val Tyr Ala Thr Leu Glu Glu
290                 295                 300
Leu Glu Met Phe Thr Asp Ile Val Gln Arg Trp Asp Val Lys Ala Val
305                 310                 315                 320
Lys Asp Leu Pro Glu Tyr Met Lys Leu Cys Phe Leu Ala Leu Phe Asn
                325                 330                 335
Thr Val Asn Glu Met Val Tyr Thr Leu Lys Glu Gln Gly Val Asp
            340                 345                 350
Ile Leu Pro Tyr Leu Thr Lys Ala Trp Gly Asp Ile Cys Lys Ala Phe
        355                 360                 365
Leu Gln Glu Thr Lys Trp Arg Tyr Lys Arg Thr Pro Ser Ser Glu
370                 375                 380
```

```
Asp Tyr Leu Asp Asn Ala Trp Ile Ser Val Ser Gly Ala Leu Leu Leu
385                 390                 395                 400

Ile His Ala Tyr Phe Leu Met Ser Pro Ser Ile Thr Asp Arg Ala Leu
            405                 410                 415

Lys Gly Leu Glu Asp Tyr His Asn Ile Leu Arg Trp Pro Ser Ile Ile
        420                 425                 430

Phe Arg Leu Thr Asn Asp Leu Gly Thr Ser Thr Ala Glu Leu Glu Arg
            435                 440                 445

Gly Glu Thr Ala Asn Ser Ile Leu Cys Tyr Met Arg Glu Thr Ser Arg
        450                 455                 460

Ser Glu Asp Phe Ala Arg Glu His Ile Ser Asn Leu Ile Asp Lys Thr
465                 470                 475                 480

Trp Lys Lys Met Asn Lys Asp Arg Phe Ser Asp Ser Pro Phe Glu Glu
                485                 490                 495

Pro Phe Leu Glu Thr Ala Ile Asn Leu Ala Arg Ile Ser His Cys Ile
            500                 505                 510

Tyr Gln His Gly Asp Gly His Gly Ala Pro Asp Thr Arg Thr Lys Asp
        515                 520                 525

Arg Val Leu Ser Leu Ile Ile Glu Pro Ile Pro Cys Tyr Asp Pro Ser
530                 535                 540

Thr Asn Phe His Ser Gln Ile His Leu
545                 550
```

<210> SEQ ID NO 27
<211> LENGTH: 549
<212> TYPE: PRT
<213> ORGANISM: Artificial Sequence
<220> FEATURE:
<223> OTHER INFORMATION: Synthetic Construct

<400> SEQUENCE: 27

```
Met Glu Thr Arg Arg Ser Ala Asn Tyr Gln Pro Ser Val Trp Thr Tyr
1               5                   10                  15

Asn Tyr Leu Gln Ser Leu Val Ala Asp Asp Ile Arg Arg Ser Arg Arg
            20                  25                  30

Glu Val Glu Gln Glu Arg Glu Lys Ala Gln Ile Leu Glu Glu Asp Val
        35                  40                  45

Arg Gly Ala Leu Asn Asp Gly Asn Ala Glu Pro Met Ala Ile Phe Ala
    50                  55                  60

Leu Val Asp Asp Ile Gln Arg Leu Gly Leu Gly Arg Tyr Phe Glu Glu
65                  70                  75                  80

Asp Ile Ser Lys Ala Leu Arg Arg Cys Leu Ser Gln Tyr Ala Val Thr
                85                  90                  95

Gly Ser Leu Gln Lys Ser Leu His Gly Thr Ala Leu Ser Phe Arg Val
            100                 105                 110

Leu Arg Gln His Gly Phe Glu Val Ser Gln Asp Val Phe Lys Ile Phe
        115                 120                 125

Met Asp Glu Ser Gly Ser Phe Met Lys Thr Leu Gly Gly Asp Val Gln
    130                 135                 140

Gly Met Leu Ser Leu Tyr Glu Ala Ser His Leu Ala Phe Glu Glu Glu
145                 150                 155                 160

Asp Ile Leu His Lys Ala Lys Thr Phe Ala Ile Lys His Leu Glu Asn
                165                 170                 175

Leu Asn His Asp Ile Asp Gln Asp Leu Gln Asp His Val Asn His
            180                 185                 190
```

```
Leu Glu Leu Pro Leu His Arg Arg Met Pro Leu Leu Glu Ala Arg Arg
            195                 200                 205

Phe Ile Glu Ala Tyr Ser Arg Arg Ser Asn Val Asn Pro Arg Ile Leu
210                 215                 220

Glu Leu Ala Val Met Lys Phe Asn Ser Ser Gln Leu Thr Leu Gln Arg
225                 230                 235                 240

Asp Leu Gln Asp Met Leu Gly Trp Trp Asn Asn Val Gly Leu Ala Lys
            245                 250                 255

Arg Leu Ser Phe Ala Arg Asp Arg Leu Met Glu Cys Phe Phe Trp Ala
            260                 265                 270

Val Gly Ile Ala Arg Glu Pro Ala Leu Ser Asn Cys Arg Lys Gly Val
            275                 280                 285

Thr Lys Ala Phe Ser Leu Ile Leu Val Leu Asp Asp Val Tyr Asp Val
            290                 295                 300

Phe Gly Thr Leu Asp Glu Leu Glu Leu Phe Thr Asp Ala Val Arg Arg
305                 310                 315                 320

Trp His Glu Asp Ala Val Glu Asn Leu Pro Gly Tyr Met Lys Leu Cys
            325                 330                 335

Phe Leu Ala Leu Tyr Asn Ser Val Asn Asp Met Ala Tyr Glu Thr Leu
            340                 345                 350

Lys Glu Thr Gly Glu Asn Val Thr Pro Tyr Leu Thr Lys Val Trp Tyr
            355                 360                 365

Asp Leu Cys Lys Ala Phe Leu Gln Glu Ala Lys Trp Ser Tyr Asn Lys
            370                 375                 380

Ile Thr Pro Gly Val Glu Tyr Leu Asn Asn Gly Trp Val Ser Ser
385                 390                 395                 400

Ser Gly Gln Val Met Leu Thr His Ala Tyr Phe Leu Ser Ser Pro Ser
            405                 410                 415

Leu Arg Lys Glu Glu Leu Glu Ser Leu Glu His Tyr His Asp Leu Leu
            420                 425                 430

Arg Leu Pro Ser Leu Ile Phe Arg Leu Thr Asn Asp Leu Ala Thr Ser
            435                 440                 445

Ser Ala Glu Leu Gly Arg Gly Glu Thr Thr Asn Ser Ile Leu Cys Tyr
450                 455                 460

Met Arg Glu Lys Gly Phe Ser Glu Ser Glu Ala Arg Lys Gln Val Ile
465                 470                 475                 480

Glu Gln Ile Asp Thr Ala Trp Arg Gln Met Asn Lys Tyr Met Val Asp
            485                 490                 495

His Ser Thr Phe Asn Arg Ser Phe Met Gln Met Thr Tyr Asn Leu Ala
            500                 505                 510

Arg Met Ala His Cys Val Tyr Gln Asp Gly Asp Ala Ile Gly Ala Pro
            515                 520                 525

Asp Asp Gln Ser Trp Asn Arg Val His Ser Leu Ile Ile Lys Pro Val
530                 535                 540

Ser Leu Ala Pro Cys
545

<210> SEQ ID NO 28
<211> LENGTH: 544
<212> TYPE: PRT
<213> ORGANISM: Artificial Sequence
<220> FEATURE:
<223> OTHER INFORMATION: Synthetic Construct

<400> SEQUENCE: 28
```

-continued

```
Met Glu Thr Arg Arg Ser Ala Asn Tyr Glu Pro Asn Ser Trp Asp Tyr
 1               5                  10                  15

Asp Tyr Leu Leu Ser Ser Asp Thr Glu Asp Ala Ile Glu Val Tyr Lys
                20                  25                  30

Asp Lys Ala Lys Lys Leu Asp Ala Glu Val Arg Ser Lys Ile Asn Asn
            35                  40                  45

Glu Thr Ala Glu Phe Leu Thr Gln Leu Glu Leu Ile Asp Thr Ile Gln
        50                  55                  60

Arg Leu Gly Leu Gly Tyr Arg Phe Glu Ser Asp Ile Arg Arg Ala Leu
 65                  70                  75                  80

Asp Arg Phe Val Ser Ser Gly Gly Phe Glu Ala Val Ala Lys Thr Ser
                85                  90                  95

Leu Gln Ala Thr Ala Leu Ser Phe Arg Leu Leu Arg Gln His Gly Phe
            100                 105                 110

Glu Val Ser Gln Glu Val Phe Asn Gly Phe Lys Asp Gln Asn Gly Asn
        115                 120                 125

Phe Met Glu Asp Leu Lys Glu Asp Ile Lys Ala Leu Leu Ser Leu His
        130                 135                 140

Glu Ala Ser Phe Leu Ala Leu Glu Gly Glu Asn Ile Leu Asp Glu Ala
145                 150                 155                 160

Lys Val Phe Thr Ile Ser His Leu Lys Glu Leu Asn Glu Glu Lys Ile
                165                 170                 175

Gly Lys Asp Met Val Glu Gln Val Asn His Ala Leu Glu Leu Pro Leu
            180                 185                 190

His Arg Arg Thr Gln Arg Leu Glu Ala Val Trp Ser Ile Glu Ala Tyr
        195                 200                 205

Arg Lys Lys Glu Asp Ala Asn Arg Val Leu Leu Glu Leu Ala Ile Leu
210                 215                 220

Asp Tyr Asn Met Val Gln Ser Val Tyr Gln Arg Asp Leu Arg Glu Thr
225                 230                 235                 240

Ser Arg Trp Trp Arg Arg Val Gly Leu Ala Thr Lys Leu His Phe Ala
                245                 250                 255

Arg Asp Arg Leu Ile Glu Ser Phe Tyr Trp Ala Val Gly Val Ala Phe
            260                 265                 270

Glu Pro Gln Tyr Ser Asp Cys Arg Ile Ser Val Ala Lys Met Phe Ser
        275                 280                 285

Phe Val Thr Ile Ile Asp Asp Ile Tyr Asp Val Tyr Gly Thr Leu Glu
        290                 295                 300

Glu Leu Glu Leu Phe Thr Asp Ala Val Glu Arg Trp Asp Val Ser Ala
305                 310                 315                 320

Ile Asp Asp Leu Pro Asp Tyr Met Lys Leu Cys Phe Leu Ala Leu Tyr
                325                 330                 335

Asn Thr Ile Asn Glu Ile Ala Tyr Asp Asn Leu Lys Glu Lys Gly Glu
            340                 345                 350

Asn Ile Leu Pro Tyr Leu Thr Lys Ala Trp Ala Asp Leu Cys Asn Ala
        355                 360                 365

Phe Leu Gln Glu Ala Arg Phe Leu Tyr Asn Lys Ser Thr Pro Thr Phe
        370                 375                 380

Ser Asp Tyr Phe Gly Asn Ala Trp Lys Ser Ser Gly Pro Leu Gln
385                 390                 395                 400

Leu Val Phe Ala Tyr Phe Ala Val Val Gln Asn Ile Lys Lys Glu Glu
                405                 410                 415
```

```
Thr Glu Asn Leu Leu Lys Tyr His Asp Ile Ile Ser Trp Pro Ser Tyr
            420                 425                 430

Ile Phe Arg Leu Cys Asn Asp Leu Ala Ser Ala Ser Ala Glu Ile Ala
        435                 440                 445

Arg Gly Glu Thr Ala Asn Ser Val Ser Cys Tyr Met Arg Thr Lys Gly
    450                 455                 460

Ile Ser Glu Glu Leu Ala Thr Glu Ser Val Met Asn Leu Ile Asp Glu
465                 470                 475                 480

Thr Trp Lys Lys Met Asn Lys Glu Lys Leu Gly Asp Ser Leu Phe Ala
                485                 490                 495

Lys His Phe Val Glu Thr Ala Ile Asn Leu Ala Arg Gln Ser His Cys
            500                 505                 510

Thr Tyr His Asn Gly Asp Ala His Thr Ser Pro Asp Glu Leu Thr Arg
        515                 520                 525

Lys Arg Val Leu Ser Val Ile Thr Glu Pro Ile Leu Pro Leu Glu Arg
    530                 535                 540
```

<210> SEQ ID NO 29
<211> LENGTH: 518
<212> TYPE: PRT
<213> ORGANISM: Artificial Sequence
<220> FEATURE:
<223> OTHER INFORMATION: Synthetic Construct

<400> SEQUENCE: 29

```
Asp Ile Arg Tyr Glu Asp Lys Ala Lys Lys Leu Leu Glu Glu Val Arg
1               5                   10                  15

Arg Met Ile Lys Asp Glu Asn Thr Asp Ile Trp Ile Lys Leu Glu Leu
            20                  25                  30

Ile Asp Asp Val Lys Arg Leu Gly Ile Gly Tyr Ser Phe Asp Met Glu
        35                  40                  45

Ile Gly Glu Ala Leu His Arg Cys Leu Ser Ser Glu Thr Phe Ile Asp
    50                  55                  60

Thr Ile Thr His Asn His Arg Ser Leu His Glu Thr Ala Leu Ser Phe
65                  70                  75                  80

Arg Val Leu Arg Glu Tyr Gly Tyr Asp Val Thr Thr Asp Ile Phe Glu
                85                  90                  95

Arg Phe Lys Asp Tyr Asn Gly Asn Phe Lys Ala Ile Leu Ser Arg Asp
            100                 105                 110

Val Lys Gly Met Leu Ser Leu Tyr Glu Ala Ser Phe Leu Ser Tyr Glu
        115                 120                 125

Gly Glu Gln Ile Leu Asp Glu Ala Lys Ala Phe Thr Ser Phe His Leu
    130                 135                 140

Lys Gly Ala Leu Lys Glu Gly Arg Ser Asn Thr Met Ile Leu Glu Gln
145                 150                 155                 160

Val Asn His Ala Met Glu Leu Pro Leu His His Arg Ile Gln Arg Leu
                165                 170                 175

Glu Ala Arg Trp Tyr Ile Glu Ser Tyr Ala Lys Arg Lys Asp Ala Asn
            180                 185                 190

Met Val Leu Leu Glu Ala Ala Lys Leu Asp Phe Asn Ile Val Gln Ser
        195                 200                 205

Thr Leu Gln Thr Asp Leu Gln Glu Met Ser Arg Trp Trp Lys Gly Met
    210                 215                 220

Gly Leu Ala Ser Lys Leu Ser Phe Ser Arg Asp Arg Leu Met Glu Cys
225                 230                 235                 240
```

Phe Phe Trp Thr Val Gly Met Val Phe Glu Pro Gln Leu Ser Asp Leu
            245                 250                 255

Arg Lys Gly Leu Thr Lys Val Ala Ser Leu Ile Thr Ile Asp Asp
        260                 265                 270

Val Tyr Asp Val Tyr Gly Thr Leu Asp Glu Leu Glu Leu Phe Thr Ala
        275                 280                 285

Ala Val Glu Ser Trp Asp Val Lys Ala Val Gln Val Leu Pro Asp Tyr
    290                 295                 300

Met Lys Ile Cys Phe Leu Ala Leu Tyr Asn Thr Val Asn Glu Phe Ala
305                 310                 315                 320

Tyr Asp Ala Leu Lys Glu Gln Gly Gln Asn Ile Leu Pro Tyr Leu Thr
                325                 330                 335

Lys Ala Trp Ser Asn Met Leu Lys Ala Phe Leu Glu Glu Ala Lys Trp
            340                 345                 350

Ser Arg Asp Lys His Val Pro Lys Phe Asp Asp Tyr Leu Asn Asn Ala
        355                 360                 365

Trp Val Ser Val Ser Gly Val Val Ile Leu Thr His Ala Tyr Phe Leu
    370                 375                 380

Leu Asn His Ser Ile Thr Lys Glu Ala Leu Gln Ser Leu Glu Asn Tyr
385                 390                 395                 400

His Ala Leu Leu Arg Arg Ser Ser Thr Ile Phe Arg Leu Cys Asn Asp
                405                 410                 415

Leu Gly Thr Ser Lys Ala Glu Leu Glu Arg Gly Glu Ala Ala Ser Ser
            420                 425                 430

Ile Val Cys Tyr Met Arg Glu Ser Gly Ala Ser Glu Glu Gly Ala Tyr
        435                 440                 445

Lys His Ile Arg Arg Leu Leu Asn Glu Thr Trp Lys Lys Met Asn Lys
    450                 455                 460

Asp Lys Val Ser Gln Ser Pro Phe Pro Lys Pro Phe Ile Glu Ile Ala
465                 470                 475                 480

Ile Asn Leu Gly Arg Ile Ser Gln Cys Thr Tyr Gln Tyr Gly Asp Gly
                485                 490                 495

His Gly Ala Pro Asp Ser Thr Val Glu Asn Arg Ile Arg Ser Leu Ile
            500                 505                 510

Ile Glu Pro Ile Ala Ile
        515

<210> SEQ ID NO 30
<211> LENGTH: 125
<212> TYPE: DNA
<213> ORGANISM: Artificial Sequence
<220> FEATURE:
<223> OTHER INFORMATION: Synthetic Construct

<400> SEQUENCE: 30
aattcatata aaaacatac agataaccat ctgcggtgat aaattatctc tggcggtgtt      60
gacataaata ccactggcgg tgatactgag cacatcagca ggacgcactg accaccatga    120
aggtg                                                                125

<210> SEQ ID NO 31
<211> LENGTH: 547
<212> TYPE: PRT
<213> ORGANISM: Artificial Sequence
<220> FEATURE:
<223> OTHER INFORMATION: Synthetic Construct

<400> SEQUENCE: 31

```
Lys Ser Ala Asn Tyr Gln Pro Asn Leu Trp Asn Tyr Asp Phe Leu Gln
  1               5                  10                  15

Ser Leu Lys Asn Asp Tyr Ala Asp Val Lys Tyr Glu Ile Met Ala Arg
             20                  25                  30

Lys Leu Glu Glu Val Arg Arg Met Ile Lys Asp Glu Asn Ser Glu Ile
         35                  40                  45

Trp Val Thr Leu Asp Leu Ile Asp Asn Val Lys Arg Leu Gly Leu Ser
     50                  55                  60

Tyr His Phe Asp Lys Glu Ile Arg Glu Ala Leu His Arg Phe Leu Ser
 65                  70                  75                  80

Leu Glu Arg Cys Asn Ala Thr Asn Ile His Thr Gly Leu His Glu Thr
                 85                  90                  95

Ala Leu Ser Phe Arg Leu Leu Arg Glu Tyr Gly Asp Asp Val Ser Ala
             100                 105                 110

Asp Val Phe Glu Arg Phe Glu Asp Asn Gly Asn Phe Lys Ala Ser
             115                 120                 125

Leu Ser Arg Asp Met Lys Gly Met Leu Ser Leu Tyr Glu Ala Ser Phe
     130                 135                 140

Leu Ser Tyr Glu Glu Leu Ile Leu Asp Lys Thr Lys Ala Phe Ser
145                 150                 155                 160

Ser Phe His Leu Arg Gly Ala Leu Lys Glu Gly Arg Ser Asn Ser Met
                 165                 170                 175

Leu Leu Glu Gln Val Asn His Ala Leu Glu Leu Pro Leu His His Arg
             180                 185                 190

Ile Gln Arg Leu Glu Ala Arg Trp Tyr Ile Glu Ser Tyr Ala Lys Arg
         195                 200                 205

Lys Asp Ala Asn Trp Val Leu Leu Glu Ala Ala Lys Leu Asp Phe Asn
210                 215                 220

Ile Val Gln Ser Thr Leu Gln Lys Asp Leu Gln Glu Met Ser Arg Trp
225                 230                 235                 240

Trp Lys Arg Met Gly Leu Ala Pro Lys Leu Ser Phe Ser Arg Asp Arg
             245                 250                 255

Leu Met Glu Cys Phe Phe Trp Ser Met Gly Met Ala Phe Glu Pro Gln
             260                 265                 270

Phe Ser Asp Leu Arg Lys Gly Leu Thr Lys Val Thr Ser Leu Ile Thr
     275                 280                 285

Thr Ile Asp Asp Val Tyr Asp Val Tyr Gly Ser Leu Asp Glu Leu Glu
     290                 295                 300

Leu Phe Thr Lys Ala Val Glu Ser Trp Asp Ile Lys Ala Val Gln Val
305                 310                 315                 320

Met Pro Glu Tyr Met Lys Ile Cys Phe Leu Ala Leu Tyr Asn Thr Val
             325                 330                 335

Asn Glu Phe Ala Tyr Asp Ala Leu Lys Ile Lys Gly Gln Asn Ile Leu
             340                 345                 350

Pro His Leu Thr Lys Ala Trp Ser Val Met Leu Lys Ala Phe Leu Gln
             355                 360                 365

Glu Ala Lys Trp Cys Arg Asp Lys Tyr Leu Pro Pro Phe Glu Asp Tyr
     370                 375                 380

Leu Asn Asn Ala Trp Val Ser Val Ser Gly Val Val Ile Leu Thr His
385                 390                 395                 400

Ala Tyr Phe Leu Leu Asn Asp Asn Ile Thr Lys Asp Ala Leu Asp Ser
                 405                 410                 415
```

```
Leu Asp Asn Tyr His Asp Leu Leu Arg Arg Pro Ser Ile Ile Phe Arg
            420                 425                 430

Leu Cys Asn Asp Leu Gly Thr Ser Arg Ala Glu Leu Gln Arg Gly Glu
        435                 440                 445

Ala Ala Ser Ser Ile Val Cys Asn Met Arg Glu Ser Cys Val Thr Glu
    450                 455                 460

Glu Gly Ala Tyr Lys Asn Ile His Ser Leu Leu Asp Glu Thr Trp Lys
465                 470                 475                 480

Lys Met Asn Lys Asp Arg Ala Met His Ser Pro Phe Ser Lys Pro Phe
                485                 490                 495

Val Glu Ala Ala Ile Asn Leu Ala Arg Ile Ser His Cys Thr Tyr Leu
            500                 505                 510

Asn Gly Asp Gly His Gly Ala Pro Asp Ile Ala Ala Lys Asn Arg Ile
        515                 520                 525

Arg Ser Leu Ile Ile Glu Pro Ile Pro Leu Arg Glu Ile Asn Ala Asp
    530                 535                 540

Ile Val Gln
545

<210> SEQ ID NO 32
<211> LENGTH: 6858
<212> TYPE: DNA
<213> ORGANISM: Artificial Sequence
<220> FEATURE:
<223> OTHER INFORMATION: Synthetic Construct

<400> SEQUENCE: 32
gtttgacagc ttatcatcga ctgcacggtg caccaatgct tctggcgtca ggcagccatc      60
ggaagctgtg gtatggctgt gcaggtcgta aatcactgca taattcgtgt cgctcaaggc     120
gcactcccgt tctggataat gttttttgcg ccgacatcat aacggttctg caaatattc     180 tgaaatgagc tgttgacaat taatcatccg gctcgtataa tgtgtggaat tgtgagcgga     240
taacaatttc acacaggaaa cagcgccgct gagaaaaagc gaagcggcac tgctctttaa     300
caatttatca gacaatctgt gtgggcactc gaccggaatt atcgattaac tttattatta     360
aaaattaaag aggtatatat taatgtatcg attaaataag gaggaataaa ccatgaacac     420
ccgtcgcagc gccaattacc agccgaacct gtgggatttc gagttttgc aaagcgtcga     480 aaacgacttg caggtggaac gcctggaaga gcgtgcacgt aagctggaag aagaagtgcg     540
tggtctgatg aaaaaggtcg agattgagcc gttgagcctg ctggaactga tggacaacgt     600
tgagcgcctg gtctgaccct acaaattcga agaggacatc aaaagcgcgt tgaataaccg     660
cattgtccca ctgttgcatc accatactat caataagtac ggtctgcacg ccacggctct     720
gagcttccgt ttcctgcgtc aacacgcctt tcacgtcagc ccggatgttt ttgaaagctt     780
caaagaagaa ggtaagttca gaaagagat tagcggcgac gtgctgggtc tgctgaacct     840
gtacgagact agctacctgg gctttgaagg tgaaaccatt ctggacgagg cacgcgcctt     900
cagcgctacc catctgaaaa atctgttgca aaccaaccag gtgcagaata aagttatggc     960
ggagaaggtc cgccatgcgt tggagctgcc gtatcaccgt cgtgttcacc gtttggaagc    1020
ccgctggttt attgagcgct atgagcagaa agaggcgcat gatggtgcct tgctggagct    1080
ggcgaaactg gatttcaaca tggttcagtc tgtgatgaag aaagagctgc aagagctgag    1140
ccgctggtgg cgtgagatcg gtctgaccag caagctggac ttcgtgcgtg atcgtctgat    1200
ggaagtgtac ttttgggcgc tgggtatggc tccgcacccg cagctgacgg agtgccgtaa    1260
```

```
agcagtgacc aagatgtttg gcctggttac catcattgac gatgtttacg atgtgtatgg      1320
caccctggac gagctgcaac tgtttacgga tgcggttgac cgttgggacg ttaacgcagt      1380
cgaaacgctg ccggactaca tgaaactgtg ttacctggcg ctgtataact ccgttaatga      1440
cacggcatat agcactctgc gtgagaaggg tgacaatagc ctgcctcact ggcaaagtc       1500 gtggcgtgat ctgtgtaagg cgtttctgca agaggcgaag tggagcaata acaagatcat      1560
tccgccgttc gatgcgtaca tccgcaacgc atctgtcagc agcagcggcg gtgctctgtt     1620
ggcgccatgt tacttctccg ttacgcaaga cagcacgagc caggccatcg attctattac      1680
gaactaccac ggcatcgtcc gttcgagctg cgcaatcttc cgcctgtgca atgacctggc      1740
gacctctgct gcggagctgg agcgtggcga aaccaccaat tccatcacgt cctatatgac      1800
cgaaaatggc accaccgaag aagaggcgcg tgaaagcctg ggtaaactga ttgaccaaga      1860
gtggaagaaa atgaatcgtg atgtggtcct ggaaagcgcg tatccgaacg tgtttaaaga      1920
aattgcgatt aacatggcac gcgttagcca ttgcacctat cagtatgcg atggtctggg     1980 tcgtccggat gatactgcgg agaatcgtat caagctgtct ctgatcgaac cgattccgat      2040
caactaactg cataaaggag gtaaaaaaac atggtatcct gttctgcgcc gggtaagatt      2100
tacctgttcg gtgaacacgc cgtagtttat ggcgaaactg caattgcgtg tgcggtggaa      2160
ctgcgtaccc gtgttcgcgc ggaactcaat gactctatca ctattcagag ccagatcggc      2220
cgcaccggtc tggatttcga aaagcaccct tatgtgtctg cggtaattga aaaatgcgc      2280 aaatctattc ctattaacgg tgtttttcttg accgtcgatt ccgacatccc ggtgggctcc      2340
ggtctgggta gcagcgcagc cgttactatc gcgtctattg gtgcgctgaa cgagctgttc      2400
ggctttggcc tcagcctgca agaaatcgct aaactgggcc acgaaatcga aattaaagta      2460
cagggtgccg cgtccccaac cgatacgtat gtttctacct tcggcggcgt ggttaccatc      2520
ccggaacgtc gcaaactgaa aactccggac tgcggcattg tgattggcga taccggcgtt      2580
ttctcctcca ccaaagagtt agtagctaac gtacgtcagc tgcgcgaaag ctacccggat      2640
ttgatcgaac cgctgatgac ctctattggc aaaatctctc gtatcggcga acaactggtt      2700
ctgtctggcg actacgcatc catcggccgc ctgatgaacg tcaaccaggg tctcctggac      2760
gccctgggcg ttaacatctt agaactgagc cagctgatct attccgctcg tgcggcaggt      2820
gcgtttggcg ctaaaatcac gggcgctggc ggcggtggct gtatggttgc gctgaccgct      2880
ccggaaaaat gcaaccaagt ggcagaagcg gtagcaggcg ctggcggtaa agtgactatc      2940
actaaaccga ccgagcaagg tctgaaagta gattaaagtc tagttaaagt ttaaacggtc      3000
tccagcttgg ctgttttggc ggatgagaga agatttttcag cctgatacag attaaatcag      3060
aacgcagaag cggtctgata aaacagaatt tgcctggcgg cagtagcgcg gtggtcccac      3120
ctgaccccat gccgaactca gaagtgaaac gccgtagcgc cgatggtagt gtgggtctc       3180 cccatgcgag agtagggaac tgccaggcat caaataaaac gaaaggctca gtcgaaagac      3240
tgggcctttc gttttatctg ttgtttgtcg gtgaacgctc tcctgagtag acaaatccg       3300 ccgggagcgg atttgaacgt tgcgaagcaa cggcccggag ggtggcgggc aggacgcccg      3360
ccataaactg ccaggcatca aattaagcag aaggccatcc tgacggatgg ccttttttgcg      3420 tttctacaaa ctcttttttgt ttatttttct aaatacattc aaatatgtat ccgctcatga      3480
gacaataacc ctgataaatg cttcaataat attgaaaaag gaagagtatg agtattcaac      3540
atttccgtgt cgcccttatt cccttttttg cggcattttg ccttcctgtt tttgctcacc      3600
cagaaacgct ggtgaaagta aaagatgctg aagatcagtt gggtgcacga gtgggttaca      3660
```

```
tcgaactgga tctcaacagc ggtaagatcc ttgagagttt tcgcccgaa gaacgttttc    3720 caatgatgag cacttttaaa gttctgctat gtggcgcggt attatcccgt gttgacgccg    3780
ggcaagagca actcggtcgc cgcatacact attctcagaa tgacttggtt gagtactcac    3840
cagtcacaga aaagcatctt acggatggca tgacagtaag agaattatgc agtgctgcca    3900
taaccatgag tgataacact gcggccaact tacttctgac aacgatcgga ggaccgaagg    3960
agctaaccgc ttttttgcac aacatggggg atcatgtaac tcgccttgat cgttgggaac    4020
cggagctgaa tgaagccata ccaaacgacg agcgtgacac cacgatgcct gtagcaatgg    4080
caacaacgtt gcgcaaacta ttaactggcg aactacttac tctagcttcc cggcaacaat    4140
taatagactg gatggaggcg gataaagttg caggaccact tctgcgctcg gcccttccgg    4200
ctggctggtt tattgctgat aaatctggag ccggtgagcg tgggtctcgc ggtatcattg    4260
cagcactggg gccagatggt aagccctccc gtatcgtagt tatctacacg acggggagtc    4320
aggcaactat ggatgaacga atagacaga tcgctgagat aggtgcctca ctgattaagc    4380
attggtaact gtcagaccaa gtttactcat atatacttta gattgattta aaacttcatt    4440
tttaatttaa aaggatctag gtgaagatcc tttttgataa tctcatgacc aaaatccctt    4500
aacgtgagtt ttcgttccac tgagcgtcag accccgtaga aaagatcaaa ggatcttctt    4560
gagatccttt ttttctgcgc gtaatctgct gcttgcaaac aaaaaaacca ccgctaccag    4620
cggtggtttg tttgccggat caagagctac caactctttt tccgaaggta actggcttca    4680
gcagagcgca gataccaaat actgtccttc tagtgtagcc gtagttaggc caccacttca    4740
agaactctgt agcaccgcct acatacctcg ctctgctaat cctgttacca gtggctgctg    4800
ccagtggcga taagtcgtgt cttaccgggt tggactcaag acgatagtta ccggataagg    4860
cgcagcggtc gggctgaacg ggggggttcgt gcacacagcc cagcttggag cgaacgacct    4920
acaccgaact gagataccta cagcgtgagc tatgagaaag cgccacgctt cccgaaggga    4980
gaaaggcgga caggtatccg gtaagcggca gggtcggaac aggagagcgc acgagggagc    5040
ttccaggggg aaacgcctgg tatctttata gtcctgtcgg gtttcgccac ctctgacttg    5100
agcgtcgatt tttgtgatgc tcgtcagggg ggcggagcct atggaaaaac gccagcaacg    5160 cggcctttt acggttcctg gccttttgct ggccttttgc tcacatgttc tttcctgcgt    5220 tatccctga ttctgtggat aaccgtatta ccgcctttga gtgagctgat accgctcgcc    5280
gcagccgaac gaccgagcgc agcgagtcag tgagcgagga agcggaagag cgcctgatgc    5340
ggtattttct ccttacgcat ctgtgcggta tttcacaccg catatggtgc actctcagta    5400
caatctgctc tgatgccgca tagttaagcc agtatacact ccgctatcgc tacgtgactg    5460
ggtcatggct gcgccccgac acccgccaac cccgctgac gcgccctgac gggcttgtct    5520
gctcccggca tccgcttaca gacaagctgt gaccgtctcc gggagctgca tgtgtcagag    5580
gttttcaccg tcatcaccga aacgcgcgag gcagcagatc aattcgcgcg cgaaggcgaa    5640
gcggcatgca tttacgttga caccatcgaa tggtgcaaaa cctttcgcgg tatggcatga    5700
tagcgcccgg aagagagtca attcagggtg gtgaatgtga aaccagtaac gttatacgat    5760
gtcgcagagt atgccggtgt ctcttatcag accgtttccc gcgtggtgaa ccaggccagc    5820
cacgtttctg cgaaaacgcg ggaaaaagtg gaagcggcga tggcggagct gaattacatt    5880
cccaaccgcg tggcacaaca actggcgggc aaacagtcgt tgctgattgg cgttgccacc    5940
tccagtctgg ccctgcacgc gccgtcgcaa attgtcgcgg cgattaaatc tcgcgccgat    6000
```

```
caactgggtg ccagcgtggt ggtgtcgatg gtagaacgaa gcggcgtcga agcctgtaaa    6060
gcggcggtgc acaatcttct cgcgcaacgc gtcagtgggc tgatcattaa ctatccgctg    6120
gatgaccagg atgccattgc tgtggaagct gcctgcacta atgttccggc gttatttctt    6180
gatgtctctg accagacacc catcaacagt attattttct cccatgaaga cggtacgcga    6240
ctgggcgtgg agcatctggt cgcattgggt caccagcaaa tcgcgctgtt agcgggccca    6300
ttaagttctg tctcggcgcg tctgcgtctg gctggctggc ataaatatct cactcgcaat    6360
caaattcagc cgatagcgga acgggaaggc gactggagtg ccatgtccgg ttttcaacaa    6420
accatgcaaa tgctgaatga gggcatcgtt cccactgcga tgctggttgc aacgatcag    6480 atggcgctgg gcgcaatgcg cgccattacc gagtccgggc tgcgcgttgg tgcggatatc    6540
tcggtagtgg gatacgacga taccgaagac agctcatgtt atatcccgcc gtcaaccacc    6600
atcaaacagg attttcgcct gctggggcaa accagcgtgg accgcttgct gcaactctct    6660
cagggccagg cggtgaaggg caatcagctg ttgcccgtct cactggtgaa aagaaaaacc    6720
accctggcgc ccaatacgca aaccgcctct ccccgcgcgt tggccgattc attaatgcag    6780
ctggcacgac aggtttcccg actggaaagc gggcagtgag cgcaacgcaa ttaatgtgag    6840
ttagcgcgaa ttgatctg                                                  6858
```

<210> SEQ ID NO 33
<211> LENGTH: 543
<212> TYPE: PRT
<213> ORGANISM: Artificial Sequence
<220> FEATURE:
<223> OTHER INFORMATION: Synthetic Construct

<400> SEQUENCE: 33

```
Met Glu Thr Arg Lys Ser Ala Asn Tyr Gln Pro Asn Ile Trp Asn Tyr
 1               5                  10                  15

Asp Tyr Leu Gln Ser Leu Lys Leu Gly Tyr Ala Asp Ala His Tyr Glu
            20                  25                  30

Asp Met Ala Lys Lys Leu Gln Glu Glu Val Arg Arg Ile Ile Lys Asp
        35                  40                  45

Asp Lys Ala Glu Ile Trp Thr Thr Leu Glu Leu Ile Asp Asp Val Lys
    50                  55                  60

Arg Leu Gly Leu Gly Tyr His Phe Glu Lys Glu Ile Arg Glu Val Leu
65                  70                  75                  80

Asn Lys Phe Leu Ser Leu Asn Thr Cys Val His Arg Ser Leu Asp Lys
                85                  90                  95

Thr Ala Leu Cys Phe Arg Leu Leu Arg Glu Tyr Gly Ser Asp Val Ser
           100                 105                 110

Ala Asp Ile Phe Glu Arg Phe Leu Asp Gln Asn Gly Asn Phe Lys Thr
       115                  120                 125

Ser Leu Val Asn Asn Val Lys Gly Met Leu Ser Leu Tyr Glu Ala Ser
   130                  135                 140

Phe Leu Ser Tyr Glu Gly Glu Gln Ile Leu Asp Lys Ala Asn Ala Phe
145                 150                 155                 160

Thr Ser Phe His Leu Lys Ser Ile His Glu Glu Asp Ile Asn Asn Ile
                165                 170                 175

Leu Leu Glu Gln Val Asn His Ala Leu Glu Leu Pro Leu His Arg Arg
            180                 185                 190

Ile His Arg Leu Glu Ala Arg Trp Tyr Thr Glu Ser Tyr Ser Arg Arg
        195                 200                 205
```

```
Lys Asp Ala Asn Trp Val Leu Leu Glu Ala Ala Lys Leu Asp Phe Asn
    210                 215                 220
Met Val Gln Ser Thr Leu Gln Lys Asp Leu Gln Glu Met Ser Arg Trp
225                 230                 235                 240
Trp Lys Gly Met Gly Leu Ala Pro Lys Leu Ser Phe Ser Arg Asp Arg
                245                 250                 255
Leu Met Glu Cys Phe Phe Trp Thr Val Gly Met Ala Phe Glu Pro Lys
            260                 265                 270
Tyr Ser Asp Leu Arg Lys Gly Leu Thr Lys Val Thr Ser Leu Ile Thr
        275                 280                 285
Thr Ile Asp Asp Ile Tyr Asp Val His Gly Thr Leu Glu Glu Leu Glu
290                 295                 300
Leu Phe Thr Ala Ile Val Glu Ser Trp Asp Ile Lys Ala Met Gln Val
305                 310                 315                 320
Leu Pro Glu Tyr Met Lys Ile Ser Phe Leu Ala Leu Tyr Asn Thr Val
                325                 330                 335
Asn Glu Leu Ala Tyr Asp Ala Leu Arg Glu Gln Gly His Asp Ile Leu
            340                 345                 350
Pro Tyr Leu Thr Lys Ala Trp Ser Asp Met Leu Lys Ala Phe Leu Gln
        355                 360                 365
Glu Ala Lys Trp Cys Arg Glu Lys His Leu Pro Lys Phe Glu His Tyr
370                 375                 380
Leu Asn Asn Ala Trp Val Ser Val Ser Gly Val Val Ile Leu Thr His
385                 390                 395                 400
Ala Tyr Phe Leu Leu Asn His Asn Thr Thr Lys Glu Val Leu Glu Ala
                405                 410                 415
Leu Glu Asn Tyr His Ala Leu Leu Lys Arg Pro Ser Ile Ile Phe Arg
            420                 425                 430
Leu Cys Asn Asp Leu Gly Thr Ser Thr Ala Glu Leu Gln Arg Gly Glu
        435                 440                 445
Val Ala Asn Ser Ile Leu Ser Cys Met His Glu Asn Asp Ile Gly Glu
450                 455                 460
Glu Ser Ala His Gln His Ile His Ser Leu Leu Asn Glu Thr Trp Lys
465                 470                 475                 480
Lys Met Asn Arg Asp Arg Phe Ile His Ser Pro Phe Pro Glu Pro Phe
                485                 490                 495
Val Glu Ile Ala Thr Asn Leu Ala Arg Ile Ala Gln Cys Thr Tyr Gln
            500                 505                 510
Thr Gly Asp Gly His Gly Ala Pro Asp Ser Ile Ala Lys Asn Arg Val
        515                 520                 525
Lys Ser Leu Ile Ile Glu Pro Ile Val Leu Asn Gly Asp Ile Tyr
530                 535                 540

<210> SEQ ID NO 34
<211> LENGTH: 6909
<212> TYPE: DNA
<213> ORGANISM: Artificial Sequence
<220> FEATURE:
<223> OTHER INFORMATION: Synthetic Construct

<400> SEQUENCE: 34
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcgggggc tccctttagg      180
```

```
gttccgattt agtgctttac ggcacctcga ccccaaaaaa cttgattagg gtgatggttc    240
acgtagtggg ccatcgccct gatagacggt ttttcgccct ttgacgttgg agtccacgtt    300
ctttaatagt ggactcttgt tccaaactgg aacaacactc aaccctatct cggtctattc    360
ttttgattta tagggatttt tgccgatttc ggcctattgg ttaaaaaatg agctgattta    420
acaaaaattt aacgcgaatt ttaacaaaat attaacgttt acaatttcag gtggcacttt    480
tcggggaaat gtgcgcggaa cccctatttg tttattttc taaatacatt caaatatgta    540
tccgctcatg aattaattct tagaaaaact catcgagcat caaatgaaac tgcaatttat    600
tcatatcagg attatcaata ccatattttt gaaaaagccg tttctgtaat gaaggagaaa    660
actcaccgag gcagttccat aggatggcaa gatcctggta tcggtctgcg attccgactc    720
gtccaacatc aatacaacct attaatttcc cctcgtcaaa aataaggtta tcaagtgaga    780
aatcaccatg agtgacgact gaatccggtg agaatggcaa aagtttatgc atttctttcc    840
agacttgttc aacaggccag ccattacgct cgtcatcaaa atcactcgca tcaaccaaac    900
cgttattcat tcgtgattgc gcctgagcga gacgaaatac gcgatcgctg ttaaaaggac    960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
cccttgtatt actgtttatg taagcagaca gttttattgt tcatgaccaa aatcccttaa   1440
cgtgagtttt cgttccactg agcgtcagac cccgtagaaa agatcaaagg atcttcttga   1500
gatccttttt ttctgcgcgt aatctgctgc ttgcaaacaa aaaaaccacc gctaccagcg   1560
gtggtttgtt tgccggatca agagctacca actctttttc cgaaggtaac tggcttcagc   1620
agagcgcaga taccaaatac tgtccttcta gtgtagccgt agttaggcca ccacttcaag   1680
aactctgtag caccgcctac atacctcgct ctgctaatcc tgttaccagt ggctgctgcc   1740
agtggcgata gtcgtgtct taccgggttg gactcaagac gatagttacc ggataaggcg   1800
cagcggtcgg gctgaacggg gggttcgtgc acacagccca gcttggagcg aacgacctac   1860
accgaactga tacctacag cgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcagggggg cggagcctat ggaaaaacgc cagcaacgcg   2100 gccttttttac ggttcctggc cttttgctgg ccttttgctc acatgttctt tcctgcgtta   2160 tccccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
```

```
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg gggtaatga taccgatgaa   2760 acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacga aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag gtggtttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
atcccactac cgagatatcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa gagacaccgg   4560
catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttcccccatc ggtgatgtcg gcgatatagg cgccagcaac cgcacctgtg   4920
```

```
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa cttaagaag gagatataca tatggaagca cgtcgctctg cgaactacga     5100
acctaacagc tgggactatg attacctgct gtcctccgac acggacgagt ccatcgaagt    5160
atacaaagac aaagcgaaaa agctggaagc cgaagttcgt cgcgagatta taacgaaaa    5220
agcagaattt ctgaccctgc tggaactgat tgacaacgtc cagcgcctgg gcctgggtta    5280
ccgtttcgag tctgatatcc gtggtgcgct ggatcgcttc gtttcctccg gcggcttcga    5340
tgcggtaacc aagacttccc tgcacggtac ggcactgtct ttccgtctgc tgcgtcaaca    5400
cggttttgag gtttctcagg aagcgttcag cggcttcaaa gaccaaaacg gcaacttcct    5460
ggagaacctg aaggaagata tcaaagctat cctgagcctg tacgaggcca gcttcctggc    5520
tctggaaggc gaaaacatcc tggacgaggc gaaggttttc gcaatctctc atctgaaaga    5580
actgtctgaa gaaagatcg gtaaagagct ggcagaacag gtgaaccatg cactggaact     5640
gccactgcat cgccgtactc agcgtctgga agcagtatgt tctatcgagg cctaccgtaa    5700
aaaggaggac gcgaatcagg ttctgctgga gctggcaatt ctggattaca acatgatcca    5760
gtctgtatac cagcgtgatc tgcgtgaaac gtcccgttgg tggcgtcgtg tgggtctggc    5820
gaccaaactg cactttgctc gtgaccgcct gattgagagc ttctactggg ccgtgggtgt    5880
agcattcgaa ccgcaatact ccgactgccg taactccgtc gcaaaaatgt ttctttcgt    5940
aaccattatc gacgatatct acgatgtata cggcacccta gacgaactgg agctgtttac    6000
tgatgcagtt gagcgttggg acgtaaacgc catcaacgac ctgccggatt acatgaaact    6060
gtgctttctg gctctgtata acactattaa cgaaatcgcc tacgacaacc tgaaagataa    6120
aggtgagaac atcctgccgt atctgaccaa agcctgggct gacctgtgca acgctttcct    6180
gcaagaagcc aagtggctgt acaacaaatc tactccgacc tttgacgact acttcggcaa    6240
cgcatggaaa tcctcttctg gcccgctgca actggtgttc gcttacttcg ctgtcgtgca    6300
gaacattaaa aaggaagaga tcgaaaacct gcaaaaatac catgacacca tctctcgtcc    6360
ttcccatatc ttccgtctgt gcaatgacct ggctagcgcg tctgcggaaa ttgcgcgtgg    6420
tgaaaccgca aatagcgttt cttgttacat gcgcactaaa ggtatctccg aagaactggc    6480
taccgaaagc gtgatgaatc tgatcgatga aacctggaaa aagatgaaca aggaaaaact    6540
gggtggtagc ctgttcgcga accgttcgt ggaaaccgcg atcaacctgg cacgtcaatc     6600
tcactgcact tatcataacg gcgacgcgca tacctctccg gatgagctga cccgcaaacg    6660
cgttctgtct gtaatcactg aaccgattct gccgtttgaa cgctaaggat ccgaattcga    6720
gctccgtcga caagcttgcg gccgcactcg agcaccacca ccaccaccac tgagatccgg    6780
ctgctaacaa agcccgaaag gaagctgagt tggctgctgc caccgctgag caataactag    6840
cataacccct ggggcctct  aaacgggtct tgaggggttt tttgctgaaa ggaggaacta    6900
tatccggat                                                           6909
```

<210> SEQ ID NO 35
<211> LENGTH: 500
<212> TYPE: PRT
<213> ORGANISM: Artificial Sequence
<220> FEATURE:
<223> OTHER INFORMATION: Synthetic Construct

<400> SEQUENCE: 35

Glu Glu Val Lys Arg Met Ile Lys Asp Glu Asn Val Asn Ile Leu Glu

-continued

```
  1               5              10              15
Leu Ile Asp Thr Val Lys Gln Leu Gly Leu Ser Tyr His Phe Glu Glu
                 20                  25                  30

Glu Ile Gly Glu Ala Leu Asp Arg Phe Leu Ser Leu Glu Lys Cys Ser
                 35                  40                  45

Gly Arg Asn Asn Phe Gly Arg Ser Leu His Glu Thr Ala Leu Arg Phe
 50                  55                  60

Arg Leu Leu Arg Glu Tyr Gly Tyr Asp Ile Ser Pro Asp Ile Phe Glu
 65                  70                  75                  80

Lys Phe Lys Asp His Asn Gly Asn Phe Lys Ala Cys Leu Val Gln Asp
                 85                  90                  95

Ile Lys Gly Met Leu Ser Leu Tyr Asp Ala Ser Phe Leu Ser Tyr Glu
                100                 105                 110

Gly Glu Gln Ile Leu Asp Glu Ala Asn Ala Phe Thr Ser Ile His Leu
                115                 120                 125

Lys Asp Leu Ser Glu Gly Arg Ser Ser Ile Leu Ile Asp Gln Val Asn
                130                 135                 140

His Ser Leu Glu Leu Pro Leu Tyr Arg Arg Val Gln Ser Leu Glu Ala
145                 150                 155                 160

Arg Trp Phe Ile Asp Ser Tyr Glu Asn Arg Lys Asp Ala Asn Lys Val
                165                 170                 175

Leu Leu Glu Ala Ala Lys Leu Asn Phe Asn Ile Val Gln Ser Thr Leu
                180                 185                 190

Gln Gln Asp Leu Lys Glu Met Ser Arg Trp Trp Lys Gly Met Gly Leu
                195                 200                 205

Ala Pro Arg Leu Ser Phe Gly Arg Asp Arg Leu Met Glu Cys Phe Phe
210                 215                 220

Trp Ala Ala Gly Met Thr Pro Phe Glu Pro Gln Phe Ser Asn Ile Arg
225                 230                 235                 240

Lys Gly Leu Thr Lys Val Cys Ser Leu Ile Thr Leu Ile Asp Asp Ile
                245                 250                 255

Tyr Asp Val Tyr Gly Thr Leu Asp Glu Leu Glu Leu Phe Thr Thr Ala
                260                 265                 270

Val Glu Ser Trp Asp Ile Asn Ala Ile Gln Ile Leu Pro Glu Tyr Met
                275                 280                 285

Lys Ile Phe Phe Leu Ala Leu Tyr Thr Thr Val Asn Asp Phe Thr Tyr
                290                 295                 300

Asp Thr Ile Lys Glu Thr Gly His Asp Ile Leu Pro Tyr Leu Val Lys
305                 310                 315                 320

Val Trp Ser Asp Met Leu Lys Ala Phe Leu Gln Glu Ala Lys Trp Cys
                325                 330                 335

His Asn Lys His Met Pro Lys Phe Asp Asp Tyr Leu Asn Asn Ala Trp
                340                 345                 350

Val Ser Val Ser Gly Val Val Leu Leu Thr His Ser Tyr Phe Leu Leu
                355                 360                 365

Asn Arg Asn Ile Thr Lys Glu Gly Leu Gly Tyr Leu Glu Asn Cys Pro
                370                 375                 380

Met Leu Leu Gln Thr Pro Ser Ile Ile Phe Arg Leu Cys Asn Asp Leu
385                 390                 395                 400

Ala Thr Ser Ser Ala Glu Leu Glu Arg Gly Glu Gly Ala Asn Ser Ile
                405                 410                 415

Ile Cys Tyr Met Asn Glu Asn Gly Val Ser Glu Glu Val Ala Tyr Lys
                420                 425                 430
```

His Ile Gln Asn Leu Leu Asp Gln Thr Trp Lys Lys Met Asn Lys Asp
        435                 440                 445

Arg Val Ile Asn Ser Pro Ser Ser Lys Tyr Phe Ser Glu Thr Ile Ile
    450                 455                 460

Asn Leu Ala Arg Ile Ser His Cys Thr Tyr Gln Tyr Gly Asp Gly His
465                 470                 475                 480

Gly Ala Pro Asp Thr Leu Ala Lys Asn Arg Ile Lys Ala Leu Ile Leu
            485                 490                 495

Glu Pro Ile Asn
            500

<210> SEQ ID NO 36
<211> LENGTH: 22
<212> TYPE: DNA
<213> ORGANISM: Artificial Sequence
<220> FEATURE:
<223> OTHER INFORMATION: Synthetic Construct

<400> SEQUENCE: 36
acaatttcac acaggaaaca gc                                          22

<210> SEQ ID NO 37
<211> LENGTH: 23
<212> TYPE: DNA
<213> ORGANISM: Artificial Sequence
<220> FEATURE:
<223> OTHER INFORMATION: Synthetic Construct

<400> SEQUENCE: 37
ccaggcaaat tctgttttat cag                                         23

<210> SEQ ID NO 38
<211> LENGTH: 23
<212> TYPE: DNA
<213> ORGANISM: Artificial Sequence
<220> FEATURE:
<223> OTHER INFORMATION: Synthetic Construct

<400> SEQUENCE: 38
gacagcttat catcgactgc acg                                         23

<210> SEQ ID NO 39
<211> LENGTH: 23
<212> TYPE: DNA
<213> ORGANISM: Artificial Sequence
<220> FEATURE:
<223> OTHER INFORMATION: Synthetic Construct

<400> SEQUENCE: 39
cgaaaagcac ccttatgtgt ctg                                         23

<210> SEQ ID NO 40
<211> LENGTH: 30
<212> TYPE: DNA
<213> ORGANISM: Artificial Sequence
<220> FEATURE:
<223> OTHER INFORMATION: Synthetic Construct

<400> SEQUENCE: 40
ggaataaacc atgaacaccc gtcgcagcgc                                  30

<210> SEQ ID NO 41
<211> LENGTH: 32

```
<212> TYPE: DNA
<213> ORGANISM: Artificial Sequence
<220> FEATURE:
<223> OTHER INFORMATION: Synthetic Construct

<400> SEQUENCE: 41
ctttatgcag ttagttgatc ggaatcggtt cg                                    32

<210> SEQ ID NO 42
<211> LENGTH: 37
<212> TYPE: DNA
<213> ORGANISM: Artificial Sequence
<220> FEATURE:
<223> OTHER INFORMATION: Synthetic Construct

<400> SEQUENCE: 42
gatcaactaa ctgcataaag gaggtaaaaa aacatgg                               37

<210> SEQ ID NO 43
<211> LENGTH: 34
<212> TYPE: DNA
<213> ORGANISM: Artificial Sequence
<220> FEATURE:
<223> OTHER INFORMATION: Synthetic Construct

<400> SEQUENCE: 43
gggtgttcat ggtttattcc tccttattta atcg                                  34

<210> SEQ ID NO 44
<211> LENGTH: 22
<212> TYPE: DNA
<213> ORGANISM: Artificial Sequence
<220> FEATURE:
<223> OTHER INFORMATION: Synthetic Construct

<400> SEQUENCE: 44
ctgacctaca aattcgaaga gg                                               22

<210> SEQ ID NO 45
<211> LENGTH: 20
<212> TYPE: DNA
<213> ORGANISM: Artificial Sequence
<220> FEATURE:
<223> OTHER INFORMATION: Synthetic Construct

<400> SEQUENCE: 45
ggtggcgtga gatcggtctg                                                  20

<210> SEQ ID NO 46
<211> LENGTH: 20
<212> TYPE: DNA
<213> ORGANISM: Artificial Sequence
<220> FEATURE:
<223> OTHER INFORMATION: Synthetic Construct

<400> SEQUENCE: 46
gcatcgtccg ttcgagctgc                                                  20

<210> SEQ ID NO 47
<211> LENGTH: 2439
<212> TYPE: DNA
<213> ORGANISM: Artificial Sequence
<220> FEATURE:
<223> OTHER INFORMATION: Synthetic Construct

<400> SEQUENCE: 47
```

```
atggttaaag acattgtaat aattgatgcc ctccgtactc ccatcggtaa gtaccgcggt    60
cagctctcaa agatgacggc ggtggaattg ggaaccgcag ttacaaaggc tctgttcgag   120
aagaacgacc aggtcaaaga ccatgtagaa caagtcattt ttggcaacgt tttacaggca   180
gggaacggcc agaatcccgc ccgtcagatc gcccttaatt ctggcctgtc cgcagagata   240
ccggcttcga ctattaacca ggtgtgtggt tctggcctga agcaataag catggcgcgc    300
caacagatcc tactcggaga agcggaagta atagtagcag gaggtatcga atccatgacg   360
aatgcgccga gtattacata ttataataaa gaagaagaca ccctctcaaa gcctgttcct   420
acgatgacct tcgatggtct gaccgacgcg tttagcggaa agattatggg tttaacagcc   480
gaaaatgttg ccgaacagta cggcgtatca cgtgaggccc aggacgcctt tgcgtatgga   540
tcgcagatga aagcagcaaa ggcccaagaa cagggcattt tcgcagctga aatactgcct   600
cttgaaatag gggacgaagt tattactcag gacgaggggg ttcgtcaaga gaccaccctc   660
gaaaaattaa gtctgcttcg gaccattttt aaagaagatg gtactgttac agcgggcaac   720
gcctcaacga tcaatgatgg cgcctcagcc gtgatcattg catcaaagga gtttgctgag   780
acaaaccaga ttccctacct tgcgatcgta catgatatta cagagatagg cattgatcca   840
tcaataatgg gcattgctcc cgtgagtgcg atcaataaac tgatcgatcg taaccaaatt   900
agcatggaag aaatcgatct cttttgaaatt aatgaggcat ttgcagcatc ctcggtggta   960
gttcaaaaag agttaagcat tcccgatgaa aagatcaata ttggcggttc cggtattgca  1020
ctaggccatc ctcttggcgc cacaggagcg cgcattgtaa ccaccctagc gcaccagttg  1080
aaacgtacac acggacgcta tggtattgcc tccctgtgca ttggcggtgg ccttggccta  1140
gcaatattaa tagaagtgcc tcaggaagat cagccggtta aaaaatttta tcaattggcc  1200
cgtgaggacc gtctggctag acttcaggag caagccgtga tcagcccagc tacaaaacat  1260
gtactggcag aaatgacact tcctgaagat attgccgaca atctgatcga aaatcaaata  1320
tctgaaatgg aaatccctct tggtgtggct ttgaatctga gggtcaatga taagagttat  1380
accatcccac tagcaactga ggaaccgagt gtaatcgctg cctgtaataa tggtgcaaaa  1440
atggcaaacc acctgggcgg ttttcagtca gaattaaaag atggtttcct gcgtgggcaa  1500
attgtactta tgaacgtcaa agaacccgca actatcgagc atacgatcac ggcagagaaa  1560
gcggcaattt tcgtgccgc agcgcagtca catccatcga ttgtgaaacg aggtgggggt  1620
ctaaaagaga tagtagtgcg tacgttcgat gatgatccga cgttcctgtc tattgatctg  1680
atagttgata ctaaagacgc aatgggcgct aacatcatta acaccattct cgagggtgta  1740
gccggctttc tgagggaaat ccttaccgaa gaaattctgt tctctatttt atctaattac  1800
gcaaccgaat caattgtgac cgccagctgt cgcataccct acgaagcact gagtaaaaaa  1860
ggtgatggta acgaatcgc tgaaaaagtg gctgctgcat ctaaatttgc ccagttagat  1920
ccttatcgag ctgcaaccca caacaaaggt attatgaatg gtattgaggc cgtcgttttg  1980
gcctcaggaa atgacacacg gcggtcgcg gcagccgcac atgcgtatgc ttcacgcgat  2040
cagcactatc ggggcttaag ccagtggcag gttgcagaag gcgcgttaca cggggagatc  2100
agtctaccac ttgcactcgg cagcgttggc ggtgcaattg aggtcttgcc taaagcgaag  2160
gcggcattcg aaatcatggg gatcacagag gcgaaggagc tggcagaagt cacagctgcg  2220
gtagggctgg cgcaaaacct ggcggcgtta agagcgcttg ttagtgaagg aatacagcaa  2280
ggtcacatgt cgctccaggc tcgctctctt gcattatcgg taggtgctac aggcaaggaa  2340
gttgaaatcc tggccgaaaa attacagggc tctcgtatga atcaggcgaa cgctcagacc  2400
```

```
atactcgcag agatcagatc gcaaaaagtt gaattgtga                         2439
```

<210> SEQ ID NO 48
<211> LENGTH: 1158
<212> TYPE: DNA
<213> ORGANISM: Artificial Sequence
<220> FEATURE:
<223> OTHER INFORMATION: Synthetic Construct

<400> SEQUENCE: 48

```
atgaccatga acgttggaat cgataaaatg tcattctttg ttccaccta ctttgtggac     60
atgactgatc tggcagtagc acgggatgtc gatcccaata agtttctgat tggtattggc    120
caggaccaga tggcagttaa tccgaaaacg caggatattg tgacatttgc cacaaatgct    180
gccaaaaaca tactgtcagc tgaggacctt gataaaattg atatggtcat agtcggcacc    240
gagagtggaa tcgatgaatc caaagcgagt gccgtagtgc ttcacaggtt gctcggtatc    300
cagaagtttg ctcgctcctt tgaaatcaaa gaagcctgtt atgggggtac cgcggcttta    360
cagttcgctg taaaccacat taggaatcat cctgaatcaa aggttcttgt agttgcatca    420
gatatcgcga aatacggcct ggcttctgga ggtgaaccaa cgcaaggtgc aggcgctgtg    480
gctatgctcg tctcaactga ccctaagatc attgctttca cgacgatag cctcgcgctt    540
acacaagata tctatgactt ctggcgacca gttggacatg actatcctat ggtcgacggg    600
cctcttagta cagagaccta catccagtca tttcagaccg tatggcagga atacacaaaa    660
cggtcgcagc atgcactggc agactttgct gcccttagct ttcatatccc gtatactaaa    720
atgggcaaaa aggcgctgct tgcaatcctt gaaggcgaat cagaggaggc tcagaaccgt    780
atactagcaa atatgaaaaa gagtatagcc tactccagaa aggcgggtaa cctgtatacc    840
ggtagcctgt atctaggact tatttcactt ctggaaaatg cagaagacct taaagctggt    900
gatttaatag gcctctttc ttacggttcc ggtgctgttg cggagttttt ctcaggaagg    960
ctggttgagg actatcagga acagctactt aaaacaaaac atgccgaaca gctggcccat   1020
agaaagcaac tgacaatcga ggagtacgaa acgatgttct ccgatcgctt ggacgtggac   1080
aaagacgccg aatacgaaga cacattagct tatagcattt cgtcagtccg aaacaccgta   1140
cgtgagtaca ggagttga                                                 1158
```

<210> SEQ ID NO 49
<211> LENGTH: 2442
<212> TYPE: DNA
<213> ORGANISM: Artificial Sequence
<220> FEATURE:
<223> OTHER INFORMATION: Synthetic Construct

<400> SEQUENCE: 49

```
atgaaagaag tggttatgat tgatgcggct cgcacaccca ttgggaaata cagaggtagt     60
cttagtcctt ttacagcggt ggagctgggg acactggtca cgaaagggct gctggataaa    120
acaaagctta agaaagacaa gatagaccaa gtgatattcg gcaatgtgct tcaggcagga    180
aacggacaaa acgttgcaag acaaatagcc ctgaacagtg gcttaccagt tgacgtgccg    240
gcgatgacta ttaacgaagt ttgcgggtcc ggaatgaaag cggtgatttt agcccgccag    300
ttaatacagt tagggaggc agagttggtc attgcagggg gtacggagtc aatgtcacaa    360
gcacccatgc tgaaaccta ccagtcagag accaacgaat acggagagcc gatatcatca    420
atggttaatg acgggctgac ggatgcgttt tccaatgctc acatgggtct tactgccgaa    480
```

```
aaggtggcga cccagttttc agtgtcgcgc gaggaacaag accggtacgc attgtccagc    540
caattgaaag cagcgcacgc ggttgaagcc ggggtgttct cagaagagat tattccggtt    600
aagattagcg acgaggatgt cttgagtgaa gacgaggcag taagaggcaa cagcactttg    660
gaaaaactgg gcaccttgcg gacggtgttt tctgaagagg gcacggttac cgctggcaat    720
gcttcaccgc tgaatgacgg cgctagtgtc gtgattcttg catcaaaaga atacgcggaa    780
aacaataatc tgccttacct ggcgacgata aggaggttg cggaagttgg tatcgatcct    840
tctatcatgg gtattgcccc aataaaggcc attcaaaagt taacagatcg gtcgggcatg    900
aacctgtcca cgattgatct gttcgaaatt aatgaagcat tcgcggcatc tagcattgtt    960
gtttctcaag agctgcaatt ggacgaagaa aaagtgaata tctatggcgg ggcgatagct   1020
ttaggccatc caatcggcgc aagcggagcc cggatactga caaccttagc atacggcctc   1080
ctgcgtgagc aaaagcgtta tggtattgcg tcattatgta tcggcggtgg tcttggtctg   1140
gccgtgctgt tagaagctaa tatggagcag acccacaaag acgttcagaa gaaaaagttt   1200
taccagctta ccccctccga gcggagatcg cagcttatcg agaagaacgt tctgactcaa   1260
gaaacggcac ttattttcca ggagcagacg ttgtccgaag aactgtccga tcacatgatt   1320
gagaatcagg tctccgaagt ggaaattcca atgggaattg cacaaaattt tcagattaat   1380
ggcaagaaaa aatggattcc tatggcgact gaagaacctt cagtaatagc ggcagcatcg   1440
aacggcgcca aaatctgcgg gaacatttgc gcggaaacgc ctcagcggct tatgcgcggg   1500
cagattgtcc tgtctggcaa atcagaatat caagccgtga taaatgccgt gaatcatcgc   1560
aaagaagaac tgattctttg cgcaaacgag tcgtacccga gtattgttaa acgcggggga   1620
ggtgttcagg atatttctac gcgggagttt atgggttctt ttcacgcgta tttatcaatc   1680
gactttctgg tggacgtcaa ggacgcaatg ggggcaaaca tgatcaactc tattctcgaa   1740
agcgttgcaa ataaactgcg tgaatggttc ccggaagagg aaatactgtt ctccatcctg   1800
tcaaacttcg ctacggagtc cctggcatct gcatgttgcg agattccttt tgaaagactt   1860
ggtcgtaaca agaaattgg tgaacagatc gccaagaaaa ttcaacaggc aggggaatat   1920
gctaagcttg acccttaccg cgcggcaacc cataacaagg ggattatgaa cggtatcgaa   1980
gccgtcgttg ccgcaacggg aaacgacaca cgggctgttt ccgcttctat tcacgcatac   2040
gccgcccgta tggcttgta ccaaggttta acggattggc agatcaaggg cgataaactg   2100
gttggtaaat aacagtcccc actggctgtg gcgactgtcg gtggcgcgtc gaacatatta   2160
ccaaaagcca aagcttccct cgccatgctg gatattgatt ccgcaaaaga actggcccaa   2220
gtgatcgccg cggtaggttt agcacagaat ctggcggcgt tacgtgcatt agtgacagaa   2280
ggcattcaga aggacacat gggcttgcaa gcacgttctt tagcgatttc gataggtgcc   2340
atcggtgagg agatagagca agtcgcgaaa aaactgcgtg aagctgaaaa aatgaatcag   2400
caaacggcaa tacagatttt agaaaaaatt cgcgagaaat ga                      2442
```

<210> SEQ ID NO 50
<211> LENGTH: 1155
<212> TYPE: DNA
<213> ORGANISM: Artificial Sequence
<220> FEATURE:
<223> OTHER INFORMATION: Synthetic Construct

<400> SEQUENCE: 50

```
atgaaaatcg gtattgaccg tctgtccttc ttcatcccga atttgtattt ggacatgact    60
gagctggcag aatcacgcgg ggatgatcca gctaaatatc atattggaat cggacaagat   120
```

```
cagatggcag tgaatcgcgc aaacgaggac atcataacac tgggtgcaaa cgctgcgagt    180
aagatcgtga cagagaaaga ccgcgagttg attgatatgg taatcgttgg cacggaatca    240
ggaattgacc actccaaagc aagcgccgtg attattcacc atctccttaa aattcagtcg    300
ttcgcccgtt ctttcgaggt aaaagaagct tgctatggcg gaactgctgc cctgcacatg    360
gcgaaggagt atgtcaaaaa tcatccggag cgtaaggtct tggtaattgc gtcagacatc    420
gcgcgttatg gtttggccag cggaggagaa gttactcaag gcgtggggc cgtagccatg     480 atgattacac aaaaccccg gattctttcg attgaagacg atagtgtttt tctcacagag     540
gatatctatg atttctggcg gcctgattac tccgagttcc ctgtagtgga cgggccctt     600 tcaaactcaa cgtatataga gagttttcag aaagtttgga accggcacaa ggaattgtcc    660
ggaagagggc tggaagatta tcaagctatt gcttttcaca taccctatac gaagatgggt    720
aagaaagcgc tccagagtgt tttagaccaa accgatgaag ataaccagga gcgcttaatg    780
gctagatatg aggagtctat tcgctatagc cggagaattg gtaacctgta cacaggcagc    840
ttgtaccttg gtcttacaag cttgttggaa aactctaaaa gtttacaacc gggagatcgg    900
atcggcctct tttcctatgg cagtggtgcg gtgtccgagt tctttaccgg gtatttagaa    960
gaaaattacc aagagtacct gttcgctcaa agccatcaag aaatgctgga tagccggact   1020
cggattacgg tcgatgaata cgagaccatc ttttcagaga ctctgccaga acatggtgaa   1080
tgcgccgaat atacgagcga cgtcccctt tctataacca agattgagaa cgacattcgt    1140
tattataaaa tctga                                                     1155
```

<210> SEQ ID NO 51
<211> LENGTH: 2448
<212> TYPE: DNA
<213> ORGANISM: Artificial Sequence
<220> FEATURE:
<223> OTHER INFORMATION: Synthetic Construct

<400> SEQUENCE: 51

```
atggaagaag tggtaattat agatgcacgt cggactccga ttggtaaata tcacgggtcg     60
ttgaagaagt tttcagcggt ggcgctgggg acggccgtgg ctaaagacat gttcgaacgc    120
aaccagaaaa tcaaagagga gatcgcgcag gtcataattg gtaatgtctt gcaggcagga    180
aatggccaga accccgcgcg gcaagttgct cttcaatcag ggttgtccgt tgacattccc    240
gcttctacaa ttaacgaggt ttgtgggtct ggtttgaaag ctatcttgat gggcatggaa    300
caaatccaac tcggcaaagc gcaagtagtg ctggcaggcg gcattgaatc aatgacaaat    360
gcgccaagcc tgtcccacta taacaaggcg gaggatacgt atagtgtccc agtgtcgagc    420
atgacactgg atggtctgac agacgcattt tctagtaaac ctatgggatt aacagcggaa    480
aacgtcgcac agcgctacgg tatctcccgt gaggcgcaag atcaattcgc atatcaatct    540
cagatgaaag cagcaaaagc gcaggcagaa acaaattcg ctaaggaaat tgtgccactg     600
gcgggtgaaa ctaaaaccat cacagctgac gaagggatca gatcccaaac aacgatggag    660
aaactggcaa gtctcaaacc tgttttaaa accgatggca ctgtaaccgc agggaatgct    720
agcaccatta tgacggggc cgcccttgtg ctgcttgcta gcaaaactta ctgcgaaact    780
aatgacatac cgtaccttgc gacaatcaaa gaaattgttg aagttggaat cgatccggag    840
attatgggca tctctccgat aaaagcgata caaacattgt tacaaaatca aaaagttagc    900
ctcgaagata ttggagtttt tgaaataaat gaagcctttg ccgcaagtag catagtggtt    960
```

```
gaatctgagt tgggattaga tccggctaaa gttaaccgtt atgggggtgg tatatcctta    1020
ggtcatgcaa ttggggcaac cggcgctcgc ctggccactt cactggtgta tcaaatgcag    1080
gagatacaag cacgttatgg tattgcgagc ctgtgcgttg gtggtggact tggactggca    1140
atgcttttag aacgtccaac tattgagaag gctaaaccga cagacaaaaa gttctatgaa    1200
ttgtcaccag ctgaacggtt gcaagagctg gaaaatcaac agaaaatcag ttctgaaact    1260
aaacagcagt tatctcagat gatgcttgcc gaggacactg caaaccattt gatagaaaat    1320
caaatatcag agattgaact cccaatgggc gtcgggatga acctgaaggt tgatgggaaa    1380
gcctatgttg tgccaatggc gacggaagag ccgtccgtca tcgcggccat gtctaatggt    1440
gccaaaatgg ccggcgaaat tcacactcag tcgaaagaac ggctgctcag aggtcagatt    1500
gttttcagcg cgaagaatcc gaatgaaatc aacagagaa tagctgagaa ccaagctttg    1560
attttcgaac gtgccgaaca gtcctatcct tccattgtga aaagagaggg aggtctccgc    1620
cgcattgcac ttcgtcattt tcctgccgat tctcagcagg agtctgcgga ccagtccaca    1680
tttttatcag tggaccttt tgtagatgtg aaagacgcga tgggggcaaa tatcataaat    1740
gcaatacttg agggcgtcgc agccctgttt cgcgaatggt tccccaatga ggaaattctt    1800
ttttctattc tctcgaactt ggctacggag agcttagtca cggctgtttg tgaagtccca    1860
tttagtgcac ttagcaagag aggtggtgca acggtggccc agaaaattgt gcaggcgtcg    1920
ctcttcgcaa agacagaccc ataccgcgca gtgacccaca caaagggat tatgaacggt    1980 gtagaggctg ttatgcttgc cacaggcaac gacacgcgcg cagtctcagc cgcttgtcat    2040
ggatacgcag cgcgcaccgg tagctatcag ggtctgacta actggacgat tgagtcggat    2100
cgcctggtag gcgagataac actgccgctg gccatcgcta cagttggagg cgctaccaaa    2160
gtgttgccca agctcaagc ggcactggag attagtgatg ttcactcttc tcaagagctt    2220
gcagccttag cggcgtcagt aggtttagta caaaatctcg cggccctgcg cgcactggtt    2280
tccgaaggta tacaaaaagg gcacatgtcc atgcaagccc ggtctctcgc aatcgcggtc    2340
ggtgctgaaa aagccgagat cgagcaggtc gccgaaaagt tgcggcagaa cccgccaatg    2400
aatcagcagc aggcgctccg ttttcttggc gagatccgcg aacaatga              2448
```

<210> SEQ ID NO 52  
<211> LENGTH: 1155  
<212> TYPE: DNA  
<213> ORGANISM: Artificial Sequence  
<220> FEATURE:  
<223> OTHER INFORMATION: Synthetic Construct

<400> SEQUENCE: 52

```
atgaacgtcg gcattgacaa aattaatttt ttcgttccac cgtattatct ggatatggtc      60
gacctggccc acgcacgcga agtggacccg aacaaattta caattggaat tggacaggat     120
cagatggctc tgagcaaaaa gacgcacgat atcgtaacat tcgcggctag tgccgcgaag     180
gaaattttag aacctgagga cttgcaagct atagacatgt ttatagttgg taccgaatcg     240
ggcattgacg agagcaaagc atccgcggtc gttttacatc gtttgttggg cgtacaacct     300
ttcgctcgca gttttgaaat taagaagcc tgttacgggg caaccgcagg cattcagttt     360
gccaagactc atatacaagc gaacccggag agcaaggtcc tggtaattgc aagcgatata     420
gctcggtatg tcttcggtc aggtggagag cccacacaag gcgcaggggc agttgctatg     480
cttctcacgc caaatcccag aatcctgacc ttcgaaaacg acaatctgat gttaacgcag     540
gatatttatg acttctggag accacttggt cacgcttacc ctatggtaga tggccacctt     600
```

```
tccaatcaag tctatattga cagttttaag aaggtctggc aagcacattg cgaacgcaat    660
caagcttcta tatccgacta tgccgcgatt agttttcata ttccgtatac aaaaatgggt    720
aagaaagccc tgctcgctgt ttttgcagat gaagtggaaa ctgaacagga acgcgttatg    780
gcacggtatg aagagtctat cgtatattca cgccggatcg gcaacttgta tacgggatca    840
ttgtacctgg ggctgatatc cttattggaa aacagttctc acctgtcggc gggcgaccgg    900
ataggattgt ttagttatgg gagtggcgct gtcagcgaat ttttctccgg tcgtttagtg    960
gcaggctatg aaaatcaatt gaacaaagag gcgcataccc agctcctgga tcagcgtcag   1020
aagctttcca tcgaagagta tgaggcgatt tttacagatt ccttagaaat tgatcaggat   1080
gcagcgttct cggatgacct gccatattcc atccgcgaga taaaaaacac gattcggtac   1140
tataaggaga gctga                                                   1155
```

<210> SEQ ID NO 53
<211> LENGTH: 2475
<212> TYPE: DNA
<213> ORGANISM: Artificial Sequence
<220> FEATURE:
<223> OTHER INFORMATION: Synthetic Construct

<400> SEQUENCE: 53

```
atggaagaag ttgtcatcat tgacgcactg cgtactccaa taggaaagta ccacggttcg     60
ctgaaagatt acacagctgt tgaactgggg acagtagcag caaggcgtt gctggcacga    120 aatcagcaag caaagaaca catagcgcaa gttattattg caacgtcct gcaagccgga     180 agtgggcaga atccaggccg acaagtcagt ttacagtcag gattgtcttc tgatatcccc    240
gctagcacga tcaatgaagt gtgtggctcg ggtatgaaag cgattctgat gggtatggag    300
caaattcagc tgaacaaagc ctctgtggtc ttaacaggcg gaattgaaag catgaccaac    360
gcgccgctgt ttagttatta caacaaggct gaggatcaat attcggcgcc ggttagcaca    420
atgatgcacg atggtctaac agatgctttc agttccaaac caatgggctt aaccgcagag    480
accgtcgctg agagatatgg aattacgcgt aaggaacaag atgaatttgc ttatcactct    540
caaatgaagg cggccaaagc ccaggcggcg aaaaagtttg atcaggaaat tgtaccctg     600 acggaaaaat ccggaacggt tctccaggac gaaggcatca gagccgcgac aacagtcgag    660
aagctagctg agcttaaaac ggtgttcaaa aagacggaa cagttacagc gggtaacgcc    720
tctacgataa atgatggcgc tgctatggta ttaatagcat caaaatctta ttgcgaagaa    780
caccagattc cttatctggc cgttataaag agatcgttg aggtgggttt tgcccccgaa     840
ataatgggta tttcccccat taaggctata gacaccctgc tgaaaaatca agcactgacc    900
atagaggata taggaatatt tgagattaat gaagcctttg ctgcgagttc gattgtggta    960
gaacgcgagt tgggcctgga ccccaaaaaa gttaatcgct atggcggtgg tatatcactc   1020
ggccacgcaa ttgggcgac gggagctcgc attgcgacga ccgttgctta tcagctgaaa   1080
gatacccagg agcgctacgg tatagcttcc ttatgcgttg gtggggtct tggattggcg   1140 atgcttctgg aaaacccatc ggccactgcc tcacaaacta attttgatga ggaatctgct   1200
tccgaaaaaa ctgagaagaa gaagttttat gcgctagctc ctaacgaacg cttagcgttt   1260
ttggaagccc aaggcgctat taccgctgct gaaaaccctgg tcttccagga tgatgaccta  1320
aacaaagaga cagccaatca cttaatcgaa accaaatca gcgaagttga aattccttta   1380
ggcgtgggcc tgaacttaca ggtgaatggg aaagcgtata atgttcctct ggccacggag   1440
```

| | |
|---|---|
| gaaccgtccg ttatcgctgc gatgtcgaat ggcgccaaaa tggctggtcc tattacaaca | 1500 |
| acaagtcagg agaggctgtt acggggtcag attgtcttca tggacgtaca ggacccagaa | 1560 |
| gcaatattag cgaaagttga atccgagcaa gctaccattt tcgcggtggc aaatgaaaca | 1620 |
| tacccgtcta tcgtgaaaag aggaggaggt ctgcgtagag tcattggcag gaatttcagt | 1680 |
| ccggccgaaa gtgacttagc cacggcgtat gtatcaattg acctgatggt agatgttaag | 1740 |
| gatgcaatgg gtgctaatat catcaatagt atcctagaag gtgttgcgga attgtttaga | 1800 |
| aaatggttcc cagaagaaga atcctgttc tcaattctct ccaatctcgc gacagaaagt | 1860 |
| ctggtaacgg cgacgtgctc agttccgttt gataaattgt ccaaaactgg aatggtcga | 1920 |
| caagtagctg gtaaaatagt gcacgcggcg gactttgcta agatagatcc atacagagct | 1980 |
| gccacacaca ataaaggtat tatgaatggc gttgaagcgt taatcttagc caccggtaat | 2040 |
| gacacccgtg cggtgtcggc tgcatgccac ggttacgcgg cacgcaatgg gcgaatgcaa | 2100 |
| gggcttacct cttggacgat tatcgaagat cggctgatag gctctatcac attacctttg | 2160 |
| gctattgcga cagtgggggg tgccacaaaa atcttgccaa aagcacaggc cgccctggcg | 2220 |
| ctaactggcg ttgagacggc gtcggaactg gccagcctgg cggcgagtgt gggattagtt | 2280 |
| caaaatttgg ccgctttacg agcactagtg agcgagggca ttcagcaagg gcacatgagt | 2340 |
| atgcaagcta gatccctggc cattagcgta ggtgcgaaag gtactgaaat agagcaacta | 2400 |
| gctgcgaagc tgagggcagc gacgcaaatg aatcaggagc aggctcgtaa atttctgacc | 2460 |
| gaaataagaa attaa | 2475 |

<210> SEQ ID NO 54
<211> LENGTH: 1161
<212> TYPE: DNA
<213> ORGANISM: Artificial Sequence
<220> FEATURE:
<223> OTHER INFORMATION: Synthetic Construct

<400> SEQUENCE: 54

| | |
|---|---|
| atgaacgttg gaattgataa aatcaatttt ttcgttccgc cctatttcat tgatatggtg | 60 |
| gatctcgctc atgcaagaga agttgacccc aacaagttca ctataggaat aggccaagat | 120 |
| cagatggcag taaacaagaa aacgcaagat atcgtaacgt tcgcgatgca cgccgcgaag | 180 |
| gatattctga ctaaggaaga tttacaggcc atagatatgg taatagtggg gactgagtct | 240 |
| gggatcgacg agagcaaggc aagtgctgtc gtattgcatc ggcttttagg tattcagcct | 300 |
| tttgcgcgct cctttgaaat taaggaggca tgctatgggg ccactgccgg ccttcagttt | 360 |
| gcaaaagctc atgtgcaggc taatccccag agcaaggtcc tggtggtagc ttccgatata | 420 |
| gcacgctacg gactggcatc cggaggagaa ccgactcaag gtgtaggtgc tgtggcaatg | 480 |
| ttgatttccg ctgatccagc tatcttgcag ttagaaaatg ataatctcat gttgacccaa | 540 |
| gatatatacg attttggcg cccggtcggg catcaatatc ctatggtaga cggccatctg | 600 |
| tctaatgccg tctatataga cagctttaaa caagtctggc aagcacattg cgagaaaaac | 660 |
| caacggactg ctaaagatta tgctgcattg tcgttccata ttccgtacac gaaaatgggt | 720 |
| aagaaagctc tgttagcggt ttttgcggag gaagatgaga cagaacaaaa gcggttaatg | 780 |
| gcacgttatg aagaatcaat tgtatacagt cgtcggactg gaaatctgta tactggctca | 840 |
| ctctatctgg gcctgattc cttactggag aatagtagca gtttacaggc gaacgatcgc | 900 |
| ataggtctgt ttagctatgg ttcagggccc gttgcggaat ttttcagtgg cctcttggta | 960 |
| ccggggttacg agaaacaatt agcgcaagct gcccatcaag ctcttctgga cgaccggcaa | 1020 |

```
aaactgacta tcgcagagta cgaagccatg tttaatgaaa ccattgatat tgatcaggac    1080
cagtcatttg aggatgactt actgtactcc atcagagaga tcaaaaacac tattcgctac    1140
tataacgagg agaatgaata a                                              1161
```

<210> SEQ ID NO 55
<211> LENGTH: 329
<212> TYPE: PRT
<213> ORGANISM: Artificial Sequence
<220> FEATURE:
<223> OTHER INFORMATION: Synthetic Construct

<400> SEQUENCE: 55

```
Met Thr Asp Val Arg Phe Arg Ile Ile Gly Thr Gly Ala Tyr Val Pro
 1               5                  10                  15

Glu Arg Ile Val Ser Asn Asp Glu Val Gly Ala Pro Ala Gly Val Asp
             20                  25                  30

Asp Asp Trp Ile Thr Arg Lys Thr Gly Ile Arg Gln Arg Arg Trp Ala
         35                  40                  45

Ala Asp Gln Ala Thr Ser Asp Leu Ala Thr Ala Ala Gly Arg Ala
     50                  55                  60

Ala Leu Lys Ala Ala Gly Ile Thr Pro Glu Gln Leu Thr Val Ile Ala
 65                  70                  75                  80

Val Ala Thr Ser Thr Pro Asp Arg Pro Gln Pro Pro Thr Ala Ala Tyr
                 85                  90                  95

Val Gln His His Leu Gly Ala Thr Gly Thr Ala Ala Phe Asp Val Asn
            100                 105                 110

Ala Val Cys Ser Gly Thr Val Phe Ala Leu Ser Ser Val Ala Gly Thr
        115                 120                 125

Leu Val Tyr Arg Gly Gly Tyr Ala Leu Val Ile Gly Ala Asp Leu Tyr
    130                 135                 140

Ser Arg Ile Leu Asn Pro Ala Asp Arg Lys Thr Val Val Leu Phe Gly
145                 150                 155                 160

Asp Gly Ala Gly Ala Met Val Leu Gly Pro Thr Ser Thr Gly Thr Gly
                165                 170                 175

Pro Ile Val Arg Arg Val Ala Leu His Thr Phe Gly Gly Leu Thr Asp
            180                 185                 190

Leu Ile Arg Val Pro Ala Gly Gly Ser Arg Gln Pro Leu Asp Thr Asp
        195                 200                 205

Gly Leu Asp Ala Gly Leu Gln Tyr Phe Ala Met Asp Gly Arg Glu Val
    210                 215                 220

Arg Arg Phe Val Thr Glu His Leu Pro Gln Leu Ile Lys Gly Phe Leu
225                 230                 235                 240

His Glu Ala Gly Val Asp Ala Ala Asp Ile Ser His Phe Val Pro His
                245                 250                 255

Gln Ala Asn Gly Val Met Leu Asp Glu Val Phe Gly Glu Leu His Leu
            260                 265                 270

Pro Arg Ala Thr Met His Arg Thr Val Glu Thr Tyr Gly Asn Thr Gly
        275                 280                 285

Ala Ala Ser Ile Pro Ile Thr Met Asp Ala Ala Val Arg Ala Gly Ser
    290                 295                 300

Phe Arg Pro Gly Glu Leu Val Leu Leu Ala Gly Phe Gly Gly Gly Met
305                 310                 315                 320

Ala Ala Ser Phe Ala Leu Ile Glu Trp
                325
```

<210> SEQ ID NO 56
<211> LENGTH: 538
<212> TYPE: PRT
<213> ORGANISM: Artificial Sequence
<220> FEATURE:
<223> OTHER INFORMATION: Synthetic Construct

<400> SEQUENCE: 56

```
Ala Arg Arg Ser Ala Asn Tyr Glu Pro Asn Ser Trp Asp Tyr Asp Tyr
 1               5                  10                  15

Leu Leu Ser Ser Asp Thr Asp Glu Ser Ile Glu Val Tyr Lys Asp Lys
            20                  25                  30

Ala Lys Lys Leu Glu Ala Glu Val Arg Arg Glu Ile Asn Asn Glu Lys
        35                  40                  45

Ala Glu Phe Leu Thr Leu Leu Glu Leu Ile Asp Asn Val Gln Arg Leu
    50                  55                  60

Gly Leu Gly Tyr Arg Phe Glu Ser Asp Ile Arg Gly Ala Leu Asp Arg
65                  70                  75                  80

Phe Val Ser Ser Gly Gly Phe Asp Ala Val Thr Lys Thr Ser Leu His
                85                  90                  95

Gly Thr Ala Leu Ser Phe Arg Leu Leu Arg Gln His Gly Phe Glu Val
            100                 105                 110

Ser Gln Glu Ala Phe Ser Gly Phe Lys Asp Gln Asn Gly Asn Phe Leu
        115                 120                 125

Glu Asn Leu Lys Glu Asp Ile Lys Ala Ile Leu Ser Leu Tyr Glu Ala
    130                 135                 140

Ser Phe Leu Ala Leu Glu Gly Glu Asn Ile Leu Asp Glu Ala Lys Val
145                 150                 155                 160

Phe Ala Ile Ser His Leu Lys Glu Leu Ser Glu Glu Lys Ile Gly Lys
                165                 170                 175

Glu Leu Ala Glu Gln Val Asn His Ala Leu Glu Leu Pro Leu His Arg
            180                 185                 190

Arg Thr Gln Arg Leu Glu Ala Val Trp Ser Ile Glu Ala Tyr Arg Lys
        195                 200                 205

Lys Glu Asp Ala Asn Gln Val Leu Leu Glu Leu Ala Ile Leu Asp Tyr
    210                 215                 220

Asn Met Ile Gln Ser Val Tyr Gln Arg Asp Leu Arg Glu Thr Ser Arg
225                 230                 235                 240

Trp Trp Arg Arg Val Gly Leu Ala Thr Lys Leu His Phe Ala Arg Asp
                245                 250                 255

Arg Leu Ile Glu Ser Phe Tyr Trp Ala Val Gly Val Ala Phe Glu Pro
            260                 265                 270

Gln Tyr Ser Asp Cys Arg Asn Ser Val Ala Lys Met Phe Ser Phe Val
        275                 280                 285

Thr Ile Ile Asp Asp Ile Tyr Asp Val Tyr Gly Thr Leu Asp Glu Leu
    290                 295                 300

Glu Leu Phe Thr Asp Ala Val Glu Arg Trp Asp Val Asn Ala Ile Asn
305                 310                 315                 320

Asp Leu Pro Asp Tyr Met Lys Leu Cys Phe Leu Ala Leu Tyr Asn Thr
                325                 330                 335

Ile Asn Glu Ile Ala Tyr Asp Asn Leu Lys Asp Lys Gly Glu Asn Ile
            340                 345                 350

Leu Pro Tyr Leu Thr Lys Ala Trp Ala Asp Leu Cys Asn Ala Phe Leu
        355                 360                 365
```

Gln Glu Ala Lys Trp Leu Tyr Asn Lys Ser Thr Pro Thr Phe Asp Asp
    370                 375                 380

Tyr Phe Gly Asn Ala Trp Lys Ser Ser Ser Gly Pro Leu Gln Leu Val
385                 390                 395                 400

Phe Ala Tyr Phe Ala Val Val Gln Asn Ile Lys Lys Glu Glu Ile Glu
                405                 410                 415

Asn Leu Gln Lys Tyr His Asp Thr Ile Ser Arg Pro Ser His Ile Phe
            420                 425                 430

Arg Leu Cys Asn Asp Leu Ala Ser Ala Ser Glu Ile Ala Arg Gly
        435                 440                 445

Glu Thr Ala Asn Ser Val Ser Cys Tyr Met Arg Thr Lys Gly Ile Ser
    450                 455                 460

Glu Glu Leu Ala Thr Glu Ser Val Met Asn Leu Ile Asp Glu Thr Trp
465                 470                 475                 480

Lys Lys Met Asn Lys Glu Lys Leu Gly Gly Ser Leu Phe Ala Lys Pro
                485                 490                 495

Phe Val Glu Thr Ala Ile Asn Leu Ala Arg Gln Ser His Cys Thr Tyr
                500                 505                 510

His Asn Gly Asp Ala His Thr Ser Pro Asp Glu Leu Thr Arg Lys Arg
            515                 520                 525

Val Leu Ser Val Ile Thr Glu Pro Ile Leu
        530                 535

<210> SEQ ID NO 57
<211> LENGTH: 540
<212> TYPE: PRT
<213> ORGANISM: Artificial Sequence
<220> FEATURE:
<223> OTHER INFORMATION: Synthetic Construct

<400> SEQUENCE: 57

Thr Arg Arg Ser Ala Asn Tyr Gln Pro Asn Leu Trp Asp Phe Glu Phe
1               5                   10                  15

Leu Gln Ser Val Glu Asn Asp Leu Gln Val Glu Arg Leu Glu Glu Arg
            20                  25                  30

Ala Arg Lys Leu Glu Glu Glu Val Arg Gly Leu Met Lys Lys Val Glu
        35                  40                  45

Ile Glu Pro Leu Ser Leu Leu Glu Leu Met Asp Asn Val Glu Arg Leu
    50                  55                  60

Gly Leu Thr Tyr Lys Phe Glu Glu Asp Ile Lys Ser Ala Leu Asn Asn
65                  70                  75                  80

Arg Ile Val Pro Leu Leu His His Thr Ile Asn Lys Tyr Gly Leu
            85                  90                  95

His Ala Thr Ala Leu Ser Phe Arg Phe Leu Arg Gln His Ala Phe His
            100                 105                 110

Val Ser Pro Asp Val Phe Glu Ser Phe Lys Glu Glu Gly Lys Phe Lys
        115                 120                 125

Lys Glu Ile Ser Gly Asp Val Leu Gly Leu Leu Asn Leu Tyr Glu Thr
    130                 135                 140

Ser Tyr Leu Gly Phe Glu Gly Glu Thr Ile Leu Asp Glu Ala Arg Ala
145                 150                 155                 160

Phe Ser Ala Thr His Leu Lys Asn Leu Leu Gln Thr Asn Gln Val Gln
                165                 170                 175

Asn Lys Val Met Ala Glu Lys Val Arg His Ala Leu Glu Leu Pro Tyr
            180                 185                 190

His Arg Arg Val His Arg Leu Glu Ala Arg Trp Phe Ile Glu Arg Tyr
            195                 200                 205

Glu Gln Lys Glu Ala His Asp Gly Ala Leu Leu Glu Leu Ala Lys Leu
            210                 215                 220

Asp Phe Asn Met Val Gln Ser Val Met Lys Lys Glu Leu Gln Glu Leu
225                 230                 235                 240

Ser Arg Trp Trp Arg Glu Ile Gly Leu Thr Ser Lys Leu Asp Phe Val
            245                 250                 255

Arg Asp Arg Leu Met Glu Val Tyr Phe Trp Ala Leu Gly Met Ala Pro
            260                 265                 270

His Pro Gln Leu Thr Glu Cys Arg Lys Ala Val Thr Lys Met Phe Gly
            275                 280                 285

Leu Val Thr Ile Ile Asp Asp Val Tyr Asp Val Tyr Gly Thr Leu Asp
            290                 295                 300

Glu Leu Gln Leu Phe Thr Asp Ala Val Asp Arg Trp Asp Val Asn Ala
305                 310                 315                 320

Val Glu Thr Leu Pro Asp Tyr Met Lys Leu Cys Tyr Leu Ala Leu Tyr
            325                 330                 335

Asn Ser Val Asn Asp Thr Ala Tyr Ser Thr Leu Arg Glu Lys Gly Asp
            340                 345                 350

Asn Ser Leu Pro His Leu Ala Lys Ser Trp Arg Asp Leu Cys Lys Ala
            355                 360                 365

Phe Leu Gln Glu Ala Lys Trp Ser Asn Asn Lys Ile Ile Pro Pro Phe
            370                 375                 380

Asp Ala Tyr Ile Arg Asn Ala Ser Val Ser Ser Gly Gly Ala Leu
385                 390                 395                 400

Leu Ala Pro Cys Tyr Phe Ser Val Thr Gln Asp Ser Thr Ser Gln Ala
            405                 410                 415

Ile Asp Ser Ile Thr Asn Tyr His Gly Ile Val Arg Ser Ser Cys Ala
            420                 425                 430

Ile Phe Arg Leu Cys Asn Asp Leu Ala Thr Ser Ala Ala Glu Leu Glu
            435                 440                 445

Arg Gly Glu Thr Thr Asn Ser Ile Thr Ser Tyr Met Thr Glu Asn Gly
            450                 455                 460

Thr Thr Glu Glu Glu Ala Arg Glu Ser Leu Gly Lys Leu Ile Asp Gln
465                 470                 475                 480

Glu Trp Lys Lys Met Asn Arg Asp Val Val Leu Glu Ser Ala Tyr Pro
            485                 490                 495

Asn Val Phe Lys Glu Ile Ala Ile Asn Met Ala Arg Val Ser His Cys
            500                 505                 510

Thr Tyr Gln Tyr Gly Asp Gly Leu Gly Arg Pro Asp Asp Thr Ala Glu
            515                 520                 525

Asn Arg Ile Lys Leu Ser Leu Ile Glu Pro Ile Pro
            530                 535                 540

<210> SEQ ID NO 58
<211> LENGTH: 543
<212> TYPE: PRT
<213> ORGANISM: Artificial Sequence
<220> FEATURE:
<223> OTHER INFORMATION: Synthetic Construct

<400> SEQUENCE: 58

Met His Thr Arg Arg Ser Ala Asn Tyr Gln Pro Asn Leu Trp Asn Phe
1               5                   10                  15

```
Glu Phe Leu Gln Ser Leu Gln Asn His His Gln Val Phe Thr Met Phe
                20                  25                  30

Arg Arg Lys Leu Glu Lys Glu Val Arg Cys Met Met Asn Lys Ala Asp
            35                  40                  45

Ala Glu Ala Leu Ser Leu Leu Glu Leu Ile Asp Asp Val Gln Arg Leu
50                  55                  60

Gly Leu Thr Tyr Arg Phe Glu Lys Asp Ile Ile Lys Val Leu Glu Lys
65                  70                  75                  80

Ile Val Ser Leu Asp Glu Ile Glu Lys His Gln Ser Gly Leu His Ala
                85                  90                  95

Thr Ala Leu Thr Phe Arg Leu Leu Arg Gln His Gly Phe His Gln Val
                100                 105                 110

Ser Gln Asp Met Phe Lys Arg Phe Lys Asp Lys Glu Gly Gly Phe Asn
            115                 120                 125

Asp Glu Leu Lys Gly Asp Val Gln Gly Leu Leu Ser Leu Tyr Glu Ala
            130                 135                 140

Ser Tyr Leu Gly Phe Glu Gly Glu Tyr Leu Leu Asp Glu Ala Arg Ala
145                 150                 155                 160

Phe Ser Ile Thr His Leu Asn Asn Ser Leu Lys Gln Gly Ile Asn Thr
                165                 170                 175

Lys Leu Ala Glu Gln Val Ser His Ala Leu Gln Leu Pro His His Arg
            180                 185                 190

Arg Leu His Arg Leu Glu Ala Arg Trp Gln Leu Asp Lys Tyr Glu Pro
            195                 200                 205

Lys Glu Pro His His His Leu Leu His Leu Ala Lys Leu Asp Phe
            210                 215                 220

Asn Ile Leu Gln Ser Leu Tyr Gln Asn Glu Leu Arg Glu Leu Ser Arg
225                 230                 235                 240

Trp Trp Arg Glu Met Gly Leu Thr Ser Lys Leu Glu Phe Val Arg Asp
                245                 250                 255

Arg Leu Met Glu Val Tyr Phe Trp Ala Leu Gly Met Ala Pro His Pro
            260                 265                 270

Glu Phe Ser Glu Cys Arg Lys Ala Ile Thr Lys Met Phe Gly Leu Val
            275                 280                 285

Thr Ile Ile Asp Asp Val Tyr Asp Val Tyr Gly Thr Leu Asp Glu Leu
290                 295                 300

Gln Leu Phe Thr Asp Ala Val Glu Arg Trp Asp Val Asn Val Val Asn
305                 310                 315                 320

Thr Leu Pro Tyr Tyr Met Lys Leu Cys Tyr Leu Ala Leu Tyr Asn Thr
                325                 330                 335

Val Asn Glu Thr Ser Tyr Ser Ile Leu Lys Glu Asn Gly His Asn Ser
                340                 345                 350

Leu Ser Tyr Leu Ala Lys Ser Trp Cys Glu Leu Cys Lys Ala Phe Leu
            355                 360                 365

Glu Glu Ala Lys Trp Ser Lys Lys Val Ile Pro Ala Leu Asn Arg
            370                 375                 380

Tyr Leu Glu Asn Ala Trp Val Ser Ser Gly Val Ala Leu Leu Ala
385                 390                 395                 400

Pro Cys Tyr Phe Ser Val Cys Lys Glu Glu Lys Ile Ser Asp Glu
                405                 410                 415

Ala Leu His Ser Leu Thr Asn Phe His Gly Leu Val Arg Ser Ser Cys
            420                 425                 430
```

Ala Ile Phe Arg Leu Tyr Asn Asp Leu Ala Thr Ser Ala Ala Glu Leu
435                 440                 445

Glu Arg Asp Glu Thr Thr Asn Ser Met Thr Cys Tyr Met His Glu Asn
450                 455                 460

Gly Ser Cys Glu Glu Gln Ala Arg Glu Leu Arg Lys Met Ile Glu
465                 470                 475                 480

Val Glu Trp Lys Lys Met Asn Gln Gly Val Leu Asp Cys Thr Leu
                485                 490                 495

Pro Thr Ala Phe Lys Glu Ile Ala Met Asn Met Ala Arg Val Ser His
                500                 505                 510

Cys Thr Tyr Gln His Gly Asp Gly Leu Gly Arg Pro Asp Tyr Thr Thr
                515                 520                 525

Gln Asn Arg Ile Lys Leu Leu Leu Ile Asp Pro Leu Pro Ile Asn
530                 535                 540

<210> SEQ ID NO 59
<211> LENGTH: 543
<212> TYPE: PRT
<213> ORGANISM: Artificial Sequence
<220> FEATURE:
<223> OTHER INFORMATION: Synthetic Construct

<400> SEQUENCE: 59

Met Asn Thr Arg Arg Ser Ala Asn Tyr His Pro Asn Leu Trp Asn Phe
1               5                   10                  15

Glu Phe Leu Gln Ser Leu Glu Asn Asp Pro Lys Ile Glu Lys Leu Glu
                20                  25                  30

Glu Lys Ala Thr Lys Leu Val Glu Val Arg His Met Met Asn Lys
            35                  40                  45

Ala Glu Thr Glu Pro Leu Ser Leu Leu Glu Leu Ile Asp Asp Val Gln
50                  55                  60

Arg Leu Gly Leu Thr Tyr Lys Phe Glu Lys Asp Ile Ile Asn Ala Leu
65                  70                  75                  80

Glu Lys Thr Ile Ser Leu Asp Glu Asn Gln Lys His Ile Ser Gly Leu
                85                  90                  95

His Ala Thr Ser Leu Ser Phe Arg Leu Leu Arg Gln His Gly Phe Glu
                100                 105                 110

Val Ser Gln Asp Val Phe Lys Lys Phe Lys Asp Glu Asp Gly Gly Phe
            115                 120                 125

Ser Ala Glu Leu Lys Gly Asp Val Gln Gly Leu Leu Ser Leu Tyr Glu
130                 135                 140

Ala Ser Tyr Leu Gly Phe Glu Gly Glu Asn Leu Leu Asp Glu Ala Arg
145                 150                 155                 160

Glu Phe Ser Ile Glu His Leu Lys Asn Asn Leu Asn Lys Gly Ile Thr
                165                 170                 175

Thr Lys Val Ala Glu Gln Val Ser His Ala Leu Glu Leu Pro Tyr His
            180                 185                 190

Arg Arg Ile His Arg Leu Glu Ala Arg Trp Phe Leu Asp Lys Tyr Glu
        195                 200                 205

Pro Lys Glu Ser Gln His Lys Leu Leu Leu Glu Leu Ala Lys Leu Asp
    210                 215                 220

Phe Asn Met Val Gln Ser Leu His Gln Lys Glu Leu Arg Glu Leu Ser
225                 230                 235                 240

Met Trp Trp Arg Glu Ile Gly Leu Thr Ser Lys Leu Asp Phe Val Arg
                245                 250                 255

-continued

```
Asp Arg Leu Met Glu Val Tyr Phe Trp Ala Leu Gly Met Ala Pro Asp
            260                 265                 270

Pro Gln Phe Ser Glu Cys Arg Lys Ala Val Thr Lys Met Phe Gly Leu
            275                 280                 285

Val Thr Ile Ile Asp Asp Val Tyr Asp Val Tyr Gly Thr Leu Asp Glu
            290                 295                 300

Leu Gln Leu Phe Thr Asp Ala Val Glu Arg Trp Asp Val Asn Ala Ile
305                 310                 315                 320

Asn Thr Leu Pro Asp Tyr Met Lys Leu Cys Phe Leu Ala Leu Tyr Asn
                325                 330                 335

Thr Val Asn Asp Thr Thr Tyr Ser Ile Leu Lys Glu Lys Gly His Asn
                340                 345                 350

Asn Ile Ser Tyr Leu Thr Lys Ser Trp Cys Glu Leu Cys Lys Ala Phe
                355                 360                 365

Leu Gln Glu Ala Lys Trp Ser Asn Asn Lys Ile Ile Pro Thr Phe Asn
    370                 375                 380

Lys Tyr Leu Arg Asn Ala Ser Val Ser Ser Ser Gly Val Ala Leu Leu
385                 390                 395                 400

Ala Pro Ser Phe Phe Leu Val Cys Gln Glu Gln Asp Ile Ser Glu Gln
                405                 410                 415

Ala Leu His Ser Leu Ile Asn Phe His Gly Leu Val Arg Ser Ser Cys
                420                 425                 430

Val Ile Phe Arg Leu Cys Asn Asp Leu Ala Thr Ser Ala Ala Glu Leu
            435                 440                 445

Glu Arg Gly Glu Thr Thr Asn Ser Ile Thr Ser Tyr Met His Glu Asn
    450                 455                 460

Gly Thr Ser Glu Glu Gln Ala Arg Gln Glu Leu Arg Ile Leu Ile Asp
465                 470                 475                 480

Ala Glu Trp Lys Asn Met Asn Gln Glu Arg Tyr Leu Asp Ser Thr Leu
                485                 490                 495

Pro Asp Ala Phe Met Glu Ile Thr Ile Asn Leu Ala Arg Val Ser His
                500                 505                 510

Cys Thr Tyr Gln Tyr Gly Asp Gly Leu Gly Arg Pro Asp Tyr Thr Thr
            515                 520                 525

Lys Asn Arg Ile Lys Leu Leu Leu Ile Asp Pro Leu Pro Ile Asn
530                 535                 540
```

LEGUME ISOPRENE SYNTHASE FOR PRODUCTION OF ISOPRENE

CROSS-REFERENCE TO RELATED APPLICATIONS

This application claims priority to U.S. Provisional Patent Application No. 61/641,861, filed May 2, 2012, the disclosure of which is incorporated by reference herein in its entirety.

INCORPORATION BY REFERENCE

The Sequence Listing submitted in an ASCII text file, in accordance with 37 C.F.R. §1.821(c) and (e), is incorporated herein by reference. The text file name is "643842004600_SEQUENCE_LISTING.txt", the date of creation of the text file is Jul. 23, 2013, and the size of the ASCII text file in bytes is 185,821.

FIELD OF THE INVENTION

The present invention provides methods and compositions comprising isoprene synthases for improved production of isoprene. In particular, the present invention provides legume isoprene synthases for increased isoprene production in host cells.

BACKGROUND OF THE INVENTION

Isoprene (2-methyl-1,3-butadiene) is a volatile hydrocarbon that is insoluble in water and soluble in alcohol. Commercially viable quantities of isoprene can be obtained by direct isolation from petroleum C5 cracking fractions or by dehydration of C5 isoalkanes or isoalkenes (Weissermel and Arpe, Industrial Organic Chemistry, 4$^{th}$ ed., Wiley-VCH, pp. 117-122, 2003). The C5 skeleton can also be synthesized from smaller subunits. It would be desirable, however, to have a commercially viable method of producing isoprene that was independent of nonrenewable resources.

Isoprene monomer is employed in the manufacture of polyisoprene and various copolymers (with isobutylene, butadiene, styrene, or other monomers). Building a strain (prokaryotic or eukaryotic) capable of producing commercially viable levels of isoprene requires optimization of part of or the entire DXP or MVA pathway or both MVA and DXP pathways. A key enzyme in the pathway is isoprene synthase (IspS), which converts the precursor DMAPP to isoprene. Isoprene synthases (IspS) that have been identified include those from plants such as poplar, English oak and kudzu vine. Some of the identified plant IspS enzymes have been partially characterized in part by expression in *E. coli* and some of the kinetic parameters of these enzymes have been determined in vitro with purified protein. However, kinetic parameters, including $K_m$, $K_i$, and $K_{cat}$, of the native IspS enzymes and even some of the recombinant enzymes are insufficient for commercial production of isoprene in a biological host. In addition, commercial use of some IspS enzymes can be limited due to insufficient expression levels. Thus, one problem to be solved is the provision of isoprene synthases that have improved properties such that a greater amount of isoprene can be biologically produced for commercial use. To solve this problem as described herein, an isoprene synthase with improved properties may be expressed in a host (e.g. a bacterial host). In particular, the present invention provides legume isoprene synthases that exhibit improved properties for increased isoprene production in host cells.

All patents, patent applications, publications, documents, nucleotide and protein sequence database accession numbers, the sequences to which they refer, and articles cited herein are all incorporated herein by reference in their entireties.

BRIEF SUMMARY OF THE INVENTION

The invention provided herein discloses, inter alia, compositions of polypeptides having isoprene synthase activity with improved properties for production of isoprene and methods for identifying, producing and using such polypeptides for the production of isoprene. In some aspects, the present invention provides legume isoprene synthases for increased isoprene production in host cells.

Accordingly, in some aspects, the invention provides for an isolated polypeptide from a legume having isoprene synthase activity, wherein said polypeptide comprises at least 40% sequence identity to SEQ ID NO: 1, wherein said polypeptide has one or more amino acid residue(s) corresponding to one or more amino acid residue(s) corresponding to SEQ ID NO:1, and wherein said one or more amino acid residue(s) are selected from the group consisting of F287, G397, N438, E451, and Y514. In other aspects, the isolated polypeptide is not from *P. montana*. In some aspects, the isolated polypeptide is an isoprene synthase selected from the group consisting of *Arachis* sp., *Mucana* sp., *Cajanus* sp., *Glycine* sp., *Lotus* sp., and *Medicago* sp. In further aspects, the isolated polypeptide is an isoprene synthase selected from the group consisting of *A. hypogaea, M. pruriens, C. cajans, G. max, G. soja, L. japonicus*, and *M. truncatula*. In yet a further aspect, the isolated polypeptide of claim 2, wherein the isolated polypeptide is an *A. hypogaea* isoprene synthase. In yet another aspect, the isolated polypeptide is an *M. pruriens* isoprene synthase. In some aspects, the invention provides legume isoprene synthases with at least one improved property as compared to a poplar isoprene synthase. In some aspects, at least one improved property is selected from but not limited to the group consisting of: specific productivity, yield, cellular performance index and protein expression. In some aspects, at least one improved property is selected from but not limited to the group consisting of: specific activity, $K_{cat}$, $K_i$, and $K_m$. In any of the aspects herein, the isolated polypeptide has a reduced substrate inhibition as compared to a poplar isoprene synthase. In any of the aspects herein, the isolated polypeptide has increased isoprene synthase activity as compared to a poplar isoprene synthase. In some aspects, the increased isoprene synthase activity is indicated by a host cell comprising the isoprene synthase displaying improved growth in the presence of mevalonic acid compared to a host cell comprising a poplar isoprene synthase. In any of the aspects herein, the isolated polypeptide is an isoprene synthase selected from the group consisting of: *A. hypogaea* (SEQ ID NO:3), *G. max* 1 (SEQ ID NO:5), *G. max* 2 (SEQ ID NO:7), *M. pruriens* (SEQ ID NO:9), and *C. cajans* (SEQ ID NO:11). In further aspects, the isolated polypeptide is an *A. hypogaea* isoprene synthase comprising the amino acid sequence of SEQ ID NO:3.

Additionally, in some aspects, the invention provides for an isolated polypeptide from a legume having isoprene synthase activity comprising at least 70% sequence identity to SEQ ID NO: 3. In any of the aspects herein, an isolated polypeptide from a legume having isoprene synthase activity, wherein said isoprene synthase has a $K_{cat}$ value of at least about 1.3 is provided. In any of the aspects herein, an isolated polypeptide from a legume having isoprene synthase activity, wherein said isoprene synthase has a $K_m$ value of at least about 2.5 is provided. In any of the aspects herein, an isolated polypeptide from a legume having isoprene synthase activity, wherein said isoprene synthase has a $K_{iDMAPP}$ value of at least about 13.0 is provided.

In addition, in some aspects, the invention provides for an isolated polypeptide from a legume having isoprene synthase activity, wherein said polypeptide comprises at least 40% sequence identity to SEQ ID NO: 1, and wherein said polypeptide has a $K_{cat}$ value of at least about 1.3. In other aspects, the invention provides for an isolated polypeptide from a legume having isoprene synthase activity, wherein said polypeptide comprises at least 40% sequence identity to SEQ ID NO: 1, and wherein said polypeptide has a $K_m$ value of at least about 2.5. In yet other aspects, the invention provides for an isolated polypeptide from a legume having isoprene synthase activity, wherein said polypeptide comprises at least 40% sequence identity to SEQ ID NO: 1, and wherein said polypeptide has a $K_{iDMAPP}$ value of at least about 13.0. In any of the aspects herein, a host cell comprising a heterologous polynucleotide sequence encoding an isoprene synthase in operable combination with a promoter is provided. In some aspects, the polynucleotide sequence is contained within a plasmid. In other aspects, the polynucleotide sequence is integrated into a chromosome of the host cell. In yet other aspects, the host is selected from the group consisting of gram-positive bacterial cells, gram-negative bacterial cells, filamentous fungal cells, and yeast cells. In other aspects, the host is selected from the group consisting of Escherichia sp. (E. coli), Panteoa sp. (P. citrea), Bacillus sp. (B. subtilis), Yarrowia sp. (Y. lipolytica), Trichoderma (T. reesei) and Saccharomyces (S. cerevisiae). In some aspects, the host cell is cultured in a medium comprising a carbon source selected from the group consisting of glucose, glycerol, glycerine, dihydroxyacetone, yeast extract, biomass, molasses, sucrose, and oil. In any of the aspects herein, the host cell further comprises one or more heterologous or native nucleic acid(s) encoding one or more mevalonate (MVA) pathway polypeptides. In some aspects, the host cell further comprises a heterologous nucleic acid encoding a mevalonate (MVA) pathway polypeptide selected from the group consisting of an MVA pathway polypeptide from Saccharomyces cerevisiae, Enterococcus faecalis, E. casseliflavus and E. gallinarum. In some other aspects, the host cell further comprising one or more nucleic acids encoding a heterologous or native nucleic acid encoding an IDI polypeptide is provided. In some aspects, the host cell further comprises a heterologous or native nucleic acid encoding an IDI polypeptide and/or a heterologous or native nucleic acid encoding a DXS polypeptide, optionally in combination with the native DXP pathway. In some aspects, the host cell further comprises one or more nucleic acids encoding an IDI polypeptide and the DXS polypeptide. In some further aspects, the host cell comprises one vector encoding the isoprene synthase, the IDI polypeptide, and the DXS polypeptide. In still other aspects, the host cell further comprises one or more nucleic acids encoding an MVA pathway polypeptide and/or a DXS polypeptide. In a further aspect, the host cell further comprises one or more nucleic acids encoding a DXS polypeptide, an IDI polypeptide, or one or more of the rest of the DXP pathway polypeptides, and a MVA pathway polypeptide. In some further aspects, the host cell further comprising DXS is provided.

Additionally, in some aspects, the invention provides a method of producing isoprene, comprising: (a) culturing the host cells in any of the aspects herein under suitable culture conditions for production of isoprene; and (b) producing the isoprene. In some further aspects, the method further comprising (c) recovering the isoprene is provided. In yet some further aspects, the method further comprising (d) polymerizing isoprene is provided.

In addition, in some aspects, the invention provides a method of detecting isoprene synthase activity, comprising: (a) culturing a host cell comprising the expression vector under conditions suitable for producing a legume isoprene synthase; (b) lysing the host cells with a lysis buffer comprising lysozyme to produce a cell lysate; and (c) detecting isoprene synthase activity in the cell lysate by measuring isoprene production from dimethylallyl diphosphate (DMAPP). In some aspects, the host cell is selected from the group consisting of gram-positive bacterial cells, gram-negative bacterial cells, filamentous fungal cells, and yeast cells. In some further aspects, wherein the host cell is selected from the group consisting of Escherichia sp. (E. coli), Panteoa sp. (P. citrea), Bacillus sp. (B. subtilis), Yarrowia sp. (Y. lipolytica), Trichoderma (T. reesei), and Saccharomyces (S. cerevisiae) is provided. In other aspects, the host cell is cultured in a medium that includes a carbon source selected from the group consisting of glucose, glycerol, glycerine, dihydroxyacetone, yeast extract, biomass, molasses, sucrose, and oil.

In some aspects, the invention provides a method of detecting isoprene in a plurality of samples in a high-throughput screening comprising: (a) providing: i) a plurality of samples each comprising isoprene synthase; ii) a glass plate comprising a plurality of wells; and iii) a seal for the glass plate; (b) placing the plurality of samples in the plurality of wells of the glass plate; (c) sealing the glass plate with the seal to produce a sealed glass plate having a headspace associated with the sample in each of the plurality of wells; (d) incubating the glass plate under conditions in which the isoprene synthase is active; and (e) detecting isoprene in the headspace. In one aspect, the isoprene is detected by gas chromatography-mass spectrometry (GC-MS). In further aspects, the method wherein the plurality of samples comprise host cells comprising an expression vector comprising a polynucleotide sequence encoding an isoprene synthase variant in operable combination with a promoter is provided. In other further aspects, the method wherein the plurality of samples comprise a lysate of the host cells, lysozyme, and dimethylallyl diphosphate (DMAPP) is provided. In yet other further aspects, the method wherein the glass plate is a deep-well glass block is provided. In still yet other further aspects, the method wherein the plurality of wells comprises at least 24 wells is provided. In some further aspects, the method wherein the plurality of wells each comprise a volume of 2 ml or less is provided.

BRIEF DESCRIPTION OF THE DRAWINGS

FIG. 1 is an amino acid sequence alignment between A. hypogaea isoprene synthase (also indicated as "peanut") and MEA P. alba isoprene synthase. These sequences are shown as starting from residue 3. (SEQ ID NOS: 56, 57)

Figure 2C:
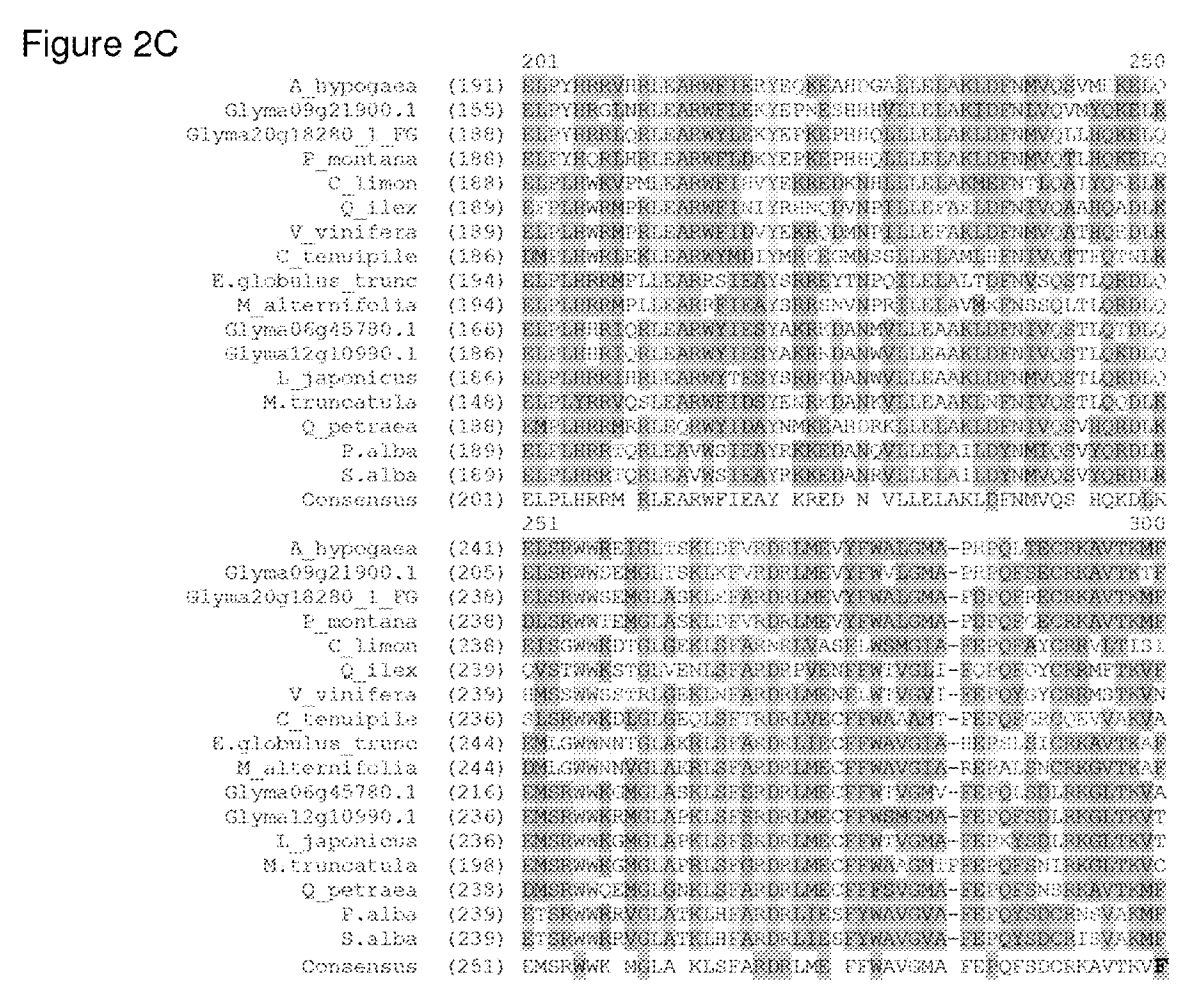
Figure 2F:
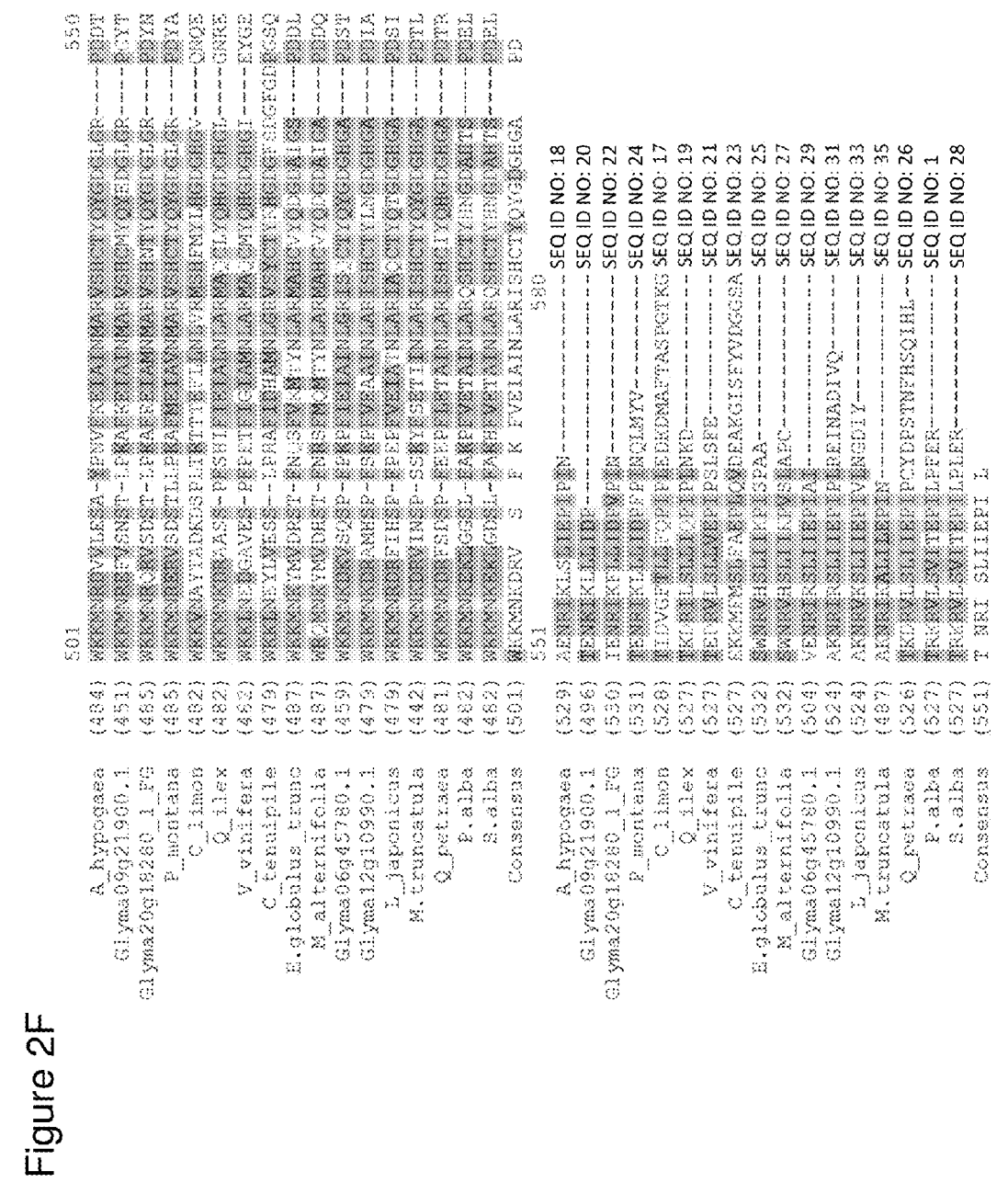

FIG. 2A-F is an amino acid sequence alignment of putative isoprene synthase enzymes with MEA P. alba isoprene synthase as a reference sequence. The consensus sequence is depicted at the bottom of the sequence alignment. (SEQ ID NOS: 18, 20, 22, 24, 17, 19, 21, 23, 25, 27, 29, 31, 33, 35, 26, 1, 28 respectively)

Figure 3B:
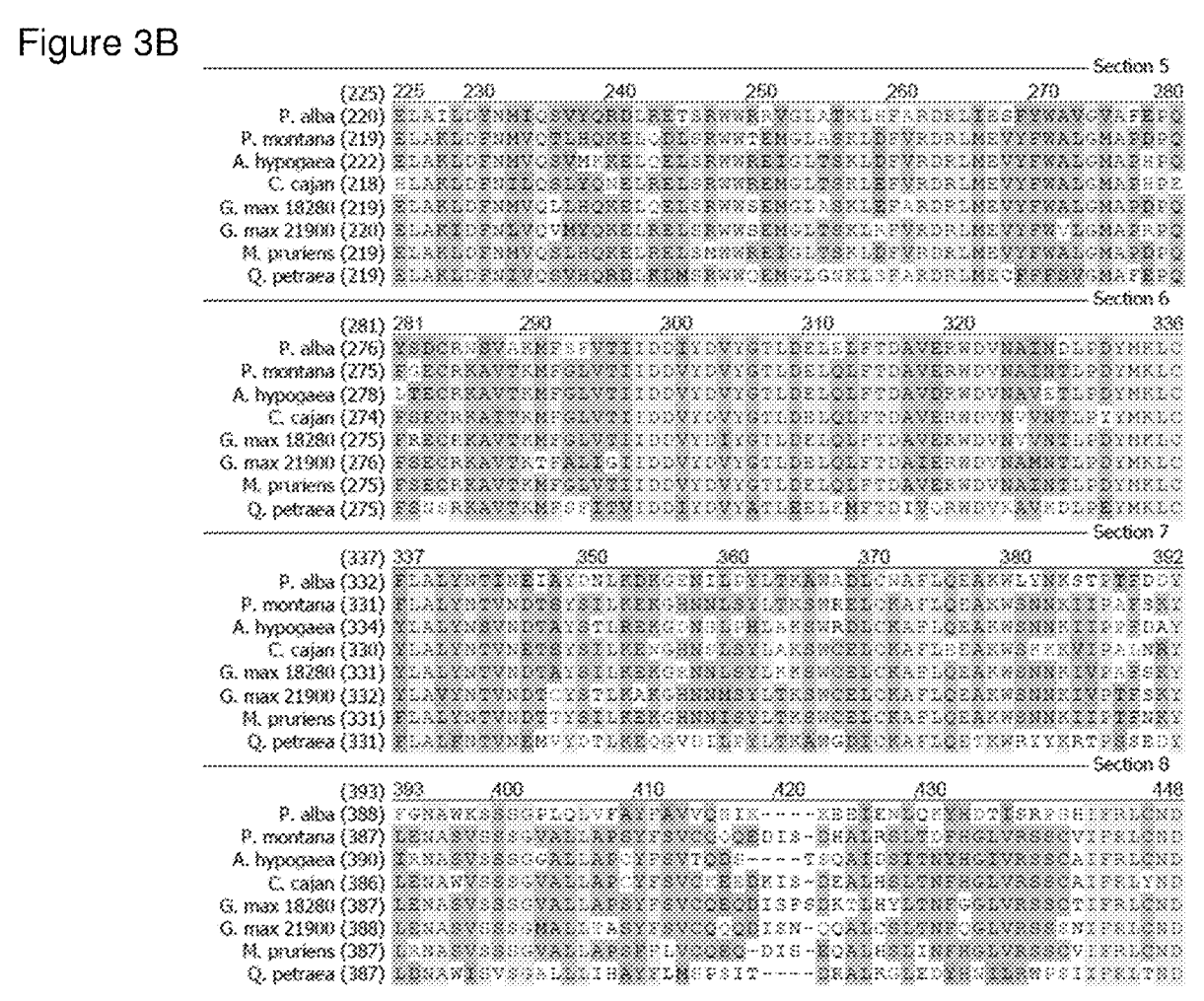

FIG. 3A-C is an amino acid sequence alignment of putative isoprene synthase enzymes with P. alba isoprene synthase and P. montana isoprene synthase as reference sequences. (SEQ ID NOS: 1, 15, 3, 58, 7, 5, 59, 13, respectively)

DETAILED DESCRIPTION

Figure 2A:
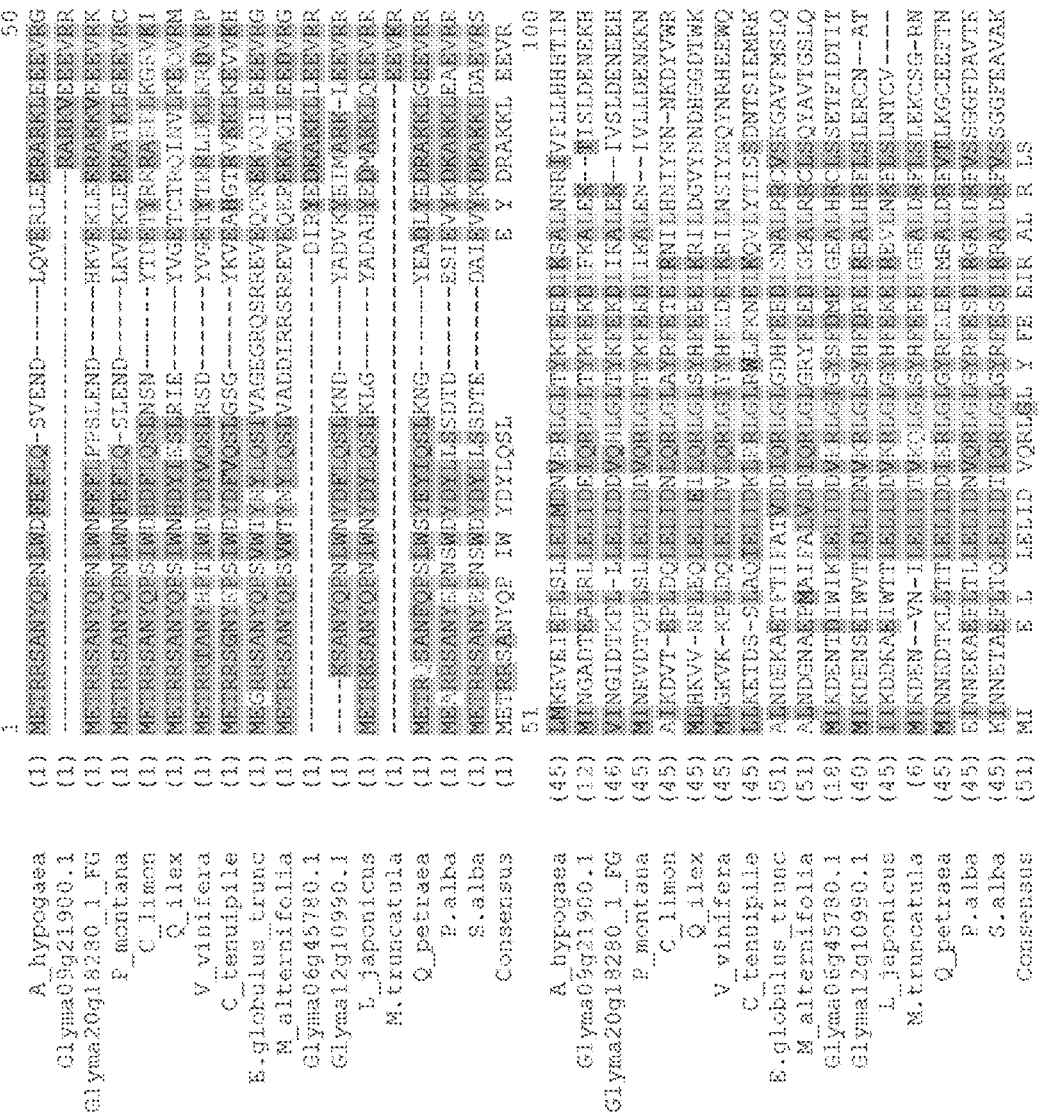
Figure 2B:
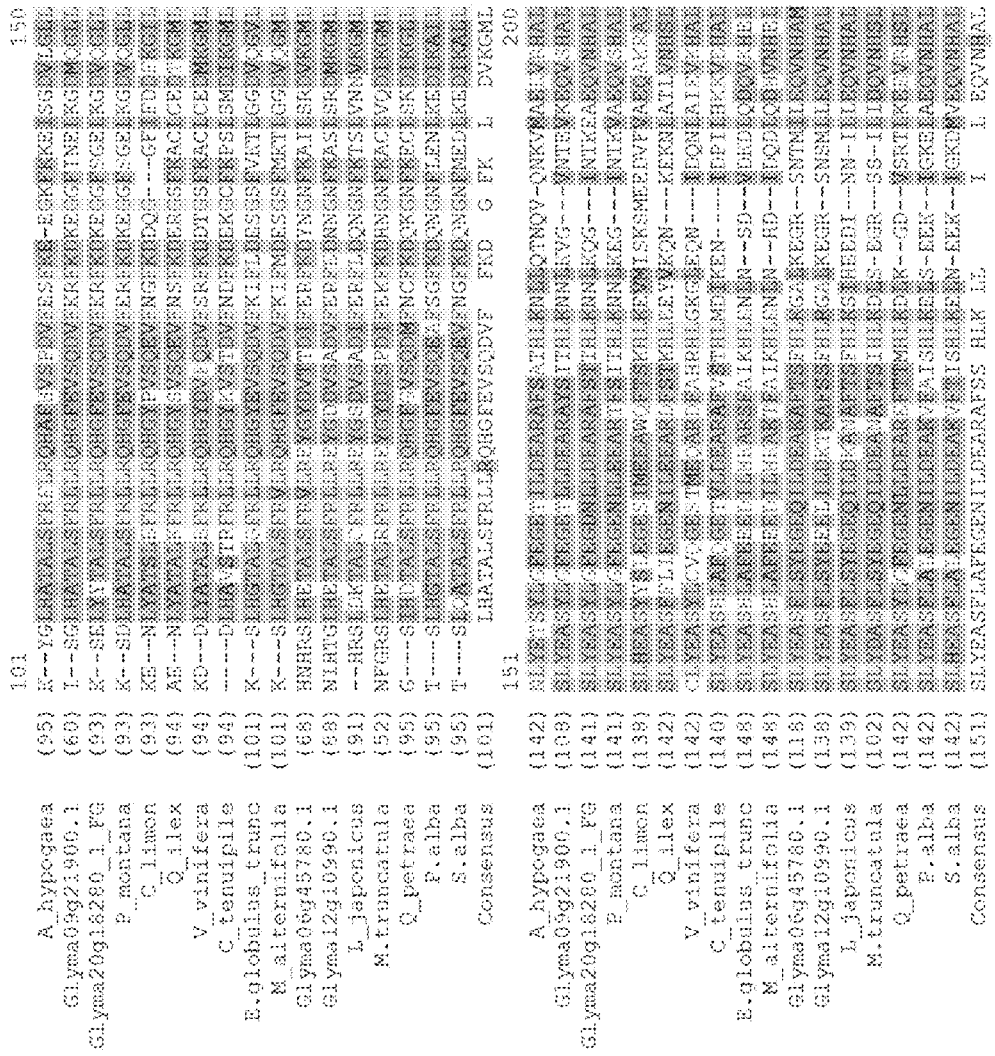
Figure 2D:
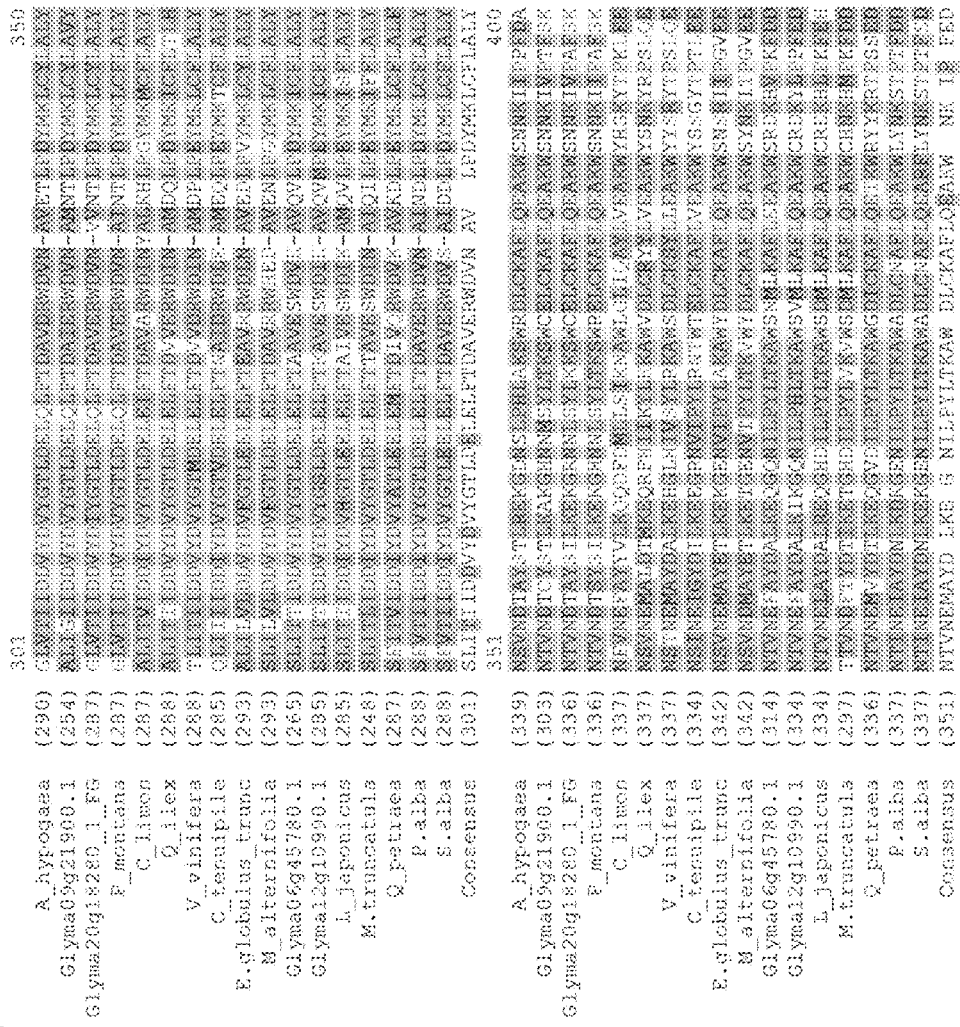
Figure 2E:
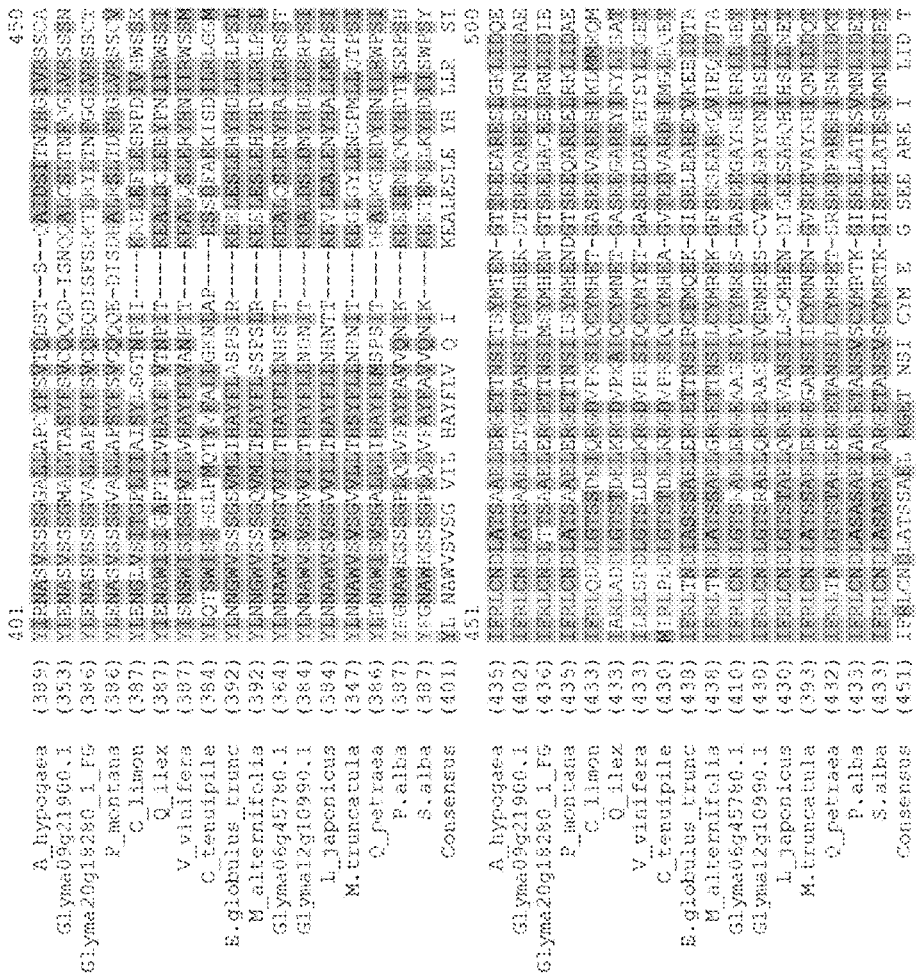
Figure 3A:
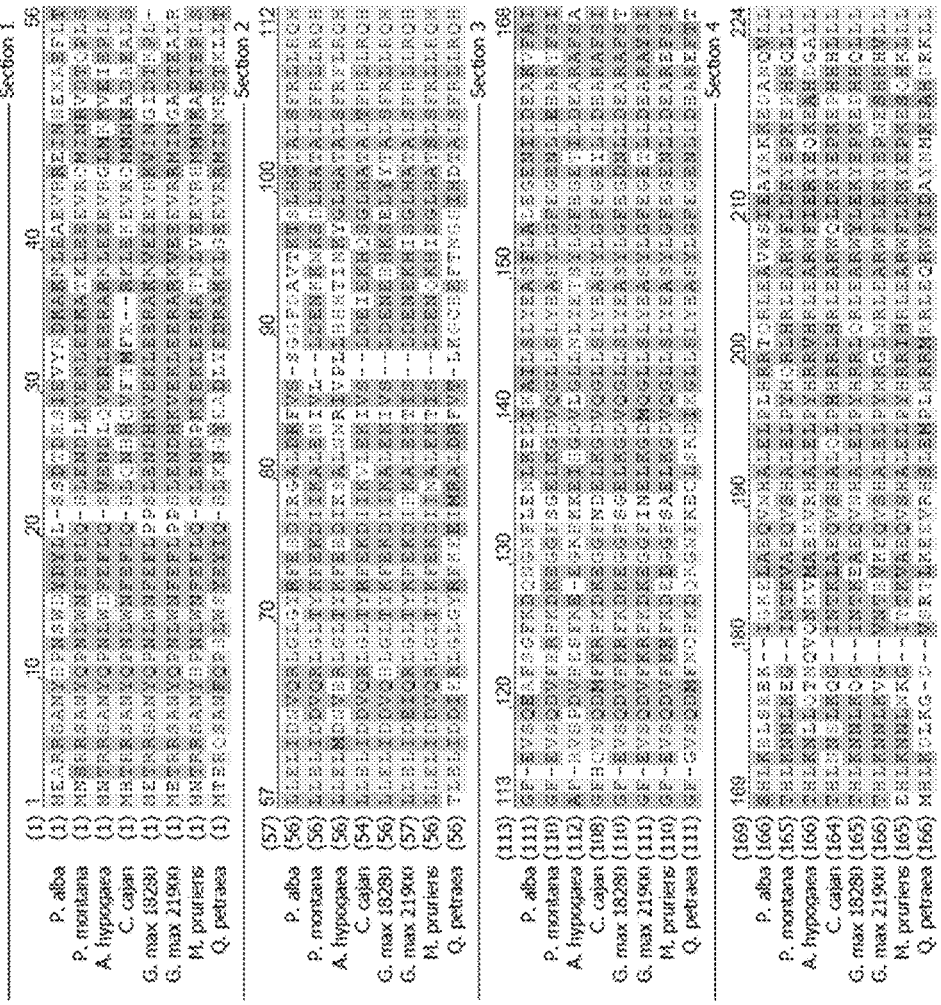
Figure 3C:
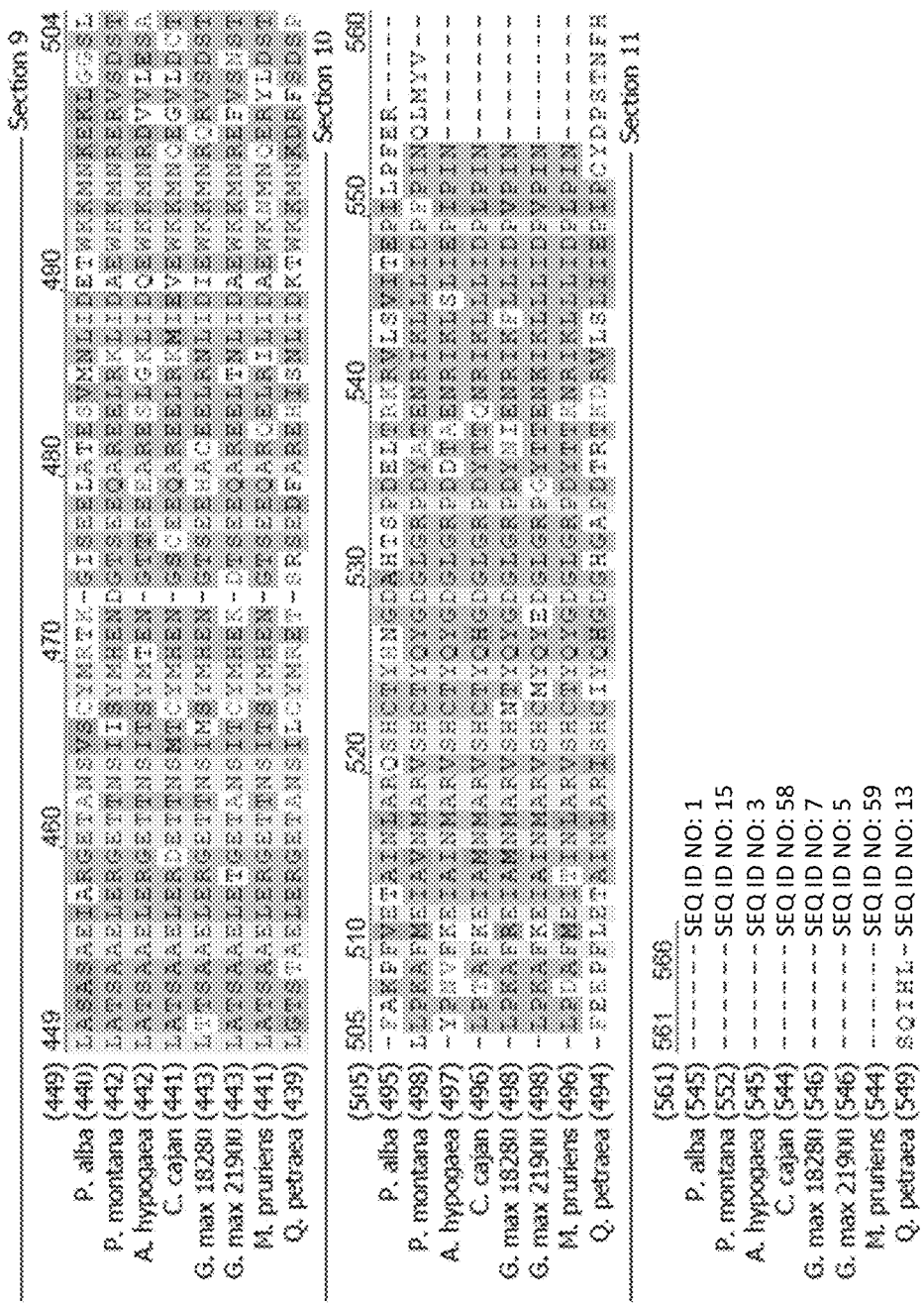

The present invention provides methods and compositions comprising at least one legume isoprene synthase enzyme with improved properties. The legume isoprene synthase comprises at least 40% sequence identity to SEQ ID NO: 1, wherein the legume isoprene synthase has one or more amino acid residue(s) corresponding to one or more amino acid residue(s) corresponding to SEQ ID NO: 1. In some aspects, one or more amino acid residue(s) can be F287, G397, N438, E451, and Y514. In some embodiments, the legume isoprene synthase is not from *P. montana*. The invention provides legume isoprene synthases with at least one improved property as compared to a poplar isoprene synthase. In some preferred embodiments, at least one improved property is selected from but not limited to the group consisting of: specific productivity, yield, cellular performance index and protein expression. In some particularly preferred embodiments, at least one improved property is selected from but not limited to the group consisting of: specific activity, $K_{cat}$, $K_i$, and $K_m$. In particular, the present invention provides legume isoprene synthases for increased isoprene production in host cells. Biosynthetically produced isoprene of the present invention finds use in the manufacture of rubber, polymers, and elastomers.

Furthermore, the headings provided herein are not limitations of the various aspects or embodiments of the invention, which can be had by reference to the specification as a whole. Accordingly, the terms defined immediately below are more fully defined by reference to the specification as a whole. Nonetheless, in order to facilitate understanding of the invention, a number of terms are defined below.

I. General Techniques

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, "*Molecular Cloning: A Laboratory Manual*", second edition (Sambrook et al., 1989); "*Oligonucleotide Synthesis*" (M. J. Gait, ed., 1984); "*Animal Cell Culture*" (R. I. Freshney, ed., 1987); "*Methods in Enzymology*" (Academic Press, Inc.); "*Current Protocols in Molecular Biology*" (F. M. Ausubel et al., eds., 1987, and periodic updates); "*PCR: The Polymerase Chain Reaction*", (Mullis et al., eds., 1994). Singleton et al., "*Dictionary of Microbiology and Molecular Biology*" 2nd ed., J. Wiley & Sons (New York, N.Y. 1994), Baltz et al., "*Manual of Industrial Microbiology and Biotechnology*" 3$^{rd}$ ed., (Washington, D.C.: ASM Press, 2010), and March, *Advanced Organic Chemistry Reactions, Mechanisms and Structure* 4th ed., John Wiley & Sons (New York, N.Y. 1992), provide one skilled in the art with a general guide to many of the terms used in the present application.

II. Definitions

Unless defined otherwise herein, all technical and scientific terms used herein have the same meaning as commonly understood by one of ordinary skill in the art to which this invention pertains. Although any methods and materials similar or equivalent to those described herein find use in the practice of the present invention, the preferred methods and materials are described herein. Accordingly, the terms defined immediately below are more fully described by reference to the Specification as a whole.

As used herein, the term "polypeptides" includes polypeptides, proteins, peptides, fragments of polypeptides, and fusion polypeptides.

As used herein, an "isolated polypeptide" is not part of a library of polypeptides, such as a library of 2, 5, 10, 20, 50 or more different polypeptides and is separated from at least one component with which it occurs in nature. An isolated polypeptide can be obtained, for example, by expression of a recombinant nucleic acid encoding the polypeptide.

By "heterologous polypeptide" is meant a polypeptide encoded by a nucleic acid sequence derived from a different organism, species, or strain than the host cell. In some aspects, a heterologous polypeptide is not identical to a wild-type polypeptide that is found in the same host cell in nature. Examples of heterologous proteins include enzymes such as isoprene synthases. In some embodiments, the genes encoding the proteins are naturally occurring genes, while in other embodiments mutated and/or synthetic genes are used.

An "endogenous polypeptide" is a polypeptide whose amino acid sequence is naturally found in the host cell. In some embodiments, an endogenous polypeptide is identical to a wild-type polypeptide that is found in the host cell in nature.

As used herein, a "nucleic acid" refers to two or more deoxyribonucleotides and/or ribonucleotides covalently joined together in either single or double-stranded form. It is to be understood that mutations, including single nucleotide mutations, can occur within a nucleic acid as defined herein.

By "recombinant nucleic acid" is meant a nucleic acid of interest that is free of one or more nucleic acids (e.g., genes) which, in the genome occurring in nature of the organism from which the nucleic acid of interest is derived, flank the nucleic acid of interest. The term therefore includes, for example, a recombinant DNA which is incorporated into a vector, into an autonomously replicating plasmid or virus, or into the genomic DNA of a prokaryote or eukaryote, or which exists as a separate molecule (e.g., a cDNA, a genomic DNA fragment, or a cDNA fragment produced by PCR or restriction endonuclease digestion) independent of other sequences. A recombinant nucleic acid may be obtained using molecular biology techniques that are known in the art, or part or all of a recombinant nucleic acid may be chemically synthesized.

By "heterologous nucleic acid" is meant a nucleic acid sequence derived from a different organism, species or strain than the host cell. In some aspects, the heterologous nucleic acid is not identical to a wild-type nucleic acid that is found in the same host cell in nature. In some aspects, a heterologous nucleic acid is not identical to a wild-type nucleic acid that is found in the same host cell in nature.

An "endogenous nucleic acid" is a nucleic acid whose nucleic acid sequence is naturally found in the host cell. In some embodiments, an endogenous nucleic acid is identical to a wild-type nucleic acid that is found in the host cell in nature. In some embodiments, one or more copies of endogenous nucleic acids are introduced into a host cell.

A nucleic acid or protein of the invention may be in isolated or purified form. As used herein, "isolated," with respect to nucleic acid or protein, means separated from other components, such as, but not limited to a cell or cell culture. It is preferably in a homogeneous state although it can be in either a dry or aqueous solution. Purity and homogeneity are typically determined using analytical chemistry techniques, such as polyacrylamide gel electrophoresis or high performance liquid chromatography. A protein or nucleic acid that is the predominant species present in a preparation is substantially purified. The term "purified" denotes that a nucleic acid or protein gives rise to essentially one band in an electrophoretic gel. Particularly, "purified" means that when isolated, the isolate contains at least 90%, at least 95%, at least 98%, or more preferably at least 99% of nucleic acid or protein by weight of the isolate. Purified polypeptides may be obtained by a number of methods including, for example, laboratory synthesis, chromatography, preparative electrophoresis, gel electrophoresis, centrifugation, precipitation, affinity purification, etc. (see, generally, R Scopes, Protein Purification, Springer-Verlag, N.Y. (1982), Deutscher, Methods in Enzymology Vol. 182: Guide to Protein Purification, Academic Press, Inc. N.Y. (1990)).

As used herein, an "expression control sequence" means a nucleic acid sequence that directs transcription of a nucleic acid of interest. An expression control sequence can be a promoter, such as a constitutive or an inducible promoter, or an enhancer. An expression control sequence can be "native" or heterologous. A native expression control sequence is derived from the same organism, species, or strain as the gene being expressed. A heterologous expression control sequence is derived from a different organism, species, or strain as the gene being expressed. An "inducible promoter" is a promoter that is active under environmental or developmental regulation.

By "operably linked" is meant a functional linkage between a nucleic acid expression control sequence (such as a promoter) and a second nucleic acid sequence, wherein the expression control sequence directs transcription of the nucleic acid corresponding to the second sequence.

The term "isoprene" refers to 2-methyl-1,3-butadiene (CAS#78-79-5). It can be the direct and final volatile C5 hydrocarbon product from the elimination of pyrophosphate from 3,3-dimethylallyl diphosphate DMAPP. It may not involve the linking or polymerization of IPP molecules to DMAPP molecules. The term "isoprene" is not generally intended to be limited to its method of production unless indicated otherwise herein.

As used herein, the terms "isoprene synthase," "isoprene synthase variant", and "IspS," refer to enzymes that catalyze the elimination of pyrophosphate from diemethylallyl diphosphate (DMAPP) to form isoprene. An "isoprene synthase" may be a wild type sequence or an isoprene synthase variant.

As used herein, the term "naturally-occurring" refers to anything (e.g., proteins, amino acids, or nucleic acid sequences) that is found in nature (e.g., has not been manipulated by means of recombinant or chemical methods). As used herein, the term "non-naturally occurring" refers to anything that is not found in nature (e.g., recombinantly produced or chemically synthesized proteins, amino acids, or nucleic acid sequences produced in the laboratory).

As used herein, an amino acid residue of an amino acid sequence of interest that "corresponds to" or is "corresponding to" or in "correspondence with" an amino acid residue of a reference amino acid sequence indicates that the amino acid residue of the sequence of interest is at a location homologous or equivalent to an enumerated residue in the reference amino acid sequence. One skilled in the art can determine whether a particular amino acid residue position in a polypeptide corresponds to that of a homologous reference sequence. For example, the sequence of an isoprene synthase polypeptide may be aligned with that of a reference sequence (e.g. SEQ ID NO: 1 using known techniques (e.g., basic local alignment search tool (BLAST), ClustalW2, Structure based sequences alignment program (STRAP), or the like). In addition, crystal structure coordinates of a reference sequence may be used as an aid in determining a homologous polypeptide residue's three dimensional structure (see, for example, PCT/US2010/032134). In another aspect, equivalent residues may be identified by determining homology at the level of tertiary structure. Using such methods, the amino acid residues of an isoprene synthase polypeptide or isoprene synthase variant may be numbered according to the corresponding amino acid residue position numbering of the reference sequence. For example, the amino acid sequence of SEQ ID NO: 1 may be used for determining amino acid residue position numbering of each amino acid residue of an isoprene synthase of interest.

As used herein, "homology" refers to sequence similarity or identity, with identity being preferred. Homology may be determined using standard techniques known in the art (see, e.g., Smith and Waterman, Adv. Appl. Math. 2:482 (1981); Needleman and Wunsch, J. Mol. Biol. 48:443 (1970); Pearson and Lipman, Proc. Natl. Acad. Sci. USA 85:2444 (1988); software programs such as GAP, BESTFIT, FASTA, and TFASTA in the Wisconsin Genetics Software Package (Genetics Computer Group, Madison, Wis.); and Devereux et al., Nucl. Acid Res. 12:387-395 (1984)). One example of a useful algorithm is PILEUP. PILEUP creates a multiple sequence alignment from a group of related sequences using progressive, pair-wise alignments. It can also plot a tree showing the clustering relationships used to create the alignment. PILEUP uses a simplification of the progressive alignment method of Feng and Doolittle (see Feng and Doolittle, J. Mol. Evol. 35:351-360 (1987)). The method is similar to that described by Higgins and Sharp (see Higgins and Sharp, CABIOS 5:151-153 (1989)). Useful PILEUP parameters including a default gap weight of 3.00, a default gap length weight of 0.10, and weighted end gaps. Another example of a useful algorithm is the BLAST algorithm, described by Altschul et al., (see Altschul et al., J. Mol. Biol. 215:403-410 (1990); and Karlin and Altschul, Proc. Natl. Acad. Sci. USA 90:5873-5787 (1993)). A particularly useful BLAST program is the WU-BLAST-2 program (see Altschul et al., Meth. Enzymol. 266:460-480 (1996)). WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched. However, the values may be adjusted to increase sensitivity.

The percent sequence identity between a reference sequence and a test sequence of interest may be readily determined by one skilled in the art. The percent identity shared by polynucleotide or polypeptide sequences is determined by direct comparison of the sequence information between the molecules by aligning the sequences and determining the identity by methods known in the art. An example of an algorithm that is suitable for determining sequence similarity is the BLAST algorithm, (see Altschul, et al., J. Mol. Biol., 215:403-410 (1990)). Software for performing BLAST analyses is publicly available through the National Center for Biotechnology Information. This algorithm involves first identifying high scoring sequence pairs (HSPs) by identifying short words of length W in the query sequence that either match or satisfy some positive-valued threshold score T when aligned with a word of the same length in a database sequence. These initial neighborhood word hits act as starting points to find longer HSPs containing them. The word hits are expanded in both directions along each of the two sequences being compared for as far as the cumulative alignment score can be increased. Extension of the word hits is stopped when: the cumulative alignment score falls off by the quantity X from a maximum achieved value; the cumulative score goes to zero or below; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff and Henikoff, Proc. Natl. Acad. Sci. USA 89:10915 (1992)) alignments (B) of 50, expectation (E) of 10, M'S, N'-4, and a comparison of both strands.

The BLAST algorithm then performs a statistical analysis of the similarity between two sequences (see, e.g., Karlin and Altschul, supra). One measure of similarity provided by the BLAST algorithm is the smallest sum probability (P(N)), which provides an indication of the probability by which a match between two nucleotide or amino acid sequences would occur by chance. For example, a nucleic acid is considered similar to a isoprene synthase nucleic acid of this invention if the smallest sum probability in a comparison of the test nucleic acid to a isoprene synthase nucleic acid is less than about 0.1, more preferably less than about 0.01, and most preferably less than about 0.001. Where the test nucleic acid encodes an isoprene synthase polypeptide, it is considered similar to a specified isoprene synthase nucleic acid if the comparison results in a smallest sum probability of less than about 0.5, and more preferably less than about 0.2.

Percent "identical" or "identity" in the context of two or more nucleic acid or polypeptide sequences refers to two or more sequences that are the same or have a specified percentage of nucleic acid residues or amino acid residues, respectively, that are the same, when compared and aligned for maximum similarity, as determined using a sequence comparison algorithm or by visual inspection. "Percent sequence identity" or "% identity" or "% sequence identity or "% amino acid sequence identity" of a subject amino acid sequence to a reference amino acid sequence means that the subject amino acid sequence is identical (i.e., on an amino acid-by-amino acid basis) by a specified percentage to the reference amino acid sequence over a comparison length when the sequences are optimally aligned. Thus, 80% amino acid sequence identity or 80% identity with respect to two amino acid sequences means that 80% of the amino acid residues in two optimally aligned amino acid sequences are identical.

"Percent sequence identity" or "% identity" or "% sequence identity" of a subject nucleic acid sequence to a reference nucleic acid sequence means that the subject nucleic acid sequence is identical (i.e., on a nucleotide-by-nucleotide basis for a polynucleotide sequence) by a specified percentage to the reference sequence over a comparison length when the sequences are optimally aligned. Thus, 80% nucleotide sequence identity or 80% identity with respect to two nucleic acid sequences means that 80% of the nucleotide residues in two optimally aligned nucleic acid sequences are identical.

The "percent sequence identity" or "% sequence identity" or "% identity" of a subject sequence to a reference sequence can be calculated by optimally aligning the two sequences and comparing the two optimally aligned sequences over the comparison length. The number of positions in the optimal alignment at which identical residues occur in both sequences is determined, thereby providing the number of matched positions, and the number of matched positions is then divided by the total number of positions of the comparison length (which, unless otherwise specified, is the length of the reference sequence). The resulting number is multiplied by 100 to yield the percent sequence identity of the subject sequence to the reference sequence.

"Optimal alignment" or "optimally aligned" refers to the alignment of two (or more) sequences giving the highest percent identity score. For example, optimal alignment of two polypeptide sequences can be achieved by manually aligning the sequences such that the maximum number of identical amino acid residues in each sequence are aligned together or by using software programs or procedures described herein or known in the art. Optimal alignment of two nucleic acid sequences can be achieved by manually aligning the sequences such that the maximum number of identical nucleotide residues in each sequence are aligned together or by using software programs or procedures described herein or known in the art.

Two sequences (e.g., polypeptide sequences) may be deemed "optimally aligned" when they are aligned using defined parameters, such as a defined amino acid substitution matrix, gap existence penalty (also termed gap open penalty), and gap extension penalty, so as to achieve the highest similarity score possible for that pair of sequences. The BLOSUM62 scoring matrix (see Henikoff and Henikoff, supra) is often used as a default scoring substitution matrix in polypeptide sequence alignment algorithms (e.g., BLASTP). The gap existence penalty is imposed for the introduction of a single amino acid gap in one of the aligned sequences, and the gap extension penalty is imposed for each residue position in the gap. Exemplary alignment parameters employed are: BLOSUM62 scoring matrix, gap existence penalty=11, and gap extension penalty=1. The alignment score is defined by the amino acid positions of each sequence at which the alignment begins and ends (e.g., the alignment window), and optionally by the insertion of a gap or multiple gaps into one or both sequences, so as to achieve the highest possible similarity score.

Optimal alignment between two or more sequences can be determined manually by visual inspection or by using a computer, such as, but not limited to e.g., the BLASTP program for amino acid sequences and the BLASTN program for nucleic acid sequences (see, e.g., Altschul et al., Nucleic Acids Res. 25(17):3389-3402 (1997); see also the National Center for Biotechnology Information (NCBI) website) or CLUSTALW program.

The term "identical" in the context of two nucleic acids or polypeptide sequences refers to the residues in the two sequences that are the same when aligned for maximum correspondence, as measured using one of the following sequence comparison or analysis algorithms.

A polypeptide of interest may be said to be "substantially identical" to a reference polypeptide if the polypeptide of interest comprises an amino acid sequence having at least about 40%, at least about 50%, at least about 60%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 99.5% sequence identity to the amino acid sequence of the reference polypeptide. The percent identity between two such polypeptides can be determined manually by inspection of the two optimally aligned polypeptide sequences or by using software programs or algorithms (e.g., BLAST, ALIGN, CLUSTAL) using standard parameters. One indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, e.g., where the two peptides differ only by a conservative amino acid substitution or one or more conservative amino acid substitutions.

A nucleic acid of interest may be said to be "substantially identical" to a reference nucleic acid if the nucleic acid of interest comprises a nucleotide sequence having at least about 40%, at least about 50%, at least about 60%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 99.5% sequence identity to the nucleotide sequence of the reference nucleic acid. The percent identity between two such nucleic acids can be determined manually by inspection of the two optimally aligned nucleic acid sequences or by using software programs or algorithms (e.g., BLAST, ALIGN, CLUSTAL) using standard parameters. One indication that two nucleic acid sequences are substantially identical is that the two nucleic acid molecules hybridize to each other under stringent conditions (e.g., within a range of medium to high stringency).

As used herein, the term "mass yield" refers to the mass of the product produced by the recombinant (e.g., bacterial) cells divided by the mass of the glucose consumed by the recombinant cells multiplied by 100, or expressed as a percentage.

By "specific productivity," it is meant the mass of the product produced by the recombinant (bacterial) cell divided by the product of the time for production, the cell density, and the volume of the culture.

By "titer," it is meant the mass of the product produced by the recombinant (e.g., bacterial) cells divided by the volume of the culture.

As used herein, the term "cell productivity index (CPI)" refers to the mass of the product produced by the recombinant (e.g., bacterial) cells divided by the mass of the recombinant cells produced in the culture.

As used herein, the singular terms "a," "an," and "the" include the plural reference unless the context clearly indicates otherwise.

Unless otherwise indicated, nucleic acids are written left to right in 5' to 3' orientation; amino acid sequences are written left to right in amino to carboxy orientation, respectively.

Reference to "about" a value or parameter herein also includes (and describes) embodiments that are directed to that value or parameter per se.

It is understood that all aspects and embodiments of the invention described herein include "comprising," "consisting," and "consisting essentially of" aspects and embodiments. It is to be understood that methods or compositions "consisting essentially of" the recited elements include only the specified steps or materials and those that do not materially affect the basic and novel characteristics of those methods and compositions.

Unless defined otherwise herein, all technical and scientific terms used herein have the same meaning as commonly understood by one of ordinary skill in the art to which this invention pertains.

It is to be understood that this invention is not limited to the particular methodology, protocols, and reagents described, as these may vary, depending upon the context they are used by those of skill in the art.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

III. Isoprene Synthase Sequences

Polypeptides can be identified as isoprene synthases by sequence alignment to a reference sequence, as well as by other characteristics (e.g., isoprene synthase activity). In some embodiments, the reference sequence is a plant isoprene synthase sequence. In some embodiments, the reference sequence is MEA *P. alba* isoprene synthase comprising the amino acid sequence of SEQ ID NO: 1. In some embodiments, the reference sequence is MEA *P. alba* synthase encoded by a nucleic acid sequence comprising the sequence of SEQ ID NO: 2. In some embodiments, the reference sequence is *P. montana* (kudzu) isoprene synthase comprising the amino acid sequence of SEQ ID NO: 15. In some embodiments, the reference sequence is *P. montana* (kudzu) synthase encoded by a nucleic acid sequence comprising the sequence of SEQ ID NO: 16. In any aspects of the invention, sequence alignment to a reference sequence can be based on sequence alignment with mature polypeptide sequences, wherein said mature polypeptides are defined as having undergone and completed processing of immature signal sequence(s). In any aspects of the invention, sequence alignment to a reference sequence can be based on sequence alignment with the C-terminal region of the reference sequence, wherein the C-terminal region contains a catalytically active site. In aspects of the invention, sequence alignment of polypeptide sequences to a reference sequence will result in the identification of a consensus sequence, wherein said consensus sequence determines that the polypeptide has isoprene synthase activity. In one embodiment, the consensus sequence is shown in FIG. 2A-F. In some embodiments, the reference sequence is a plant isoprene synthase sequence. In some embodiments, the reference sequence is MEA *P. alba* isoprene synthase comprising the amino acid sequence of SEQ ID NO: 1. In some embodiments, the reference sequence is *P. montana* (kudzu) isoprene synthase comprising the amino acid sequence of SEQ ID NO: 15. In any aspects of the invention, identification of a polypeptide with isoprene synthase activity includes, but is not limited to, said polypeptide having one or more amino acid residue(s) corresponding to one or more consensus poplar isoprene synthase amino acid residue(s). In some embodiments, the poplar isoprene synthase comprises the amino acid sequence of SEQ ID NO: 1. In some embodiments, the one or more consensus poplar isoprene synthase residue(s) are selected from the group consisting of F287, G397, N438, E451, and Y514. In some aspects of the invention, consensus sequence refers to an archetypical amino acid sequence against which all candidate isoprene synthase sequences and sequence of interest are compared. In other aspects of the invention, consensus sequences refers to a sequence that sets forth the nucleotides that are most often present in a DNA sequence of interest. For each position of a gene, the consensus sequence gives the amino acid that is most abundant in that position in the multiple sequence alignment. In some aspects of the invention, multiple sequence alignment refers to the sequences of multiple homologs of a reference sequence that are aligned using an algorithm (e.g., Clustal W). In some embodiments, the reference sequence is a plant isoprene synthase sequence. In some embodiments, the reference sequence is MEA *P. alba* synthase comprising the amino acid sequence of SEQ ID NO: 1. In some embodiments, the reference sequence is MEA *P. alba* synthase encoded by a nucleic acid sequence comprising the sequence of SEQ ID NO: 2. In some embodiments, the reference sequence is *P. montana* (kudzu) comprising the amino acid sequence of SEQ ID NO: 15. In some embodiments, the reference sequence is *P. montana* (kudzu) synthase encoded by a nucleic acid sequence comprising the sequence of SEQ ID NO: 16.

In some aspects of the invention, an isolated polypeptide from a legume having isoprene synthase comprises at least 40% sequence identity to SEQ ID NO: 1, wherein the legume isoprene synthase has one or more amino acid residue(s) corresponding to one or more amino acid residue(s) corresponding to SEQ ID NO: 1, wherein the one or more amino acid residue(s) are selected from the group consisting of F287, G397, N438, E451, and Y514. In some embodiments, the legume isoprene synthase is not from *P. montana*.

In any aspects of the invention, the polypeptide having isoprene activity is an isoprene synthase polypeptide. In some embodiments, the isoprene synthase polypeptide is from the family Leguminosae, the family Fagaceae, the family Rutaceae, the family Lauraceae, the family Vitaceae, or the family Myrtaceae. In some embodiments, the isoprene synthase polypeptide or nucleic acid is a naturally-occurring polypeptide or nucleic acid from a legume including, but not limited to, peanut (such *Arachis hypogaea*), velvet bean (such as *Mucuna pruriens*), pigeon pea (such as *Cajanus cajans*), soybean (such as *Glycine max*), wild legume (such as *Lotus japonicus*), or clover-like plant (such as *Medicago truncatula*). In some embodiments, the isoprene synthase polypeptide or nucleic acid is a naturally-occurring polypeptide or nucleic acid from a citrus including, but not limited to, lemon (such *Citrus limon*). In some embodiments, the isoprene synthase polypeptide or nucleic acid is a naturally-occurring polypeptide or nucleic acid from *Cinnamomum tenuipile*. In some embodiments, the isoprene synthase polypeptide or nucleic acid is a naturally-occurring polypeptide or nucleic acid from a grape including, but not limited to, wine grape (such as *Vitis vinifera*). In some embodiments, the isoprene synthase polypeptide or nucleic acid is a naturally-occurring polypeptide or nucleic acid from an oak such as *Querus petraea* or *Querus ilex*. In some embodiments, the isoprene synthase polypeptide or nucleic acid is a naturally-occurring polypeptide or nucleic acid from *Eucalyptus globulus* or *Melaleuca alternifolia*. In some embodiments, the isoprene synthase polypeptide or nucleic acid is not from *P. montana*. Isoprene synthases of the present invention include, but are not limited to, those identified by JGI Accession Nos. Glyma09g21900.1, Glyma20g18280.1, Glyma06g45780.1, and Glyma12g10990.1. Isoprene synthases of the present invention include, but are not limited to, those identified by a FGENESH predicted polypeptide encoded from a *G. max* genomic sequence, such as the polypeptide identified by Glyma20g18280__1_FG. In any aspects of the invention, an isolated polypeptide from a legume having isoprene synthase activity has at least about 40%, at least about 50%, at least about 60%, at least about 70%, at least about 80%, at least about 90%, at least about 92%, at least about 94%, at least about 96%, at least about 98%, at least about 99% sequence identity with *A. hypogaea* isoprene synthase comprising the amino acid sequence of SEQ ID NO: 3. In any aspects of the invention, an isolated polypeptide from a legume having isoprene synthase activity has at least about 40%, at least about 50%, at least about 60%, at least about 70%, at least about 80%, at least about 90%, at least about 92%, at least about 94%, at least about 96%, at least about 98%, at least about 99% sequence identity with *A. hypogaea* isoprene synthase encoded by a nucleic acid sequence comprising the sequence of SEQ ID NO: 4.

In any aspects of the invention, the isoprene synthase polypeptide has at least about 40%, at least about 50%, at least about 60%, at least about 70%, at least about 80%, at least about 90%, at least about 92%, at least about 94%, at least about 96%, at least about 98%, at least about 99% sequence identity with MEA *P. alba* synthase comprising the amino acid sequence of SEQ ID NO: 1. In other embodiments, the isoprene synthase polypeptide has at least about 40%, at least about 50%, at least about 60%, at least about 70%, at least about 80%, at least about 90%, at least about 92%, at least about 94%, at least about 96%, at least about 98%, at least about 99% sequence identity with MEA *P. alba* synthase encoded by a nucleic acid sequence comprising the sequence of SEQ ID NO: 2. In any aspects of the invention, the isoprene synthase polypeptide has at least about 40%, at least about 50%, at least about 60%, at least about 70%, at least about 80%, at least about 90%, at least about 92%, at least about 94%, at least about 96%, at least about 98%, at least about 99% sequence identity with *P. montana* (kudzu) comprising the amino acid sequence of SEQ ID NO: 15. In other embodiments, the isoprene synthase polypeptide has at least about 40%, at least about 50%, at least about 60%, at least about 70%, at least about 80%, at least about 90%, at least about 92%, at least about 94%, at least about 96%, at least about 98%, at least about 99% sequence identity with *P. montana* (kudzu) synthase encoded by a nucleic acid sequence comprising the sequence of SEQ ID NO: 16.

Isoprene synthase variants may be generated from an isoprene synthase of the present invention, wherein the isoprene synthase may be an isoprene synthase as described herein, including wild type and non-wild type isoprene synthases. In some embodiments, the isoprene synthase is a legume isoprene synthase. Exemplary isoprene synthase nucleic acids include nucleic acids that encode a polypeptide, fragment of a polypeptide, peptide, or fusion polypeptide that has at least one activity of an isoprene synthase polypeptide. Exemplary isoprene synthase polypeptides and nucleic acids include naturally-occurring polypeptides and nucleic acids from any of the source organisms described herein as well as variant polypeptides and nucleic acids derived from any of the source organisms described herein. In some embodiments, the isoprene synthase variants have one or more amino acid substitution(s) at one or more amino acid residues corresponding to one or more amino acid residue(s) corresponding to SEQ ID NO:1, wherein said one or more amino acid residue(s) corresponding to SEQ ID NO: 1 are selected from the group consisting of T481, K463, K393, L376, K161, S288, T240, E472, G389, and R242. In some embodiments, the amino acid substitution is S288C.

Several methods are known in the art that are suitable for generating variants of the isoprene synthases of the present invention, including but not limited to site-saturation mutagenesis, scanning mutagenesis, insertional mutagenesis, random mutagenesis, site-directed mutagenesis, and directed-evolution, as well as various other recombinatorial approaches.

IV. Isoprene Synthase Properties

In any aspects of the invention described herein, the polypeptide having isoprene synthase activity has at least one improved property over a reference sequence. In some embodiments, the reference sequence is a plant isoprene synthase sequence. In some embodiments, the reference sequence is MEA *P. alba* synthase comprising the amino acid sequence of SEQ ID NO: 1. In some embodiments, the reference sequence is MEA *P. alba* synthase encoded by a nucleic acid sequence comprising the sequence of SEQ ID NO: 2. In some embodiments, the reference sequence is *P. montana* (kudzu) comprising the amino acid sequence of SEQ ID NO: 15. In some embodiments, the reference sequence is *P. montana* (kudzu) synthase encoded by a nucleic acid sequence comprising the sequence of SEQ ID NO: 16. In some preferred embodiments, at least one improved property is selected from but not limited to the group consisting of: specific productivity, yield, cellular performance index and protein expression. In some particularly preferred embodiments, at least one improved property is selected from but not limited to the group consisting of: specific activity, $K_{cat}$, $K_i$, and $K_m$. In some embodiments, the polypeptide has a $K_{cat}$ value of at least about 1.3. In some embodiments, the polypeptide has a $K_m$ value of at least about 2.5. In some embodiments, the polypeptide has a $K_{iDMAPP}$ value of at least about 13.0.

Properties of interest include, but are not limited to: increased intracellular activity, specific productivity, yield, and cellular performance index. In some embodiments, specific productivity increase at least about 2, 3, 4, 5, 6 7, 8, 9, 10 times or more. In one embodiment, specific productivity is about 20 mg/L/OD/hr. In other embodiments, yield increase at least about 2, 3, 4, 5 times or more. In other embodiments, cell performance index increase at least about 2, 3, 4, 5 times or more. In other embodiments, intracellular activity increase at least about 2, 3, 4, 5, 6, 7, 8, 9, 10 times or more.

Without being bound by theory, these properties can be achieved by one or a combination of any of the following properties of IspS of the present invention: increased cellular viability, increased $k_{cat}$, decreased $K_m$, increased $K_m$, increased $K_i$, increased specific productivity, increased specific activity, increased solubility, decreased insolubility, improved ribosome binding, increased translation initiation rate, increased translation elongation rate, increased transcription initiation rate, increased transcription elongation rate, decreased secondary structure of DNA, decreased secondary structure of RNA, increased secondary structure of DNA, increased secondary structure of RNA, increased folding rates, increased affinity for intracellular chaperones, increased stability, decreased protein turnover, increased protein expression levels, decreased exposure to intracellular protease, decreased affinity for intracellular protease, decreased localization to the periplasm, improved localization to the cytoplasm, decreased inclusion body formation, decreased membrane localization, increased expression due to a more favorable codon, increased DNA stability, increased RNA stability, and decreased RNA degradation. Any mutation that has a positive effect on the properties of nucleic acid sequences (DNA and RNA) encoding or expressing the IspS, or the biochemical properties of the IspS enzyme itself, could allow for greater activity within the cell. Other properties of interest include pH optima, temperature stability (e.g., $T_m$ value), as well as sensitivity to potential inhibitors including substrate or product inhibition. Oxidative and proteolytic stability are also of interest. Furthermore, activation or inhibition due to metal ion effects and ionic strength is of interest.

Growth index or performance index of a host cell comprising a nucleic acid encoding an isoprene synthase of the present invention may also be used to indicate whether a particular isoprene synthase has a property of interest. Growth index and performance index may be determined according to methods known to one of skill in the art and/or as taught herein. Growth and performance index may be determined for a particular isoprene synthase by comparison with a reference sequence. In some embodiments, the reference sequence is a plant isoprene synthase sequence. In some embodiments, the reference sequence is MEA *P. alba* synthase comprising the amino acid sequence of SEQ ID NO: 1. In some embodiments, the reference sequence is MEA *P. alba* synthase encoded by a nucleic acid sequence comprising the sequence of SEQ ID NO: 2. In some embodiments, the reference sequence is *P. montana* (kudzu) comprising the amino acid sequence of SEQ ID NO: 15. In some embodiments, the reference sequence is *P. montana* (kudzu) synthase encoded by a nucleic acid sequence comprising the sequence of SEQ ID NO: 16. In various embodiments, the growth index of the isoprene synthase is at least about 0.8, at least about 0.9, at least about 1.0, at least about 1.1, at least about 1.2, at least about 1.3, as compared with the reference sequence. In various embodiments, the performance index of the isoprene synthase is at least about 0.7, at least about 0.8, at least about 0.9, at least about 1.0, at least about 1.1, at least about 1.2, as compared with the reference sequence.

Methods for determining the properties of interest are known tone of skill in the art. Certain methods are further described herein in the Examples. Polypeptides having isoprene synthase activity can be assessed based on the desired outcome or property to be improved. For example, an isoprene synthase can be tested for the conversion of DMAPP to isoprene in vitro with purified or partially purified isoprene synthase or in vivo in the context of a host organism such as *E. coli*. In some cases, the *E. coli* may also express the DXP pathway, the MVA pathway, or both. Improved activity is assessed in comparison with other isoprene synthases; for example, a *P. alba* isoprene synthase, a *P. alba* variant isoprene synthase, or other reference polypeptide. It is contemplated that enzymes having various degrees of e.g. stability, solubility, activity, and/or expression level in one or more of test conditions will find use in the present invention for the production of isoprene in a diversity of hosts. High throughput methods may provide an investigation of these properties in an economical manner.

There is a strong correlation between increased intracellular DMAPP levels and growth inhibition of *E. coli*, which can be alleviated by the expression of *P. alba* isoprene synthase (IspS). Without being bound by theory, increased levels of IspS activity should therefore allow for better growth due to more rapid conversion of DMAPP to isoprene. By monitoring the growth rates of *E. coli* expressing polypeptides of interest under these conditions, the inventors have identified IspS enzymes that display increased ability to convert DMAPP to isoprene within the cell. In some embodiments, the IspS is a legume IspS. In some embodiments, the IspS is *A. hypogaea* IspS. In other embodiments, the IspS is *M. pruriens* IspS.

The invention also contemplates methods for screening polypeptides for isoprene synthase activity, comprising: (a) contacting a host cell with a medium comprising about 10 µM to about 70 µM IPTG, and about 5 mM to about 20 mM mevalonic acid (MVA), wherein the host cell comprises a nucleic acid encoding a polypeptide of interest in operable combination with a promoter; and (b) measuring the growth rate of the host cell. The isoprene synthase growth rate may be compared to that of a reference isoprene synthase (e.g. *P. alba* WT isoprene synthase, MEA *P. alba* isoprene synthase, *P. alba* variant, or *P. montana*). The methods may be used to screen for polypeptides having isoprene synthase activity for a particular property of interest, for example, one or more of the properties described herein. In some embodiments, an increased growth rate indicates an isoprene synthase with an increased ability to convert DMAPP to isoprene within the host cell synthase. Growth rates may be analyzed, for example, according to methods known in the art, or as exemplified in the Examples below. In some embodiments, the method further comprises determining a growth index for the isoprene synthase. In some embodiments, the method further comprises determining a performance index for the isoprene synthase. Growth rate of the cells in exponential phase and/or final density of the cells may be taken into consideration as factors when selecting isoprene synthases with improved properties.

In some embodiments, the IPTG is present in the medium at a concentration from about 10 µM to about 60 µM. In some embodiments, the IPTG is present in the medium at a concentration from about 20 µM to about 60 µM. In some embodiments, the IPTG is present in the medium at a concentration from about 40 µM to about 60 µM. In some embodiments, the IPTG is present in the medium at a concentration of about 50 µM. In some embodiments, the MVA is present in the medium at a concentration of about 5 mM to about 75 mM. In some embodiments, the MVA is present in the medium at a concentration of about 10 mM to about 60 mM. In some embodiments, the MVA is present in the medium at a concentration of about 15 mM to about 45 mM. In some embodiments, the MVA is present in the medium at a concentration of about 5 mM to about 30 mM. In some embodiments, the MVA is present in the medium at a concentration of about 5 mM to about 15 mM. In some embodiments, the MVA is present in the medium at a concentration of about 15 mM.

V. Legume Isoprene Synthase for the Production of Isoprene

The invention features compositions and methods for the production of increased amounts of isoprene. In particular, these compositions and methods may increase the rate of isoprene production and the total amount of isoprene that is produced. The biosynthetic processes for isoprene production described herein are a desirable alternative to using natural rubber. As discussed further below, the amount of isoprene produced by cells can be greatly increased by introducing a heterologous nucleic acid encoding a isoprene synthase (IspS) of the present invention into the cells. In some embodiments, the isoprene synthase is a legume isoprene synthase.

A. Recombinant Cells for the Production of Isoprene

Isoprene (2-methyl-1,3-butadiene) is an important organic compound used in a wide array of applications. For instance, isoprene is employed as an intermediate or a starting material in the synthesis of numerous chemical compositions and polymers, including in the production of synthetic rubber. Isoprene is also an important biological material that is synthesized naturally by many plants and animals.

Isoprene is produced from DMAPP by the enzymatic action of isoprene synthase. Therefore, without being bound to theory, it is thought that increasing the cellular production of isopentenyl pyrophosphate from mevalonate via the alternative lower MVA pathway in recombinant cells by any of the compositions and methods described above will likewise result in the production of higher amounts of isoprene. Increasing the molar yield of isopentenyl pyrophosphate production from glucose translates into higher molar yields of isoprene produced from glucose when combined with appropriate enzymatic activity levels of mevalonate kinase, phosphomevalonate decarboxylase, isopentenyl kinase, and other appropriate enzymes for isoprene production.

In some aspects, any of the cells used for the production of isoprene can express one or more heterologous nucleic acids encoding one or more polypeptides which increase the cellular production of isoprene. In other aspects, the cells can also harbor specific genomic mutations which either enhance the production of isoprene or which increase carbon availability through the metabolic pathways responsible for the production of isoprene (such as the MVA pathway).

As described herein, the present invention provides recombinant cells capable of producing of isoprene, wherein the cells comprise one or more nucleic acids encoding one or more polypeptides of the MVA pathway, and a heterologous nucleic acid encoding an isoprene synthase polypeptide, wherein culturing the cells in a suitable media provides for the production of isoprene. In a further embodiment, the recombinant cells further comprise one or more nucleic acids encoding an isopentenyl diphosphate isomerase (IDI) polypeptide. In certain embodiments, the present invention provides recombinant cells capable of isoprene production, wherein the cells comprise one or more nucleic acids encoding one or more polypeptides of the MVA pathway, and a heterologous nucleic acid encoding an isoprene synthase polypeptide, wherein the cells produce increased amounts of isoprene compared to isoprene-producing cells that do not comprise a nucleic acid encoding a polypeptide having phosphomevalonate decarboxylase activity and/or a nucleic acid encoding a polypeptide having isopentenyl kinase activity. In a further embodiment, the recombinant cells further comprise one or more nucleic acids encoding an isopentenyl diphosphate isomerase (IDI) polypeptide.

Production of isoprene can also be made by using any of the recombinant host cells described herein further comprising one or more of the enzymatic pathways manipulations wherein enzyme activity is modulated to increase carbon flow towards mevalonate production. The recombinant cells described herein that have various enzymatic pathways manipulated for increased carbon flow to mevalonate production can be used to produce isoprene. In one embodiment, the recombinant cells further comprise a nucleic acid encoding a phosphoketolase. In another embodiment, the recombinant cells can be further engineered to increase the activity of one or more of the following genes selected from the group consisting of ribose-5-phosphate isomerase (rpiA and/or rpiB), D-ribulose-5-phosphate 3-epimerase (rpe), transketolase (tktA and/or tktB), transaldolase B (tal B), phosphate acetyltransferase (pta and/or eutD). In another embodiment, these recombinant cells can be further engineered to decrease the activity of one or more genes of the following genes including glucose-6-phosphate dehydrogenase (zwf), 6-phosphofructokinase-1 (pfkA and/or pfkB), fructose bisphosphate aldolase (fba, fbaA, fbaB, and/or fbaC), glyceraldehyde-3-phosphate dehydrogenase (gapA and/or gapB), acetate kinase (ackA), citrate synthase (gltA), EI (ptsI), EIICB$^{Glc}$ (ptsG), EIIA$^{Glc}$ (crr), and/or HPr (ptsH).

1. Isoprene Synthase Nucleic Acids and Polypeptides

In some aspects of the invention, the recombinant cells described in any of the compositions or methods described herein express one or more nucleic acids encoding an isoprene synthase polypeptide or a polypeptide having isoprene synthase activity. In some aspects of the invention, the cells described in any of the compositions or methods described herein (including host cells that have been modified as described herein) further comprise one or more nucleic acids encoding an isoprene synthase polypeptide or a polypeptide having isoprene synthase activity. The nucleic acids and/or polypeptides can be either endogenous or heterologous. In some aspects, the isoprene synthase polypeptide is an endogenous polypeptide. In some aspects, the endogenous nucleic acid encoding an isoprene synthase polypeptide is operably linked to a constitutive promoter. In some aspects, the endogenous nucleic acid encoding an isoprene synthase polypeptide is operably linked to an inducible promoter. In some aspects, the endogenous nucleic acid encoding an isoprene synthase polypeptide is operably linked to a strong promoter. In some aspects, more than one endogenous nucleic acid encoding an isoprene synthase polypeptide is used (e.g, 2, 3, 4, or more copies of an endogenous nucleic acid encoding an isoprene synthase polypeptide).

In some aspects, the isoprene synthase polypeptide is a heterologous polypeptide. In some aspects, the cells comprise more than one copy of a heterologous nucleic acid encoding an isoprene synthase polypeptide. In some aspects, the heterologous nucleic acid encoding an isoprene synthase polypeptide is operably linked to a constitutive promoter. In some aspects, the heterologous nucleic acid encoding an isoprene synthase polypeptide is operably linked to an inducible promoter. In some aspects, the heterologous nucleic acid encoding an isoprene synthase polypeptide is operably linked to a strong promoter. In some aspects, the heterologous nucleic acid encoding an isoprene synthase polypeptide is operably linked to a weak promoter. In some aspects, the isoprene synthase polypeptide is a polypeptide or variant thereof from *Pueraria* or *Populus* or a hybrid such as *Populus alba×Populus tremula*. In some aspects, the isoprene synthase polypeptide is a polypeptide or variant thereof from *Pueraria montana* or *Pueraria lobata, Populus tremuloides, Populus alba, Populus nigra*, and *Populus trichocarpa*. In some aspects, the isoprene synthase polypeptide is from *Eucalyptus*.

The nucleic acids encoding an isoprene synthase polypeptide(s) can be integrated into a genome of the host cells or can be stably expressed in the cells. The nucleic acids encoding an isoprene synthase polypeptide(s) can additionally be on a vector.

In a particular aspect, the cells are engineered to overexpress the endogenous isoprene synthase pathway polypeptide relative to wild-type cells. In some aspects, the endogenous nucleic acid encoding an isoprene synthase polypeptide is operably linked to a weak promoter.

In some aspects, the isoprene synthase polypeptide is a polypeptide from the family Leguminosae, the family Fagaceae, the family Rutaceae, the family Lauraceae, the family Vitaceae, or the family Myrtaceae. In some embodiments, the isoprene synthase polypeptide is from a legume. In some embodiments, the legume isoprene synthase is *Arachis hypogaea* (SEQ ID: NO 3), *Glycine max* 1 (SEQ ID NO: 5), *Glycine max* 2 (SEQ ID NO: 7), *M. pruriens* (SEQ ID NO: 9), *C. cajans* (SEQ ID NO: 11), *Lotus japonicas* (SEQ ID NO: 33), or *Medicago truncatula* (SEQ ID NO: 35). In some embodiments, the isoprene synthase polypeptide is from a citrus including, but not limited to, *Citrus limon* (SEQ ID NO: 17). In some embodiments, the isoprene synthase polypeptide is from *Cinnamomum tenuipile* (SEQ ID NO: 23). In some embodiments, the isoprene synthase polypeptide is from a grape including, but not limited to, *Vitis vinifera* (SEQ ID NO: 21). In some embodiments, the isoprene synthase polypeptide is from an oak such as *Querus petraea* (SEQ ID NO: 13) or *Querus ilex* (SEQ ID NO: 19). In some embodiments, the isoprene synthase polypeptide is from *Eucalyptus globulus* (SEQ ID NO: 25) or *Melaleuca alternifolia* (SEQ ID NO: 27). Isoprene synthase of the present invention include, but are not limited to, those identified by JGI Accession Nos. Glyma09g21900.1, Glyma20g18280.1, Glyma06g45780.1, and Glyma12g10990.1. Isoprene synthases of the present invention include, but are not limited to, those identified by a FGENESH predicted polypeptide encoded from a *G. max* genomic sequence, such as the polypeptide identified by Glyma20g18280_1_FG.

In any aspects of the invention, an isolated polypeptide from a legume having isoprene synthase activity has at least about 40%, at least about 50%, at least about 60%, at least about 70%, at least about 80%, at least about 90%, at least about 92%, at least about 94%, at least about 96%, at least about 98%, at least about 99% sequence identity with *A. hypogaea* isoprene synthase comprising the amino acid sequence of SEQ ID NO: 3. In any aspects of the invention, an isolated polypeptide from a legume having isoprene synthase activity has at least about 40%, at least about 50%, at least about 60%, at least about 70%, at least about 80%, at least about 90%, at least about 92%, at least about 94%, at least about 96%, at least about 98%, at least about 99% sequence identity with *Glycine max* 1 isoprene synthase comprising the amino acid sequence of SEQ ID NO: 5. In any aspects of the invention, an isolated polypeptide from a legume having isoprene synthase activity has at least about 40%, at least about 50%, at least about 60%, at least about 70%, at least about 80%, at least about 90%, at least about 92%, at least about 94%, at least about 96%, at least about 98%, at least about 99% sequence identity with *Glycine max* 2 isoprene synthase comprising the amino acid sequence of SEQ ID NO: 7. In any aspects of the invention, an isolated polypeptide from a legume having isoprene synthase activity has at least about 40%, at least about 50%, at least about 60%, at least about 70%, at least about 80%, at least about 90%, at least about 92%, at least about 94%, at least about 96%, at least about 98%, at least about 99% sequence identity with *M. pruriens* isoprene synthase comprising the amino acid sequence of SEQ ID NO: 9. In any aspects of the invention, an isolated polypeptide from a legume having isoprene synthase activity has at least about 40%, at least about 50%, at least about 60%, at least about 70%, at least about 80%, at least about 90%, at least about 92%, at least about 94%, at least about 96%, at least about 98%, at least about 99% sequence identity with *C. cajans* isoprene synthase comprising the amino acid sequence of SEQ ID NO: 11. In any aspects of the invention, an isolated polypeptide from a legume having isoprene synthase activity has at least about 40%, at least about 50%, at least about 60%, at least about 70%, at least about 80%, at least about 90%, at least about 92%, at least about 94%, at least about 96%, at least about 98%, at least about 99% sequence identity with *Lotus japonicas* isoprene synthase comprising the amino acid sequence of SEQ ID NO: 33. In any aspects of the invention, an isolated polypeptide from a legume having isoprene synthase activity has at least about 40%, at least about 50%, at least about 60%, at least about 70%, at least about 80%, at least about 90%, at least about 92%, at least about 94%, at least about 96%, at least about 98%, at least about 99% sequence identity with *Medicago truncatula* isoprene synthase comprising the amino acid sequence of SEQ ID NO: 35.

In some aspects, the invention provides an isolated polypeptide having isoprene synthase activity, wherein the isolated polypeptide is not a legume. In some aspects, an isolated polypeptide from a citrus having isoprene synthase activity has at least about 40%, at least about 50%, at least about 60%, at least about 70%, at least about 80%, at least about 90%, at least about 92%, at least about 94%, at least about 96%, at least about 98%, at least about 99% sequence identity with *Citrus limon* isoprene synthase comprising the amino acid sequence of SEQ ID NO: 17. In some aspects, an isolated polypeptide from a *Cinnamomum* having isoprene synthase activity has at least about 40%, at least about 50%, at least about 60%, at least about 70%, at least about 80%, at least about 90%, at least about 92%, at least about 94%, at least about 96%, at least about 98%, at least about 99% sequence identity with *Cinnamomum tenuipile* isoprene synthase comprising the amino acid sequence of SEQ ID NO: 23.

In some aspects, an isolated polypeptide from a grape having isoprene synthase activity has at least about 40%, at least about 50%, at least about 60%, at least about 70%, at least about 80%, at least about 90%, at least about 92%, at least about 94%, at least about 96%, at least about 98%, at least about 99% sequence identity with *Vitis vinifera* isoprene synthase comprising the amino acid sequence of SEQ ID NO: 21. In some aspects, an isolated polypeptide from an oak having isoprene synthase activity has at least about 40%, at least about 50%, at least about 60%, at least about 70%, at least about 80%, at least about 90%, at least about 92%, at least about 94%, at least about 96%, at least about 98%, at least about 99% sequence identity with *Querus petraea* isoprene synthase comprising the amino acid sequence of SEQ ID NO: 13. In some aspects, an isolated polypeptide from an oak having isoprene synthase activity has at least about 40%, at least about 50%, at least about 60%, at least about 70%, at least about 80%, at least about 90%, at least about 92%, at least about 94%, at least about 96%, at least about 98%, at least about 99% sequence identity with *Querus ilex* isoprene synthase comprising the amino acid sequence of SEQ ID NO: 19. In some aspects, an isolated polypeptide from a eucalyptus having isoprene synthase activity has at least about 40%, at least about 50%, at least about 60%, at least about 70%, at least about 80%, at least about 90%, at least about 92%, at least about 94%, at least about 96%, at least about 98%, at least about 99% sequence identity with *Eucalyptus globulus* isoprene synthase comprising the amino acid sequence of SEQ ID NO: 25. In some aspects, an isolated polypeptide from a manuka having isoprene synthase activity has at least about 40%, at least about 50%, at least about 60%, at least about 70%, at least about 80%, at least about 90%, at least about 92%, at least about 94%, at least about 96%, at least about 98%, at least about 99% sequence identity with *Melaleuca alternifolia* isoprene synthase comprising the amino acid sequence of SEQ ID NO: 27.

The nucleic acids encoding an isoprene synthase polypeptide(s) can be integrated into a genome of the host cells or can be stably expressed in the cells. The nucleic acids encoding an isoprene synthase polypeptide(s) can additionally be on a vector (include multiple vectors).

Exemplary isoprene synthase nucleic acids include nucleic acids that encode a polypeptide, fragment of a polypeptide, peptide, or fusion polypeptide that has at least one activity of an isoprene synthase polypeptide. Isoprene synthase polypeptides convert dimethylallyl diphosphate (DMAPP) into isoprene. Exemplary isoprene synthase polypeptides include polypeptides, fragments of polypeptides, peptides, and fusions polypeptides that have at least one activity of an isoprene synthase polypeptide. Exemplary isoprene synthase polypeptides and nucleic acids include naturally-occurring polypeptides and nucleic acids from any of the source organisms described herein. In addition, variants of isoprene synthase can possess improved activity such as improved enzymatic activity. In some aspects, an isoprene synthase variant has other improved properties, such as improved stability (e.g., thermo-stability), and/or improved solubility.

Standard methods can be used to determine whether a polypeptide has isoprene synthase polypeptide activity by measuring the ability of the polypeptide to convert DMAPP into isoprene in vitro, in a cell extract, or in vivo. Isoprene synthase polypeptide activity in the cell extract can be measured, for example, as described in Silver et al., J. Biol. Chem. 270:13010-13016, (1995). In one exemplary assay, DMAPP (Sigma) can be evaporated to dryness under a stream of nitrogen and rehydrated to a concentration of 100 mM in 100 mM potassium phosphate buffer pH 8.2 and stored at −20° C. To perform the assay, a solution of 5 μL of 1M MgCl$_2$, 1 mM (250 μg/ml) DMAPP, 65 μL of Plant Extract Buffer (PEB) (50 mM Tris-HCl, pH 8.0, 20 mM MgCl$_2$, 5% glycerol, and 2 mM DTT) can be added to 25 μL of cell extract in a 20 ml Headspace vial with a metal screw cap and teflon coated silicon septum (Agilent Technologies) and cultured at 370 C for 15 minutes with shaking. The reaction can be quenched by adding 200 μL of 250 mM EDTA and quantified by GC/MS.

In some aspects, the isoprene synthase polypeptide is a plant isoprene synthase polypeptide or a variant thereof. In some aspects, the isoprene synthase polypeptide is an isoprene synthase from *Pueraria* or a variant thereof. In some aspects, the isoprene synthase polypeptide is an isoprene synthase from *Populus* or a variant thereof. In some aspects, the isoprene synthase polypeptide is a poplar isoprene synthase polypeptide or a variant thereof. In some aspects, the isoprene synthase polypeptide is a kudzu isoprene synthase polypeptide or a variant thereof. In some aspects, the isoprene synthase polypeptide is a willow isoprene synthase polypeptide or a variant thereof. In some aspects, the isoprene synthase polypeptide is a eucalyptus isoprene synthase polypeptide or a variant thereof. In some aspects, the isoprene synthase polypeptide is a polypeptide from *Pueraria* or *Populus* or a hybrid, *Populus alba*×*Populus tremula*, or a variant thereof. In some aspects, the isoprene synthase polypeptide is from *Robinia, Salix,* or *Melaleuca* or variants thereof.

In some embodiments, the plant isoprene synthase is from the family Fabaceae, the family Salicaceae, or the family Fagaceae. In some aspects, the isoprene synthase polypeptide or nucleic acid is a polypeptide or nucleic acid from *Pueraria montana* (kudzu) (Sharkey et al., *Plant Physiology* 137: 700-712, (2005)), *Pueraria lobata*, poplar (such as *Populus alba, Populus nigra, Populus trichocarpa,* or *Populus alba*× *tremula* (CAC35696) (Miller et al., Planta 213: 483-487, (2001)), aspen (such as *Populus tremuloides*) (Silver et al., JBC 270(22): 13010-1316, (1995)), English Oak (*Quercus robur*) (Zimmer et al., WO 98/02550), or a variant thereof. In some aspects, the isoprene synthase polypeptide is an isoprene synthase from *Pueraria montana, Pueraria lobata, Populus tremuloides, Populus alba, Populus nigra,* or *Populus trichocarpa* or a variant thereof. In some aspects, the isoprene synthase polypeptide is an isoprene synthase from *Populus alba* or a variant thereof. In some aspects, the isoprene synthase is *Populus balsamifera* (Genbank JN173037), *Populus deltoides* (Genbank JN173039), *Populus fremontii* (Genbank JN173040), *Populus granididenta* (Genbank JN173038), *Salix* (Genbank JN173043), *Robinia pseudoacacia* (Genbank JN173041), *Wisteria* (Genbank JN173042), *Eucalyptus globulus* (Genbank AB266390) or *Melaleuca alterniflora* (Genbank AY279379) or variant thereof. In some aspects, the nucleic acid encoding the isoprene synthase (e.g., isoprene synthase from *Populus alba* or a variant thereof) is codon optimized.

In some aspects, the isoprene synthase polypeptide is a legume isoprene synthase polypeptide or a variant thereof. In some aspects, the isoprene synthase polypeptide is an isoprene synthase from *Arachis* or a variant thereof. In some aspects, the isoprene synthase polypeptide is an isoprene synthase from *Mucuna* or a variant thereof. In some aspects, the isoprene synthase polypeptide is an isoprene synthase from *Cajanus* or a variant thereof. In some aspects, the isoprene synthase polypeptide is an isoprene synthase from *Glycine* or a variant thereof. In some aspects, the isoprene synthase polypeptide is an isoprene synthase from *Lotus* or a variant thereof. In some aspects, the isoprene synthase polypeptide is an isoprene synthase from *Medicago* or a variant thereof. In some aspects, the isoprene synthase polypeptide is a poplar isoprene synthase polypeptide or a variant thereof. In some aspects, the isoprene synthase polypeptide is a kudzu isoprene synthase polypeptide or a variant thereof.

In any aspects of the invention, the isoprene synthase polypeptide is encoded by a nucleic acid from the family Leguminosae, the family Fagaceae, the family Rutaceae, the family Lauraceae, the family Vitaceae, or the family Myrtaceae. In some embodiments, the isoprene synthase polypeptide is encoded by a nucleic acid from a legume. In some embodiments, the nucleic acid encoding legume isoprene synthase is from *Arachis hypogaea* (SEQ ID: NO 4), *Glycine max* 1 (SEQ ID NO: 6), *Glycine max* 2 (SEQ ID NO: 8), *M. pruriens* (SEQ ID NO: 10), *C. cajans* (SEQ ID NO: 12), wild legume (such as *Lotus japonicus*), or clover-like plant (such as *Medicago truncatula*). In some embodiments, the isoprene synthase polypeptide is encoded by a nucleic acid from a citrus including, but not limited to, lemon (such *Citrus limon*). In some embodiments, the isoprene synthase polypeptide is encoded by a nucleic acid from *Cinnamomum tenuipile*. In some embodiments, the isoprene synthase polypeptide is encoded by a nucleic acid from a grape including, but not limited to, wine grape (such as *Vitis vinifera*). In some embodiments, the isoprene synthase polypeptide is encoded by a nucleic acid from an oak such as *Querus petraea* (SEQ ID NO: 14) or *Querus ilex*. In some embodiments, the isoprene synthase polypeptide is encoded by a nucleic acid from *Eucalyptus globulus* or *Melaleuca alternifolia*. Isoprene synthase of the present invention include, but are not limited to, those identified by JGI Accession Nos. Glyma09g21900.1, Glyma20g18280.1, Glyma06g45780.1, and Glyma12g10990.1. Isoprene synthases of the present invention include, but are not limited to, those identified by a FGENESH predicted polypeptide encoded from a *G. max* genomic sequence, such as the polypeptide identified by Glyma20g18280_1_FG.

In any aspects of the invention, an isolated polypeptide from a legume having isoprene synthase activity has at least about 40%, at least about 50%, at least about 60%, at least about 70%, at least about 80%, at least about 90%, at least about 92%, at least about 94%, at least about 96%, at least about 98%, at least about 99% sequence identity with *A. hypogaea* isoprene synthase encoded by a nucleic acid sequence comprising the sequence of SEQ ID NO: 4. In any aspects of the invention, an isolated polypeptide from a legume having isoprene synthase activity has at least about 40%, at least about 50%, at least about 60%, at least about 70%, at least about 80%, at least about 90%, at least about 92%, at least about 94%, at least about 96%, at least about 98%, at least about 99% sequence identity with *Glycine max* 1 isoprene synthase encoded by a nucleic acid sequence comprising the sequence of SEQ ID NO: 6. In any aspects of the invention, an isolated polypeptide from a legume having isoprene synthase activity has at least about 40%, at least about 50%, at least about 60%, at least about 70%, at least about 80%, at least about 90%, at least about 92%, at least about 94%, at least about 96%, at least about 98%, at least about 99% sequence identity with *Glycine max* 2 isoprene synthase encoded by a nucleic acid sequence comprising the sequence of SEQ ID NO: 8. In any aspects of the invention, an isolated polypeptide from a legume having isoprene synthase activity has at least about 40%, at least about 50%, at least about 60%, at least about 70%, at least about 80%, at least about 90%, at least about 92%, at least about 94%, at least about 96%, at least about 98%, at least about 99% sequence identity with *M. pruriens* isoprene synthase encoded by a nucleic acid sequence comprising the sequence of SEQ ID NO: 10. In any aspects of the invention, an isolated polypeptide from a legume having isoprene synthase activity has at least about 40%, at least about 50%, at least about 60%, at least about 70%, at least about 80%, at least about 90%, at least about 92%, at least about 94%, at least about 96%, at least about 98%, at least about 99% sequence identity with *C. cajans* isoprene synthase encoded by a nucleic acid sequence comprising the sequence of SEQ ID NO: 12.

In some aspects, the isoprene synthase nucleic acid or polypeptide is a naturally-occurring polypeptide or nucleic acid (e.g., naturally-occurring polypeptide or nucleic acid from *Populus*). In some aspects, the isoprene synthase nucleic acid or polypeptide is not a wild-type or naturally-occurring polypeptide or nucleic acid. In some aspects, the isoprene synthase nucleic acid or polypeptide is a variant of a wild-type or naturally-occurring polypeptide or nucleic acid (e.g., a variant of a wild-type or naturally-occurring polypeptide or nucleic acid from *Populus*).

In some aspects, the isoprene synthase nucleic acid or polypeptide is a naturally-occurring polypeptide or nucleic acid (e.g., naturally-occurring polypeptide or nucleic acid from *Arachis*). In some aspects, the isoprene synthase nucleic acid or polypeptide is not a wild-type or naturally-occurring polypeptide or nucleic acid. In some aspects, the isoprene synthase nucleic acid or polypeptide is a variant of a wild-type or naturally-occurring polypeptide or nucleic acid (e.g., a variant of a wild-type or naturally-occurring polypeptide or nucleic acid from *Arachis*).

In some aspects, the isoprene synthase polypeptide is a legume isoprene synthase. In some aspects, the isoprene synthase polypeptide is a wild-type or naturally occurring legume isoprene synthase. In some aspects, the legume isoprene synthase has improved activity such as improved catalytic activity as compared to a reference isoprene synthase such MEA *P. alba* isoprene synthase comprising the amino acid sequence of SEQ ID NO: 1. The increase in activity (e.g., catalytic activity) can be at least about any of 10%, 20%, 30%, 40%, 50%, 60%, 70%, 80%, 90%, or 95%. In some aspects, the increase in activity such as catalytic activity is at least about any of 1 fold, 2 folds, 5 folds, 10 folds, 20 folds, 30 folds, 40 folds, 50 folds, 75 folds, or 100 folds. In some aspects, the increase in activity such as catalytic activity is about 10% to about 100 folds (e.g., about 20% to about 100 folds, about 50% to about 50 folds, about 1 fold to about 25 folds, about 2 folds to about 20 folds, or about 5 folds to about 20 folds). In some aspects, the legume isoprene synthase has improved solubility compared to a reference isoprene synthase such MEA *P. alba* isoprene synthase comprising the amino acid sequence of SEQ ID NO: 1 The increase in solubility can be at least about any of 10%, 20%, 30%, 40%, 50%, 60%, 70%, 80%, 90%, or 95%. The increase in solubility can be at least about any of 1 fold, 2 folds, 5 folds, 10 folds, 20 folds, 30 folds, 40 folds, 50 folds, 75 folds, or 100 folds. In some aspects, the increase in solubility is about 10% to about 100 folds (e.g., about 20% to about 100 folds, about 50% to about 50 folds, about 1 fold to about 25 folds, about 2 folds to about 20 folds, or about 5 folds to about 20 folds).

In some aspects, the $k_{cat}$ is at least about 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0. In other aspects, the kcat is at least about 3.1, 3.2, 3.3, 3.4, 3.5, 3.6, 3.7, 3.8, 3.9, 4.0, 4.1, 4.2, 4.3, 4.4, 4.5, 4.6. 4.7, 4.8, 4.9, 5.0, 5.1, 5.2, 5.3, 5.4, 5.5, 5.6, 5.7, 5.8. 5.9 or 6.0.

In some aspects, the $K_m$ is at least about 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 16, 17, 17.5, 18, 18.5, 19, 19.5, 20, 20.5, 21, 21.5, 22, 22.5, 23, 23.5, 24, 24.5 or 25.

In some aspects, $K_{iDMAPP}$ values at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60.

In some aspects, the legume isoprene synthase has at least about 10%, at least about 20%, at least about 30%, at least about 40%, at least about 50%, at least about 60%, at least about 70%, at least about 80%, at least about 90%, at least about 100%, at least about 110%, at least about 120%, at least about 130%, at least about 140%, at least about 150%, at least about 160%, at least about 170%, at least about 180%, at least about 190%, at least about 200% to MEA *P. alba* isoprene synthase comprising the amino acid sequence of SEQ ID NO: 1. The legume isoprene synthase can share sequence similarity MEA *P. alba* isoprene synthase comprising the amino acid sequence of SEQ ID NO: 1. In some aspects, a legume isoprene synthase can have at least about any of 40%, 50%, 60%, 70%, 75%, 80%, 90%, 91%, 92%, 93%, 94%, 95%, 96%, 97%, 98%, 99%, 99.5%, or 99.9% amino acid sequence identity as that of the MEA *P. alba* isoprene synthase comprising the amino acid sequence of SEQ ID NO: 1. In some aspects, a legume isoprene synthase has any of about 70% to about 99.9%, about 75% to about 99%, about 80% to about 98%, about 85% to about 97%, or about 90% to about 95% amino acid sequence identity as that of MEA *P. alba* isoprene synthase comprising the amino acid sequence of SEQ ID NO: 1.

In some aspects, the isoprene synthase polypeptide is a variant. In some aspects, the isoprene synthase polypeptide is a variant of a wild-type or naturally occurring isoprene synthase. In some aspects, the variant has improved activity such as improved catalytic activity compared to the wild-type or naturally occurring isoprene synthase.

In any aspects of the invention, an isoprene synthase variant comprises a mutation in the wild-type or naturally occurring isoprene synthase. In some aspects, the isoprene synthase variant has at least one amino acid substitution, at least one amino acid insertion, and/or at least one amino acid deletion. In some aspects, the isoprene synthase variant has at least one amino acid substitution. In some aspects, the number of differing amino acid residues between the variant and wild-type or naturally occurring isoprene synthase can be one or more, e.g. 1, 2, 3, 4, 5, 10, 15, 20, 30, 40, 50, or more amino acid residues. Naturally occurring isoprene synthases can include any isoprene synthases from plants, for example, peanut (such *Arachis hypogaea*), velvet bean (such as *Mucuna pruriens*), pigeon pea (such as *Cajanus cajans*), soybean (such as *Glycine max*), wild legume (such as *Lotus japonicus*), clover-like plant (such as *Medicago truncatula*), citrus (such *Citrus limon*), *Cinnamomum tenuipile*, wine grape (such as *Vitis vinifera*), oak (such as *Querus petraea* or *Querus ilex*), *Eucalyptus globulus* or *Melaleuca alternifolia*. In some aspects, the variant is a variant of isoprene synthase from *Arachis hypogaea*. In some aspects, the variant of isoprene synthase from *Arachis hypogaea* has at least one amino acid substitution, at least one amino acid insertion, and/or at least one amino acid deletion. In some aspects, the variant is a truncated *Arachis hypogaea* isoprene synthase. In some aspects, the nucleic acid encoding variant (e.g., variant of isoprene synthase from *Arachis hypogaea*) is codon optimized (for example, codon optimized based on host cells where the heterologous isoprene synthase is expressed). In some aspects, the variant is a variant of isoprene synthase from *Mucuna pruriens*. In some aspects, the variant of isoprene synthase from *Mucuna pruriens* has at least one amino acid substitution, at least one amino acid insertion, and/or at least one amino acid deletion. In some aspects, the variant is a truncated *Mucuna pruriens* isoprene synthase. In some aspects, the nucleic acid encoding variant (e.g., variant of isoprene synthase from *Mucuna pruriens*) is codon optimized (for example, codon optimized based on host cells where the heterologous isoprene synthase is expressed).

The isoprene synthase polypeptide provided herein can be any of the isoprene synthases or isoprene synthase variants described in WO 2009/132220, WO 2010/124146, and U.S. Patent Application Publication No.: 2010/0086978, the contents of which are expressly incorporated herein by reference in their entirety with respect to the isoprene synthases and isoprene synthase variants.

Any one of the promoters described herein (e.g., promoters described herein and identified in the Examples of the present disclosure including inducible promoters and constitutive promoters) can be used to drive expression of any of the isoprene synthases described herein.

Suitable isoprene synthases include, but are not limited to, those identified by JGI Accession Nos. Glyma09g21900.1, Glyma20g18280.1, Glyma06g45780.1, and Glyma12g10990.1. Suitable isoprene synthases include, but are not limited to, those identified by a FGENESH predicted polypeptide encoded from a *G. max* genomic sequence, such as the polypeptide identified by Glyma20g18280_1_FG. Types of isoprene synthases which can be used in any one of the compositions or methods including methods of making microorganisms encoding isoprene synthase described herein are also described in International Patent Application Publication Nos. WO 2009/076676, WO 2010/003007, WO 2009/132220, WO 2010/031062, WO 2010/031068, WO 2010/031076, WO 2010/013077, WO 2010/031079, WO 2010/148150, WO 2010/124146, WO 2010/078457, and WO 2010/148256, U.S. patent application Ser. No. 13/283,564, and Sharkey et al., "*Isoprene Synthase Genes Form A Monophyletic Clade Of Acyclic Terpene Synthases In The Tps-B Terpene Synthase Family*", Evolution (2012) (available on line at DOI: 10.1111/evo.12013), the contents of which are expressly incorporated herein by reference in their entirety with respect to the isoprene synthases and isoprene synthase variants.

2. MVA Pathway Nucleic Acids and Polypeptides

The complete MVA pathway can be subdivided into two groups: an upper and lower pathway. In the upper portion of the MVA pathway, acetyl Co-A produced during cellular metabolism is converted to mevalonate via the actions of polypeptides having either: (a) (i) thiolase activity or (ii) acetoacetyl-CoA synthase activity, (b) HMG-CoA reductase, and (c) HMG-CoA synthase enzymatic activity. First, acetyl Co-A is converted to acetoacetyl CoA via the action of a thiolase or an acetoacetyl-CoA synthase (which utilizes acetyl-CoA and malonyl-CoA). Next, acetoacetyl-CoA is converted to 3-hydroxy-3-methylglutaryl-CoA (HMG-CoA) by the enzymatic action of HMG-CoA synthase. This Co-A derivative is reduced to mevalonate by HMG-CoA reductase, which is the rate-limiting step of the mevalonate pathway of isoprenoid production. In the lower MVA pathway, mevalonate is then converted into mevalonate-5-phosphate via the action of mevalonate kinase which is subsequently transformed into 5-diphosphomevalonate by the enzymatic activity of phosphomevalonate kinase. Finally, IPP is formed from 5-diphosphomevalonate by the activity of the enzyme mevalonate-5-pyrophosphate decarboxylase. The mevalonate-dependent biosynthetic pathway is particularly important for the production of the isoprenoid precursor molecules dimethylallyl diphosphate (DMAPP) and isopentenyl pyrophosphate (IPP).

Exemplary MVA pathway polypeptides include, but are not limited to: 3-hydroxy-3-methylglutaryl-CoA synthase (HMG-CoA synthase) polypeptides (e.g., an enzyme encoded by mvaS), 3-hydroxy-3-methylglutaryl-CoA reductase (HMG-CoA reductase) polypeptides (e.g., enzyme encoded by mvaR or enzyme encoded by mvaE that has been modified to be thiolase-deficient but still retains its reductase activity), mevalonate kinase (MVK) polypeptides, phosphomevalonate kinase (PMK) polypeptides, diphosphomevalonte decarboxylase (MVD) polypeptides, phosphomevalonate decarboxylase (PMDC) polypeptides, isopentenyl phosphate kinase (IPK) polypeptides, IPP isomerase polypeptides, IDI polypeptides, and polypeptides (e.g., fusion polypeptides) having an activity of two or more MVA pathway polypeptides. In particular, MVA pathway polypeptides include polypeptides, fragments of polypeptides, peptides, and fusions polypeptides that have at least one activity of an MVA pathway polypeptide. Exemplary MVA pathway nucleic acids include nucleic acids that encode a polypeptide, fragment of a polypeptide, peptide, or fusion polypeptide that has at least one activity of an MVA pathway polypeptide. Exemplary MVA pathway polypeptides and nucleic acids include naturally-occurring polypeptides and nucleic acids from any of the source organisms described herein. In addition, variants of MVA pathway polypeptide that confer the result of better isoprene production can also be used as well.

Non-limiting examples of MVA pathway polypeptides which can be used are described in International Patent Application Publication No. WO 2009/076676; WO 2010/003007 and WO 2010/148150.

a. Nucleic Acids Encoding Polypeptides of the Upper MVA Pathway

The upper portion of the MVA pathway uses acetyl Co-A produced during cellular metabolism as the initial substrate for conversion to mevalonate via the actions of polypeptides having either: (a) (i) thiolase activity or (ii) acetoacetyl-CoA synthase activity, (b) HMG-CoA reductase, and (c) HMG-CoA synthase enzymatic activity. First, acetyl Co-A is converted to acetoacetyl CoA via the action of a thiolase or an acetoacetyl-CoA synthase (which utilizes acetyl-CoA and malonyl-CoA). Next, acetoacetyl-CoA is converted to 3-hydroxy-3-methylglutaryl-CoA (HMG-CoA) by the enzymatic action of HMG-CoA synthase. This Co-A derivative is reduced to mevalonate by HMG-CoA reductase, which is a rate-limiting step of the mevalonate pathway of isoprenoid production.

Non-limiting examples of upper MVA pathway polypeptides include: acetyl-CoA acetyltransferase (AA-CoA thiolase) polypeptides, acetoacetyl-CoA synthase polypeptides, 3-hydroxy-3-methylglutaryl-CoA synthase (HMG-CoA synthase) polypeptides, 3-hydroxy-3-methylglutaryl-CoA reductase (HMG-CoA reductase) polypeptides. Upper MVA pathway polypeptides can include polypeptides, fragments of polypeptides, peptides, and fusions polypeptides that have at least one activity of an upper MVA pathway polypeptide. Exemplary upper MVA pathway nucleic acids include nucleic acids that encode a polypeptide, fragment of a polypeptide, peptide, or fusion polypeptide that has at least one activity of an upper MVA pathway polypeptide. Exemplary MVA pathway polypeptides and nucleic acids include naturally-occurring polypeptides and nucleic acids from any of the source organisms described herein. Thus, it is contemplated herein that any gene encoding an upper MVA pathway polypeptide can be used in the present invention.

In certain embodiments, various options of mvaE and mvaS genes from *L. grayi, E. faecium, E. gallinarum, E. casseliflavus* and/or *E. faecalis* alone or in combination with one or more other mvaE and mvaS genes encoding proteins from the upper MVA pathway are contemplated within the scope of the invention. In other embodiments, an acetoacetyl-CoA synthase gene is contemplated within the scope of the present invention in combination with one or more other genes encoding: (i) 3-hydroxy-3-methylglutaryl-CoA synthase (HMG-CoA synthase) polypeptides and 3-hydroxy-3-methylglutaryl-CoA reductase (HMG-CoA reductase) polypeptides. Thus, in certain aspects, any of the combinations of genes contemplated herein can be expressed in recombinant cells in any of the ways described herein.

Additional non-limiting examples of upper MVA pathway polypeptides which can be used herein are described in International Patent Application Publication No. WO 2009/076676; WO 2010/003007 and WO 2010/148150.

(i) Acetoacetyl-CoA Synthase Nucleic Acids and Polypeptides

The acetoacetyl-CoA synthase gene (aka nphT7) is a gene encoding an enzyme having the activity of synthesizing acetoacetyl-CoA from malonyl-CoA and acetyl-CoA and having minimal activity (e.g., no activity) of synthesizing acetoacetyl-CoA from two acetyl-CoA molecules. See, e.g., Okamura et al., PNAS Vol 107, No. 25, pp. 11265-11270 (2010), the contents of which are expressly incorporated herein for teaching about nphT7. An acetoacetyl-CoA synthase gene from an actinomycete of the genus *Streptomyces* CL190 strain was described in JP Patent Publication (Kokai) No. 2008-61506 A and US 2010/0285549. Acetoacetyl-CoA synthase can also be referred to as acetyl CoA:malonyl CoA acyltransferase. A representative acetoacetyl-CoA synthase (or acetyl CoA:malonyl CoA acyltransferase) that can be used is Genbank AB540131.1.

In one embodiment, acetoacetyl-CoA synthase of the present invention synthesizes acetoacetyl-CoA from malonyl-CoA and acetyl-CoA via an irreversible reaction. The use of acetoacetyl-CoA synthase to generate acetyl-CoA provides an additional advantage in that this reaction is irreversible while acetoacetyl-CoA thiolase enzyme's action of synthesizing acetoacetyl-CoA from two acetyl-CoA molecules is reversible. Consequently, the use of acetoacetyl-CoA synthase to synthesize acetoacetyl-CoA from malonyl-CoA and acetyl-CoA can result in significant improvement in productivity for isoprene compared with using thiolase to generate the end same product.

Furthermore, the use of acetoacetyl-CoA synthase to produce isoprene provides another advantage in that acetoacetyl-CoA synthase can convert malonyl CoA to acetyl CoA via decarboxylation of the malonyl CoA. Thus, stores of starting substrate are not limited by the starting amounts of acetyl CoA. The synthesis of acetoacetyl-CoA by acetoacetyl-CoA synthase can still occur when the starting substrate is only malonyl-CoA. In one embodiment, the pool of starting malonyl-CoA is increased by using host strains that have more malonyl-CoA. Such increased pools can be naturally occurring or be engineered by molecular manipulation. See, for example Fowler, et al., Applied and Environmental Microbiology, Vol. 75, No. 18, pp. 5831-5839 (2009).

In any of the aspects or embodiments described herein, an enzyme that has the ability to synthesize acetoacetyl-CoA from malonyl-CoA and acetyl-CoA can be used. Non-limiting examples of such an enzyme are described herein. In certain embodiments described herein, an acetoacetyl-CoA synthase gene derived from an actinomycete of the genus *Streptomyces* having the activity of synthesizing acetoacetyl-CoA from malonyl-CoA and acetyl-CoA can be used. An example of such an acetoacetyl-CoA synthase gene is the gene encoding a protein having the amino acid sequence of SEQ ID NO: 15. Such a protein having the amino acid sequence of SEQ ID NO: 15 corresponds to an acetoacetyl-CoA synthase having activity of synthesizing acetoacetyl- CoA from malonyl-CoA and acetyl-CoA and having no activity of synthesizing acetoacetyl-CoA from two acetyl-CoA molecules.

```
Sequence of acetoacetyl-CoA synthase
                                    (SEQ ID NO: 15)
MTDVRFRIIGTGAYVPERIVSNDEVGAPAGVDDDWITRKTGIRQRRWAAD

DQATSDLATAAGRAALKAAGITPEQLTVIAVATSTPDRPQPPTAAYVQHH

LGATGTAAFDVNAVCSGTVFALSSVAGTLVYRGGYALVIGADLYSRILNP

ADRKTVVLFGDGAGAMVLGPTSTGTGPIVRRVALHTFGGLTDLIRVPAGG

SRQPLDTDGLDAGLQYFAMDGREVRRFVTEHLPQLIKGFLHEAGVDAADI

SHFVPHQANGVMLDEVFGELHLPRATMHRTVETYGNTGAASIPITMDAAV

RAGSFRPGELVLLAGFGGGMAASFALIEW.
```

The acetoacetyl-CoA synthase activity of a polypeptide can be evaluated as described below. Specifically, a gene encoding a polypeptide to be evaluated is first introduced into a host cell such that the gene can be expressed therein, followed by purification of the protein by a technique such as chromatography. Malonyl-CoA and acetyl-CoA are added as substrates to a buffer containing the obtained protein to be evaluated, followed by, for example, incubation at a desired temperature (e.g., 10° C. to 60° C.). After the completion of reaction, the amount of substrate lost and/or the amount of product (acetoacetyl-CoA) produced are determined. Thus, it is possible to evaluate whether or not the protein being tested has the function of synthesizing acetoacetyl-CoA from malonyl-CoA and acetyl-CoA and to evaluate the degree of synthesis. In such case, it is possible to examine whether or not the protein has the activity of synthesizing acetoacetyl-CoA from two acetyl-CoA molecules by adding acetyl-CoA alone as a substrate to a buffer containing the obtained protein to be evaluated and determining the amount of substrate lost and/or the amount of product produced in a similar manner.

(ii) Genes Encoding mvaE and mvaS Polypeptides

In certain embodiments, various options of mvaE and mvaS genes from L. grayi, E. faecium, E. gallinarum, E. casseliflavus and/or E. faecalis alone or in combination with one or more other mvaE and mvaS genes encoding proteins from the upper MVA pathway are contemplated within the scope of the invention. In some embodiments, the mvaE gene encodes a polypeptide that possesses both thiolase and HMG-CoA reductase activities (Hedl, et al., J. Bacteriol. 2002 April; 184(8): 2116-2122). In L. grayi, E. faecium, E. gallinarum, E. casseliflavus, and E. faecalis, the mvaE gene encodes a polypeptide that possesses both thiolase and HMG-CoA reductase activities. In fact, the mvaE gene product represented the first bifunctional enzyme of IPP biosynthesis found in eubacteria and the first example of HMG-CoA reductase fused to another protein in nature (Hedl, et al., J. Bacteriol. 2002 April; 184(8): 2116-2122). The mvaS gene, on the other hand, can encode a polypeptide having an HMG-CoA synthase activity.

Accordingly, recombinant cells (e.g., E. coli) can be engineered to express one or more mvaE and mvaS genes from L. grayi, E. faecium, E. gallinarum, E. casseliflavus and/or E. faecalis to produce isoprene. The one or more mvaE and mvaS genes can be expressed on a multicopy plasmid. The plasmid can be a high copy plasmid, a low copy plasmid, or a medium copy plasmid. Alternatively, the one or more mvaE and mvaS genes can be integrated into the host cell's chromosome. For both heterologous expression of the one or more mvaE and mvaS genes on a plasmid or as an integrated part of the host cell's chromosome, expression of the genes can be driven by either an inducible promoter or a constitutively expressing promoter. The promoter can be a strong driver of expression, it can be a weak driver of expression, or it can be a medium driver of expression of the one or more mvaE and mvaS genes.

The mvaE gene encodes a polypeptide that possesses both thiolase and HMG-CoA reductase activities. The thiolase activity of the polypeptide encoded by the mvaE gene converts acetyl Co-A to acetoacetyl CoA whereas the HMG-CoA reductase enzymatic activity of the polypeptide converts 3-hydroxy-3-methylglutaryl-CoA to mevalonate. Exemplary mvaE polypeptides and nucleic acids include naturally-occurring polypeptides and nucleic acids from any of the source organisms described herein as well as mutant polypeptides and nucleic acids derived from any of the source organisms described herein that have at least one activity of a mvaE polypeptide.

Mutant mvaE polypeptides include those in which one or more amino acid residues have undergone an amino acid substitution while retaining mvaE polypeptide activity (i.e., the ability to convert acetyl Co-A to acetoacetyl CoA as well as the ability to convert 3-hydroxy-3-methylglutaryl-CoA to mevalonate). The amino acid substitutions can be conservative or non-conservative and such substituted amino acid residues can or cannot be one encoded by the genetic code. The standard twenty amino acid "alphabet" has been divided into chemical families based on similarity of their side chains. Those families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). A "conservative amino acid substitution" is one in which the amino acid residue is replaced with an amino acid residue having a chemically similar side chain (i.e., replacing an amino acid having a basic side chain with another amino acid having a basic side chain). A "non-conservative amino acid substitution" is one in which the amino acid residue is replaced with an amino acid residue having a chemically different side chain (i.e., replacing an amino acid having a basic side chain with another amino acid having an aromatic side chain).

Amino acid substitutions in the mvaE polypeptide can be introduced to improve the functionality of the molecule. For example, amino acid substitutions that increase the binding affinity of the mvaE polypeptide for its substrate, or that improve its ability to convert acetyl Co-A to acetoacetyl CoA and/or the ability to convert 3-hydroxy-3-methylglutaryl-CoA to mevalonate can be introduced into the mvaE polypeptide. In some aspects, the mutant mvaE polypeptides contain one or more conservative amino acid substitutions.

In one aspect, mvaE proteins that are not degraded or less prone to degradation can be used for the production of isoprene. Examples of gene products of mvaEs that are not degraded or less prone to degradation which can be used include, but are not limited to, those from the organisms E. faecium, E. gallinarum, E. casseliflavus, E. faecalis, and L. grayi. One of skill in the art can express mvaE protein in E. coli BL21 (DE3) and look for absence of fragments by any standard molecular biology techniques. For example, absence of fragments can be identified on Safestain stained SDS-PAGE gels following His-tag mediated purification or when expressed in mevalonate or isoprene producing *E. coli* BL21 using the methods of detection described herein.

Standard methods, such as those described in Hedl et al., (J. Bacteriol. 2002, April; 184(8): 2116-2122) can be used to determine whether a polypeptide has mvaE activity, by measuring acetoacetyl-CoA thiolase as well as HMG-CoA reductase activity. In an exemplary assay, acetoacetyl-CoA thiolase activity is measured by spectrophotometer to monitor the change in absorbance at 302 nm that accompanies the formation or thiolysis of acetoacetyl-CoA. Standard assay conditions for each reaction to determine synthesis of acetoacetyl-CoA, are 1 mM acetyl-CoA, 10 mM $MgCl_2$, 50 mM Tris, pH 10.5 and the reaction is initiated by addition of enzyme. Assays can employ a final volume of 200 µl. For the assay, 1 enzyme unit (eu) represents the synthesis or thiolysis in 1 min of 1 µmol of acetoacetyl-CoA. In another exemplary assay, of HMG-CoA reductase activity can be monitored by spectrophotometer by the appearance or disappearance of NADP(H) at 340 nm. Standard assay conditions for each reaction measured to show reductive deacylation of HMG-CoA to mevalonate are 0.4 mM NADPH, 1.0 mM (R,S)-HMG-CoA, 100 mM KCl, and 100 mM $K_xPO_4$, pH 6.5. Assays employ a final volume of 200 µl. Reactions are initiated by adding the enzyme. For the assay, 1 eu represents the turnover, in 1 min, of 1 µmol of NADP(H). This corresponds to the turnover of 0.5 µmol of HMG-CoA or mevalonate.

Exemplary mvaE nucleic acids include nucleic acids that encode a polypeptide, fragment of a polypeptide, peptide, or fusion polypeptide that has at least one activity of a mvaE polypeptide. Exemplary mvaE polypeptides and nucleic acids include naturally-occurring polypeptides and nucleic acids from any of the source organisms described herein as well as mutant polypeptides and nucleic acids derived from any of the source organisms described herein. Exemplary mvaE nucleic acids include, for example, mvaE nucleic acids isolated from *Listeria grayi*_DSM 20601, *Enterococcus faecium*, *Enterococcus gallinarum* EG2, *Enterococcus faecalis*, and/or *Enterococcus casseliflavus*. The mvaE nucleic acid encoded by the *Listeria grayi*_DSM 20601 mvaE gene can have at least about 99%, 98%, 97%, 96%, 95%, 95%, 93%, 92%, 91%, 90%, 89%, 88%, 87%, 86%, or 85% sequence identity to SEQ ID NO:47. The mvaE nucleic acid encoded by the *Enterococcus faecium* mvaE gene can have at least about 99%, 98%, 97%, 96%, 95%, 95%, 93%, 92%, 91%, 90%, 89%, 88%, 87%, 86%, or 85% sequence identity to SEQ ID NO:48. The mvaE nucleic acid encoded by the *Enterococcus gallinarum* EG2 mvaE gene can have at least about 99%, 98%, 97%, 96%, 95%, 95%, 93%, 92%, 91%, 90%, 89%, 88%, 87%, 86%, or 85% sequence identity to SEQ ID NO:49. The mvaE nucleic acid encoded by the *Enterococcus casseliflavus* mvaE gene can have at least about 99%, 98%, 97%, 96%, 95%, 95%, 93%, 92%, 91%, 90%, 89%, 88%, 87%, 86%, or 85% sequence identity to SEQ ID NO:50. The mvaE nucleic acid encoded by the *Enterococcus faecalis* mvaE gene can have at least about 99%, 98%, 97%, 96%, 95%, 95%, 93%, 92%, 91%, 90%, 89%, 88%, 87%, 86%, or 85% sequence identity to the mvaE gene previously disclosed in *E. coli* to produce mevalonate (see US 2005/0287655 A1; Tabata, K. and Hashimoto, S.-I. Biotechnology Letters 26: 1487-1491, 2004).

```
Sequence of Listeria grayi DSM 20601 mvaE
                                                                    (SEQ ID NO: 47)
atggttaaagacattgtaataattgatgccctccgtactcccatcggtaagtaccgcggtcagctctcaaagatgacggcggtggaattgggaacc gcagttacaaaggctctgttcgagaagaacgaccaggtcaaagaccatgtagaacaagtcattttttggcaacgttttacaggcagggaacggcc agaatcccgcccgtcagatcgcccttaattctggcctgtccgcagagataccggcttcgactattaaccaggtgtgtggttctggcctgaaagcaa taagcatggcgcgccaacagatcctactcggagaagcggaagtaatagtagcaggaggtatcgaatccatgacgaatgcgccgagtattacat attataataaagaagaagacaccctctcaaagcctgttcctacgatgaccttcgatggtctgaccgacgcgtttagcggaaagattatgggtttaac agccgaaaatgttgccgaacagtacggcgtatcacgtgaggcccaggacgcctttgcgtatggatcgcagatgaaagcagcaaaggcccaag aacagggcattttcgcagctgaaatactgcctcttgaaatagggagcgaagttattactcaggacgaggggttcgtcaagagaccaccctcga aaaattaagtctgcttcggaccatttttaaagaagatggtactgttacagcgggcaacgcctcaacgatcaatgatgcgcctcagccgtgatcatt gcatcaaaggagtttgctgagacaaaccagattccctaccttgcgatcgtacatgatattacagagataggcattgatccatcaataatgggcattg ctcccgtgagtgcgatcaataaactgatcgatcgtaaccaaattagcatggaagaaatcgatctctttgaaattaatgaggcatttgcagcatcctc ggtggtagttcaaaaagagttaagcattcccgatgaaaagatcaatattggcggttccggtattgcactaggccatcctcttggcgccacaggagc gcgcattgtaaccacctagcgcaccagttgaaacgtacacacggacgctatggtattgcctccctgtgcattggcggtggccttggcctagcaa tattaatagaagtgcctcaggaagatcagccggttaaaaaattttatcaattggcccgtgaggaccgtctggctagacttcaggagcaagccgtga tcagcccagctacaaaacatgtactggcagaaatgacacttcctgaagatattgccgacaatctgatcgaaatcaaatatctgaaatggaaatcc ctcttggtgtggctttgaatctgagggtcaatgataagagttataccatcccactagcaactgaggaaccgagtgtaatcgctgcctgtaataatggt gcaaaaatggcaaaccacctgggcggttttcagtcagaattaaaagatggtttcctgcgtgggcaaattgtacttatgaacgtcaaagaacccgca actatcgagcatacgatcacggcagagaaagcggcaatttttcgtgccgcagcgcagtcacatccatcgattgtgaaacgaggtgggggtctaa aagagatagtagtgcgtacgttcgatgatgatccgacgttcctgtctattgatctgatagttgatactaaagacgcaatgggcgctaacatcattaac accattctcgagggtgtagccggctttctgagggaaatccttaccgaagaaattctgttctctattttatctaattacgcaaccgaatcaattgtgacc gccagctgtcgcataccttacgaagcactgagtaaaaaggtgatggtaaacgaatcgctgaaaaagtggctgctgcatctaaatttgcccagtta gatccttatcgagctgcaacccacaacaaaggtattatgaatggtattgaggccgtcgttttggcctcaggaaatgacacacgggcggtcgcggc
```

-continued agccgcacatgcgtatgcttcacgcgatcagcactatcggggcttaagccagtggcaggttgcagaaggcgcgttacacggggagatcagtct accacttgcactcggcagcgttggcggtgcaattgaggtcttgcctaaagcgaaggcggcattcgaaatcatggggatcacagaggcgaagga gctggcagaagtcacagctgcggtagggctggcgcaaaacctggcggcgttaagagcgcttgttagtgaaggaatacagcaaggtcacatgtc gctccaggctcgctctcttgcattatcggtaggtgctacaggcaaggaagttgaaatcctggccgaaaaattacagggctctcgtatgaatcaggc gaacgctcagaccatactcgcagagatcagatcgcaaaaagttgaattgtga Sequence of *Enterococcus faecium* mvaE (SEQ ID NO: 48)

atgaccatgaacgttggaatcgataaaatgtcattctttgttccaccttactttgtggacatgactgatctggcagtagcacgggatgtcgatcccaat aagtttctgattggtattggccaggaccagatggcagttaatccgaaaacgcaggatattgtgacatttgccacaaatgctgccaaaaacatactgt cagctgaggaccttgataaaattgatatggtcatagtcggcaccgagagtggaatcgatgaatccaaagcgagtgccgtagtgcttcacaggttg ctcggtatccagaagtttgctcgctcctttgaaatcaaagaagcctgttatgggggtaccgcggctttacagttcgctgtaaaccacattaggaatc atcctgaatcaaaggttcttgtagttgcatcagatatcgcgaaatacggcctggcttctggaggtgaaccaacgcaaggtgcaggcgctgtggct atgctcgtctcaactgaccctaagatcattgctttcaacgacgatagcctcgcgcttacacaagatatctatgacttctggcgaccagttggacatga ctatcctatggtcgacgggcctcttagtacagagacctacatccagtcattcagaccgtatggcaggaatacacaaaacggtcgcagcatgcac tggcagactttgctgcccttagctttcatatcccgtatactaaaatgggcaaaaaggcgctgcttgcaatccttgaaggcgaatcagaggaggctc agaaccgtatactagcaaaatatgaaaagagtatagcctactccagaaaggcgggtaacctgtataccggtagcctgtatctaggacttatttcact tctggaaaatgcagaagaccttaaagctggtgatttaataggcctcttttcttacggttccggtgctgttgcggagttttttctcaggaaggctggttga ggactatcaggaacagctacttaaaacaaaacatgccgaacagctggcccatagaaagcaactgacaatcgaggagtacgaaacgatgttctc cgatcgcttggacgtggacaaagacgccgaatacgaagacacattagcttatagcatttcgtcagtccgaaacaccgtacgtgagtacaggagtt ga Sequence of *Enterococcus gallinarum* EG2 mvaE (SEQ ID NO: 49)

atgaaagaagtggttatgattgatgcggctcgcacacccattgggaaatacagaggtagtcttagtccttttacagcggtggagctggggacact ggtcacgaaagggctgctggataaaacaaagcttaagaaagacaagatagaccaagtgatattcggcaatgtgcttcaggcaggaaacggaca aaacgttgcaagacaaatagccctgaacagtggcttaccagttgacgtgccggcgatgactattaacgaagtttgcgggtccggaatgaaagcg gtgattttagccccgccagttaatacagttaggggaggcagagttggtcattgcaggggtacggagtcaatgtcacaagcacccatgctgaaac cttaccagtcagagaccaacgaatacgagagccgatatcatcaatggttaatgacgggctgacggatgcgttttccaatgctcacatgggtctta ctgccgaaaaggtggcgacccagttttcagtgtcgcgcgaggaacaagaccggtacgcattgtccagccaattgaaagcagcgcacgcggttg aagcggggtgttctcagaagagattattccggttaagattagcgacgaggatgtcttgagtgaagacgaggcagtaagaggcaacagcacttt ggaaaaactgggcaccttgcggacggtgtttctgaagagggcacggttaccgctggcaatgcttcaccgctgaatgacggcgctagtgtcgtg attcttgcatcaaaagaatacgcggaaaacaataatctgccttacctggcgacgataaaggaggttgcggaagttggtatcgatccttctatcatgg gtattgccccaataaaggccattcaaaagttaacagatcggtcgggcatgaacctgtccacgattgatctgttcgaaattaatgaagcattcgcgg catctagcattgttgtttctcaagagctgcaattggacgaagaaaaagtgaatatctatggcggggcgatagctttaggccatcaatcggcgcaa gcggagcccggatactgacaaccttagcatacggcctcctgcgtgagcaaaagcgttatggtattgcgtcattatgtatcggcggtggtcttggtc tggccgtgctgttagaagctaatatggagcagacccacaaagacgttcagaagaaaaagttttaccagcttaccccctccgagcggagatcgca gcttatcgagaagaacgttctgactcaagaaacggcacttattttccaggagcagacgttgtccgaagaactgtccgatcacatgattgagaatca ggtctccgaagtggaaattccaatgggaattgcacaaaattttcagattaatggcaagaaaaatggattcctatggcgactgaagaaccttcagt aatagcggcagcatcgaacggcgccaaaatctgcgggaacatttgcgcggaaacgcctcagcggcttatgcgcgggcagattgtcctgtctgg caaatcagaatatcaagccgtgataaatgccgtgaatcatcgcaaagaagaactgattctcttgcgcaaacgagtcgtacccgagtattgttaaacg cgggggaggtgttcaggatatttctacgcgggagtttatgggttcttttcacgcgtatttatcaatcgactttctggtggacgtcaaggacgcaatgg gggcaaacatgatcaactctattctcgaaagcgttgcaaataaactgcgtgaatggttcccggaagaggaaatactgttctccatcctgtcaaactt cgctacggagtccctggcatctgcatgttgcgagattccttttgaaagacttggtcgtaacaaagaaattggtgaacagatcgccaagaaaattca -continued

```
acaggcaggggaatatgctaagcttgacccttaccgcgcggcaacccataacaaggggattatgaacggtatcgaagccgtcgttgccgcaac gggaaacgacacacgggctgtttccgcttctattcacgcatacgccgcccgtaatggcttgtaccaaggtttaacggattggcagatcaagggcg ataaactggttggtaaattaacagtcccactggctgtggcgactgtcggtggcgcgtcgaacatattaccaaaagccaaagcttccctcgccatgc tggatattgattccgcaaaagaactggcccaagtgatcgccgcggtaggtttagcacagaatctggcggcgttacgtgcattagtgacagaagg cattcagaaaggacacatgggcttgcaagcacgttctttagcgatttcgataggtgccatcggtgaggagatagagcaagtcgcgaaaaaactg cgtgaagctgaaaaaatgaatcagcaaacggcaatacagattttagaaaaaattcgcgagaaatga
```

Sequence of *Enterococcus casseliflavus* mvaE (SEQ ID NO: 50)

```
atgaaaatcggtattgaccgtctgtccttcttcatcccgaatttgtatttggacatgactgagctggcagaatcacgcggggatgatccagctaaata tcatattggaatcggacaagatcagatggcagtgaatcgcgcaaacgaggacatcataacactgggtgcaaacgctgcgagtaagatcgtgac agagaaagaccgcgagttgattgatatggtaatcgttggcacggaatcaggaattgaccactccaaagcaagcgccgtgattattcaccatctcct taaaattcagtcgttcgcccgttctttcgaggtaaaagaagcttgctatggcggaactgctgccctgcacatggcgaaggagtatgtcaaaaatcat ccggagcgtaaggtcttggtaattgcgtcagacatcgcgcgttatggtttggccagcggaggagaagttactcaaggcgtggggccgtagcc atgatgattacacaaaaccccggattctttcgattgaagacgatagtgtttttctcacagaggatatctatgatttctggcggcctgattactccgagt tccctgtagtggacgggccccttttcaaactcaacgtatatagagagttttcagaaagtttggaaccggcacaaggaattgtccggaagagggctg gaagattatcaagctattgcttttcacataccctatacgaagatgggtaagaaagcgctccagagtgttttagaccaaaccgatgaagataaccag gagcgcttaatggctagatatgaggagtctattcgctatagccggagaattggtaacctgtacacaggcagcttgtaccttggtcttacaagcttgtt ggaaaactctaaaagtttacaaccgggagatcggatcggcctcttttcctatggcagtggtgcggtgtccgagttctttaccgggtatttagaagaa aattaccaagagtacctgttcgctcaaagccatcaagaaatgctggatagccggactcggattacggtcgatgaatacgagaccatcttttcagag actctgccagaacatggtgaatgcgccgaatatacgagcgacgtcccctttctataaccaagattgagaacgacattcgttattataaaatctga
```

The mvaE nucleic acid can be expressed in a recombinant cell on a multicopy plasmid. The plasmid can be a high copy plasmid, a low copy plasmid, or a medium copy plasmid. Alternatively, the mvaE nucleic acid can be integrated into the host cell's chromosome. For both heterologous expression of an mvaE nucleic acid on a plasmid or as an integrated part of the host cell's chromosome, expression of the nucleic acid can be driven by either an inducible promoter or a constitutively expressing promoter. The promoter can be a strong driver of expression, it can be a weak driver of expression, or it can be a medium driver of expression of the mvaE nucleic acid.

The mvaS gene encodes a polypeptide that possesses HMG-CoA synthase activity. This polypeptide can convert acetoacetyl CoA to 3-hydroxy-3-methylglutaryl-CoA (HMG-CoA). Exemplary mvaS polypeptides and nucleic acids include naturally-occurring polypeptides and nucleic acids from any of the source organisms described herein as well as mutant polypeptides and nucleic acids derived from any of the source organisms described herein that have at least one activity of a mvaS polypeptide.

Mutant mvaS polypeptides include those in which one or more amino acid residues have undergone an amino acid substitution while retaining mvaS polypeptide activity (i.e., the ability to convert acetoacetyl CoA to 3-hydroxy-3-methylglutaryl-CoA). Amino acid substitutions in the mvaS polypeptide can be introduced to improve the functionality of the molecule. For example, amino acid substitutions that increase the binding affinity of the mvaS polypeptide for its substrate, or that improve its ability to convert acetoacetyl CoA to 3-hydroxy-3-methylglutaryl-CoA can be introduced into the mvaS polypeptide. In some aspects, the mutant mvaS polypeptides contain one or more conservative amino acid substitutions.

Standard methods, such as those described in Quant et al. (Biochem J., 1989, 262:159-164), can be used to determine whether a polypeptide has mvaS activity, by measuring HMG-CoA synthase activity. In an exemplary assay, HMG-CoA synthase activity can be assayed by spectrophotometrically measuring the disappearance of the enol form of acetoacetyl-CoA by monitoring the change of absorbance at 303 nm. A standard 1 ml assay system containing 50 mm-Tris/HCl, pH 8.0, 10 mM-MgCl2 and 0.2 mM-dithiothreitol at 30° C.; 5 mM-acetyl phosphate, 10 µM-acetoacetyl-CoA and 5 µl samples of extracts can be added, followed by simultaneous addition of acetyl-CoA (100 µM) and 10 units of PTA. HMG-CoA synthase activity is then measured as the difference in the rate before and after acetyl-CoA addition. The absorption coefficient of acetoacetyl-CoA under the conditions used (pH 8.0, 10 mM-$MgCl_2$), is $12.2 \times 10^3$ $M^{-1}$ $cm^{-1}$. By definition, 1 unit of enzyme activity causes 1 µmol of acetoacetyl-CoA to be transformed per minute.

Alternatively, production of mevalonate in recombinant cells can be measured by, without limitation, gas chromatography (see U.S. Patent Application Publication No.: US 2005/0287655 A1) or HPLC (See U.S. Patent Application Publication No.: 2011/0159557 A1). As an exemplary assay, cultures can be inoculated in shake tubes containing LB broth supplemented with one or more antibiotics and incubated for 14 h at 34° C. at 250 rpm. Next, cultures can be diluted into well plates containing TM3 media supplemented with 1% Glucose, 0.1% yeast extract, and 200 µM IPTG to final OD of 0.2. The plate are then sealed with a Breath Easier membrane (Diversified Biotech) and incubated at 34° C. in a shaker/incubator at 600 rpm for 24 hours. 1 mL of each culture is then centrifuged at 3,000×g for 5 min. Supernatant is then added to 20% sulfuric acid and incubated on ice for 5 min. The mixture is then centrifuged for 5 min at 3000×g and the supernatant was collected for HPLC analysis. The concentration of mevalonate in samples is determined by comparison to a standard curve of mevalonate (Sigma). The glucose concentration can additionally be measured by performing a glucose oxidase assay according to any method known in the art. Using HPLC, levels of mevalonate can be quantified by comparing the refractive index response of each sample versus a calibration curve generated by running various mevonate containing solutions of known concentration.

Exemplary mvaS nucleic acids include nucleic acids that encode a polypeptide, fragment of a polypeptide, peptide, or fusion polypeptide that has at least one activity of a mvaS polypeptide. Exemplary mvaS polypeptides and nucleic acids include naturally-occurring polypeptides and nucleic acids from any of the source organisms described herein as well as mutant polypeptides and nucleic acids derived from any of the source organisms described herein. Exemplary mvaS nucleic acids include, for example, mvaS nucleic acids isolated from *Listeria grayi*_DSM 20601, *Enterococcus faecium*, *Enterococcus gallinarum* EG2, *Enterococcus faecalis*, and/or *Enterococcus casseliflavus*. The mvaS nucleic acid encoded by the *Listeria grayi*_DSM 20601 mvaS gene can have at least about 99%, 98%, 97%, 96%, 95%, 95%, 93%, 92%, 91%, 90%, 89%, 88%, 87%, 86%, or 85% sequence identity to SEQ ID NO:51. The mvaS nucleic acid encoded by the *Enterococcus faecium* mvaS gene can have at least about 99%, 98%, 97%, 96%, 95%, 95%, 93%, 92%, 91%, 90%, 89%, 88%, 87%, 86%, or 85% sequence identity to SEQ ID NO:52. The mvaS nucleic acid encoded by the *Enterococcus gallinarum* EG2 mvaS gene can have at least about 99%, 98%, 97%, 96%, 95%, 95%, 93%, 92%, 91%, 90%, 89%, 88%, 87%, 86%, or 85% sequence identity to SEQ ID NO:53. The mvaS nucleic acid encoded by the *Enterococcus casseliflavus* mvaS gene can have at least about 99%, 98%, 97%, 96%, 95%, 95%, 93%, 92%, 91%, 90%, 89%, 88%, 87%, 86%, or 85% sequence identity to SEQ ID NO:54. The mvaS nucleic acid encoded by the *Enterococcus faecalis* mvaS gene can have at least about 99%, 98%, 97%, 96%, 95%, 95%, 93%, 92%, 91%, 90%, 89%, 88%, 87%, 86%, or 85% sequence identity to the mvaE gene previously disclosed in *E. coli* to produce mevalonate (see US 2005/0287655 A1; Tabata, K. and Hashimoto, S.-I. Biotechnology Letters 26: 1487-1491, 2004).

```
Sequence of Listeria grayi DSM 20601 mvaS
                                                                              (SEQ ID NO: 51)
atggaagaagtggtaattatagatgcacgtcggactccgattggtaaatatcacgggtcgttgaagaagttttcagcggtggcgctggggacggc cgtggctaaagacatgttcgaacgcaaccagaaaatcaaagaggagatcgcgcaggtcataattggtaatgtcttgcaggcaggaaatggcca gaacccccgcgcggcaagttgctcttcaatcagggttgtccgttgacattcccgcttctacaattaacgaggtttgtgggtctggtttgaaagctatctt gatgggcatggaacaaatccaactcggcaaagcgcaagtagtgctggcaggcggcattgaatcaatgacaaatgcgccaagcctgtcccacta taacaaggcggaggatacgtatagtgtcccagtgtcgagcatgacactggatggtctgacagacgcattttctagtaaacctatgggattaacagc ggaaaacgtcgcacagcgctacggtatctcccgtgaggcgcaagatcaattcgcatatcaatctcagatgaaagcagcaaaagcgcaggcag aaaacaaattcgctaaggaaattgtgccactggcgggtgaaactaaaaccatcacagctgacgaagggatcagatcccaaacaacgatggaga aactggcaagtctcaaacctgttttaaaaccgatggcactgtaaccgcagggaatgctagcaccattaatgacggggccgcccttgtgctgcttg ctagcaaaacttactgcgaaactaatgacataccgtaccttgcgacaatcaaagaaattgttgaagttggaatcgatccggagattatgggcatctc tccgataaaagcgatacaaacattgttacaaaatcaaaaagttagcctcgaagatattggagtttttgaaatcaaatgaagcctttgccgcaagtagc atagtggttgaatctgagttgggattagatccggctaaagttaaccgttatggggggtggtatatccttaggtcatgcaattggggcaaccggcgctc gcctggccacttcactggtgtatcaaatgcaggagatacaagcacgttatggtattgcgagcctgtgcgttggtggtggacttggactggcaatgc ttttagaacgtccaactattgagaaggctaaaccgacagacaaaaagttctatgaattgtcaccagctgaacggttgcaagagctggaaaatcaac ag aaaatcagttctgaaactaaacagcagttatctcagatgatgcttgccgaggacactgcaaaccatttgatagaaatcaaatatcagagattga actcccaatgggcgtcgggatgaacctgaaggttgatgggaaagcctatgttgtgccaatggcgacggaagagccgtccgtcatcgcggccat gtctaatggtgccaaaatggccggcgaaattcacactcagtcgaaagaacggctgctcagaggtcagattgttttcagcgcgaagaatccgaat gaaatcgaacagagaatagctgagaaccaagctttgattttcgaacgtgccgaacagtcctatccttccattgtgaaaagagagggaggtctccg ccgcattgcacttcgtcattttcctgccgattctcagcaggagtctgcggaccagtccacatttttatcagtggaccttttgtagatgtgaaagacgc gatgggggcaaatatcataaatgcaatacttgagggcgtcgcagccctgtttcgcgaatggttccccaatgaggaaattcttttttctattctctcgaa cttggctacggagagcttagtcacggctgtttgtgaagtcccatttagtgcacttagcaagagaggtggtgcaacggtggcccagaaaattgtgc aggcgtcgctcttcgcaaagacagacccataccgcgcagtgacccacaacaaagggattatgaacggtgtagaggctgttatgcttgccacag gcaacgacacgcgcgcagtctcagccgcttgtcatggatacgcagcgcgcaccggtagctatcagggtctgactaactggacgattgagtcgg atcgcctggtaggcgagataacactgccgctgccatcgctacagttggaggcgctaccaaagtgttgcccaaagctcaagcggcactggaga ttagtgatgttcactcttctcaagagcttgcagccttagcggcgtcagtaggtttagtacaaaatctcgcggccctgcgcgcactggtttccgaagg tatacaaaaagggcacatgtccatgcaagcccggtctctcgcaatcgcggtcggtgctgaaaaagccgagatcgagcaggtcgccgaaaagtt gcggcagaacccgccaatgaatcagcagcaggcgctccgttttcttggcgagatccgcgaacaatga
```

Sequence of *Enterococcus faecium* mvaS (SEQ ID NO: 52)

atgaacgtcggcattgacaaaattaattttttcgttccaccgtattatctggatatggtcgacctggcccacgcacgcgaagtggacccgaacaaat ttacaattggaattggacaggatcagatggctgtgagcaaaaagacgcacgatatcgtaacattcgcggctagtgccgcgaaggaaattttagaa cctgaggacttgcaagctatagacatggttatagttggtaccgaatcgggcattgacgagagcaaagcatccgcggtcgttttacatcgtttgttgg gcgtacaacctttcgctcgcagttttgaaattaaagaagcctgttacggggcaaccgcaggcattcagtttgccaagactcatatacaagcgaacc cggagagcaaggtcctggtaattgcaagcgatatagctcggtatggtcttcggtcaggtggagagccccacacaaggcgcaggggcagttgcta tgcttctcacggcaaatcccagaatcctgaccttcgaaaacgacaatctgatgttaacgcaggatatttatgacttctggagaccacttggtcacgct taccctatggtagatggccaccttccaatcaagtctatattgacagttttaagaaggtctggcaagcacattgcgaacgcaatcaagcttctatatc cgactatgccgcgattagttttcatattccgtatacaaaaatgggtaagaaagccctgctcgctgttttgcagatgaagtggaaactgaacaggaa cgcgttatggcacggtatgaagagtctatcgtatattcacgccgatcggcaacttgtatacggatcattgtacctggggctgatatccttattgga aaacagttctcacctgtcggcgggcgaccggataggattgtttagttatgggagtggcgctgtcagcgaattttctccggtcgtttagtggcaggc tatgaaaatcaattgaacaaagaggcgcatacccagctcctggatcagcgtcagaagctttccatcgaagagtatgaggcgattttttacagattcct tagaaattgatcaggatgcagcgttctcggatgacctgccatattccatccgcgagataaaaaaacacgattcggtactataaggagagctga Sequence of *Enterococcus gallinarum* EG2 mvaS (SEQ ID NO: 53)

atggaagaagttgtcatcattgacgcactgcgtactccaataggaaagtaccacggttcgctgaaagattacacagctgttgaactggggacagt agcagcaaaggcgttgctggcacgaaatcagcaagcaaaagaacacatagcgcaagttattattggcaacgtcctgcaagccggaagtgggc agaatccaggccgacaagtcagtttacagtcaggattgtcttctgatatccccgctagcacgatcaatgaagtgtgtggctcgggtatgaaagcga ttctgatgggtatggagcaaattcagctgaacaaagcctctgtggtcttaacaggcggaattgaaagcatgaccaacgcgccgctgtttagttatta caacaaggctgaggatcaatattcggcgccggttagcacaatgatgcacgatggtctaacagatgctttcagttccaaaccaatgggcttaaccg cagagaccgtcgctgagagatatgaattacgcgtaaggaacaagatgaatttgcttatcactctcaaatgaaggcggcaaaagcccaggcgg cgaaaaagtttgatcaggaaattgtaccctgacggaaaaatccggaacggttctccaggacgaaggcatcagagccgcgacaacagtcgag aagctagctgagcttaaaacggtgttcaaaaaagacggaacagttacagcgggtaacgcctctacgataaatgatgcgctgctatggtattaat agcatcaaaatcttattgcgaagaacaccagattccttatctggccgttataaaggagatcgttgaggtgggttttgcccccgaaataatgggtattt cccccattaaggctatagacaccctgctgaaaaatcaagcactgaccatagaggatataggaatatttgagattaatgaagcctttgctgcgagttc gattgtggtagaacgcgagttgggcctggaccccaaaaaagttaatcgctatggcggtggtatatcactcggccacgcaattggggcgacggg agctcgcattgcgacgaccgttgcttatcagctgaaagatacccaggagcgctacggtatagcttccttatgcgttggtggggtcttggattggc gatgcttctggaaaacccatcggccactgcctcacaaactaattttgatgaggaatctgcttccgaaaaaactgagaagaagaagtttatgcgcta gctcctaacgaacgcttagcgttttggaagcccaaggcgctattaccgctgctgaaaccctggtcttccaggagatgaccttaaacaaagagac agccaatcacttaatcgaaaaccaaatcagcgaagttgaaattcctttaggcgtgggcctgaacttacaggtgaatgggaaagcgtataatgttcc tctggccacggaggaaccgtccgttatcgctgcgatgtcgaatggcgccaaaatggctggtcctattacaacaacaagtcaggagaggctgtta cggggtcagattgtcttcatggacgtacaggacccagaagcaatattagcgaaagttgaatccgagcaagctaccattttcgcggtggcaaatga aacatacccgtctatcgtgaaaagaggaggaggtctgcgtagagtcattggcaggaatttcagtccggccgaaagtgacttagccacggcgtat gtatcaattgacctgatggtagatgttaaggatgcaatgggtgctaatatcatcaatagtatcctagaaggtgttgcggaattgttttagaaaatggttc ccagaagaagaaatcctgttctcaattctctccaatctcgcgacagaaagtctggtaacggcgacgtgctcagttccgtttgataaattgtccaaaa ctgggaatggtcgacaagtagctggtaaaatagtgcacgcggcgactttgctaagatagatccatacagagctgccacacacaataaaggtatt atgaatggcgttgaagcgttaatcttagccaccggtaatgacacccgtgcggtgtcggctgcatgccacggttacgcggcacgcaatgggcgaa tgcaagggcttacctcttggacgattatcgaagatcggctgataggctctatcacattacctttggctattgcgacagtgggggtgccacaaaaat cttgccaaaagcacaggccgccctggcgctaactggcgttgagacggcgtcggaactggccagcctggcggcgagtgtgggattagttcaaa atttggccgctttacgagcactagtgagcgagggcattcagcaagggcacatgagtatgcaagctagatccctggccattagcgtaggtgcgaa -continued

```
aggtactgaaatagagcaactagctgcgaagctgagggcagcgacgcaaatgaatcaggagcaggctcgtaaatttctgaccgaaataagaaa
ttaa
```

Sequence of *Enterococcus casseliflavus* mvaS (SEQ ID NO: 54)

```
atgaacgttggaattgataaaatcaattttttcgttccgccctatttcattgatatggtggatctcgctcatgcaagagaagttgaccccaacaagttca
ctataggaataggccaagatcagatggcagtaaacaagaaaacgcaagatatcgtaacgttcgcgatgcacgccgcgaaggatattctgactaa
ggaagatttacaggccatagatatggtaatagtggggactgagtctgggatcgacgagagcaaggcaagtgctgtcgtattgcatcggcttttag
gtattcagccttttgcgcgctcctttgaaattaaggaggcatgctatggggccactgccggccttcagtttgcaaaagctcatgtgcaggctaatcc
ccagagcaaggtcctggtggtagcttccgatatagcacgctacggactggcatccggaggagaaccgactcaaggtgtaggtgctgtggcaat
gttgatttccgctgatccagctatcttgcagttagaaaatgataatctcatgttgacccaagatatatacgattttttggcgcccggtcgggcatcaatat
cctatggtagacggccatctgtctaatgccgtctatatagacagctttaaacaagtctggcaagcacattgcgagaaaaaccaacggactgctaaa
gattatgctgcattgtcgttccatattccgtacacgaaaatgggtaagaaagctctgttagcggttttttgcggaggaagatgagacagaacaaaag
cggttaatggcacgttatgaagaatcaattgtatacagtcgtcggactggaaatctgtatactggctcactctatctgggcctgatttccttactggag
aatagtagcagtttacaggcgaacgatcgcataggtctgtttagctatggttcaggggccgttgcggaattttttcagtggcctcttggtaccgggtta
cgagaaacaattagcgcaagctgcccatcaagctcttctggacgaccggcaaaaactgactatcgcagagtacgaagccatgtttaatgaaacc
attgatattgatcaggaccagtcatttgaggatgacttactgtactccatcagagagatcaaaaacactattcgctactataacgaggagaatgaata
a
```

The mvaS nucleic acid can be expressed in a recombinant cell on a multicopy plasmid. The plasmid can be a high copy plasmid, a low copy plasmid, or a medium copy plasmid. Alternatively, the mvaS nucleic acid can be integrated into the host cell's chromosome. For both heterologous expression of an mvaS nucleic acid on a plasmid or as an integrated part of the host cell's chromosome, expression of the nucleic acid can be driven by either an inducible promoter or a constitutively expressing promoter. The promoter can be a strong driver of expression, it can be a weak driver of expression, or it can be a medium driver of expression of the mvaS nucleic acid.

Compositions of recombinant cells as described herein are contemplated within the scope of the invention as well. It is understood that recombinant cells also encompass progeny cells as well.

b. Nucleic Acids Encoding Polypeptides of the Lower MVA Pathway

In some aspects of the invention, the cells described in any of the compositions or methods described herein further comprise one or more nucleic acids encoding a lower mevalonate (MVA) pathway polypeptide(s). In some aspects, the lower MVA pathway polypeptide is an endogenous polypeptide. In some aspects, the endogenous nucleic acid encoding a lower MVA pathway polypeptide is operably linked to a constitutive promoter. In some aspects, the endogenous nucleic acid encoding a lower MVA pathway polypeptide is operably linked to an inducible promoter. In some aspects, the endogenous nucleic acid encoding a lower MVA pathway polypeptide is operably linked to a strong promoter. In a particular aspect, the cells are engineered to over-express the endogenous lower MVA pathway polypeptide relative to wild-type cells. In some aspects, the endogenous nucleic acid encoding a lower MVA pathway polypeptide is operably linked to a weak promoter.

The lower mevalonate biosynthetic pathway comprises mevalonate kinase (MVK), phosphomevalonate kinase (PMK), and diphosphomevalonte decarboxylase (MVD). In some aspects, the lower MVA pathway can further comprise isopentenyl diphosphate isomerase (IDI). Cells provided herein can comprise at least one nucleic acid encoding isoprene synthase, one or more upper MVA pathway polypeptides, and/or one or more lower MVA pathway polypeptides. Polypeptides of the lower MVA pathway can be any enzyme (a) that phosphorylates mevalonate to mevalonate 5-phosphate; (b) that converts mevalonate 5-phosphate to mevalonate 5-pyrophosphate; and (c) that converts mevalonate 5-pyrophosphate to isopentenyl pyrophosphate. More particularly, the enzyme that phosphorylates mevalonate to mevalonate 5-phosphate can be from the group consisting of *M. mazei* mevalonate kinase, *Lactobacillus* mevalonate kinase polypeptide, *Methanoccoides* mevalonate kinase polypeptide, *Methanoccoides burtonii* mevalonate kinase polypeptide, *Lactobacillus sakei* mevalonate kinase polypeptide, yeast mevalonate kinase polypeptide, *Saccharomyces cerevisiae* mevalonate kinase polypeptide, *Streptococcus* mevalonate kinase polypeptide, *Streptococcus pneumoniae* mevalonate kinase polypeptide, *Streptomyces* mevalonate kinase polypeptide, and *Streptomyces* CL190 mevalonate kinase polypeptide. In another aspect, the enzyme that phosphorylates mevalonate to mevalonate 5-phosphate is *M. mazei* mevalonate kinase.

In some aspects, the lower MVA pathway polypeptide is a heterologous polypeptide. In some aspects, the cells comprise more than one copy of a heterologous nucleic acid encoding a lower MVA pathway polypeptide. In some aspects, the heterologous nucleic acid encoding a lower MVA pathway polypeptide is operably linked to a constitutive promoter. In some aspects, the heterologous nucleic acid encoding a lower MVA pathway polypeptide is operably linked to an inducible promoter. In some aspects, the heterologous nucleic acid encoding a lower MVA pathway polypeptide is operably linked to a strong promoter. In some aspects, the heterologous nucleic acid encoding a lower MVA pathway polypeptide is operably linked to a weak promoter. In some aspects, the heterologous lower MVA pathway polypeptide is a polypeptide from *Saccharomyces cerevisiae, Enterococcus faecalis*, or *Methanosarcina mazei*.

The nucleic acids encoding a lower MVA pathway polypeptide(s) can be integrated into a genome of the cells or can be stably expressed in the cells. The nucleic acids encoding a lower MVA pathway polypeptide(s) can additionally be on a vector.

Exemplary lower MVA pathway polypeptides are also provided below: (i) mevalonate kinase (MVK); (ii) phosphomevalonate kinase (PMK); (iii) diphosphomevalonate decarboxylase (MVD); and (iv) isopentenyl diphosphate isomerase (IDI). In particular, the lower MVK polypeptide can be from the genus *Methanosarcina* and, more specifically, the lower MVK polypeptide can be from *Methanosarcina mazei*. In other aspects, the lower MVK polypeptide can be from the genus *Methanococcoides* and, more specifically, from *M. burtonii*. Additional examples of lower MVA pathway polypeptides can be found in U.S. Patent Application Publication 2010/0086978 the contents of which are expressly incorporated herein by reference in their entirety with respect to lower MVK pathway polypeptides and lower MVK pathway polypeptide variants.

Any one of the cells described herein can comprise IDI nucleic acid(s) (e.g., endogenous or heterologous nucleic acid(s) encoding IDI). Isopentenyl diphosphate isomerase polypeptides (isopentenyl-diphosphate delta-isomerase or IDI) catalyzes the interconversion of isopentenyl diphosphate (IPP) and dimethylallyl diphosphate (DMAPP) (e.g., converting IPP into DMAPP and/or converting DMAPP into IPP). Exemplary IDI polypeptides include polypeptides, fragments of polypeptides, peptides, and fusions polypeptides that have at least one activity of an IDI polypeptide. Standard methods (such as those described herein) can be used to determine whether a polypeptide has IDI polypeptide activity by measuring the ability of the polypeptide to interconvert IPP and DMAPP in vitro, in a cell extract, or in vivo. Exemplary IDI nucleic acids include nucleic acids that encode a polypeptide, fragment of a polypeptide, peptide, or fusion polypeptide that has at least one activity of an IDI polypeptide. Exemplary IDI polypeptides and nucleic acids include naturally-occurring polypeptides and nucleic acids from any of the source organisms described herein as well as mutant polypeptides and nucleic acids derived from any of the source organisms described herein.

Lower MVA pathway polypeptides include polypeptides, fragments of polypeptides, peptides, and fusions polypeptides that have at least one activity of a lower MVA pathway polypeptide. Exemplary lower MVA pathway nucleic acids include nucleic acids that encode a polypeptide, fragment of a polypeptide, peptide, or fusion polypeptide that has at least one activity of a lower MVA pathway polypeptide. Exemplary lower MVA pathway polypeptides and nucleic acids include naturally-occurring polypeptides and nucleic acids from any of the source organisms described herein. In addition, variants of lower MVA pathway polypeptides that confer the result of better isoprene production can also be used as well.

In some aspects, the lower MVA pathway polypeptide is a polypeptide from *Saccharomyces cerevisiae, Enterococcus faecalis*, or *Methanosarcina mazei*. In some aspects, the MVK polypeptide is selected from the group consisting of *Lactobacillus* mevalonate kinase polypeptide, *Lactobacillus sakei* mevalonate kinase polypeptide, yeast mevalonate kinase polypeptide, *Saccharomyces cerevisiae* mevalonate kinase polypeptide, *Streptococcus* mevalonate kinase polypeptide, *Streptococcus pneumoniae* mevalonate kinase polypeptide, *Streptomyces* mevalonate kinase polypeptide, *Streptomyces* CL190 mevalonate kinase polypeptide, *M. burtonii* mevalonate kinase polypeptide, and *Methanosarcina mazei* mevalonate kinase polypeptide. Any one of the promoters described herein (e.g., promoters described herein and identified in the Examples of the present disclosure including inducible promoters and constitutive promoters) can be used to drive expression of any of the MVA polypeptides described herein.

3. DXP Pathway Nucleic Acids and Polypeptides

In some aspects of the invention, the recombinant cells described in any of the compositions or methods described herein (including host cells that have been modified as described herein) further comprise one or more heterologous nucleic acids encoding a DXS polypeptide and/or other DXP pathway polypeptides. In some aspects, the cells further comprise a chromosomal copy of an endogenous nucleic acid encoding a DXS polypeptide and/or other DXP pathway polypeptides. In some aspects, the *E. coli* cells further comprise one or more nucleic acids encoding an IDI polypeptide and a DXS polypeptide and/or other DXP pathway polypeptides. In some aspects, one nucleic acid encodes the isoprene synthase polypeptide, IDI polypeptide, and DXS polypeptide and/or other DXP pathway polypeptides. In some aspects, one plasmid encodes the isoprene synthase polypeptide, IDI polypeptide, and DXS polypeptide and/or other DXP pathway polypeptides. In some aspects, multiple plasmids encode the isoprene synthase polypeptide, IDI polypeptide, and DXS polypeptide or other DXP pathway polypeptides.

Exemplary DXS polypeptides include polypeptides, fragments of polypeptides, peptides, and fusions polypeptides that have at least one activity of a DXS polypeptide. Standard methods (such as those described herein) can be used to determine whether a polypeptide has DXS polypeptide activity by measuring the ability of the polypeptide to convert pyruvate and D-glyceraldehyde-3-phosphate into 1-deoxy-D-xylulose-5-phosphate in vitro, in a cell extract, or in vivo. Exemplary DXS polypeptides and nucleic acids and methods of measuring DXS activity are described in more detail in International Publication No. WO 2009/076676, U.S. patent application Ser. No. 12/335,071 (US Publ. No. 2009/0203102), WO 2010/003007, US Publ. No. 2010/0048964, WO 2009/132220, and US Publ. No. 2010/0003716.

Exemplary DXP pathways polypeptides include, but are not limited to any of the following polypeptides: DXS polypeptides, DXR polypeptides, MCT polypeptides, CMK polypeptides, MCS polypeptides, HDS polypeptides, HDR polypeptides, and polypeptides (e.g., fusion polypeptides) having an activity of one, two, or more of the DXP pathway polypeptides. In particular, DXP pathway polypeptides include polypeptides, fragments of polypeptides, peptides, and fusions polypeptides that have at least one activity of a DXP pathway polypeptide. Exemplary DXP pathway nucleic acids include nucleic acids that encode a polypeptide, fragment of a polypeptide, peptide, or fusion polypeptide that has at least one activity of a DXP pathway polypeptide. Exemplary DXP pathway polypeptides and nucleic acids include naturally-occurring polypeptides and nucleic acids from any of the source organisms described herein as well as mutant polypeptides and nucleic acids derived from any of the source organisms described herein. Exemplary DXP pathway polypeptides and nucleic acids and methods of measuring DXP pathway polypeptide activity are described in more detail in International Publication No.: WO 2010/148150

Exemplary DXS polypeptides include polypeptides, fragments of polypeptides, peptides, and fusions polypeptides that have at least one activity of a DXS polypeptide. Standard methods (such as those described herein) can be used to determine whether a polypeptide has DXS polypeptide activity by measuring the ability of the polypeptide to convert pyruvate and D-glyceraldehyde-3-phosphate into 1-deoxy-D-xylulose-5-phosphate in vitro, in a cell extract, or in vivo. Exemplary DXS polypeptides and nucleic acids and methods of measuring DXS activity are described in more detail in International Publication No. WO 2009/076676, U.S. patent application Ser. No. 12/335,071 (US Publ. No. 2009/0203102), WO 2010/003007, US Publ. No. 2010/0048964, WO 2009/132220, and US Publ. No. 2010/0003716.

In particular, DXS polypeptides convert pyruvate and D-glyceraldehyde 3-phosphate into 1-deoxy-d-xylulose 5-phosphate (DXP). Standard methods can be used to determine whether a polypeptide has DXS polypeptide activity by measuring the ability of the polypeptide to convert pyruvate and D-glyceraldehyde 3-phosphate in vitro, in a cell extract, or in vivo.

DXR polypeptides convert 1-deoxy-d-xylulose 5-phosphate (DXP) into 2-C-methyl-D-erythritol 4-phosphate (MEP). Standard methods can be used to determine whether a polypeptide has DXR polypeptides activity by measuring the ability of the polypeptide to convert DXP in vitro, in a cell extract, or in vivo.

MCT polypeptides convert 2-C-methyl-D-erythritol 4-phosphate (MEP) into 4-(cytidine 5'-diphospho)-2-methyl-D-erythritol (CDP-ME). Standard methods can be used to determine whether a polypeptide has MCT polypeptides activity by measuring the ability of the polypeptide to convert MEP in vitro, in a cell extract, or in vivo.

CMK polypeptides convert 4-(cytidine 5'-diphospho)-2-C-methyl-D-erythritol (CDP-ME) into 2-phospho-4-(cytidine 5'-diphospho)-2-C-methyl-D-erythritol (CDP-MEP). Standard methods can be used to determine whether a polypeptide has CMK polypeptides activity by measuring the ability of the polypeptide to convert CDP-ME in vitro, in a cell extract, or in vivo.

MCS polypeptides convert 2-phospho-4-(cytidine 5'-diphospho)-2-C-methyl-D-erythritol (CDP-MEP) into 2-C-methyl-D-erythritol 2,4-cyclodiphosphate (ME-CPP or cMEPP). Standard methods can be used to determine whether a polypeptide has MCS polypeptides activity by measuring the ability of the polypeptide to convert CDP-MEP in vitro, in a cell extract, or in vivo.

HDS polypeptides convert 2-C-methyl-D-erythritol 2,4-cyclodiphosphate into (E)-4-hydroxy-3-methylbut-2-en-1-yl diphosphate (HMBPP or HDMAPP). Standard methods can be used to determine whether a polypeptide has HDS polypeptides activity by measuring the ability of the polypeptide to convert ME-CPP in vitro, in a cell extract, or in vivo.

HDR polypeptides convert (E)-4-hydroxy-3-methylbut-2-en-1-yl diphosphate into isopentenyl diphosphate (IPP) and dimethylallyl diphosphate (DMAPP). In one embodiment, the ispH gene can be used to encode for HDR polypeptides. IspH is also known as 1-hydroxy-2-methyl-2-(E)-butenyl 4-diphosphate reductase, 4Fe-4S protein, ECK0030, JW0027, lytB, yaaE, and b0029. Standard methods can be used to determine whether a polypeptide has HDR polypeptides activity by measuring the ability of the polypeptide to convert HMBPP in vitro, in a cell extract, or in vivo.

4. Source Organisms for MVA Pathway, Isoprene Synthase, IDI, and DXP Pathway Polypeptides Isoprene synthase, IDI, DXP pathway, and/or MVA pathway nucleic acids can be obtained from any organism that naturally contains isoprene synthase, IDI, DXP pathway, and/or MVA pathway nucleic acids. Isoprene is formed naturally by a variety of organisms, such as bacteria, yeast, plants, and animals. Some organisms contain the MVA pathway for producing isoprene. Isoprene synthase nucleic acids can be obtained, e.g., from any organism that contains an isoprene synthase. MVA pathway nucleic acids can be obtained, e.g., from any organism that contains the MVA pathway. IDI and DXP pathway nucleic acids can be obtained, e.g., from any organism that contains the IDI and DXP pathway.

The nucleic acid sequence of the isoprene synthase, DXP pathway, IDI, and/or MVA pathway nucleic acids can be isolated from a bacterium, fungus, plant, algae, or cyanobacterium. Exemplary source organisms include, for example, yeasts, such as species of *Saccharomyces* (e.g., *S. cerevisiae*), bacteria, such as species of *Escherichia* (e.g., *E. coli*), or species of *Methanosarcina* (e.g., *Methanosarcina mazei*), plants, such as kudzu or poplar (e.g., *Populus alba* or *Populus alba×tremula* CAC35696) or aspen (e.g., *Populus tremuloides*). Exemplary sources for isoprene synthases, IDI, and/or MVA pathway polypeptides which can be used are also described in International Patent Application Publication Nos. WO 2009/076676, WO 2010/003007, WO 2009/132220, WO 2010/031062, WO 2010/031068, WO 2010/031076, WO 2010/013077, WO 2010/031079, WO 2010/148150, WO 2010/078457, and WO 2010/148256.

In some aspects, the source organism is a yeast, such as *Saccharomyces* sp., *Schizosaccharomyces* sp., *Pichia* sp., or *Candida* sp.

In some aspects, the source organism is a bacterium, such as strains of *Bacillus* such as *B. lichenformis* or *B. subtilis*, strains of *Pantoea* such as *P. citrea*, strains of *Pseudomonas* such as *P. alcaligenes*, strains of *Streptomyces* such as *S. lividans* or *S. rubiginosus*, strains of *Escherichia* such as *E. coli*, strains of *Enterobacter*, strains of *Streptococcus*, or strains of Archaea such as *Methanosarcina mazei*.

As used herein, "the genus *Bacillus*" includes all species within the genus "*Bacillus*," as known to those of skill in the art, including but not limited to *B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus*, and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*." The production of resistant endospores in the presence of oxygen is considered the defining feature of the genus *Bacillus*, although this characteristic also applies to the recently named *Alicyclobacillus, Amphibacillus, Aneurinibacillus, Anoxybacillus, Brevibacillus, Filobacillus, Gracilibacillus, Halobacillus, Paenibacillus, Salibacillus, Thermobacillus, Ureibacillus*, and *Virgibacillus*.

In some aspects, the source organism is a gram-positive bacterium. Non-limiting examples include strains of *Streptomyces* (e.g., *S. lividans, S. coelicolor*, or *S. griseus*) and *Bacillus*. In some aspects, the source organism is a gram-negative bacterium, such as *E. coli* or *Pseudomonas* sp. In some aspects, the source organism is *L. acidophilus*.

In some aspects, the source organism is a plant, such as a plant from the family Fabaceae, such as the Faboideae subfamily. In some aspects, the source organism is kudzu, poplar (such as *Populus alba×tremula* CAC35696), aspen (such as *Populus tremuloides*), or *Quercus robur*.

In some aspects, the source organism is an algae, such as a green algae, red algae, glaucophytes, chlorarachniophytes, euglenids, chromista, or dinoflagellates.

In some aspects, the source organism is a cyanobacteria, such as cyanobacteria classified into any of the following groups based on morphology: Chroococcales, Pleurocapsales, Oscillatoriales, Nostocales, or Stigonematales.

5. Phosphoketolase Nucleic Acids and Polypeptides

In some aspects of the invention, the recombinant cells described in any of the compositions or methods described herein further comprise one or more nucleic acids encoding a phosphoketolase polypeptide or a polypeptide having phosphoketolase activity. In some aspects, the phosphoketolase polypeptide is an endogenous polypeptide. In some aspects, the endogenous nucleic acid encoding a phosphoketolase polypeptide is operably linked to a constitutive promoter. In some aspects, the endogenous nucleic acid encoding a phosphoketolase polypeptide is operably linked to an inducible promoter. In some aspects, the endogenous nucleic acid encoding a phosphoketolase polypeptide is operably linked to a strong promoter. In some aspects, more than one endogenous nucleic acid encoding a phosphoketolase polypeptide is used (e.g, 2, 3, 4, or more copies of an endogenous nucleic acid encoding a phosphoketolase polypeptide). In a particular aspect, the cells are engineered to overexpress the endogenous phosphoketolase polypeptide relative to wild-type cells. In some aspects, the endogenous nucleic acid encoding a phosphoketolase polypeptide is operably linked to a weak promoter.

Phosphoketolase enzymes catalyze the conversion of xylulose 5-phosphate to glyceraldehyde 3-phosphate and acetyl phosphate and/or the conversion of fructose 6-phosphate to erythrose 4-phosphate and acetyl phosphate. In certain embodiments, the phosphoketolase polypeptide catalyzes the conversion of sedoheptulose-7-phosphate to a product (e.g., ribose-5-phosphate) and acetyl phosphate. Thus, without being bound by theory, the expression of phosphoketolase as set forth herein can result in an increase in the amount of acetyl phosphate produced from a carbon source. This acetyl phosphate can be converted into acetyl-CoA which can then be utilized by the enzymatic activities of the MVA pathway to produce mevalonate, and/or isoprene. Thus the amount of these compounds produced from a carbon source may be increased. In certain embodiments, the phosphoketolase enzyme is capable of catalyzing the conversion of xylulose 5-phosphate to glyceraldehyde 3-phosphate and acetyl phosphate. In other embodiments, the phosphoketolase enzyme is capable of catalyzing the conversion of fructose 6-phosphate to erythrose 4-phosphate and acetyl phosphate. Thus, without being bound by theory, the expression of phosphoketolase as set forth herein can result in an increase in the amount of acetyl phosphate produced from a carbohydrate source. This acetyl phosphate can be converted into acetyl-CoA which can then be utilized by the enzymatic activities of the MVA pathway to produce isoprene. Thus the amount of these compounds produced from a carbohydrate substrate may be increased. Alternatively, production of Acetyl-P and AcCoA can be increased without the increase being reflected in higher intracellular concentration. In certain embodiments, intracellular acetyl-P or acetyl-CoA concentrations will remain unchanged or even decrease, even though the phosphoketolase reaction is taking place.

Accordingly, in certain embodiments, the recombinant cells described herein in any of the methods described herein further comprise one or more nucleic acids encoding a phosphoketolase polypeptide or a polypeptide having phosphoketolase activity. In some aspects, the phosphoketolase polypeptide is an endogenous polypeptide. In some aspects, the endogenous nucleic acid encoding a phosphoketolase polypeptide is operably linked to a constitutive promoter. In some aspects, the endogenous nucleic acid encoding a phosphoketolase polypeptide is operably linked to an inducible promoter. In some aspects, the endogenous nucleic acid encoding a phosphoketolase polypeptide is operably linked to a strong promoter. In some aspects, more than one endogenous nucleic acid encoding a phosphoketolase polypeptide is used (e.g, 2, 3, 4, or more copies of an endogenous nucleic acid encoding a phosphoketolase polypeptide). In a particular aspect, the cells are engineered to overexpress the endogenous phosphoketolase polypeptide relative to wild-type cells. In some aspects, the endogenous nucleic acid encoding a phosphoketolase polypeptide is operably linked to a weak promoter.

Exemplary phosphoketolase nucleic acids include nucleic acids that encode a polypeptide, fragment of a polypeptide, peptide, or fusion polypeptide that has at least one activity of a phosphoketolase polypeptide. Exemplary phosphoketolase polypeptides and nucleic acids include naturally-occurring polypeptides and nucleic acids from any of the source organisms described herein as well as mutant polypeptides and nucleic acids derived from any of the source organisms described herein. In some aspects, a nucleic acid encoding a phosphoketolase is from *Clostridium acetobutylicum, Lactobacillus reuteri, Lactobacillus plantarum, Lactobacillus paraplantarum, Bifidobacterium longum, Bifidobacterium animalis, Bifidobacterium breve, Enterococcus gallinarum, Gardnerella vaginalis, Ferrimonas balearica, Mucilaginibacter paludis, Nostoc punctiforme, Nostoc punctiforme PCC 73102, Pantoea, Pedobactor saltans, Rahnella aquatilis, Rhodopseudomonas palustris, Streptomyces griseus, Streptomyces avermitilis, Nocardiopsis dassonvillei,* and/or *Thermobifida fusca*. Additional examples of phosphoketolase enzymes which can be used herein are described in U.S. Pat. No. 7,785,858 and International Patent Application Publication No. WO 2011/159853 which are incorporated by reference herein.

Standard methods can be used to determine whether a polypeptide has phosphoketolase peptide activity by measuring the ability of the peptide to convert D-fructose 6-phosphate or D-xylulose 5-phosphate into acetyl-P. Acetyl-µ can then be converted into ferryl acetyl hydroxamate, which can be detected spectrophotometrically (Meile et al., J. Bact. 183: 2929-2936, 2001). Any polypeptide identified as having phosphoketolase peptide activity as described herein is suitable for use in the present invention.

In other aspects, exemplary phosphoketolase nucleic acids include, for example, a phosphoketolase isolated from *Lactobacillus reuteri, Bifidobacterium longum, Ferrimonas balearica, Pedobactor saltans, Streptomyces griseus,* and/or *Nocardiopsis dassonvillei*. Additional examples of phosphoketolase enzymes which can be used herein are described in U.S. Pat. No. 7,785,858, which is incorporated by reference herein.

In any of the embodiments herein, the recombinant cells can be further engineered to increase the activity of one or more of the following genes selected from the group consisting of ribose-5-phosphate isomerase (rpiA and/or rpiB), D-ribulose-5-phosphate 3-epimerase (rpe), transketolase (tktA and/or tktB), transaldolase B (tal B), phosphate acetyltransferase (pta and/or eutD). In another embodiment, the recombinant cells can be further engineered to decrease the activity of one or more genes of the following genes including glucose-6-phosphate dehydrogenase (zwf), 6-phosphofructokinase-1 (pfkA and/or pfkB), fructose bisphosphate aldolase (fba, fbaA, fbaB, and/or fbaC), glyceraldehyde-3-phosphate dehydrogenase (gapA and/or gapB), acetate kinase (ackA), citrate synthase (gltA), EI (ptsI), EIICB$^{Glc}$ (ptsG), EIIA$^{Glc}$ (crr), and/or HPr (ptsH).

Pathways Involving Glyceraldehyde 3-Phosphate

Glyceraldehyde 3-phosphate dehydrogenase (gapA and/or gapB) is a crucial enzyme of glycolysis catalyzes the conversion of glyceraldehyde 3-phosphate into 1,3-biphospho-D-glycerate (Branlant G. and Branlant C. 1985. Eur. J. Biochem. 150:61-66).

In certain aspects, recombinant cells comprising one or more expressed nucleic acids encoding monophosphate decarboxylase and/or isopentenyl kinase polypeptides as disclosed herein further compare one more nucleic acids encoding a phosphoketolase polypeptide. In order to direct carbon towards the phosphoketolase enzyme, glyceraldehyde 3-phosphate dehydrogenase expression can be modulated (e.g., decrease enzyme activity) to allow more carbon to flux towards fructose 6-phosphate and xylulose 5-phosphate, thereby increasing the eventual production of isoprene. Decrease of glyceraldehyde 3-phosphate dehydrogenase activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, 99%. Or 100%. In some aspects, the activity of glyceraldehyde 3-phosphate dehydrogenase is modulated by decreasing the activity of an endogenous glyceraldehyde 3-phosphate dehydrogenase. This can be accomplished by replacing the endogenous glyceraldehyde 3-phosphate dehydrogenase gene promoter with a synthetic constitutively low expressing promoter. The gene encoding glyceraldehyde 3-phosphate dehydrogenase can also be deleted. The gene encoding glyceraldehyde 3-phosphate dehydrogenase can also be replaced by a *Bacillus* enzyme catalyzing the same reaction but producing NADPH rather than NADH. The decrease of the activity of glyceraldehyde 3-phosphate dehydrogenase can result in more carbon flux into the mevalonate-dependent biosynthetic pathway in comparison to cells that do not have decreased expression of glyceraldehyde 3-phosphate dehydrogenase. In any aspects of the invention, provided herein are recombinant cells comprising one or more expressed nucleic acids encoding monophosphate decarboxylase and/or isopentenyl kinase polypeptides as disclosed herein and further engineered to decrease the activity of glyceraldehyde 3-phosphate dehydrogenase (gapA and/or gapB). Activity modulation (e.g., decreased) of glyceraldehyde 3-phosphate dehydrogenase isozymes is also contemplated herein. In any aspects of the invention, provided herein are recombinant cells comprising one or more heterologously expressed nucleic acids encoding monophosphate decarboxylase and/or isopentenyl kinase polypeptides as disclosed herein and further engineered to decrease the activity of a glyceraldehyde 3-phosphate dehydrogenase (gapA and/or gapB) isozyme.

a. Pathways Involving the Entner-Doudoroff Pathway

The Entner-Doudoroff (ED) pathway is an alternative to the Emden-Meyerhoff-Parnass (EMP-glycolysis) pathway. Some organisms, like *E. coli*, harbor both the ED and EMP pathways, while others have only one or the other. *Bacillus subtilis* has only the EMP pathway, while *Zymomonas mobilis* has only the ED pathway (Peekhaus and Conway. 1998. J. Bact. 180:3495-3502; Stulke and Hillen. 2000. Annu. Rev. Microbiol. 54, 849-880; Dawes et al. 1966. Biochem. J. 98:795-803). Fructose bisphophate aldolase (fba, fbaA, fbaB, and/or fbaC) interacts with the Entner-Doudoroff pathway and reversibly catalyzes the conversion of fructose 1,6-bisphosphate into dihydroxyacetone phosphate (DHAP) and glyceraldehyde 3-phosphate (GAP) (Baldwin S. A., et. al., Biochem J. (1978) 169(3):633-41).

Phosphogluconate dehydratase (edd) removes one molecule of $H_2O$ from 6-phospho-D-gluconate to form 2-dehydro-3-deoxy-D-gluconate 6-phosphate, while 2-keto-3-deoxygluconate 6-phosphate aldolase (eda) catalyzes an aldol cleavage (Egan et al. 1992. J. Bact. 174:4638-4646). The two genes are in an operon.

Metabolites that can be directed into the phosphoketolase pathway can also be diverted into the ED pathway. To avoid metabolite loss to the ED-pathway, phosphogluconate dehydratase gene (e.g., the endogenous phosphogluconate dehydratase gene) and/or an 2-keto-3-deoxygluconate 6-phosphate aldolase gene (e.g., the endogenous 2-keto-3-deoxygluconate 6-phosphate aldolase gene) activity is attenuated. One way of achieving attenuation is by deleting phosphogluconate dehydratase (edd) and/or 2-keto-3-deoxygluconate 6-phosphate aldolase (eda). This can be accomplished by replacing one or both genes with a chloramphenicol or kanamycin cassette followed by looping out of the cassette. Without these enzymatic activities, more carbon can flux through the phosphoketolase enzyme, thus increasing the yield of isoprene.

The activity of phosphogluconate dehydratase (edd) and/or 2-keto-3-deoxygluconate 6-phosphate aldolase (eda) can also be decreased by other molecular manipulations of the enzymes. The decrease of enzyme activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%.

In some cases, attenuating the activity of the endogenous phosphogluconate dehydratase gene and/or the endogenous 2-keto-3-deoxygluconate 6-phosphate aldolase gene results in more carbon flux into the mevalonate dependent biosynthetic pathway in comparison to cells that do not have attenuated endogenous phosphogluconate dehydratase gene and/or endogenous acetate kinase2-keto-3-deoxygluconate 6-phosphate aldolase gene expression.

b. Pathways Involving the Oxidative Branch of the Pentose Phosphate Pathway

*E. coli* uses the pentose phosphate pathway to break down hexoses and pentoses and to provide cells with intermediates for various anabolic pathways. It is also a major producer of NADPH. The pentose phosphate pathway is composed from an oxidative branch (with enzymes like glucose 6-phosphate 1-dehydrogenase (zwf), 6-phosphogluconolactonase (pgl) or 6-phosphogluconate dehydrogenase (gnd)) and a non-oxidative branch (with enzymes such as transketolase (tktA), transaldolase (talA or talB), ribulose-5-phosphate-epimerase and (or) ribose-5-phosphate epimerase) (Sprenger. 1995. Arch. Microbiol. 164:324-330).

In order to direct carbon towards the phosphoketolase enzyme, the non-oxidative branch of the pentose phosphate pathway (transketolase, transaldolase, ribulose-5-phosphate-epimerase and (or) ribose-5-phosphate epimerase) expression can be modulated (e.g., increase enzyme activity) to allow more carbon to flux towards fructose 6-phosphate and xylulose 5-phosphate, thereby increasing the eventual production of isoprene. Increase of transketolase, transaldolase, ribulose-5-phosphate-epimerase and (or) ribose-5-phosphate epimerase activity can be any amount of increase of specific activity or total activity as compared to when no manipulation has been effectuated. In some instances, the enzyme activity is increased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, 99%, or 100%. In some aspects, the activity of transketolase, transaldolase, ribulose-5-phosphate-epimerase and (or) ribose-5-phosphate epimerase is modulated by increasing the activity of an endogenous transketolase, transaldolase, ribulose-5-phosphate-epimerase and (or) ribose-5-phosphate epimerase. This can be accomplished by replacing the endogenous transketolase, transaldolase, ribulose-5-phosphate-epimerase and (or) ribose-5-phosphate epimerase gene promoter with a synthetic constitutively high expressing promoter. The genes encoding transketolase, transaldolase, ribulose-5-phosphate-epimerase and (or) ribose-5-phosphate epimerase can also be cloned on a plasmid behind an appropriate promoter. The increase of the activity of transketolase, transaldolase, ribulose-5-phosphate-epimerase and (or) ribose-5-phosphate epimerase can result in more carbon flux into the mevalonate dependent biosynthetic pathway in comparison to cells that do not have increased expression of transketolase, transaldolase, ribulose-5-phosphate-epimerase and (or) ribose-5-phosphate epimerase.

c. Pathways Involving Phosphofructokinase

Phosphofructokinase is a crucial enzyme of glycolysis which catalyzes the phosphorylation of fructose 6-phosphate. *E. coli* has two isozymes encoded by pfkA and pfkB. Most of the phosphofructokinase activity in the cell is due to pfkA (Kotlarz et al. 1975 Biochim. Biophys. Acta 381:257-268).

In order to direct carbon towards the phosphoketolase enzyme, phosphofructokinase expression can be modulated (e.g., decrease enzyme activity) to allow more carbon to flux towards fructose 6-phosphate and xylulose 5-phosphate, thereby increasing the eventual production of isoprene. Decrease of phosphofructokinase activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, 99%. Or 100%. In some aspects, the activity of phosphofructokinase is modulated by decreasing the activity of an endogenous phosphofructokinase. This can be accomplished by replacing the endogenous phosphofructokinase gene promoter with a synthetic constitutively low expressing promoter. The gene encoding phosphofructokinase can also be deleted. The decrease of the activity of phosphofructokinase can result in more carbon flux into the mevalonate dependent biosynthetic pathway in comparison to cells that do not have decreased expression of phosphofructokinase.

6. Additional Host Cell Mutations

The invention also contemplates additional host cell mutations that increase carbon flux through the MVA pathway. By increasing the carbon flow, more isoprene can be produced. The recombinant cells comprising acetoacetyl-CoA synthase as described herein can also be engineered for increased carbon flux towards mevalonate production wherein the activity of one or more enzymes from the group consisting of: (a) citrate synthase, (b) phosphotransacetylase; (c) acetate kinase; (d) lactate dehydrogenase; (e) NADP-dependent malic enzyme, and; (f) pyruvate dehydrogenase; (g) 6-phosphogluconolactonase; (h) phosphoenolpyruvate carboxylase; (i) the inhibitor of RssB activity during magnesium starvation protein; (j) the acrA component of the multidrug efflux pump acrAB-TolC; and (k) the fumarate and nitrate reduction sRNA (FNR) is modulated.

a. Citrate Synthase Pathway

Citrate synthase catalyzes the condensation of oxaloacetate and acetyl-CoA to form citrate, a metabolite of the Tricarboxylic acid (TCA) cycle (Ner, S. et al. 1983. *Biochemistry,* 22: 5243-5249; Bhayana, V. and Duckworth, H. 1984. *Biochemistry* 23: 2900-2905). In *E. coli,* this enzyme, encoded by gltA, behaves like a trimer of dimeric subunits. The hexameric form allows the enzyme to be allosterically regulated by NADH. This enzyme has been widely studied (Wiegand, G., and Remington, S. 1986. *Annual Rev. Biophysics Biophys. Chem.* 15: 97-117; Duckworth et al. 1987. *Biochem Soc Symp.* 54:83-92; Stockell, D. et al. 2003. *J. Biol. Chem.* 278: 35435-43; Maurus, R. et al. 2003. *Biochemistry.* 42:5555-5565). To avoid allosteric inhibition by NADH, replacement by or supplementation with the *Bacillus subtilis* NADH-insensitive citrate synthase has been considered (Underwood et al. 2002. *Appl. Environ. Microbiol.* 68:1071-1081; Sanchez et al. 2005. *Met. Eng.* 7:229-239).

The reaction catalyzed by citrate synthase is directly competing with the thiolase catalyzing the first step of the mevalonate pathway, as they both have acetyl-CoA as a substrate (Hedl et al. 2002. *J. Bact.* 184:2116-2122). Therefore, one of skill in the art can modulate citrate synthase expression (e.g., decrease enzyme activity) to allow more carbon to flux into the mevalonate pathway, thereby increasing the eventual production of isoprene. Decrease of citrate synthase activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%. In some aspects, the activity of citrate synthase is modulated by decreasing the activity of an endogenous citrate synthase gene. This can be accomplished by chromosomal replacement of an endogenous citrate synthase gene with a transgene encoding an NADH-insensitive citrate synthase or by using a transgene encoding an NADH-insensitive citrate synthase that is derived from *Bacillus subtilis.* The activity of citrate synthase can also be modulated (e.g., decreased) by replacing the endogenous citrate synthase gene promoter with a synthetic constitutively low expressing promoter. The decrease of the activity of citrate synthase can result in more carbon flux into the mevalonate dependent biosynthetic pathway in comparison to microorganisms that do not have decreased expression of citrate synthase. In any aspects of the invention, provided herein are recombinant cells comprising one or more expressed nucleic acids encoding monophosphate decarboxylase and/or isopentenyl kinase polypeptides as disclosed herein and further engineered to decrease the activity of citrate synthase (gltA). Activity modulation (e.g., decreased) of citrate synthase isozymes is also contemplated herein. In any aspects of the invention, provided herein are recombinant cells comprising one or more expressed nucleic acids encoding monophosphate decarboxylase and/or isopentenyl kinase polypeptides as disclosed herein and further engineered to decrease the activity of a citrate synthase isozyme.

b. Pathways Involving Phosphotransacetylase and/or Acetate Kinase

Phosphotransacetylase ((encoded in *E. coli* by (i) pta (Shimizu et al. 1969. Biochim. Biophys. Acta 191: 550-558) or (ii) eutD (Bologna et al. 2010. J of Microbiology. 48:629-636)) catalyzes the reversible conversion between acetyl-CoA and acetylphosphate (acetyl-μ), while acetate kinase (encoded in *E. coli* by ackA) (Kakuda, H. et al. 1994. J. Biochem. 11:916-922) uses acetyl-μ to form acetate. These genes can be transcribed as an operon in *E. coli*. Together, they catalyze the dissimilation of acetate, with the release of ATP. Thus, one of skill in the art can increase the amount of available acetyl Co-A by attenuating the activity of phosphotransacetylase gene (e.g., the endogenous phosphotransacetylase gene) and/or an acetate kinase gene (e.g., the endogenous acetate kinase gene). In certain embodiments, enhancement is achieved by placing an upregulated promoter upstream of the gene in the chromosome, or to place a copy of the gene behind an adequate promoter on a plasmid. In order to decrease the amount of acetyl-coA going towards acetate, the activity of acetate kinase gene (e.g., the endogenous acetate kinase gene) can be decreased or attenuated. One way of achieving attenuation is by deleting phosphotransacetylase (pta) and/or acetate kinase (ackA). This can be accomplished by replacing one or both genes with a chloramphenicol cassette followed by looping out of the cassette. Acetate is produced by *E. coli* for a variety of reasons (Wolfe, A. 2005. Microb. Mol. Biol. Rev. 69:12-50). Without being bound by theory, since ackA-pta use acetyl-CoA, deleting those genes might allow carbon not to be diverted into acetate and to increase the yield of isoprene. Without being bound by theory, deletion of ackA could result in decreased carbon being diverted into acetate production (since ackA use acetyl-CoA) and thereby increase the yield of isoprene.

In some aspects, the recombinant microorganism produces decreased amounts of acetate in comparison to microorganisms that do not have attenuated endogenous phosphotransacetylase gene and/or endogenous acetate kinase gene expression. Decrease in the amount of acetate produced can be measured by routine assays known to one of skill in the art. The amount of acetate reduction is at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99% as compared when no molecular manipulations are done.

The activity of phosphotransacetylase (pta) and/or acetate kinase (ackA) can also be decreased by other molecular manipulation of the enzymes. The decrease of enzyme activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%.

The activity of phosphotransacetylase (pta and/or eutD) can be increased by other molecular manipulations of the enzymes. The increase of enzyme activity can be and increase in any amount of specific activity or total activity as compared to when no manipulation has been effectuated. In some instances, the increase of enzyme activity is increased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%. In one embodiment the activity of pta is increased by altering the promoter and/or rbs on the chromosome, or by expressing it from a plasmid. In any aspects of the invention, provided herein are recombinant cells comprising one or more heterologously expressed nucleic acids encoding monophosphate decarboxylase and/or isopentenyl kinase polypeptides as disclosed herein and further engineered to increase the activity of phosphotransacetylase (pta and/or eutD). Activity modulation (e.g., increased) of phosphotransacetylase isozymes is also contemplated herein. In any aspects of the invention, provided herein are recombinant cells comprising one or more expressed nucleic acids encoding monophosphate decarboxylase and/or isopentenyl kinase polypeptides as disclosed herein and further engineered to increase the activity of a phosphotransacetylase (pta and/or eutD) isozyme.

The activity of acetate kinase (ackA) can also be decreased by other molecular manipulations of the enzymes. The decrease of enzyme activity can be any amount of reduction of specific activity or total activity as compared to when no manipulation has been effectuated. In some instances, the enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%. In any aspects of the invention, provided herein are recombinant cells comprising one or more heterologously expressed nucleic acids encoding phosphoketolase polypeptides as disclosed herein and further engineered to decrease the activity of acetate kinase (ackA). Activity modulation (e.g., decreased) of acetate kinase isozymes is also contemplated herein. In any aspects of the invention, provided herein are recombinant cells comprising one or more expressed nucleic acids encoding monophosphate decarboxylase and/or isopentenyl kinase polypeptides as disclosed herein and further engineered to decrease the activity of a acetate kinase isozyme.

In some cases, attenuating the activity of the endogenous phosphotransacetylase gene and/or the endogenous acetate kinase gene results in more carbon flux into the mevalonate dependent biosynthetic pathway in comparison to microorganisms that do not have attenuated endogenous phosphotransacetylase gene and/or endogenous acetate kinase gene expression.

c. Pathways Involving Lactate Dehydrogenase

In *E. coli*, D-Lactate is produced from pyruvate through the enzyme lactate dehydrogenase (encoded by ldhA) (Bunch, P. et al. 1997. Microbiol. 143:187-195). Production of lactate is accompanied with oxidation of NADH, hence lactate is produced when oxygen is limited and cannot accommodate all the reducing equivalents. Thus, production of lactate could be a source for carbon consumption. As such, to improve carbon flow through to isoprene production, one of skill in the art can modulate the activity of lactate dehydrogenase, such as by decreasing the activity of the enzyme.

Accordingly, in one aspect, the activity of lactate dehydrogenase can be modulated by attenuating the activity of an endogenous lactate dehydrogenase gene. Such attenuation can be achieved by deletion of the endogenous lactate dehydrogenase gene. Other ways of attenuating the activity of lactate dehydrogenase gene known to one of skill in the art may also be used. By manipulating the pathway that involves lactate dehydrogenase, the recombinant microorganism produces decreased amounts of lactate in comparison to microorganisms that do not have attenuated endogenous lactate dehydrogenase gene expression. Decrease in the amount of lactate produced can be measured by routine assays known to one of skill in the art. The amount of lactate reduction is at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99% as compared when no molecular manipulations are done.

The activity of lactate dehydrogenase can also be decreased by other molecular manipulations of the enzyme. The decrease of enzyme activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%.

Accordingly, in some cases, attenuation of the activity of the endogenous lactate dehydrogenase gene results in more carbon flux into the mevalonate dependent biosynthetic pathway in comparison to microorganisms that do not have attenuated endogenous lactate dehydrogenase gene expression.

d. Pathways Involving Malic Enzyme

Malic enzyme (in *E. coli* sfcA and maeB) is an anaplerotic enzyme that catalyzes the conversion of malate into pyruvate (using NAD+ or NADP+) by the equation below:

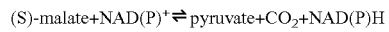

$$(S)\text{-malate} + NAD(P)^+ \rightleftharpoons pyruvate + CO_2 + NAD(P)H$$

Thus, the two substrates of this enzyme are (S)-malate and $NAD(P)^+$, whereas its 3 products are pyruvate, $CO_2$, and NADPH.

Expression of the NADP-dependent malic enzyme (maeB) (Iwikura, M. et al. 1979. J. Biochem. 85: 1355-1365) can help increase isoprene yield by 1) bringing carbon from the TCA cycle back to pyruvate, direct precursor of acetyl-CoA, itself direct precursor of the mevalonate pathway and 2) producing extra NADPH which could be used in the HMG-CoA reductase reaction (Oh, M K et al. (2002) *J. Biol. Chem.* 277: 13175-13183; Bologna, F. et al. (2007) J. Bact. 189:5937-5946).

As such, more starting substrate (pyruvate or acetyl-CoA) for the downstream production of isoprene can be achieved by modulating, such as increasing, the activity and/or expression of malic enzyme. The NADP-dependent malic enzyme gene can be an endogenous gene. One non-limiting way to accomplish this is by replacing the endogenous NADP-dependent malic enzyme gene promoter with a synthetic constitutively expressing promoter. Another non-limiting way to increase enzyme activity is by using one or more heterologous nucleic acids encoding an NADP-dependent malic enzyme polypeptide. One of skill in the art can monitor the expression of maeB RNA during fermentation or culturing using readily available molecular biology techniques.

Accordingly, in some embodiments, the recombinant microorganism produces increased amounts of pyruvate in comparison to microorganisms that do not have increased expression of an NADP-dependent malic enzyme gene. In some aspects, increasing the activity of an NADP-dependent malic enzyme gene results in more carbon flux into the mevalonate dependent biosynthetic pathway in comparison to microorganisms that do not have increased NADP-dependent malic enzyme gene expression.

Increase in the amount of pyruvate produced can be measured by routine assays known to one of skill in the art. The amount of pyruvate increase can be at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99% as compared when no molecular manipulations are done.

The activity of malic enzyme can also be increased by other molecular manipulations of the enzyme. The increase of enzyme activity can be any amount of increase of specific activity or total activity as compared to when no manipulation has been effectuated. In some instances, the increase of enzyme activity is at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%.

e. Pathways Involving Pyruvate Dehydrogenase Complex

The pyruvate dehydrogenase complex, which catalyzes the decarboxylation of pyruvate into acetyl-CoA, is composed of the proteins encoded by the genes aceE, aceF and lpdA. Transcription of those genes is regulated by several regulators. Thus, one of skill in the art can increase acetyl-CoA by modulating the activity of the pyruvate dehydrogenase complex. Modulation can be to increase the activity and/or expression (e.g., constant expression) of the pyruvate dehydrogenase complex. This can be accomplished by different ways, for example, by placing a strong constitutive promoter, like PL.6 (aattcatataaaaaacatacagataac-catctgcggtgataaattatctctggcg-gtgttgacataaataccactggcggtgatactgagcacatca gcaggacgcact-gaccaccatgaaggtg (SEQ ID NO:30) lambda promoter, GenBank NC_001416), in front of the operon or using one or more synthetic constitutively expressing promoters.

Accordingly, in one aspect, the activity of pyruvate dehydrogenase is modulated by increasing the activity of one or more genes of the pyruvate dehydrogenase complex consisting of (a) pyruvate dehydrogenase (E1), (b) dihydrolipoyl transacetylase, and (c) dihydrolipoyl dehydrogenase. It is understood that any one, two or three of these genes can be manipulated for increasing activity of pyruvate dehydrogenase. In another aspect, the activity of the pyruvate dehydrogenase complex can be modulated by attenuating the activity of an endogenous pyruvate dehydrogenase complex repressor gene, further detailed below. The activity of an endogenous pyruvate dehydrogenase complex repressor can be attenuated by deletion of the endogenous pyruvate dehydrogenase complex repressor gene.

In some cases, one or more genes of the pyruvate dehydrogenase complex are endogenous genes. Another way to increase the activity of the pyruvate dehydrogenase complex is by introducing into the microorganism one or more heterologous nucleic acids encoding one or more polypeptides from the group consisting of (a) pyruvate dehydrogenase (E1), (b) dihydrolipoyl transacetylase, and (c) dihydrolipoyl dehydrogenase.

By using any of these methods, the recombinant microorganism can produce increased amounts of acetyl Co-A in comparison to microorganisms wherein the activity of pyruvate dehydrogenase is not modulated. Modulating the activity of pyruvate dehydrogenase can result in more carbon flux into the mevalonate dependent biosynthetic pathway in comparison to microorganisms that do not have modulated pyruvate dehydrogenase expression.

f. Combinations of Mutations

It is understood that for any of the enzymes and/or enzyme pathways described herein, molecular manipulations that modulate any combination (two, three, four, five or six) of the enzymes and/or enzyme pathways described herein is expressly contemplated. For ease of the recitation of the combinations, citrate synthase (OA) is designated as A, phosphotransacetylase (ptaB) is designated as B, acetate kinase (ackA) is designated as C, lactate dehydrogenase (ldhA) is designated as D, malic enzyme (sfcA or maeB) is designated as E, pyruvate decarboxylase (aceE, aceF, and/or lpdA) is designated as F, 6-phosphogluconolactonase (ybhE) is designated as G, and phosphoenolpyruvate carboxylase (ppl) is designated as H. As discussed above, aceE, aceF, and/or lpdA enzymes of the pyruvate decarboxylase complex can be used singly, or two of three enzymes, or three of three enzymes for increasing pyruvate decarboxylase activity.

Accordingly, for combinations of any two of the enzymes A-H, non-limiting combinations that can be used are: AB, AC, AD, AE, AF, AG, AH, BC, BD, BE, BF, BG, BH, CD, CE, CF, CG, CH, DE, DF, DG, DH, EF, EG, EH, and GH. For combinations of any three of the enzymes A-H, non-limiting combinations that can be used are: ABC, ABD, ABE, ABF, ABG, ABH, BCD, BCE, BCF, BCG, BCH, CDE, CDF, CDG, CDH, DEF, DEH, ACD, ACE, ACF, ACG, ACH, ADE, ADF, ADG, ADH, AEF, AEG, AEH, BDE, BDF, BDG, BDH, BEF, BEG, BEH, CEF, CEG, CEH, CFG, CFH, and CGH. For combinations of any four of the enzymes A-H, non-limiting combinations that can be used are: ABCD, ABCE, ABCF, ABCG, ABCH, ABDE, ABDF, ABDG, ABDH, ABEF, ABEG, ABEH, BCDE, BCDF, BCDG, BCDH, CDEF, CDEG, CDEH, ACDE, ACDF, ACDG, ACDH, ACEF, ACEG, ACEH, BCEF, BDEF, BGEF, BHEF, ADEF. For combinations of any five of the enzymes A-H, non-limiting combinations that can be used are: ABCDE, ABCDF, ABCDG, ABCDH, ABDEF, ABDEG, ABDEH, BCDEF, BCDEG, BCDEH, ACDEF, ACDEG, ACEDH, ABCEF, ABCEG, and ABCEH. For combinations of any six of the enzymes A-H, non-limiting combinations that can be used are: ABCDEF, ABCDEG, ABCDEH, BCDEFG, BCDEFH, and CDEFGH. For combinations of any seven of the enzymes A-H, non-limiting combinations that can be used are: ABCDEFG, ABCDEFH, BCDEFGH. In another aspect, all eight enzyme combinations are used ABCDEFGH.

Accordingly, the recombinant microorganism as described herein can achieve increased mevalonate production that is increased compared to microorganisms that are not grown under conditions of tri-carboxylic acid (TCA) cycle activity, wherein metabolic carbon flux in the recombinant microorganism is directed towards mevalonate production by modulating the activity of one or more enzymes from the group consisting of (a) citrate synthase, (b) phosphotransacetylase; (c) acetate kinase; (d) lactate dehydrogenase; (e) NADP-dependent malic enzyme, and; (f) pyruvate dehydrogenase; (g) 6-phosphogluconolactonase; (h) phosphoenolpyruvate carboxylase; (i) the inhibitor of RssB activity during magnesium starvation protein; (j) the acrA component of the multidrug efflux pump acrAB-TolC; and (k) the fumarate and nitrate reduction sRNA (FNR).

7. Other Regulators and Factors for Increased Isoprene Production

Other molecular manipulations can be used to increase the flow of carbon towards isoprene production. One method is to reduce, decrease or eliminate the effects of negative regulators for pathways that feed into the mevalonate pathway. For example, in some cases, the genes aceEF-lpdA are in an operon, with a fourth gene upstream pdhR. pdhR is a negative regulator of the transcription of its operon. In the absence of pyruvate, it binds its target promoter and represses transcription. It also regulates ndh and cyoABCD in the same way (Ogasawara, H. et al. 2007. J. Bact. 189:5534-5541). In one aspect, deletion of pdhR regulator can improve the supply of pyruvate, and hence the production of isoprene via the alternative lower MVA pathway (e.g., MVK, PMevDC, IPK, and/or IDI).

In other embodiments, any of the resultant strains described above can be further engineered to modulate the activity of the Entner-Doudoroff pathway. The gene coding for phosphogluconate dehydratase or aldolase can be attenuated or deleted. In other embodiments, any of the resultant strains described above may also be engineered to decrease or remove the activity of acetate kinase or citrate synthase. In other embodiments, any of the strains the resultant strain may also be engineered to decrease or remove the activity of phosphofructokinase. In other embodiments, any of the resultant strains described above may also be engineered to modulate the activity of glyceraldehyde-3-phosphate dehydrogenase. The activity of glyceraldehyde-3-phosphate dehydrogenase can be modulated by decreasing its activity. In other embodiments, the enzymes from the non-oxidative branch of the pentose phosphate pathway, such as transketolase, transaldolase, ribulose-5-phosphate-epimerase and (or) ribose-5-phosphate epimerase can be overexpressed.

In other aspects, the host cells can be further engineered to increase intracellular acetyl-phospate concentrations by introducing heterologous nucleic acids encoding sedoheptulose-1,7-bisphosphatase/fructose-1,6-bisphosphate aldolase and sedoheptulose-1,7-bisphosphatase/fructose-1,6-bisphosphate phosphatase. In certain embodiments, the host cells having these molecular manipulations can be combined with attenuated or deleted transaldolase (talB) and phosphofructokinase (pfkA and/or pfkB) genes, thereby allowing faster conversion of erythrose 4-phosphate, dihydroxyacetone phosphate, and glyceraldehyde 3-phosphate into sedoheptulose 7-phosphate and fructose 1-phosphate.

In other aspects, the introduction of 6-phosphogluconolactonase (PGL) into microorganisms (such as various E. coli strains) which lack PGL can be used to improve production of isoprene. PGL may be introduced using chromosomal integration or extra-chromosomal vehicles, such as plasmids. In yet other aspects, PGL may be deleted from the genome of cells (for example, microorganisms, such as various E. coli strains) which express a PGL to improve production of mevalonate and/or isoprene. In another aspect, a heterologous nucleic acid encoding a PGL polypeptide can be expressed in a cell which does not endogenously express PGL. In some aspects, deletion of PGL results in any of about 10%, 20%, 30%, 40%, 50%, 60%, 70%, 80%, 90%, or 100%, inclusive, such as any values in between these percentages, higher percent yield of isoprene in comparison to microorganisms that express PGL. In other aspects, deletion of PGL results in any of about 10%, 20%, 30%, 40%, 50%, 60%, 70%, 80%, 90%, or 100%, inclusive, including any values in between these percentages, higher instantaneous percent yield of isoprene in comparison to microorganisms that express PGL. In other aspects, deletion of PGL results in any of about 10%, 20%, 30%, 40%, 50%, 60%, 70%, 80%, 90%, or 100%, inclusive, including any values in between these percentages, higher cell productivity index for isoprene in comparison to microorganisms that express PGL. In other aspects, deletion of PGL results in any of about 10%, 20%, 30%, 40%, 50%, 60%, 70%, 80%, 90%, or 100%, inclusive, including any values in between these percentages, higher volumetric productivity of isoprene in comparison to microorganisms that express PGL. In other aspects, deletion of PGL results in any of about 10%, 20%, 30%, 40%, 50%, 60%, 70%, 80%, 90%, or 100%, inclusive, including any values in between these percentages, higher peak specific productivity of isoprene in comparison to microorganisms that express PGL. In some aspects the deletion of PGL results in peak specific productivity being maintained for a longer period of time in comparison to microorganisms that express PGL.

8. Vectors

Suitable vectors can be used for any of the compositions and methods described herein. For example, suitable vectors can be used to optimize the expression of one or more copies of a gene encoding an isoprene synthase, an acetoacetyl co-A synthase, an MVA pathway enzyme, a DXP pathway enzyme, a phosphoketolase, and/or a polyprenyl pyrophosphate synthase, in a cell. In some aspects, the vector contains a selective marker. Examples of selectable markers include, but are not limited to, antibiotic resistance nucleic acids (e.g., kanamycin, ampicillin, carbenicillin, gentamicin, hygromycin, phleomycin, bleomycin, neomycin, or chloramphenicol) and/or nucleic acids that confer a metabolic advantage, such as a nutritional advantage on the host cell. In some aspects, one or more copies of an isoprene synthase, an acetoacetyl co-A synthase, an MVA pathway enzyme, a DXP pathway enzyme, a phosphoketolase, and/or a polyprenyl pyrophosphate synthases nucleic acid(s) integrate into the genome of host cells without a selective marker.

Any one of the vectors characterized or used in the Examples of the present disclosure can be used.

9. Exemplary Host Cells

One of skill in the art will recognize that expression vectors are designed to contain certain components which optimize gene expression for certain host strains. Such optimization components include, but are not limited to origin of replication, promoters, and enhancers. The vectors and components referenced herein are described for exemplary purposes and are not meant to narrow the scope of the invention.

Any microorganism or progeny thereof that can be used to heterologously express genes can be used for modulation of any of the genes described herein for increased production of isoprene (e.g., citrate synthase, phosphotransacetylase, acetate kinase, lactate dehydrogenase, malic enzyme, pyruvate dehydrogenase, 6-phosphogluconolactonase, phosphoenolpyruvate carboxylase and/or FNR). Also, any microorganism or progeny thereof that can be used to heterologously express genes can be used to express one or more heterologous nucleic acids encoding an isoprene synthase, acetoacetyl co-A synthase, MVA pathway enzyme, DXP pathway enzyme, phosphoketolase, and/or a polyprenyl pyrophosphate synthase polypeptides in a cell. In some aspects, any microorganism or progeny thereof can be used to heterologously express one or more genes encoding isoprene synthase (such as, but not limited to, isoprene synthase genes from *A. hypogaea, M. pruriens, C. cajans, G. max, G. soja, L. japonicus, M. truncatula, C. limon, C. tenuipile, V. vinifera, Q. petraea, Q. ilex, E. globulus*, and/or *M. alternifolia*). Bacteria cells, including gram positive or gram negative bacteria can be used to express any of the nucleic acids or polypeptides described above. In some embodiments, the host cell is a gram-positive bacterium. Non-limiting examples include strains of *Streptomyces* (e.g., *S. lividans, S. coelicolor, S. rubiginosus*, or *S. griseus*), *Streptococcus, Bacillus* (e.g., *B. lichenformis* or *B. subtilis*), *Listeria* (e.g., *L. monocytogenes*), *Corynebacteria*, or *Lactobacillus* (e.g., *L.* spp). In some embodiments, the source organism is a gram-negative bacterium. Non-limiting examples include strains of *Escherichia* (e.g., *E. coli*), *Pseudomonas* (e.g., *P. alcaligenes*), *Pantoea* (e.g., *P. citrea*), *Enterobacter*, or *Helicobacter* (*H. pylori*). In particular, one or more copies of a nucleic acid encoding an isoprene synthase, acetoacetyl co-A synthase, MVA pathway enzyme, DXP pathway enzyme, phosphoketolase, and/or a polyprenyl pyrophosphate synthase polypeptides can be expressed in any one of *P. citrea, B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus, B. thuringiensis, S. albus, S. lividans, S. coelicolor, S. griseus, Pseudomonas* sp., and *P. alcaligenes* cells. In some aspects, the host cell can be a *Lactobacilis* spp., such as *Lactobacillus* lactis or a *Lactobacillus plantarum*.

Exemplary host cells include, for example, yeasts, such as species of *Saccharomyces* (e.g., *S. cerevisiae*), bacteria, such as species of *Escherichia* (e.g., *E. coli*), archaea, such as species of *Methanosarcina* (e.g., *Methanosarcina mazei*), plants, such as kudzu or poplar (e.g., *Populus alba* or *Populus alba×tremula* CAC35696) or aspen (e.g., *Populus tremuloides*).

There are numerous types of anaerobic cells that can be used as host cells in the compositions and methods of the present invention. In one aspect of the invention, the cells described in any of the compositions or methods described herein are obligate anaerobic cells and progeny thereof. Obligate anaerobes typically do not grow well, if at all, in conditions where oxygen is present. It is to be understood that a small amount of oxygen may be present, that is, there is some tolerance level that obligate anaerobes have for a low level of oxygen. In one aspect, obligate anaerobes engineered to produce isoprene can serve as host cells for any of the methods and/or compositions described herein and are grown under substantially oxygen-free conditions, wherein the amount of oxygen present is not harmful to the growth, maintenance, and/or fermentation of the anaerobes.

In another aspect of the invention, the host cells described and/or used in any of the compositions or methods described herein are facultative anaerobic cells and progeny thereof. Facultative anaerobes can generate cellular ATP by aerobic respiration (e.g., utilization of the TCA cycle) if oxygen is present. However, facultative anaerobes can also grow in the absence of oxygen. This is in contrast to obligate anaerobes which die or grow poorly in the presence of greater amounts of oxygen. In one aspect, therefore, facultative anaerobes can serve as host cells for any of the compositions and/or methods provided herein and can be engineered to produce isoprene. Facultative anaerobic host cells can be grown under substantially oxygen-free conditions, wherein the amount of oxygen present is not harmful to the growth, maintenance, and/or fermentation of the anaerobes, or can be alternatively grown in the presence of greater amounts of oxygen.

The host cell can additionally be a filamentous fungal cell and progeny thereof. (See, e.g., Berka & Barnett, *Biotechnology Advances*, (1989), 7(2):127-154). In some aspects, the filamentous fungal cell can be any of *Trichoderma longibrachiatum, T. viride, T. koningii, T. harzianum, Penicillium* sp., *Humicola insolens, H. lanuginose, H. grisea, Chrysosporium* sp., *C. lucknowense, Gliocladium* sp., *Aspergillus* sp., such as *A. oryzae, A. niger, A sojae, A. japonicus, A. nidulans*, or *A. awamori, Fusarium* sp., such as *F. roseum, F. graminum F. cerealis, F. oxysporuim*, or *F. venenatum, Neurospora* sp., such as *N. crassa, Hypocrea* sp., *Mucor* sp., such as *M. miehei, Rhizopus* sp. or *Emericella* sp. In some aspects, the fungus is *A. nidulans, A. awamori, A. oryzae, A. aculeatus, A. niger, A. japonicus, T. reesei, T. viride, F. oxysporum*, or *F. solani*. In certain embodiments, plasmids or plasmid components for use herein include those described in U.S. patent pub. No. US 2011/0045563.

The host cell can also be a yeast, such as *Saccharomyces* sp., *Schizosaccharomyces* sp., *Pichia* sp., or *Candida* sp. In some aspects, the *Saccharomyces* sp. is *Saccharomyces cerevisiae* (See, e.g., Romanos et al., *Yeast*, (1992), 8(6):423-488). In certain embodiments, plasmids or plasmid components for use herein include those described in U.S. Pat. No. 7,659,097 and U.S. patent pub. No. US 2011/0045563.

The host cell can also be a species of plant, such as a plant from the family Fabaceae, such as the Faboideae subfamily. In some aspects, the host cell is kudzu, poplar (such as *Populus alba×tremula* CAC35696), aspen (such as *Populus tremuloides*), or *Quercus robur*.

The host cell can additionally be a species of algae, such as a green algae, red algae, glaucophytes, chlorarachniophytes, euglenids, chromista, or dinoflagellates. (See, e.g., Saunders & Warmbrodt, "*Gene Expression in Algae and Fungi, Including Yeast*," (1993), National Agricultural Library, Beltsville, Md.). In certain embodiments, plasmids or plasmid components for use herein include those described in U.S. Patent Pub. No. US 2011/0045563. In some aspects, the host cell is a cyanobacterium, such as cyanobacterium classified into any of the following groups based on morphology: Chlorococcales, Pleurocapsales, Oscillatoriales, Nostocales, or Stigonematales (See, e.g., Lindberg et al., Metab. Eng., (2010) 12(1):70-79). In certain embodiments, plasmids or plasmid components for use herein include those described in U.S. Patent Pub. No.: US 2010/0297749; US 2009/0282545 and Intl. Pat. Appl. No. WO 2011/034863.

*E. coli* host cells can be used to express one or more isoprene synthase, acetoacetyl co-A synthase, MVA pathway enzyme, DXP pathway enzyme, phosphoketolase, and/or a polyprenyl pyrophosphate synthase polypeptides in the compositions and methods described herein. In one aspect, the host cell is a recombinant cell of an *Escherichia coli* (*E. coli*) strain, or progeny thereof, capable of producing isoprene, that expresses one or more nucleic acids encoding isoprene synthase, acetoacetyl co-A synthase, MVA pathway enzyme, DXP pathway enzyme, phosphoketolase, and/or a polyprenyl pyrophosphate synthase polypeptide. The *E. coli* host cells can produce isoprene in amounts, peak titers, and cell productivities greater than that of the same cells lacking one or more heterologously expressed nucleic acids encoding isoprene synthase, acetoacetyl co-A synthase, MVA pathway enzyme, DXP pathway enzyme, phosphoketolase, and/or a polyprenyl pyrophosphate synthase polypeptide. In addition, the one or more heterologously expressed nucleic acids encoding isoprene synthase, acetoacetyl co-A synthase, MVA pathway enzyme, DXP pathway enzyme, phosphoketolase, and/or a polyprenyl pyrophosphate synthase polypeptide in *E. coli* can be chromosomal copies (e.g., integrated into the *E. coli* chromosome). In other aspects, the *E. coli* cells are in culture.

In other aspects, the host cell can be a species of yeast other than *S. cerevisiae* such as, but not limited to, a *Pichia* spp., a *Candida* spp., a *Hansenula* spp., a *Kluyveromyces* spp., a *Kluyveromyces* spp., or a *Schizosaccharomyces* spp. In still other aspects, the host cell can be a species of bacterium including, but not limited to, an *Arthrobacter* spp., a *Zymomonas* spp., a *Brevibacterium* spp., a *Clostridium* spp., an *Aerococcus* spp., a *Bacillus* spp., an *Actinobacillus* spp. (such as, but not limited to, *A. succinogens*), a *Carbobacterium* spp., a *Corynebacterium* spp., an *Enterococcus* spp., an *Erysipelothrix* spp., a *Gemella* spp., a *Geobacillus* spp., a *Globicatella* spp., a *Lactobacillus* spp. (such as, but not limited to, *L. lactis* and *L. rhammosus*), a *Lactococcus* spp., a *Leuconostoc* spp., a *Pediococcus* spp., a *Streptococcus* spp., a *Tetragenococcus* spp., an *Actinobacillus* spp., or a *Vagococcus* spp., In other aspects, the fermenting organism can be a fungus such as, but not limited to, a *Rhizopus* spp.

In other aspects, the host cell can be a lactic acid bacteria, such as those of the genera *Aerococcus, Bacillus, Carbobacterium, Enterococcus, Erysipelothrix, Gemella, Globicatella, Lactobacillus, Lactococcus, Leuconostoc, Pediococcus, Streptococcus, Tetragenococcus* and *Vagococcus*. For example, other bacteria of the genus *Lactobacillus* which may be substituted include, but are not limited to, *L. heiveticus, L. delbrueckii, L. casei, L, acidophilus, L. amylovorus, L. leichmanii* or *L. bulgaricus. L. amylovorus*, and *L. pentosus*.

Other exemplary host cells that can be used are described in US Pub. 2009/0203102, WO 2009/076676, WO 2010/003007, WO 2009/132220, WO 2010/031062, WO 2010/031068, WO 2010/031076, WO 2010/031077, and WO 2010/031079.

B. Methods for the Production of Isoprene

Provided herein are methods of producing isoprene by culturing any of the recombinant cells described herein under conditions such as those disclosed herein using any isoprene as described herein. In one aspect, isoprene can be produced by culturing recombinant cells expressing one or more nucleic acids encoding: (a) an isoprene synthase polypeptide, wherein the isoprene synthase polypeptide is encoded by a heterologous nucleic acid; and (b) one or more mevalonate (MVA) pathway polypeptides in culture media. In one aspect, one or more heterologous nucleic acids encoding a thiolase, HMG-CoA reductase, a lower MVA pathway polypeptide, and an isoprene synthase polypeptide can be used. In another aspect, isoprene can be produced by culturing recombinant cells comprising one or more heterologous nucleic acids encoding a thiolase, HMG-CoA reductase and HMG-CoA synthase, a lower MVA pathway polypeptide, and an isoprene synthase polypeptide. In yet another aspect, one or more heterologous nucleic acids encoding one or more upper MVA pathway polypeptides, one or more lower MVA pathway polypeptides, and/or one or more DXP pathway polypeptides can be used. In some aspects, the recombinant cells described herein exhibit any of about 10%, 15%, 20%, 25%, 30%, 35%, 40%, 45%, 50%, 55%, 60%, 65%, 70%, 75%, 80%, 95%, or 100%, inclusive, including any value in between these percentages, increased isoprene production in comparison to cells which do not comprise one or more heterologous nucleic acids encoding an isoprene synthase polypeptide and one or more MVA pathway polypeptides. The isoprene can be produced from any of the cells described herein and according to any of the methods described herein. Any of the cells can be used for the purpose of producing isoprene using any isoprene synthase as described herein.

The cells can further express one or more nucleic acid molecules encoding the lower MVA pathway polypeptide(s) described above (e.g., MVK, PMK, MVD, and/or IDI), any of the upper MVA pathways polypeptide(s) described above (e.g., a thiolase, an acetoacetyl-CoA synthase, an HMG-CoA reductase, and/or an HMG-CoA synthase) and/or any of the isoprene synthase polypeptide(s) described above (e.g. *A. hypogaea* isoprene synthase). In some aspects, the recombinant (e.g., bacterial) cells can be any of the cells described herein. Any of the isoprene synthases or variants thereof described herein, any of the bacterial strains described herein, any of the promoters described herein, and/or any of the vectors described herein can also be used to produce isoprene. In some aspects, the method of producing isoprene further comprises a step of recovering the isoprene.

In some aspects, the amount of isoprene produced is measured at a productivity time point. In some aspects, the productivity for the cells is about any of the amounts of isoprene disclosed herein. In some aspects, the cumulative, total amount of isoprene produced is measured. In some aspects, the cumulative total productivity for the cells is about any of the amounts of isoprene disclosed herein.

In some aspects, any of the cells described herein (for examples the cells in culture) produce isoprene at greater than about any of or about any of 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, or more nmole of isoprene/gram of cells for the wet weight of the cells/hour (nmole/$g_{wcm}$/hr). In some aspects, the amount of isoprene is between about 2 to about 5,000 nmole/$g_{wcm}$/hr, such as between about 2 to about 100 nmole/$g_{wcm}$/hr, about 100 to about 500 nmole/$g_{wcm}$/hr, about 150 to about 500 nmole/$g_{wcm}$/hr, about 500 to about 1,000 nmole/$g_{wcm}$/hr, about 1,000 to about 2,000 nmole/$g_{wcm}$/hr, or about 2,000 to about 5,000 nmole/$g_{wcm}$/hr. In some aspects, the amount of isoprene is between about 20 to about 5,000 nmole/$g_{wcm}$/hr, about 100 to about 5,000 nmole/$g_{wcm}$/hr, about 200 to about 2,000 nmole/$g_{wcm}$/hr, about 200 to about 1,000 nmole/$g_{wcm}$/hr, about 300 to about 1,000 nmole/$g_{wcm}$/hr, or about 400 to about 1,000 nmole/$g_{wcm}$/hr.

In some aspects, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 100,000, or more ng of isoprene/gram of cells for the wet weight of the cells/hr ($ng/g_{wcm}/h$). In some aspects, the amount of isoprene is between about 2 to about 5,000 $ng/g_{wcm}/h$, such as between about 2 to about 100 $ng/g_{wcm}/h$, about 100 to about 500 $ng/g_{wcm}/h$, about 500 to about 1,000 $ng/g_{wcm}/h$, about 1,000 to about 2,000 $ng/g_{wcm}/h$, or about 2,000 to about 5,000 $ng/g_{wcm}/h$. In some aspects, the amount of isoprene is between about 20 to about 5,000 $ng/g_{wcm}/h$, about 100 to about 5,000 $ng/g_{wcm}/h$, about 200 to about 2,000 $ng/g_{wcm}/h$, about 200 to about 1,000 $ng/g_{wcm}/h$, about 300 to about 1,000 $ng/g_{wcm}/h$, or about 400 to about 1,000 $ng/g_{wcm}/h$.

In some aspects, the cells in culture produce a cumulative titer (total amount) of isoprene at greater than about any of or about any of 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 50,000, 100,000, or more mg of isoprene/L of broth ($mg/L_{broth}$, wherein the volume of broth includes the volume of the cells and the cell medium). In some aspects, the amount of isoprene is between about 2 to about 5,000 $mg/L_{broth}$, such as between about 2 to about 100 $mg/L_{broth}$, about 100 to about 500 $mg/L_{broth}$, about 500 to about 1,000 $mg/L_{broth}$, about 1,000 to about 2,000 $mg/L_{broth}$, or about 2,000 to about 5,000 $mg/L_{broth}$. In some aspects, the amount of isoprene is between about 20 to about 5,000 $mg/L_{broth}$, about 100 to about 5,000 $mg/L_{broth}$, about 200 to about 2,000 $mg/L_{broth}$, about 200 to about 1,000 $mg/L_{broth}$, about 300 to about 1,000 $mg/L_{broth}$, or about 400 to about 1,000 $mg/L_{broth}$.

In some aspects, the isoprene produced by the cells in culture (such as any of the recombinant cells described herein) comprises at least about 1, 2, 5, 10, 15, 20, or 25% by volume of the fermentation offgas. In some aspects, the isoprene comprises between about 1 to about 25% by volume of the offgas, such as between about 5 to about 15%, about 15 to about 25%, about 10 to about 20%, or about 1 to about 10%.

In some embodiments, the cells are cultured in a culture medium under conditions permitting the production of isoprene by the cells. In some embodiments, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, or more nmole of isoprene/gram of cells for the wet weight of the cells/hour (nmole/gwcm/hr). In some embodiments, the amount of isoprene is between about 2 to about 5,000 nmole/gwcm/hr, such as between about 2 to about 100 nmole/gwcm/hr, about 100 to about 500 nmole/gwcm/hr, about 150 to about 500 nmole/gwcm/hr, about 500 to about 1,000 nmole/gwcm/hr, about 1,000 to about 2,000 nmole/gwcm/hr, or about 2,000 to about 5,000 nmole/gwcm/hr. The amount of isoprene in units of nmole/gwcm/hr can be measured as disclosed in U.S. Pat. No. 5,849,970. For example, two mL of headspace (e.g., headspace from a culture such as 2 mL of culture cultured in sealed vials at 32° C. with shaking at 200 rpm for approximately 3 hours) are analyzed for isoprene using a standard gas chromatography system, such as a system operated isothermally (85° C.) with an n-octane/porasil C column (Alltech Associates, Inc., Deerfield, Ill.) and coupled to a RGD2 mercuric oxide reduction gas detector (Trace Analytical, Menlo Park, Calif.) (see, e.g., Greenberg et al, Atmos. Environ. 27A: 2689-2692, 1993; Silver et al., Plant Physiol. 97:1588-1591, 1991). The gas chromatography area units are converted to nmol isoprene via a standard isoprene concentration calibration curve. In some embodiments, the value for the grams of cells for the wet weight of the cells is calculated by obtaining the $A_{600}$ value for a sample of the cell culture, and then converting the $A_{600}$ value to grams of cells based on a calibration curve of wet weights for cell cultures with a known $A_{600}$ value. In some embodiments, the grams of the cells is estimated by assuming that one liter of broth (including cell medium and cells) with an $A_{600}$ value of 1 has a wet cell weight of 1 gram. The value is also divided by the number of hours the culture has been incubating for, such as three hours.

In some embodiments, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 100,000, or more ng of isoprene/gram of cells for the wet weight of the cells/hr (ng/gwcm/h). In some embodiments, the amount of isoprene is between about 2 to about 5,000 ng/gwcm/h, such as between about 2 to about 100 ng/gwcm/h, about 100 to about 500 ng/gwcm/h, about 500 to about 1,000 ng/gwcm/h, about 1,000 to about 2,000 ng/gwcm/h, or about 2,000 to about 5,000 ng/gwcm/h. The amount of isoprene in ng/gwcm/h can be calculated by multiplying the value for isoprene production in the units of nmole/gwcm/hr discussed above by 68.1 (as described in Equation 5 below).

In some embodiments, the cells in culture produce a cumulative titer (total amount) of isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 50,000, 100,000, or more mg of isoprene/L of broth (mg/L broth, wherein the volume of broth includes the volume of the cells and the cell medium). In some embodiments, the amount of isoprene is between about 2 to about 5,000 mg/L broth, such as between about 2 to about 100 mg/L broth, about 100 to about 500 mg/L broth, about 500 to about 1,000 mg/L broth, about 1,000 to about 2,000 mg/L broth, or about 2,000 to about 5,000 mg/L broth. The specific productivity of isoprene in mg of isoprene/L of headspace from shake flask or similar cultures can be measured by taking a 1 ml sample from the cell culture at an $OD_{600}$ value of approximately 1.0, putting it in a 20 mL vial, incubating for 30 minutes, and then measuring the amount of isoprene in the headspace. If the $OD_{600}$ value is not 1.0, then the measurement can be normalized to an $OD_{600}$ value of 1.0 by dividing by the $OD_{600}$ value. The value of mg isoprene/L headspace can be converted to mg/Lbroth/hr/$OD_{600}$ of culture broth by multiplying by a factor of 38. The value in units of mg/Lbroth/hr/$OD_{600}$ can be multiplied by the number of hours and the $OD_{600}$ value to obtain the cumulative titer in units of mg of isoprene/L of broth.

The instantaneous isoprene production rate in mg/L broth/hr in a fermentor can be measured by taking a sample of the fermentor off-gas, analyzing it for the amount of isoprene (in units such as mg of isoprene per L of gas), and multiplying this value by the rate at which off-gas is passed though each liter of broth (e.g., at 1 vvm (volume of air/volume of broth/minute) this is 60 Lgas per hour). Thus, an off-gas level of 1 mg/Lgas corresponds to an instantaneous production rate of 60 mg/Lbroth/hr at air flow of 1 vvm. If desired, the value in the units mg/Lbroth/hr can be divided by the $OD_{600}$ value to obtain the specific rate in units of mg/Lbroth/hr/OD. The average value of mg isoprene/Lgas can be converted to the total product productivity (grams of isoprene per liter of fermentation broth, mg/Lbroth) by multiplying this average off-gas isoprene concentration by the total amount of off-gas sparged per liter of fermentation broth during the fermentation. Thus, an average off-gas isoprene concentration of 0.5 mg/Lbroth/hr over 10 hours at 1 vvm corresponds to a total product concentration of 300 mg isoprene/Lbroth.

In some embodiments, the cells in culture convert greater than or about 0.0015, 0.002, 0.005, 0.01, 0.02, 0.05, 0.1, 0.12, 0.14, 0.16, 0.2, 0.3, 0.4, 0.5, 0.6, 0.7, 0.8, 0.9, 1.0, 1.2, 1.4, or 1.6% of the carbon in the cell culture medium into isoprene. In some embodiments, the percent conversion of carbon into isoprene is between about 0.002 to about 1.6%, such as about 0.002 to about 0.005%, about 0.005 to about 0.01%, about 0.01 to about 0.05%, about 0.05 to about 0.15%, 0.15 to about 0.2%, about 0.2 to about 0.3%, about 0.3 to about 0.5%, about 0.5 to about 0.8%, about 0.8 to about 1.0%, or about 1.0 to about 1.6%. The percent conversion of carbon into isoprene (also referred to as "% carbon yield") can be measured by dividing the moles carbon in the isoprene produced by the moles carbon in the carbon source (such as the moles of carbon in batched and fed glucose and yeast extract). This number is multiplied by 100% to give a percentage value (as indicated in Equation 1).

% Carbon Yield=(moles carbon in isoprene produced)/(moles carbon in carbon source)*100    Equation 1%

For this calculation, yeast extract can be assumed to contain 50% w/w carbon.

% Carbon Yield=(39.1 g isoprene*1/68.1 mol/g*5 C/mol)/[(181221 g glucose*1/180 mol/g*6 C/mol)+(17780 g yeast extract*0.5*1/12 mol/g)]*100=0.042%    Equation 2%

One skilled in the art can readily convert the rates of isoprene production or amount of isoprene produced into any other units. Exemplary equations are listed below for inter-converting between units.

Units for Rate of Isoprene Production (Total and Specific)

1 g isoprene/$L_{broth}$/hr=14.7 mmol isoprene/$L_{broth}$/hr (total volumetric rate)    Equation 3

1 nmol isoprene/$g_{wcm}$/hr=1 nmol isoprene/$L_{broth}$/hr/$OD_{600}$ (This conversion assumes that one liter of broth with an $OD_{600}$ value of 1 has a wet cell weight of 1 gram.)    Equation 4

1 nmol isoprene/$g_{wcm}$/hr=68.1 ng isoprene/$g_{wcm}$/hr (given the molecular weight of isoprene)    Equation 5

1 nmol isoprene/$L_{gas}$$O_2$/hr=90 nmol isoprene/$L_{broth}$/hr (at an $O_2$ flow rate of 90 L/hr per L of culture broth)    Equation 6

1 μg isoprene/$L_{gas}$ isoprene in off-gas=60 μg isoprene/$L_{broth}$/hr at a flow rate of 60 $L_{gas}$ per $L_{broth}$ (1 vvm)    Equation 7

Units for Titer (Total and Specific)

1 nmol isoprene/mg cell protein=150 nmol isoprene/$L_{broth}$/$OD_{600}$ (This conversion assumes that one liter of broth with an $OD_{600}$ value of 1 has a total cell protein of approximately 150 mg)(specific productivity)    Equation 8

1 g isoprene/$L_{broth}$=14.7 mmol isoprene/$L_{broth}$ (total titer)    Equation 9

If desired, Equation 10 can be used to convert any of the units that include the wet weight of the cells into the corresponding units that include the dry weight of the cells.

Dry weight of cells=(wet weight of cells)/3.3    Equation 10

In some embodiments encompassed by the invention, a cell comprising a heterologous nucleic acid encoding an isoprene synthase polypeptide produces an amount of isoprene that is at least or about 2-fold, 3-fold, 5-fold, 10-fold, 25-fold, 50-fold, 100-fold, 150-fold, 200-fold, 400-fold, or greater than the amount of isoprene produced from a corresponding cell grown under essentially the same conditions without the heterologous nucleic acid encoding the isoprene synthase polypeptide.

In some embodiments encompassed by the invention, a cell comprising a heterologous nucleic acid encoding an isoprene synthase polypeptide and one or more heterologous nucleic acids encoding a DXS, IDI, and/or MVA pathway polypeptide produces an amount of isoprene that is at least or about 2-fold, 3-fold, 5-fold, 10-fold, 25-fold, 50-fold, 100-fold, 150-fold, 200-fold, 400-fold, or greater than the amount of isoprene produced from a corresponding cell grown under essentially the same conditions without the heterologous nucleic acids.

1. Transformation Methods

Nucleic acids encoding one or more copies of a nucleic acid encoding an mvaE and an mvaS polypeptide, an isoprene synthase polypeptide, MVA pathway polypeptides, DXP pathway polypeptides, phosphoketolase polypeptide, and/or polyprenyl pyrophosphate synthase polypeptides can be inserted into a microorganism using suitable techniques. Additionally, these nucleic acids or vectors containing them can be inserted into a host cell (e.g., a plant cell, a fungal cell, a yeast cell, or a bacterial cell described herein) using standard techniques for introduction of a DNA construct or vector into a host cell, such as transformation, electroporation, nuclear microinjection, transduction, transfection (e.g., lipofection mediated or DEAE-Dextrin mediated transfection or transfection using a recombinant phage virus), incubation with calcium phosphate DNA precipitate, high velocity bombardment with DNA-coated microprojectiles, and protoplast fusion. General transformation techniques are known in the art (See, e.g., *Current Protocols in Molecular Biology* (F. M. Ausubel et al. (eds.) Chapter 9, 1987; Sambrook et al., *Molecular Cloning: A Laboratory Manual*, 2$^{nd}$ ed., Cold Spring Harbor, 1989; and Campbell et al., Curr. Genet. 16:53-56, 1989). The introduced nucleic acids can be integrated into chromosomal DNA or maintained as extrachromosomal replicating sequences. Transformants can be selected by any method known in the art. Suitable methods for selecting transformants are described in International Publication No. WO 2009/076676, U.S. patent application Ser. No. 12/335,071 (US Publ. No. 2009/0203102), WO 2010/003007, US Publ. No. 2010/0048964, WO 2009/132220, and US Publ. No. 2010/0003716.

2. Exemplary Cell Culture Media

As used herein, the terms "minimal medium" or "minimal media" refer to growth medium containing the minimum nutrients possible for cell growth, generally, but not always, without the presence of amino acids (e.g., 1, 2, 3, 4, 5, 6, 7, 8, 9, 10, or more amino acids). Minimal medium can contain: (1) a carbon source for microbial growth; (2) various salts, which can vary among microbial species and growing conditions; and (3) water. The carbon source can vary significantly, from simple sugars like glucose to more complex hydrolysates of other biomass, such as yeast extract, as discussed in more detail below. The salts generally provide essential elements such as magnesium, nitrogen, phosphorus, and sulfur to allow the cells to synthesize proteins and nucleic acids. Minimal medium can also be supplemented with selective agents, such as antibiotics, to select for the maintenance of certain plasmids and the like. For example, if a microorganism is resistant to a certain antibiotic, such as ampicillin or tetracycline, then that antibiotic can be added to the medium in order to prevent cells lacking the resistance from growing. Medium can be supplemented with other compounds as necessary to select for desired physiological or biochemical characteristics, such as particular amino acids and the like.

Any minimal medium formulation can be used to cultivate the host cells. Exemplary minimal medium formulations include, for example, M9 minimal medium and TM3 minimal medium. Each liter of M9 minimal medium contains (1) 200 ml sterile M9 salts (64 g $Na_2HPO_4$-$7H_2O$, 15 g $KH_2PO_4$, 2.5 g NaCl, and 5.0 g $NH_4Cl$ per liter); (2) 2 ml of 1 M $MgSO_4$ (sterile); (3) 20 ml of 20% (w/v) glucose (or other carbon source); and (4) 100 µl of 1 M $CaCl_2$ (sterile). Each liter of TM3 minimal medium contains (1) 13.6 g $K_2HPO_4$; (2) 13.6 g $KH_2PO_4$; (3) 2 g $MgSO_4$*$7H_2O$; (4) 2 g Citric Acid Monohydrate; (5) 0.3 g Ferric Ammonium Citrate; (6) 3.2 g $(NH_4)_2SO_4$; (7) 0.2 g yeast extract; and (8) 1 ml of 1000× Trace Elements solution; pH is adjusted to ~6.8 and the solution is filter sterilized. Each liter of 1000× Trace Elements contains: (1) 40 g Citric Acid Monohydrate; (2) 30 g $MnSO_4.H_2O$; (3) 10 g NaCl; (4) 1 g $FeSO_4.7H_2O$; (4) 1 g $CoCl_2.6H_2O$; (5) 1 g $ZnSO_4.7H_2O$; (6) 100 mg $CuSO_4.5H_2O$; (7) 100 mg $H_3BO_3$; and (8) 100 mg $NaMoO_4.2H_2O$; pH is adjusted to ~3.0.

An additional exemplary minimal media includes (1) potassium phosphate $K_2HPO_4$, (2) Magnesium Sulfate $MgSO_4.7H_2O$, (3) citric acid monohydrate $C_6H_8O_7.H_2O$, (4) ferric ammonium citrate $NH_4FeC_6H_5O_7$, (5) yeast extract (from biospringer), (6) 1000× Modified Trace Metal Solution, (7) sulfuric acid 50% w/v, (8) foamblast 882 (Emerald Performance Materials), and (9) Macro Salts Solution 3.36 ml. All of the components are added together and dissolved in deionized $H_2O$ and then heat sterilized. Following cooling to room temperature, the pH is adjusted to 7.0 with ammonium hydroxide (28%) and q.s. to volume. Vitamin Solution and spectinomycin are added after sterilization and pH adjustment.

Any carbon source can be used to cultivate the host cells. The term "carbon source" refers to one or more carbon-containing compounds capable of being metabolized by a host cell or organism. For example, the cell medium used to cultivate the host cells can include any carbon source suitable for maintaining the viability or growing the host cells. In some aspects, the carbon source is a carbohydrate (such as monosaccharide, disaccharide, oligosaccharide, or polysaccharides), or invert sugar (e.g., enzymatically treated sucrose syrup).

In some aspects, the carbon source includes yeast extract or one or more components of yeast extract. In some aspects, the concentration of yeast extract is 0.1% (w/v), 0.09% (w/v), 0.08% (w/v), 0.07% (w/v), 0.06% (w/v), 0.05% (w/v), 0.04% (w/v), 0.03% (w/v), 0.02% (w/v), or 0.01% (w/v) yeast extract. In some aspects, the carbon source includes both yeast extract (or one or more components thereof) and another carbon source, such as glucose.

Exemplary monosaccharides include glucose and fructose; exemplary oligosaccharides include lactose and sucrose, and exemplary polysaccharides include starch and cellulose. Exemplary carbohydrates include C6 sugars (e.g., fructose, mannose, galactose, or glucose) and C5 sugars (e.g., xylose or arabinose).

In some aspects, the cells described herein are capable of using syngas as a source of energy and/or carbon. In some embodiments, the syngas includes at least carbon monoxide and hydrogen. In some embodiments, the syngas further additionally includes one or more of carbon dioxide, water, or nitrogen. In some embodiments, the molar ratio of hydrogen to carbon monoxide in the syngas is 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 3.0, 4.0, 5.0, or 10.0. In some embodiments, the syngas comprises 10, 20, 30, 40, 50, 60, 70, 80, or 90% by volume carbon monoxide. In some embodiments, the syngas comprises 10, 20, 30, 40, 50, 60, 70, 80, or 90% by volume hydrogen. In some embodiments, the syngas comprises 10, 20, 30, 40, 50, 60, 70, 80, or 90% by volume carbon dioxide. In some embodiments, the syngas comprises 10, 20, 30, 40, 50, 60, 70, 80, or 90% by volume water. In some embodiments, the syngas comprises 10, 20, 30, 40, 50, 60, 70, 80, or 90% by volume nitrogen.

Synthesis gas may be derived from natural or synthetic sources. The source from which the syngas is derived is referred to as a "feedstock." In some embodiments, the syngas is derived from biomass (e.g., wood, switch grass, agriculture waste, municipal waste) or carbohydrates (e.g., sugars). In other embodiments, the syngas is derived from coal, petroleum, kerogen, tar sands, oil shale, or natural gas. In other embodiments, the syngas is derived from rubber, such as from rubber tires.

Syngas can be derived from a feedstock by a variety of processes, including methane reforming, coal liquefaction, co-firing, fermentative reactions, enzymatic reactions, and biomass gasification. Biomass gasification is accomplished by subjecting biomass to partial oxidation in a reactor at temperatures above about 700° C. in the presence of less than a stoichiometric amount of oxygen. The oxygen is introduced into the bioreactor in the form of air, pure oxygen, or steam. Gasification can occur in three main steps: 1) initial heating to dry out any moisture embedded in the biomass; 2) pyrolysis, in which the biomass is heated to 300-500° C. in the absence of oxidizing agents to yield gas, tars, oils and solid char residue; and 3) gasification of solid char, tars and gas to yield the primary components of syngas. Co-firing is accomplished by gasification of a coal/biomass mixture. The composition of the syngas, such as the identity and molar ratios of the components of the syngas, can vary depending on the feedstock from which it is derived and the method by which the feedstock is converted to syngas.

Synthesis gas can contain impurities, the nature and amount of which vary according to both the feedstock and the process used in production. Fermentations may be tolerant to some impurities, but there remains the need to remove from the syngas materials such as tars and particulates that might foul the fermentor and associated equipment. It is also advisable to remove compounds that might contaminate the isoprene product such as volatile organic compounds, acid gases, methane, benzene, toluene, ethylbenzene, xylenes, $H_2S$, COS, $CS_2$, HCl, $O_3$, organosulfur compounds, ammonia, nitrogen oxides, nitrogen-containing organic compounds, and heavy metal vapors. Removal of impurities from syngas can be achieved by one of several means, including gas scrubbing, treatment with solid-phase adsorbents, and purification using gas-permeable membranes.

3. Exemplary Cell Culture Conditions

Materials and methods suitable for the maintenance and growth of the recombinant cells of the invention are described infra, e.g., in the Examples section. Other materials and methods suitable for the maintenance and growth of bacterial or cell cultures are well known in the art. Exemplary techniques can be found in International Publication No. WO 2009/076676, U.S. patent application Ser. No. 12/335,071 (U.S. Publ. No. 2009/0203102), WO 2010/003007, US Publ. No. 2010/0048964, WO 2009/132220, US Publ. No. 2010/0003716, *Manual of Methods for General Bacteriology* Gerhardt et al., eds), American Society for Microbiology, Washington, D.C. (1994) or Brock in *Biotechnology: A Textbook of Industrial Microbiology*, Second Edition (1989) Sinauer Associates, Inc., Sunderland, Mass. In some aspects, the cells are cultured in a culture medium under conditions permitting the expression of one or more MVA pathway, isoprene synthase, DXP pathway (e.g., DXS), IDI, MVA pathway, polypeptides encoded by a nucleic acid inserted into the host cells.

Standard cell culture conditions can be used to culture the cells (see, for example, WO 2004/033646 and references cited therein). In some aspects, cells are grown and maintained at an appropriate temperature, gas mixture, and pH (such as at about 20° C. to about 37° C., at about 6% to about 84% $CO_2$, and at a pH between about 5 to about 9). In some aspects, cells are grown at 35° C. in an appropriate cell medium. In some aspects, the pH ranges for fermentation are between about pH 5.0 to about pH 9.0 (such as about pH 6.0 to about pH 8.0 or about 6.5 to about 7.0). Cells can be grown under aerobic, anoxic, or anaerobic conditions based on the requirements of the host cells. In addition, more specific cell culture conditions can be used to culture the cells. For example, in some embodiments, the bacterial cells (such as *E. coli* cells) express one or more heterologous nucleic acids encoding mvaE and mvaS polypeptides under the control of a strong promoter in a low to medium copy plasmid and are cultured at 34° C.

Standard culture conditions and modes of fermentation, such as batch, fed-batch, or continuous fermentation that can be used are described in International Publication No. WO 2009/076676, U.S. patent application Ser. No. 12/335,071 (U.S. Publ. No. 2009/0203102), WO 2010/003007, US Publ. No. 2010/0048964, WO 2009/132220, US Publ. No. 2010/0003716. Batch and Fed-Batch fermentations are common and well known in the art and examples can be found in Brock, Biotechnology: *A Textbook of Industrial Microbiology*, Second Edition (1989) Sinauer Associates, Inc.

In some aspects, the cells are cultured under limited glucose conditions. By "limited glucose conditions" is meant that the amount of glucose that is added is less than or about 105% (such as about 100%, 90%, 80%, 70%, 60%, 50%, 40%, 30%, 20%, or 10%) of the amount of glucose that is consumed by the cells. In particular aspects, the amount of glucose that is added to the culture medium is approximately the same as the amount of glucose that is consumed by the cells during a specific period of time. In some aspects, the rate of cell growth is controlled by limiting the amount of added glucose such that the cells grow at the rate that can be supported by the amount of glucose in the cell medium. In some aspects, glucose does not accumulate during the time the cells are cultured. In various aspects, the cells are cultured under limited glucose conditions for greater than or about 1, 2, 3, 5, 10, 15, 20, 25, 30, 35, 40, 50, 60, or 70 hours. In various aspects, the cells are cultured under limited glucose conditions for greater than or about 5, 10, 15, 20, 25, 30, 35, 40, 50, 60, 70, 80, 90, 95, or 100% of the total length of time the cells are cultured. While not intending to be bound by any particular theory, it is believed that limited glucose conditions can allow more favorable regulation of the cells.

In some aspects, the bacterial cells are grown in batch culture. The bacterial cells can also be grown in fed-batch culture or in continuous culture. Additionally, the bacterial cells can be cultured in minimal medium, including, but not limited to, any of the minimal media described above. The minimal medium can be further supplemented with 1.0% (w/v) glucose, or any other six carbon sugar, or less. Specifically, the minimal medium can be supplemented with 1% (w/v), 0.9% (w/v), 0.8% (w/v), 0.7% (w/v), 0.6% (w/v), 0.5% (w/v), 0.4% (w/v), 0.3% (w/v), 0.2% (w/v), or 0.1% (w/v) glucose. Additionally, the minimal medium can be supplemented 0.1% (w/v) or less yeast extract. Specifically, the minimal medium can be supplemented with 0.1% (w/v), 0.09% (w/v), 0.08% (w/v), 0.07% (w/v), 0.06% (w/v), 0.05% (w/v), 0.04% (w/v), 0.03% (w/v), 0.02% (w/v), or 0.01% (w/v) yeast extract. Alternatively, the minimal medium can be supplemented with 1% (w/v), 0.9% (w/v), 0.8% (w/v), 0.7% (w/v), 0.6% (w/v), 0.5% (w/v), 0.4% (w/v), 0.3% (w/v), 0.2% (w/v), or 0.1% (w/v) glucose and with 0.1% (w/v), 0.09% (w/v), 0.08% (w/v), 0.07% (w/v), 0.06% (w/v), 0.05% (w/v), 0.04% (w/v), 0.03% (w/v), 0.02% (w/v), or 0.01% (w/v) yeast extract.

4. Exemplary Purification Methods

In some embodiments, any of the methods described herein further include a step of recovering the isoprene. For example, the isoprene produced using the compositions and methods of the invention can be recovered using standard techniques, such as gas stripping, membrane enhanced separation, fractionation, adsorption/desorption, pervaporation, thermal or vacuum desorption of isoprene from a solid phase, or extraction of isoprene immobilized or absorbed to a solid phase with a solvent (see, for example, U.S. Pat. Nos. 4,703,007 and 4,570,029, which are each hereby incorporated by reference in their entireties, particularly with respect to isoprene recovery and purification methods). In one aspect, the isoprene is recovered by absorption stripping (see, e.g., US Pub. No. 2011/0178261). In particular aspects, extractive distillation with an alcohol (such as ethanol, methanol, propanol, or a combination thereof) is used to recover the isoprene. In some embodiments, the recovery of isoprene involves the isolation of isoprene in a liquid form (such as a neat solution of isoprene or a solution of isoprene in a solvent). Gas stripping involves the removal of isoprene vapor from the fermentation off-gas stream in a continuous manner. Such removal can be achieved in several different ways including, but not limited to, adsorption to a solid phase, partition into a liquid phase, or direct condensation (such as condensation due to exposure to a condensation coil or do to an increase in pressure). In some embodiments, membrane enrichment of a dilute isoprene vapor stream above the dew point of the vapor resulting in the condensation of liquid isoprene. In some embodiments, the recovery is performed as described in U.S. Patent Application Publication No. 2011/0178261. In some aspects, the isoprene is compressed and condensed.

The recovery of isoprene may involve one step or multiple steps. In some embodiments, the removal of isoprene vapor from the fermentation off-gas and the conversion of isoprene to a liquid phase are performed simultaneously. For example, isoprene can be directly condensed from the off-gas stream to form a liquid. In some embodiments, the removal of isoprene vapor from the fermentation off-gas and the conversion of isoprene to a liquid phase are performed sequentially. For example, isoprene may be adsorbed to a solid phase and then extracted from the solid phase with a solvent. In one aspect, the isoprene is recovered by using absorption stripping as described in U.S. application Ser. No. 12/969,440 (US Publ. No. 2011/0178261).

In some embodiments, any of the methods described herein further include purifying the isoprene. For example, the isoprene produced using the compositions and methods of the invention can be purified using standard techniques. Purification refers to a process through which isoprene is separated from one or more components that are present when the isoprene is produced. In some embodiments, the isoprene is obtained as a substantially pure liquid. Examples of purification methods include (i) distillation from a solution in a liquid extractant and (ii) chromatography. As used herein, "purified isoprene" means isoprene that has been separated from one or more components that are present when the isoprene is produced. See, e.g. U.S. Patent Application Publication No.

2009/0203102, PCT publication WO 2009/076676 and U.S. patent application Ser. No. 12/496,573. In some embodiments, the isoprene is at least about 20%, by weight, free from other components that are present when the isoprene is produced. In various embodiments, the isoprene is at least or about 25%, 30%, 40%, 50%, 60%, 70%, 75%, 80%, 90%, 95%, or 99%, by weight, pure. Purity can be assayed by any appropriate method, e.g., by column chromatography, HPLC analysis, or GC-MS analysis. In some aspects, at least a portion of the gas phase remaining after one or more recovery steps for the removal of isoprene is recycled by introducing the gas phase into a cell culture system (such as a fermentor) for the production of isoprene.

In some aspects, any of the methods described herein further include a step of recovering isoprene produced by any of the recombinant cells disclosed herein. In some aspects, the isoprene is recovered by absorption stripping (See, e.g., U.S. Patent Application Publication No. 2011/0178261 A1).

In some aspects, any of the methods described herein further include a step of recovering the heterologous nucleic acid. In some aspects, any of the methods described herein further include a step of recovering the heterologous polypeptide.

Suitable purification methods are described in more detail in U.S. Patent Application Publication No. US2010/0196977 A1.

All publications and patents mentioned in the above specification are herein incorporated by reference. Various modifications and variations of the described method and system of the invention will be apparent to those skilled in the art without departing from the scope and spirit of the invention. Although the invention has been described in connection with specific embodiments, it should be understood that the invention as claimed should not be unduly limited to such specific embodiments. It is also to be understood that one, some, or all of the properties of the various embodiments described herein may be combined to form other embodiments of the present invention. These and other aspects of the invention will become apparent to one of skill in the art.

Throughout this specification, various patents, patent applications and other types of publications (e.g., journal articles) are referenced. The disclosure of all patents, patent applications, and publications cited herein are hereby incorporated by reference in their entirety for all purposes.

The invention can be more fully further understood by reference to the following examples, which are provided by way of illustration and are not meant to be limiting of the scope of the invention. All citations throughout the disclosure are hereby expressly incorporated by reference.

EXAMPLES

The following examples are provided in order to demonstrate and further illustrate certain preferred embodiments and aspects of the present invention and are not to be construed as limiting the scope thereof.

Example 1

Identification of Candidate Isoprene Synthases

Amino acid sequences encoding isoprene synthase (IspS) isolated from *P. alba* and *P. montana* were analyzed against proprietary and public sequence databases to identify polypeptides that may have isoprene synthase activity. Screening criteria for identifying candidate polypeptides with potential isoprene synthase activity included: 1) the presence of one or more immutable amino acid residue(s) that correspond to the MEA *P. alba* isoprene synthase amino acid residues F287, G397, N438, E451, Y514; 2) sequence alignment based on mature sequences defined as polypeptides that had completed processing of immature signal sequences; and 3) sequence alignment based on the C-terminal region that contains the catalytically active site for IspS. Sequence alignments resulted in the identification of several candidate isoprene synthases including *A. hypogaea* (peanut), *G. max* 1 (soybean), *G. max* 2 (soybean), *Q. petraea* (oak), *Q. ilex*, *M. pruriens* (velvet bean), and *C. cajans* (pigeon pea) (FIGS. 1, 2A-F and 3A-C).

Example 2

Analysis of Candidate Isoprene Synthases by Assessment of Isoprene Synthase Activity as Measured by Isoprene Production In Vitro The candidate isoprene synthases were analyzed for the ability to convert DMAPP to isoprene in vitro.

Materials and Methods

Codon Optimization of IspS Enzymes and Strain Construction

Figure 12:
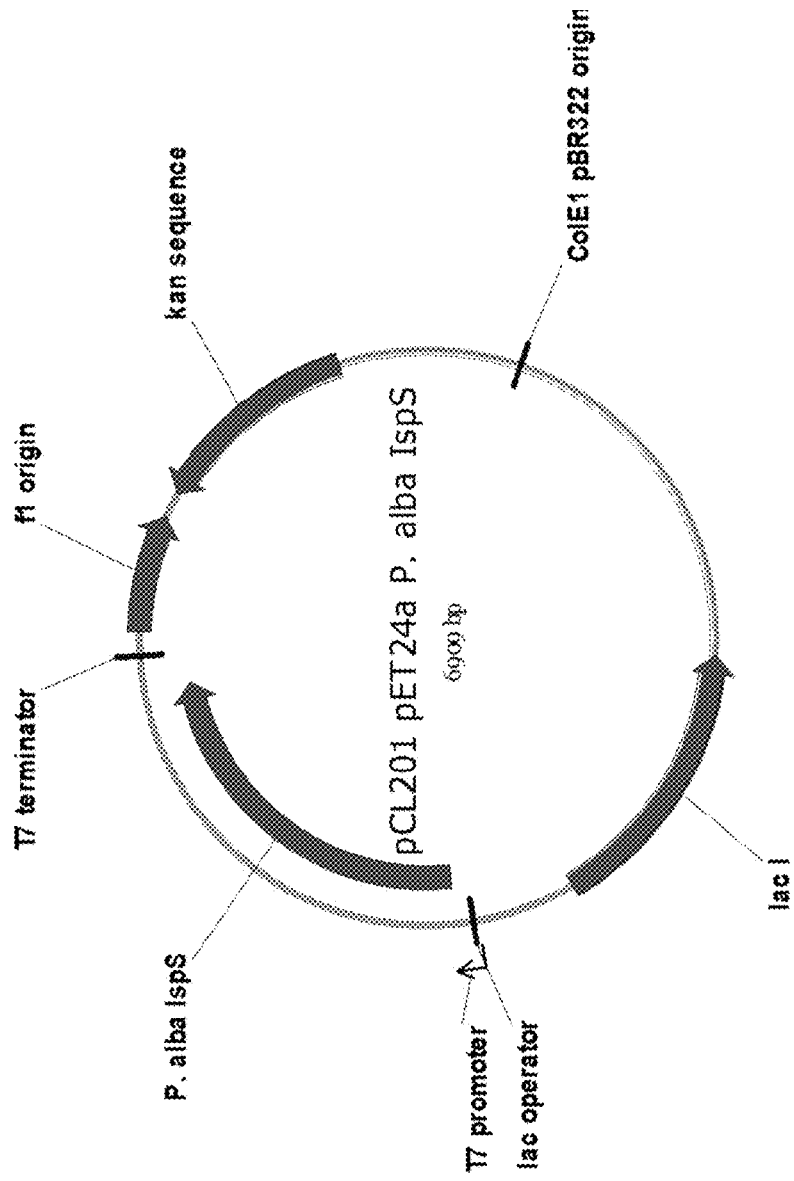
FIG. 12 shows a plasmid map for pCL201

DNA sequences encoding putative IspS enzymes from *A. hypogaea*, *C. cajans*, *G. max*, *M. pruriens* and *Q. petraea* were codon optimized, synthesized and cloned into the pCL201 expression vector by DNA2.0, in the identical orientation as the *P. alba* IspS MEA enzyme (FIG. 12). Purified plasmids were transformed into the expression host BL21 DE3 pLysS (Invitrogen) according to the manufacturer's recommended protocol, and resistant colonies harboring expression cassettes of the putative IspS enzymes were selected for further study. See Table 1 for detailed strain description.

TABLE 1

Strains used in this study

| Strain | Relevant Genotype |
|---|---|
| DW331 | BL21 DE3 pLysS (Invitrogen), pET24a PT7-*P. alba* IspS MEA, Kan50, Chlor25 |
| DW668 | BL21 DE3 pLysS (Invitrogen), pET24a PT7-*A. hypogaea* putative IspS, Kan50, Chlor25 |
| DW669 | BL21 DE3 pLysS (Invitrogen), pET24a PT7-*Q. petraea* putative IspS, Kan50, Chlor25 |
| DW688 | BL21 DE3 pLysS (Invitrogen), pET24a PT7-*G. max* 18280 putative IspS, Kan50, Chlor25 |
| DW689 | BL21 DE3 pLysS (Invitrogen), pET24a PT7-*G. max* 21900 putative IspS, Kan50, Chlor25 |
| DW731 | BL21 DE3 pLysS (Invitrogen), pET24a PT7-*M. pruriens* putative IspS, Kan50, Chlor25 |
| DW732 | BL21 DE3 pLysS (Invitrogen), pET24a PT7-*C. cajan* putative IspS, Kan50, Chlor25 |

Isoprene Synthase Specific Productivity Determination

Materials

Tris/NaCl pH 7.6, $MgCl_2$, 4-(2-Aminoethyl)benzenesulfonyl fluoride Hydrochloride (AEBSF), DNase I, DMAPP Triammonium salt (Cayman chemicals), Lysozyme (Sigma-Aldrich), 96-well Zinsser Glass Block, Seal & Sample Aluminum foil lids (Part No:538619) (Beckman coulter), Nunc MicroWell 96-Well Plates, Polypropylene, High Volume (Part No:2449946), (Thermo Scientific) (VWR).

Protein Expression and Solubility Measurement

*E. coli* transformants expressing *P. alba* MEA isoprene synthase, *P. alba* variant 3 isoprene synthase, *A. hypogaea* isoprene synthase, *G. max* 1 (G,max 21900 or Glyma09g21900.1) isoprene synthase, *G. max* 2 (G,max 18280 or Glyma20g18280_1_FG) isoprene synthase, *M. pruriens* isoprene synthase, or *C. cajans* isoprene synthase were grown in LB media, induced at $OD_{600}$~0.5 with 200 µM IPTG, and induced for 5 hours. Prior to harvesting the cells, a final $OD_{600}$ value was recorded. Cell pellets were collected by centrifugation and stored at −80° C. 3 mL of lysis buffer (100 mM Tris, 100 mM NaCl pH 7.6, 1 mg/ml BSA, 1 mg/ml lysozyme, 0.1 mg/ml DNAase, 0.5 mM AEBSF, 5 mM $MgCl2$) was added to each frozen pellet, the pellets were re-suspended, and allowed to incubate on ice for 30 min. The cell suspension was then lysed fully by passing 2-3 times through a french pressure cell (small french press cell at 800 psi/Low setting) until lysate started to look clear. The mixture was then centrifuged at 14000 rpm for 25 minutes at 4° C. The supernatant was collected for use in enzymatic activity assays. Samples from total lysate, the soluble fraction, and the pellet were analyzed for protein solubility by SDS-PAGE and Coomasie blue staining.

Isoprene Synthase Enzymatic Activity Assay

25 µL of *E. coli* supernatant, containing isoprene synthase, was incubated with 0.25, 0.5, 1, 3, 5, 7, 10, 15, 20, and 25 mM DMAPP, in 100 µL reactions containing 50 mM $MgCl_2$ and 100 mM Tris/NaCl in a Zinsser 96-well glass block sealed with aluminum foil lids for 30 minutes at 34° C. The glass blocks were then transferred to an 80° C. water bath for 2 minutes. Next, the glass blocks were analyzed by GC-FID (see below) to determine the concentration of isoprene generated in the reactions.

GC-FID Analysis
Equipment and Materials

Gas chromatograph (GC), 7890 (Agilent Technologies), Flame ionization detector (FID) 7890 (Agilent Technologies), HP-5 ms column, 5%-phenyl-methylpolysiloxane, 15 m×0.25 mm×0.25 µm (Agilent Technologies), CTC autosampler (Leap Technologies), 0.2% v/v isoprene, balance nitrogen (Air Liquide), Chemstation with Enhanced Data Analysis (D.03.00.611)

Procedure 96-well glass blocks were analyzed using GC-FID with the following parameters:

Oven:

| Rate (° C./min) | Temperature (° C.) | Time (min) |
|---|---|---|
| 0 | 37 | 28 |

Run Time: 28 minutes

| FRONT INLET | |
|---|---|
| Front Inlet Temperature | 110° C. |
| Flow Rate | 3.4 mL/min |
| Flow Mode | Constant Flow |
| Split Ratio | 50:1 |
| Carrier Gas | Helium |
| FLAME IONIZATION DETECTOR | |
| Detector Temperature | 160° C. |
| Hydrogen Flow | 40 mL/min |
| Air Flow | 400 mL/min |
| Makeup Flow | 0.1 mL/min |
| Makeup Gas Type | Helium |

Calculations

The peak areas were converted to isoprene concentrations by dividing the peak area by the response factor calculated from 0.2% v/v isoprene in nitrogen calibration standards. Specific productivity of isoprene synthase was calculated in units of mg isoprene/L/hr/OD.

Isoprene Synthase Specific Activity Determination
Expression of 6×His-tagged Isoprene Synthase N-terminally 6×His-tagged *P. alba* WT isoprene synthase, *P. alba* variant 1 isoprene synthase, *P. alba* variant 2 isoprene synthase, and *A. hypogaea* isoprene synthase were expressed and purified. The growth procedure is suitable for histidine tagged enzymes expressed in BL21(λDE3)pLysS cells. 10 ml of overnight culture was prepared for each 1 L of planned growth. The appropriate antibiotics (50 mg/ml kanamycin, 25 mg/ml chloramphenicol) were added to 10 ml of LB medium in a 25 ml flask and was inoculated with 1 colony from a fresh plate of cells or directly from glycerol frozen cell stock. Cultures were grown at 30° C. overnight with shaking at ~220 rpm. Day cultures were prepared in 1 liter of LB medium with appropriate antibiotics for each culture. Each 1 L day culture was inoculated with 10 ml of overnight culture and grown at 30-37° C. with shaking at ~220 rpm until the OD600 reached ~0.4-0.6. Day cultures were then induced with 400 µM IPTG and allowed to continue growing at 30° C. with shaking at 220 rpm for ~5-6 hours. Cells were then harvested by centrifugation at 10,000×g for 10 min, 4° C. Following harvest, cells were used directly or stored at −80° C. until ready to process.

Purification of 6×His-Tagged Isoprene Synthase

For purification of histidine tagged enzymes from BL21 (λDE3) pLysS cells, cells were gently resuspended in fresh Lysis buffer (Lysis buffer: Ni wash buffer+0.5 mM PMST, 1 mg/ml lysozyme, 0.2 mg/ml DNaseI; Ni wash buffer: 50 mM NaH2PO4, 300 mM NaCl, 20 mM Imidazole, pH 8.0). Approximately 40-50 ml of lysis buffer was used per 1 L of cell pellet. Cells were then incubated on ice for approximately 30 min. The cell suspension was then lysed fully by passing 2-3 times through a french pressure cell (large french press cell at 1200 psi/High setting) until lysate started to look clear. A sample of the lysate was saved for activity assay and gel analysis (~100 µl). The lysate was then clarified by centrifuging the lysate at 30,000×g for 30 min, 4° C. in a Sorvall Discovery 90SE ultracentrifuge. The supernatant was removed and retained. A sample of the "clarified lysate" was saved for activity assay and gel analysis (~100 µl).

The clarified lysate was run over HisTrap HP columns (GE healthcare) using a gradient from 0-100% Ni buffer B. Following loading of the lysate on the column, the column was washed with Ni wash buffer (50 mM NaH2PO4, 300 mm NaCl, 20 mM imidazole, ph 8.0). The his-tagged Isoprene Synthase was then eluted from the column using a gradient from 0-100% Ni elution buffer (50 mM NaH2PO4, 300 mM NaCl, 500 mM imidazole, ph 8.0) and fractions containing the his-tagged Isoprene Synthase were collected. The column was then washed with Ni stripping buffer (20 mM NaH2PO4, 0.5 m NaCl, 50 mM EDTA, ph 7.4). Samples were then analyzed by SDS-PAGE gel (4-12% gel NUPAGE, Invitrogen) according to manufacturer's directions. Desired fractions were concentrated on spin filters (Vivaspin-20, Sartoris) and then desalted over a Hi Prep 26/10 Desalting column (GE healthcare) packed with Sephadex G25 resin. The G-25 buffer consisted of 50 mM HEPES, 50 mM NaCl, and 1 mM DTT, pH 7.4. Fractions were then analyzed and concentrated. The samples were then stored at −80° C.

TEV Cleavage to Remove Histidine Tag

Digestion was performed with TurboTEV Protease from Eton Bioscience Inc. One unit of TurboTEV per 10 µg of purified protein was used. The digest was performed at 4° C. overnight. Samples were passed through another Ni column equilibrated in the Ni buffer to remove uncleaved enzyme, tag, TurboTEV protease (which is also tagged), and impurities. The Ni column pass through and washes were analyzed using SDS-PAGE gel (NUPAGE, Invitrogen) and DMAPP activity assays. Samples containing pure enzyme were pooled and desalted into 50 mM NaCl pH 7.4 buffer, protein concentration was determined using the absorbance at $A_{280}$, and the purified protein was then aliquoted and stored at −80° C.

Isoprene Synthase Enzymatic Activity Assay

Isoprene Synthase enzymatic assay was performed as described above.

Calculation of Isoprene Synthase Kinetic Parameters

Isoprene synthase activity is reported in units of $s^{-1}$. Isoprene concentration is determined in the DMAPP assay and multiplied by a conversion factor of $1.47\ E^{-04}$ to obtain units of µM/L/second. Isoprene synthase activity is then calculated for each variant at each substrate concentration by:

$$\text{Isoprene Synthase Activity} = \frac{\text{enzyme}\left(\frac{\mu M}{L}\right)}{\text{isoprene}\left(\frac{\mu M}{L/sec}\right)}$$

Figure 6:
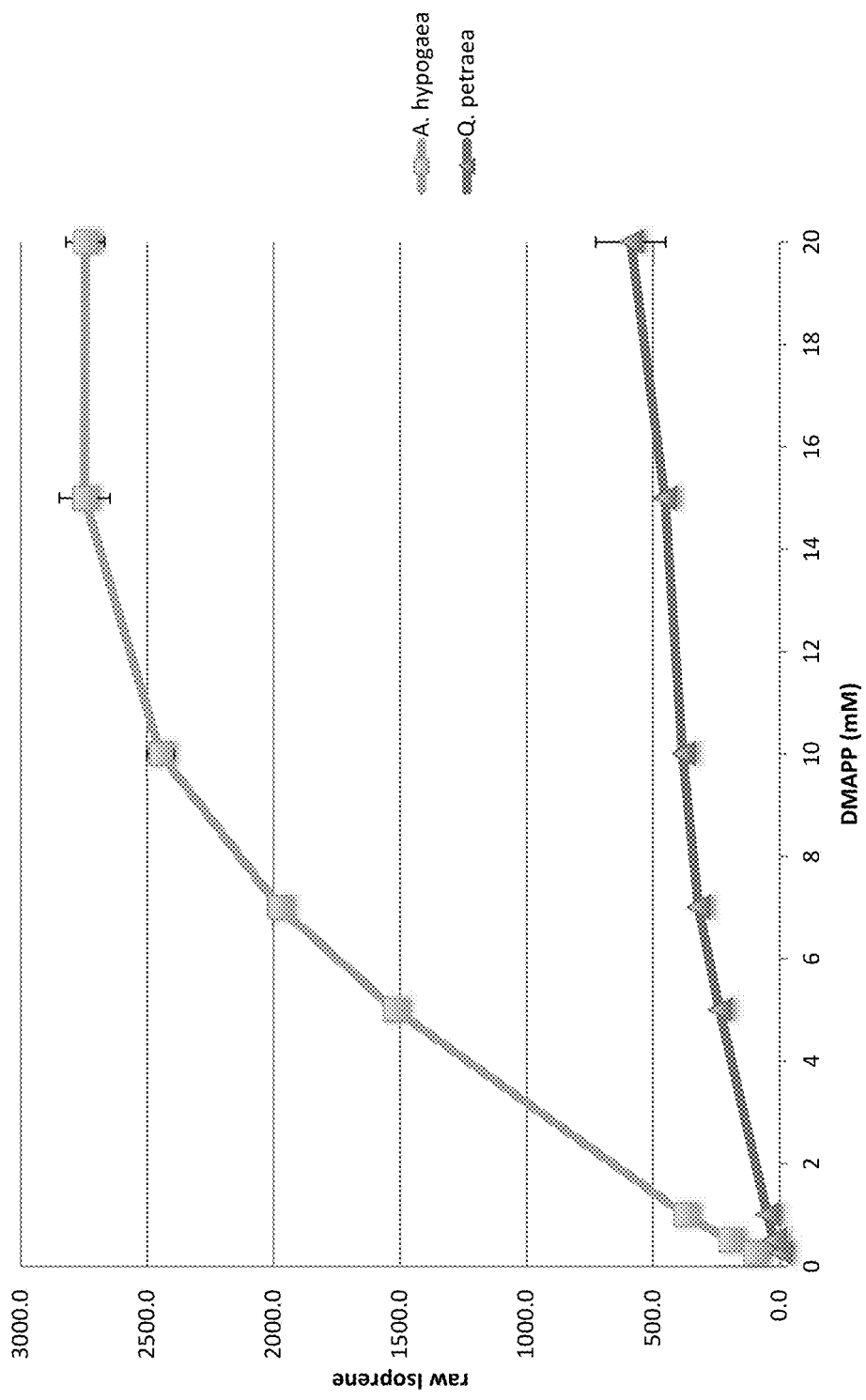
FIG. 6 is a graph demonstrating isoprene synthase enzymatic activity of putative isoprene synthases in an in vitro isoprene production assay. Supernatents prepared from lysates harvested from cells expressing a polypeptide isolated from *A. hypogaea* or *Q. petraea* were incubated with increasing concentrations of DMAPP and measured for raw isoprene production by GC-FID (Gas chromatograph-flame ionization detector).
Figure 7:
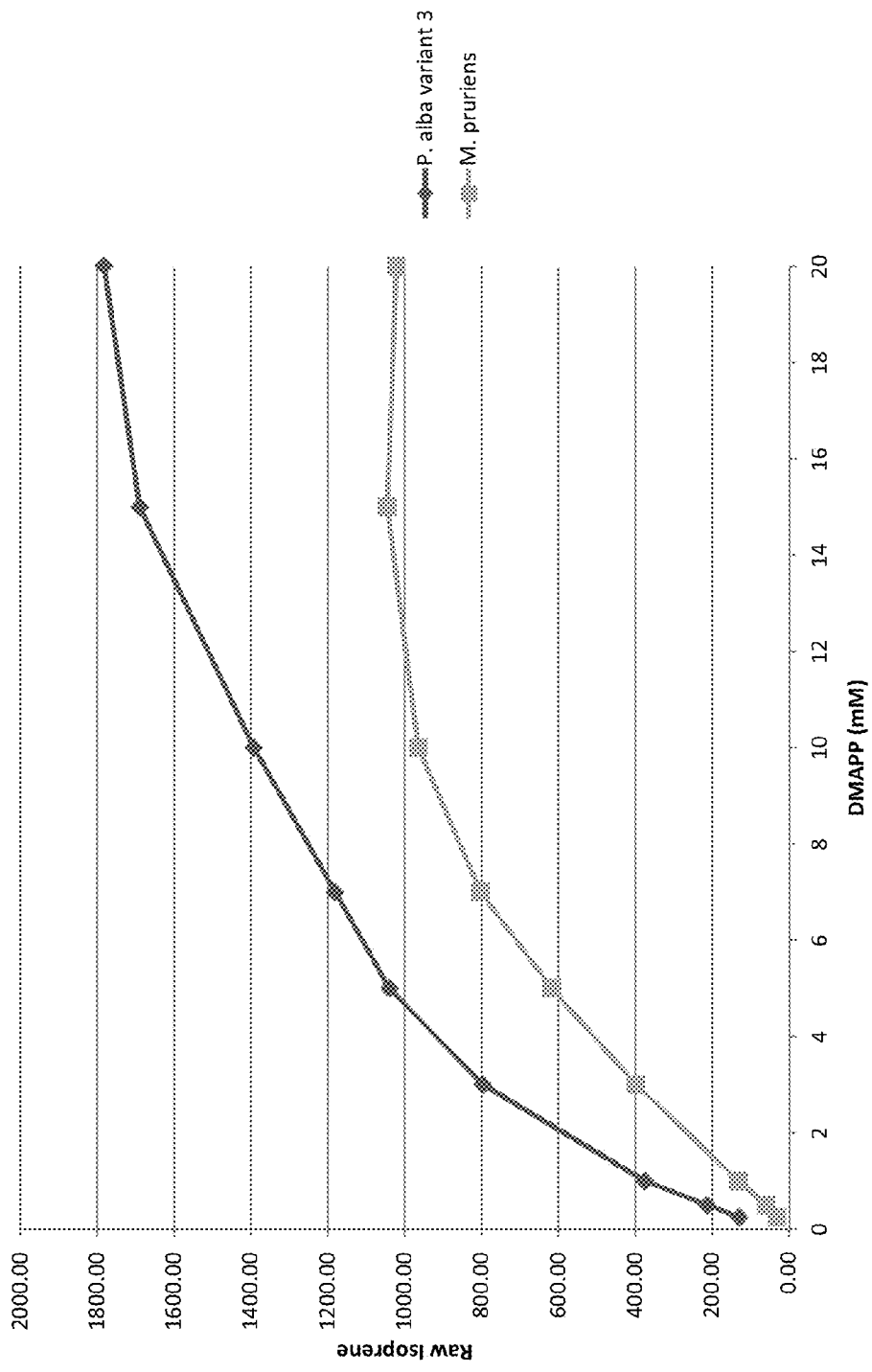
FIG. 7 is a graph demonstrating isoprene synthase enzymatic activity of putative isoprene synthases in an in vitro isoprene production assay. Supernatents prepared from lysates harvested from cells expressing a polypeptide isolated from *M. pruriens* or an isoprene synthase isolated from *P. alba* variant 3 were incubated with increasing concentrations of DMAPP and measured for raw isoprene production by GC-FID (Gas chromatograph-flame ionization detector).

Lysates from cells expressing *A. hypogaea* IspS or *Q. petraea* IspS produced isoprene in the presence of increasing concentrations of DMAPP, with lysates containing *A. hypogaea* IspS demonstrating significantly higher production of isoprene as compared to lysates from cells expressing *Q. petraea* IspS (FIG. 6). Isoprene was produced from cell lysates containing *M. pruriens* IspS when in the presence of increasing concentrations of DMAPP as indicated by comparison of isoprene production by cells lysates containing the positive control, *P. alba* variant 3 IspS (FIG. 7). These results indicate that the candidate polypeptides, *A. hypogaea* IspS, *Q. petraea* IspS, and *M. pruriens* IspS have isoprene synthase activity.

Figure 8:
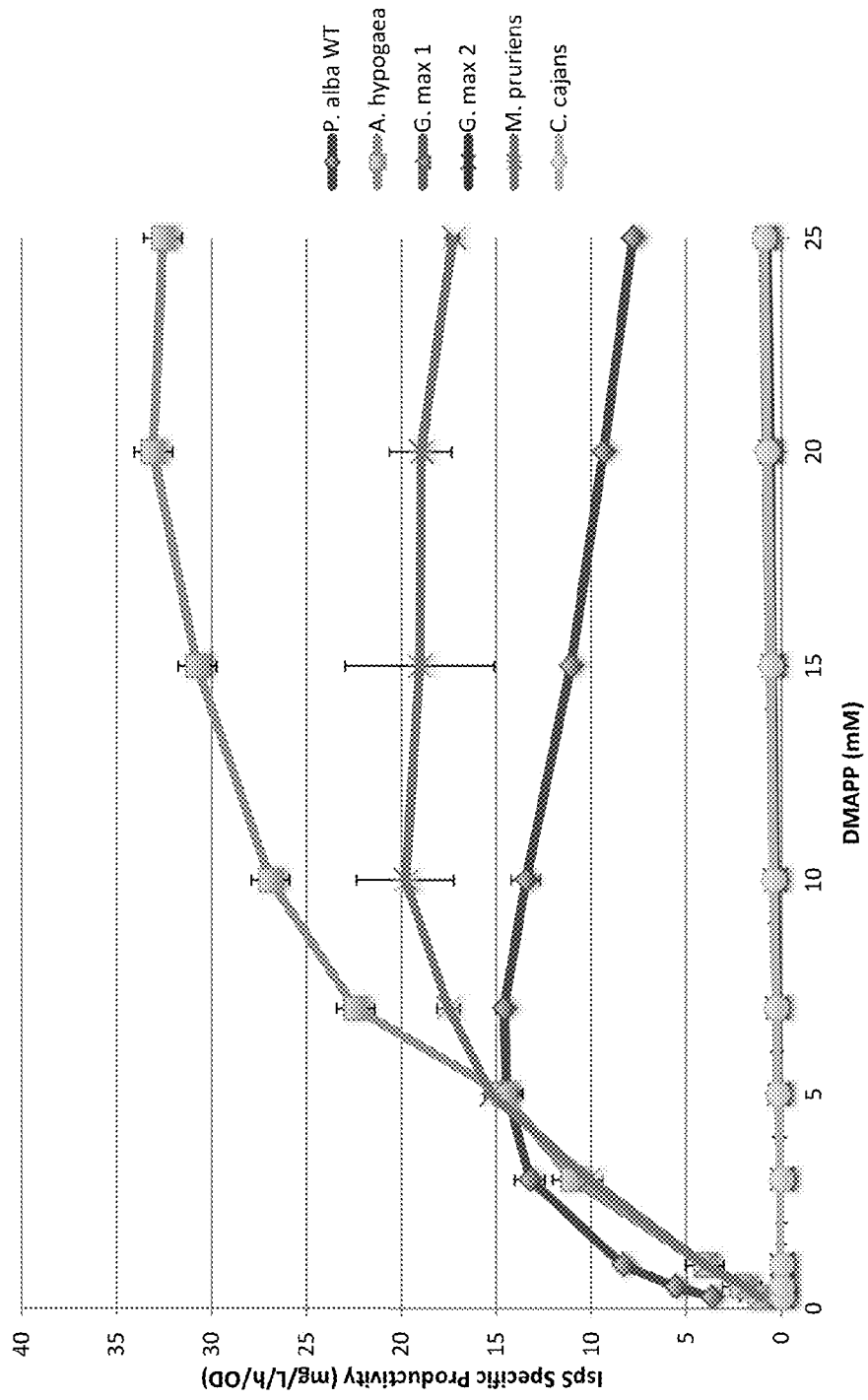
FIG. 8 is a graph demonstrating specific productivity of putative isoprene synthases as determined from an in vitro isoprene production assay. Supernatents prepared from lysates harvested from cells expressing a polypeptide isolated from *A. hypogaea*, *G. max* 1, *G. max* 2, *M. pruriens*, or *C. cajans* were incubated with increasing concentrations of DMAPP and measured for isoprene production by GC-FID. Specific productivity of isoprene synthase was calculated in units of mg isoprene/L/hr/OD. The poplar isoprene synthase from *P. alba* WT was used as a positive control.

Analysis of IspS specific productivity in lysates prepared from cells expressing the IspS candidates *A. hypogaea* (peanut), *G. max* 1 (soybean), *G. max* 2 (soybean), *M. pruriens* (velvet bean), or *C. cajans* (pigeon pea) demonstrated that *A. hypogaea* and *M. pruriens* had higher specific productivity than the other IspS candidates and *P. alba* IspS (FIG. 8 and Table 2). Cell lysates containing *G. max* 1 IspS, *G. max* 2 IspS, and *C. cajans* IspS did not produce isoprene in the presence of DMAPP.

TABLE 2

Comparison of IspS specific productivity

| DMAPP (mM) | P. alba WT SP | P. alba WT Std Dev | A. hypogaea SP | A. hypogaea Std Dev | G. max 1 SP | G. max 1 Std Dev | G. max 2 SP | G. max 2 Std Dev | M. pruriens SP | M. pruriens Std Dev | C. cajans SP | C. cajans Std Dev |
|---|---|---|---|---|---|---|---|---|---|---|---|---|
| 0.25 | 3.7 | 0.173 | 1.2 | 0.132 | 0.000 | 0.000 | 0.000 | 0.000 | 1.1 | 0.013 | 0.000 | 0.000 |
| 0.5 | 5.6 | 0.167 | 2.1 | 0.027 | 0.000 | 0.000 | 0.000 | 0.000 | 1.8 | 0.045 | 0.000 | 0.000 |
| 1 | 8.3 | 0.340 | 4.0 | 0.164 | 0.000 | 0.000 | 0.000 | 0.000 | 4.0 | 0.160 | 0.000 | 0.000 |
| 3 | 13.2 | 0.782 | 11.0 | 0.378 | 0.000 | 0.000 | 0.000 | 0.000 | 10.1 | 0.710 | 0.000 | 0.000 |
| 5 | 14.4 | 0.860 | 14.6 | 3.445 | 0.201 | 0.014 | 0.171 | 0.004 | 15.3 | 0.328 | 0.202 | 0.006 |
| 7 | 14.6 | 0.437 | 22.4 | 0.561 | 0.272 | 0.030 | 0.244 | 0.025 | 17.5 | 0.582 | 0.291 | 0.031 |
| 10 | 13.4 | 0.761 | 26.9 | 0.660 | 0.397 | 0.032 | 0.322 | 0.018 | 19.8 | 2.569 | 0.427 | 0.004 |
| 15 | 11.1 | 0.299 | 30.8 | 1.013 | 0.591 | 0.007 | 0.473 | 0.021 | 19.0 | 3.933 | 0.570 | 0.020 |
| 20 | 9.4 | 0.358 | 33.1 | 0.733 | 0.802 | 0.065 | 0.598 | 0.003 | 19.0 | 1.648 | 0.765 | 0.014 |
| 25 | 7.8 | 0.217 | 32.6 | 0.596 | 0.958 | 0.075 | 0.784 | 0.034 | 17.3 | 0.274 | 0.928 | 0.008 |

SP = Specific Productivity (mg/L/h/OD)

Data from the isoprene synthase kinetic assays were fit to the following modified version of the Henri-Michaelis-Menten equation that takes into account substrate inhibition using Kaleidagraph 4.0 (Synergy Software) to determine $K_M$, $k_{cat}$ and $k_{iDMAPP}$ values for each isoprene synthase analyzed:

$$\frac{\text{rate}}{[\text{Isoprene synthase}]} = \frac{kcat * [DMAPP]}{KM + [DMAPP]\left(1 + \frac{[DMAPP]}{KiDMAPP}\right)}$$

Results

Figure 4:
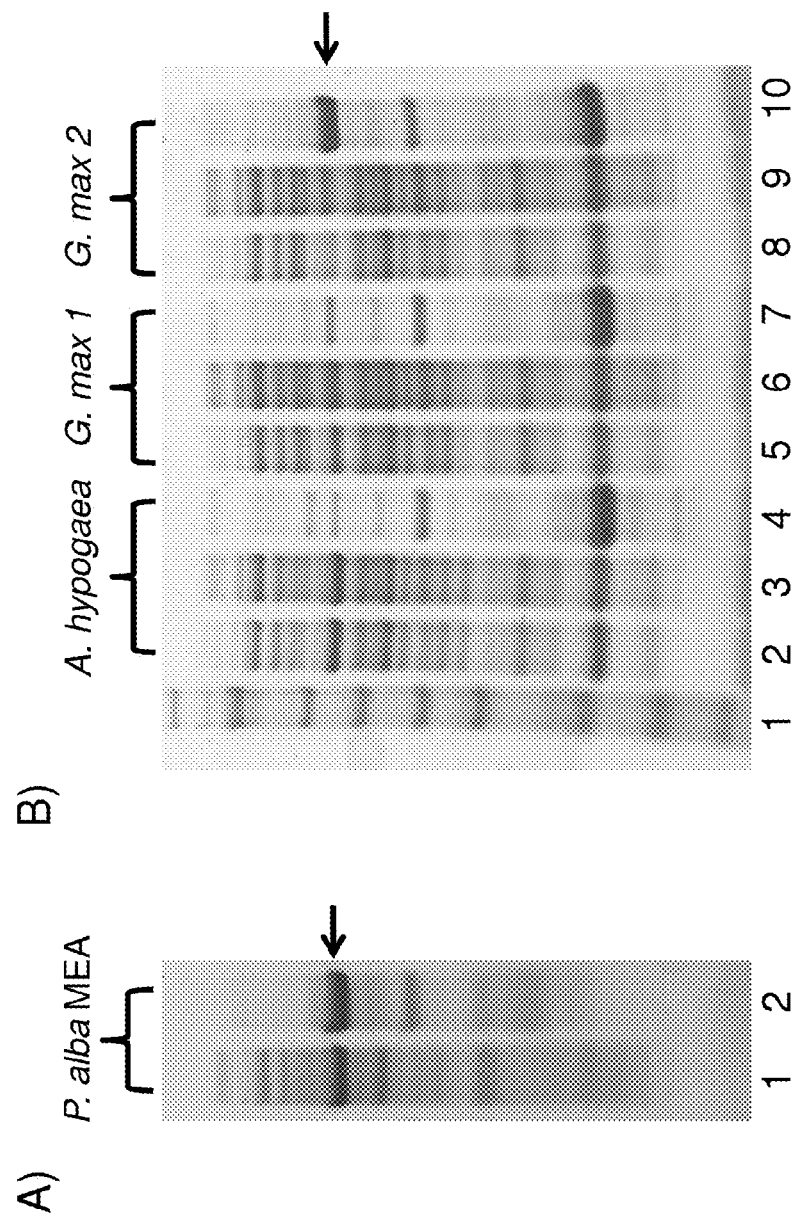
FIG. 4 is a coomassie stained SDS-PAGE gel showing solubility of putative isoprene synthase enzymes as compared to a known isoprene synthase. A) shows protein levels of MEA *P. alba* isoprene synthase in the soluble fraction (lane 1) and in the insoluble fraction (lane 2). B) shows protein levels of *A. hypogaea* isoprene synthase in the total lysate (lane 2), soluble fraction (lane 3), and insoluble pellet fraction (lane 4); protein levels of *G. max*/isoprene synthase in the total lysate (lane 5), soluble fraction (lane 6), and insoluble pellet fraction (lane 7); and protein levels of *G. max* 2 isoprene synthase in the total lysate (lane 8), soluble fraction (lane 9), and insoluble pellet fraction (lane 10). Lane 1 contains a molecular weight marker. The arrow indicates a band corresponding to molecular weight of isoprene synthase.
Figure 5:
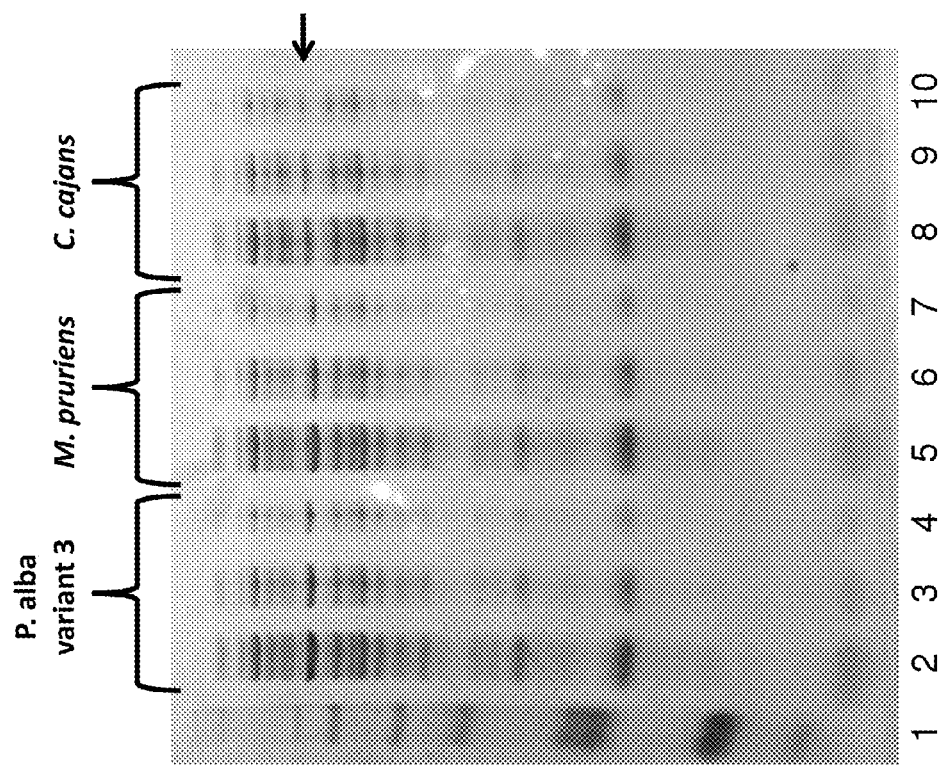
FIG. 5 is a coomassie stained SDS-PAGE gel showing solubility of putative isoprene synthase enzymes as compared to a known isoprene synthase. Three dilutions of the soluble fraction were loaded in the lanes in order of decreasing protein concentration from left to right. Protein levels of soluble *P. alba* variant 3 isoprene synthase (lanes 2, 3, and 4), *M. pruriens* (lanes 5, 6, and 7), and *C. cajans* (lanes 8, 9, and 10) are shown. Lane 1 contains a molecular weight marker. The arrow indicates a band corresponding to molecular weight of isoprene synthase.

SDS-PAGE analysis of lysates prepared from cells expressing the indicated IspS demonstrated that *A. hypogaea* IspS (FIG. 4B; lanes 3 and 4) and *G. max* 1 IspS (FIG. 4B; lanes 6 and 7) were soluble and expressed at levels comparable to *P. alba* MEA IspS (FIG. 4A; lane 2). In contrast, *G. max* 2 IspS (FIG. 4B; lanes 9 and 10) was mostly insoluble as compared to *P. alba* MEA IspS. Analysis of three dilutions prepared from the soluble fraction of cells expressing *M. pruriens* IspS (FIG. 5; lanes 5, 6 and 7) or *C. cajans* IspS (FIG. 5; lanes 8, 9 and 10) demonstrated that they were soluble and expressed at levels comparable to *P. alba* variant 3 IspS (FIG. 5; lanes 2, 3 and 4).

Production of isoprene from DMAPP that was provided to cell lysates containing the indicated IspS was measured.

Figure 9:
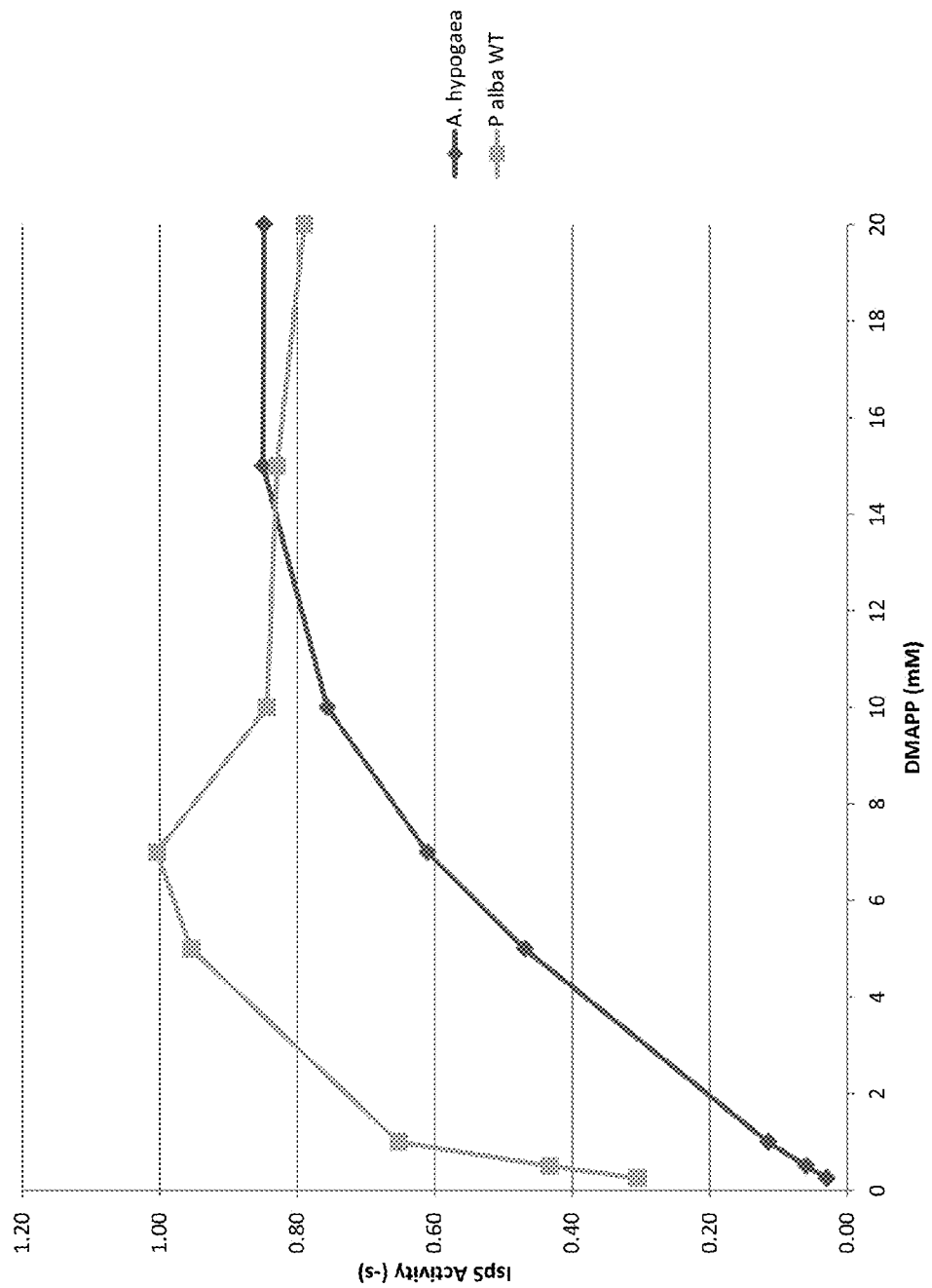
FIG. 9 is a graph showing isoprene synthase specific activity of a polypeptide isolated from the legume *A. hypogaea* in an in vitro isoprene production assay. As compared to the isoprene synthase from *P. alba*, the *A. hypogaea* isoprene synthase exhibited reduced substrate inhibition at increasing concentrations of DMAPP. Isoprene synthase activity is reported in units of $s^{-1}$.
Figure 10:
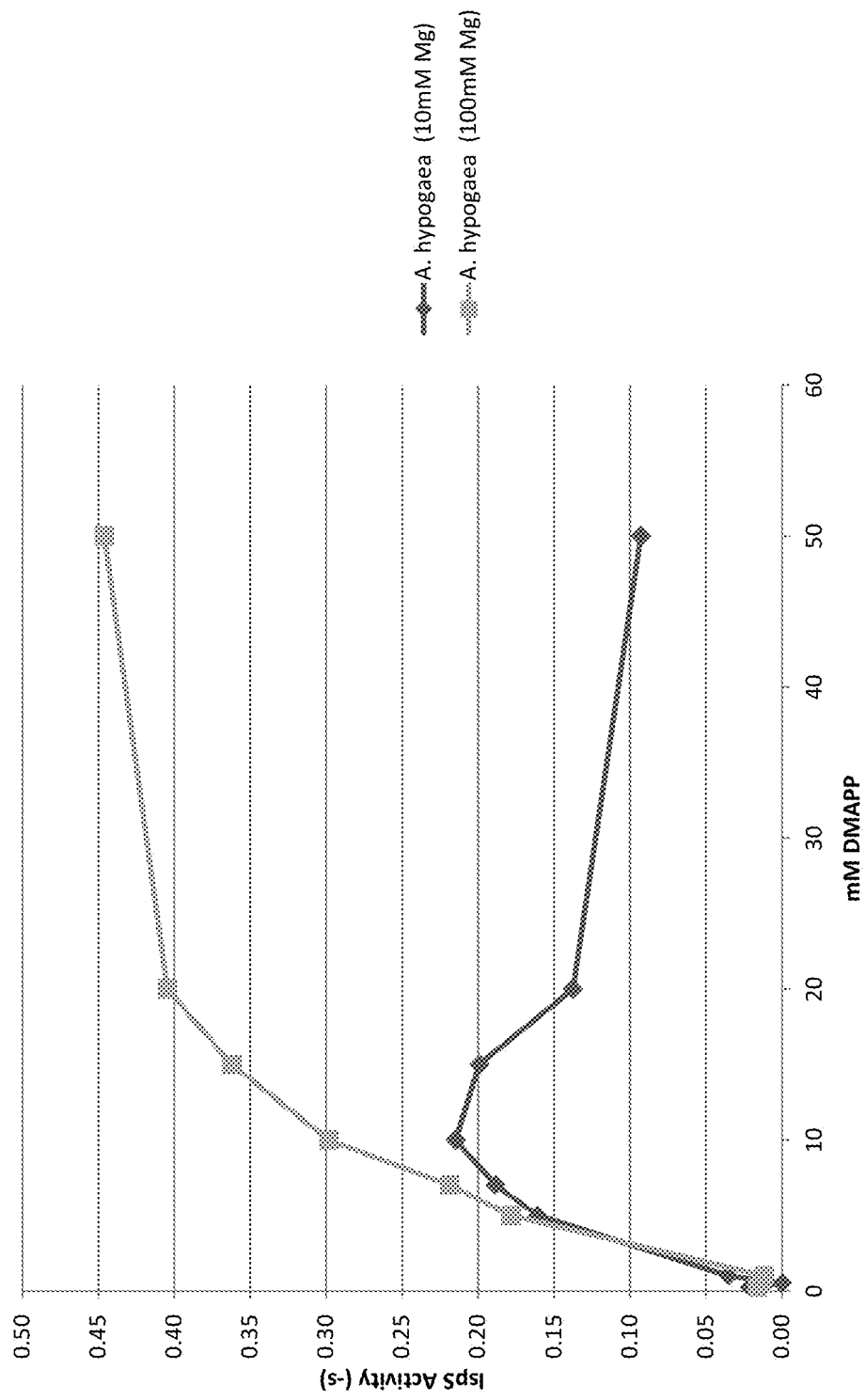
FIG. 10 is a graph showing isoprene synthase specific activity of a polypeptide isolated from the legume *A. hypogaea* in the presence of 10 mM or 100 mM magnesium (Mg) in an in vitro isoprene production assay. The *A. hypogaea* isoprene synthase exhibited reduced substrate inhibition despite the presence of increasing DMAPP concentrations when a concentration of 100 mM $Mg^{2+}$ was provided. At a lower concentration of $Mg^{2+}$, the *A. hypogaea* isoprene synthase exhibited sensitivity to substrate inhibition at low concentrations of DMAPP. Isoprene synthase activity is reported in units of $s^{-1}$.

Analysis of isoprene production when normalized to substrate provided to lysates prepared from cells expressing *P. alba* IspS demonstrated that at a concentration of about 6 mM DMAPP the enzyme exhibited substrate inhibition (FIG. 9). In contrast, *A. hypogaea* IspS did not demonstrate substrate inhibition at the highest concentration of DMAPP assayed (FIG. 9). The lack of substrate inhibition by *A. hypogaea* IspS was dependent on the presence of magnesium ($Mg^{2+}$), a cofactor required by IspS for enzymatic activity. When *A. hypogaea* IspS was provided with 10 mM $Mg^{2+}$, substrate inhibition was observed at a concentration of about 10 mM DMAPP (FIG. 10). However, when 100 mM $Mg^{2+}$ was provided, no substrate inhibition was observed at the highest concentration of DMAPP assayed (FIG. 10).

Figure 11:
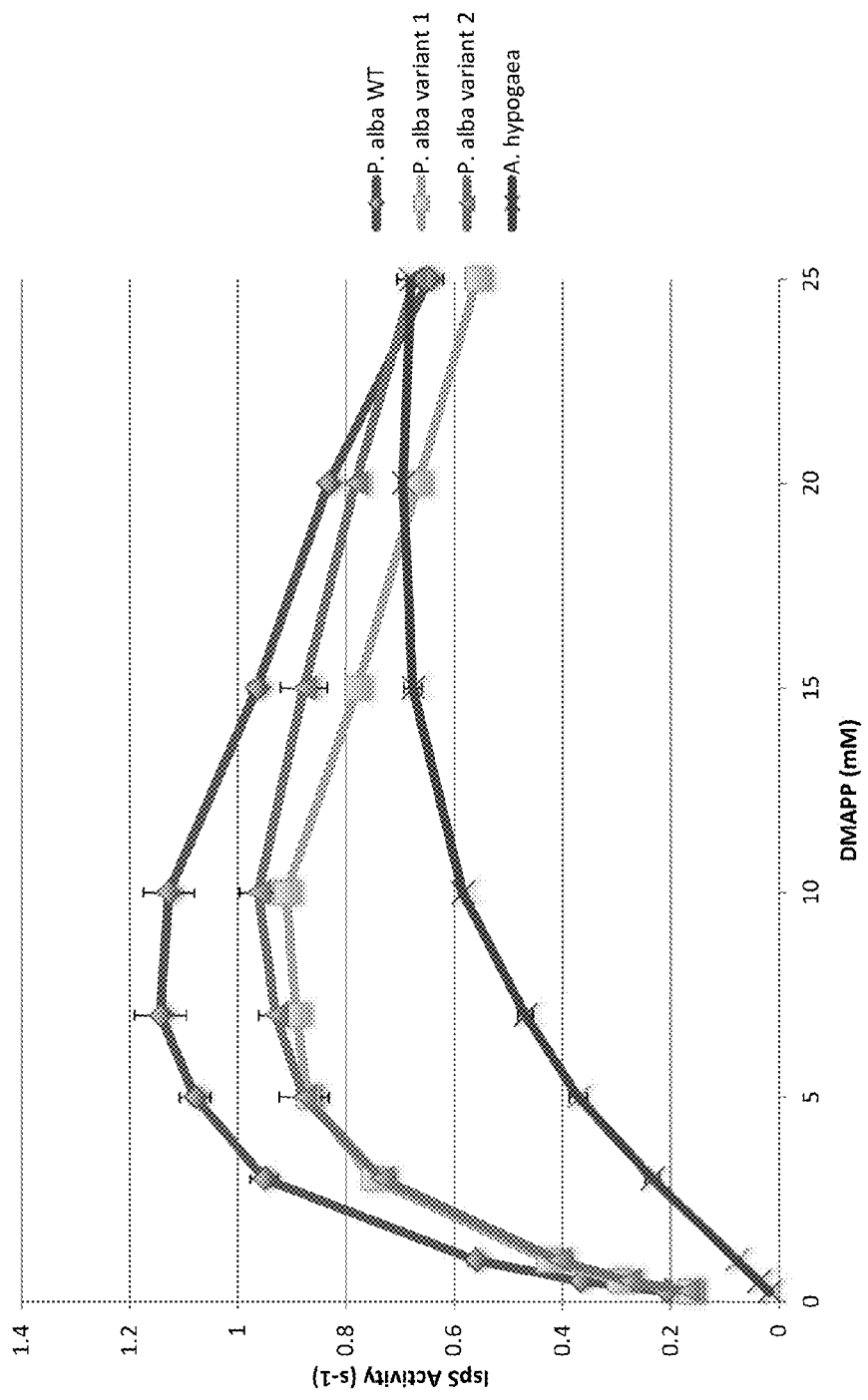
FIG. 11 is a graph showing isoprene synthase specific activity of a polypeptide isolated from the legume *A. hypogaea* in an in vitro isoprene production assay. As compared to the isoprene synthase from *P. alba* WT, the *A. hypogaea* isoprene synthase exhibited reduced substrate inhibition at increasing concentrations of DMAPP. The *A. hypogaea* isoprene synthase also exhibited reduced substrate inhibition at increasing concentrations of DMAPP when compared to variant isoprene synthases, *P. alba* variant 1 and *P. alba* variant 2, that had previously been determined to have increased isoprene synthase specific activity as compared to the parent *P. alba* sequence. Isoprene synthase activity is reported in units of $s^{-1}$.

Kinetic parameters of *A. hypogaea* IspS was determined in vitro with purified protein and compared to *P. alba* IspS (WT), *P. alba* variant 1 IspS, and *P. alba* variant 2 IspS. Analysis of isoprene production when normalized to substrate demonstrated that at a concentration of about 10 mM DMAPP, *P. alba* IspS exhibited substrate inhibition (FIG. 11 and Table 3). *P. alba* variant 1 IspS and *P. alba* variant 2 IspS both exhibited substrate inhibition at a concentration of about 15 mM DMAPP (FIG. 11 and Table 3). In comparison, *A. hypogaea* IspS exhibited substrate inhibition at a concentration of about 25 mM DMAPP (FIG. 11 and Table 3) with a higher $K_{iDMAPP}$ value at 30.6 than *P. alba* IspS (WT), *P. alba* variant 1 IspS, or *P. alba* variant 2 IspS, each having a $K_{iDMAPP}$ value of 2.17, 1.68, and 1.62, respectively (Table 4). In addition, *A. hypogaea* IspS had a $K_m$ value of 18.3 that was significantly higher than the $K_m$ value of *P. alba* IspS (WT), *P. alba* variant 1 IspS, or *P. alba* variant 2 IspS and the $K_{cat}$ value for *A. hypogaea* IspS was measured at 1.81 (Table 4).

TABLE 3

Comparison of IspS activity

| | *P. alba* WT | | *P. alba* variant 1 | | *P. alba* variant 2 | | *A. hypogaea* | |
|---|---|---|---|---|---|---|---|---|
| DMAPP (mM) | Activity (s − 1) | Std Dev | Activity (s − 1) | Std Dev | Activity (s − 1) | Std Dev | Activity (s − 1) | Std Dev |
| 0.25 | 0.208 | 0.009 | 0.166 | 0.009 | 0.168 | 0.006 | 0.018 | 0.001 |
| 0.5 | 0.366 | 0.011 | 0.295 | 0.023 | 0.277 | 0.003 | 0.036 | 0.001 |
| 1 | 0.560 | 0.013 | 0.427 | 0.021 | 0.407 | 0.025 | 0.077 | 0.001 |
| 3 | 0.951 | 0.025 | 0.751 | 0.018 | 0.734 | 0.024 | 0.233 | 0.012 |
| 5 | 1.079 | 0.028 | 0.871 | 0.037 | 0.878 | 0.045 | 0.371 | 0.016 |
| 7 | 1.144 | 0.048 | 0.892 | 0.048 | 0.930 | 0.030 | 0.468 | 0.014 |
| 10 | 1.128 | 0.047 | 0.911 | 0.020 | 0.962 | 0.034 | 0.584 | 0.007 |
| 15 | 0.965 | 0.014 | 0.779 | 0.030 | 0.878 | 0.043 | 0.677 | 0.016 |
| 20 | 0.833 | 0.008 | 0.667 | 0.023 | 0.783 | 0.009 | 0.695 | 0.007 |
| 25 | 0.646 | 0.025 | 0.558 | 0.019 | 0.674 | 0.031 | 0.680 | 0.008 |

TABLE 4

Comparison of IspS kinetic parameters

| | *P. alba* WT | | *P. alba* variant 1 | | *P. alba* variant 2 | | *A. hypogaea* | |
|---|---|---|---|---|---|---|---|---|
| | Avg Value | Avg Error | Avg Value | Avg Error | Avg Value | Avg Error | Avg Value | Avg Error |
| $K_{cat}$ | 2.17 | 0.309 | 1.68 | 0.192 | 1.62 | 0.166 | 1.81 | 0.502 |
| $K_m$ | 2.83 | 0.727 | 2.79 | 0.587 | 2.88 | 0.568 | 18.3 | 6.538 |
| $K_i$ | 13.5 | 3.5 | 14.9 | 3.3 | 22.1 | 5.1 | 30.6 | 17.1 |

Example 3

Analysis of Candidate Isoprene Synthases by DMAPP Toxicity Relief

There is a strong correlation between increased intracellular DMAPP levels and growth inhibition of *E. coli*, which can be alleviated by the expression of *P. alba* IspS. Without being bound by theory, increased levels of IspS activity should therefore allow for better growth due to more rapid conversion of DMAPP to isoprene. The growth rates of *E. coli* expressing IspS candidates were monitored to identify candidates that display the ability to convert DMAPP to isoprene within the cell.

Materials and Methods

Construction of Plasmid pEWL1036

Figure 15:
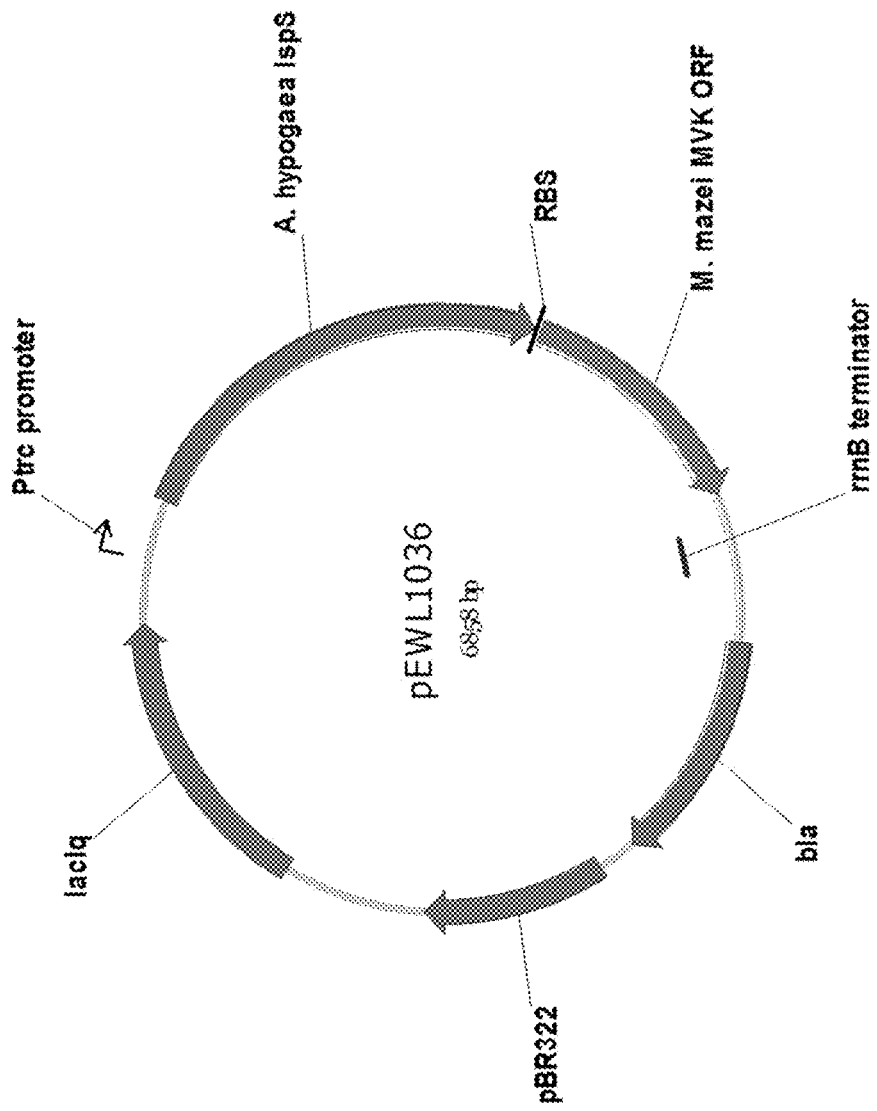
FIG. 15 shows a plasmid map for pEWL1036

The *A. hypogaea* IspS gene was optimized for expression in *E. coli* and synthesized by DNA2.0. To generate an expression construct for use in production hosts, *A. hypogaea* IspS was amplified from the DNA2.0 expression vector with PfuUltra II Fusion DNA Polymerase from Agilent Technologies (Santa Clara, Calif.) according to the manufacturer's protocol with primers EL1304 and EL1305 (Table 5). The pDW34 backbone was amplified with primers EL1306 and EL1307 (Table 5). Using the GENEART Seamless Cloning and Assembly Kit from Life Technologies (Carlsbad, Calif.), the two PCR products were purified (Qiagen) and recombined to form an in vitro circular product. The product was electroporated into strain CMP451 according to standard molecular biology protocols. Cells were recovered in non-selective liquid LB medium, plated onto LA+50 μg/μl carbenicillin+5 mM mevalonic acid plates, and incubated overnight at 37° C. The next day, transformants were screened by PCR to check for the presence of the *A. hypogaea* IspS-mMVK fragment with primers EL1005 and EL1310 (Table 5). Transformants containing the correct sized PCR products were grown overnight in LB+50 μg/μl carbenicillin, and plasmids were purified for sequencing (Qiagen). The plasmids were verified by sequencing (Quintara Biosciences) with primers EL1004, EL1005, EL1006, EL1238, EL1308, EL1309, EL1310 (Table 5). One plasmid, pEWL1036, was selected for further study (FIG. 15 and Table 6).

TABLE 5

Primer sequences

| Primer name | Primer sequence | SEQ ID NO: |
|---|---|---|
| EL1004 | ACAATTTCACACAGGAAACAGC | 37 |
| EL1005 | CCAGGCAAATTCTGTTTTATCAG | 38 |
| EL1006 | GACAGCTTATCATCGACTGCACG | 39 |
| EL1238 | CGAAAAGCACCCTTATGTGTCTG | 40 |
| EL1304 | GGAATAAACCATGAACACCCGTCGCAGCGC | 41 |
| EL1305 | CTTTATGCAGTTAGTTGATCGGAATCGGTTCG | 42 |
| EL1306 | GATCAACTAACTGCATAAAGGAGGTAAAAAAACATGG | 43 |
| EL1307 | GGGTGTTCATGGTTTATTCCTCCTTATTTAATCG | 44 |
| EL1308 | CTGACCTACAAATTCGAAGAGG | 45 |
| EL1309 | GGTGGCGTGAGATCGGTCTG | 46 |
| EL1310 | GCATCGTCCGTTCGAGCTGC | 47 |

TABLE 6

Plasmid encoding *A. hypogaea* isoprene synthase

| Plasmid name | Antibiotic resistance | Description |
|---|---|---|
| pEWL1036 | Carbenicillin | pTrc *A. hypogaea* IspS-mMVK |

Construction of Strains EWL1043, EWL1047, EWL1049, and EWL1052

For construction of strain EWL1043, the parent strain CMP1133 was co-transformed with plasmids pEWL1036 and MCM82 by electroporation according to standard molecular biology protocols. Cells were recovered in non-selective liquid LB, incubated for 2 hours at 30° C. with shaking, and selected on LA+50 µg/µl carbenicillin+50 µg/µl spectinomycin plates and incubated overnight at 37° C. An individual colony resistant to carbenicillin and spectinomycin was designated as strain EWL1043 and used for further study (Table 7).

For construction of strain EWL1047, the parent strain CMP1133 was co-transformed with plasmids pEWL1036 and pCHL276 by electroporation according to standard molecular biology protocols. Cells were recovered in non-selective liquid LB, incubated for 2 hours at 30° C. with shaking, and selected on LA+50 µg/µl carbenicillin+50 µg/µl spectinomycin plates and incubated overnight at 37° C. An individual colony resistant to carbenicillin and spectinomycin was designated as strain EWL1047 and used for further study (Table 7).

For construction of strain EWL1049, the parent strain CMP1133 was co-transformed with plasmids pEWL1036 and pCHL277 by electroporation according to standard molecular biology protocols. Cells were recovered in non-selective liquid LB, incubated for 2 hours at 30° C. with shaking, and selected on LA+50 µg/µl carbenicillin+50 µg/µl spectinomycin plates and incubated overnight at 37° C. An individual colony resistant to carbenicillin and spectinomycin was designated as strain EWL1049 and used for further study (Table 7).

For construction of strain EWL1052, the parent strain CMP1133 was co-transformed with plasmids pEWL1036 and MCM1225 by electroporation according to standard molecular biology protocols. Cells were recovered in non-selective liquid LB, incubated for 2 hours at 30° C. with shaking, and selected on LA+50 µg/µl carbenicillin+50 µg/µl spectinomycin plates and incubated overnight at 37° C. An individual colony resistant to carbenicillin and spectinomycin was designated as strain EWL1052 and used for further study (Table 7).

TABLE 7

Strains used in this study

| Strain name | Antibiotic resistance | Description |
|---|---|---|
| EWL1043 | Carbenicillin, Spectinomycin | BL21, pgl-, PL.2-mKKDyI, GI1.2-gltA, yhfS-PyddV-ispA, pTrc *A. hypogaea* IspS-mMVK, pCL Ptrc-*E. faecalis* Upper MVA |
| EWL1047 | Carbenicillin Spectinomycin | BL21, pgl-, PL.2-mKKDyI, GI1.2-gltA, yhfS-PyddV-ispA, pTrc *A. hypogaea* IspS-mMVK, pCL Ptrc-leaderless *E. faecalis* Upper MVA |
| EWL1049 | Carbenicillin, Spectinomycin | BL21, pgl-, PL.2-mKKDyI, GI1.2-gltA, yhfS-PyddV-ispA, pTrc *A. hypogaea* IspS-mMVK, pCL Ptrc-leaderless *E. casseliflavus* Upper MVA |
| EWL1052 | Carbenicillin Spectinomycin | BL21, pgl-, PL.2-mKKDyI, GI1.2-gltA, yhfS-PyddV-ispA, pTrc *A. hypogaea* IspS-mMVK, pCL Ptrc-leaderless *E. gallinarum* Upper MVA |

Growth and Specific Productivity Assay of Isoprene Production Strains

The growth and isoprene productivity assay of isoprene production strains was performed as follows: Overnight cultures were prepared from glycerol culture stocks in LB medium with appropriate antibiotics in 30 ml glass test tubes and grown at 34° C. The next day, cultures were diluted to an OD600 of 0.2 in TM3 medium with appropriate antibiotics, distributed into a 48-well block (VWR), sealed with a Breathe Easier membrane (Diversified Biotech), and grown at 34° C. at 600 rpm in a Shel Lab shaking incubator. Cultures were induced with appropriate amounts of IPTG when OD600 was between 0.4 and 0.8. Mevalonic acid was added subsequently to selected cultures one hour after induction. Both OD and isoprene were then measured every hour for 4 to 5 hours. OD600 was measured in a 96-well polystyrene plate (VWR) on a plate reader (Molecular Devices) according to standard molecular biology procedures. Isoprene measurements were conducted according to standard procedures. Briefly, 100 ul of bacterial culture was removed from the 48-well block and redistributed into a 96-well glass block (Zinsser) for analysis. Glass blocks were sealed with foil membranes, incubated on a Thermomixer (Eppendorf) for 30 minutes at 450 rpm at 34° C., and cultures were heat-killed for 2 minutes in an 80° C. water bath. Glass blocks were cooled prior to standard isoprene measurement by GC-MS. Specific productivity was calculated by dividing the grams of isoprene produced by volume, cell density, and time.

Results

Figure 13:
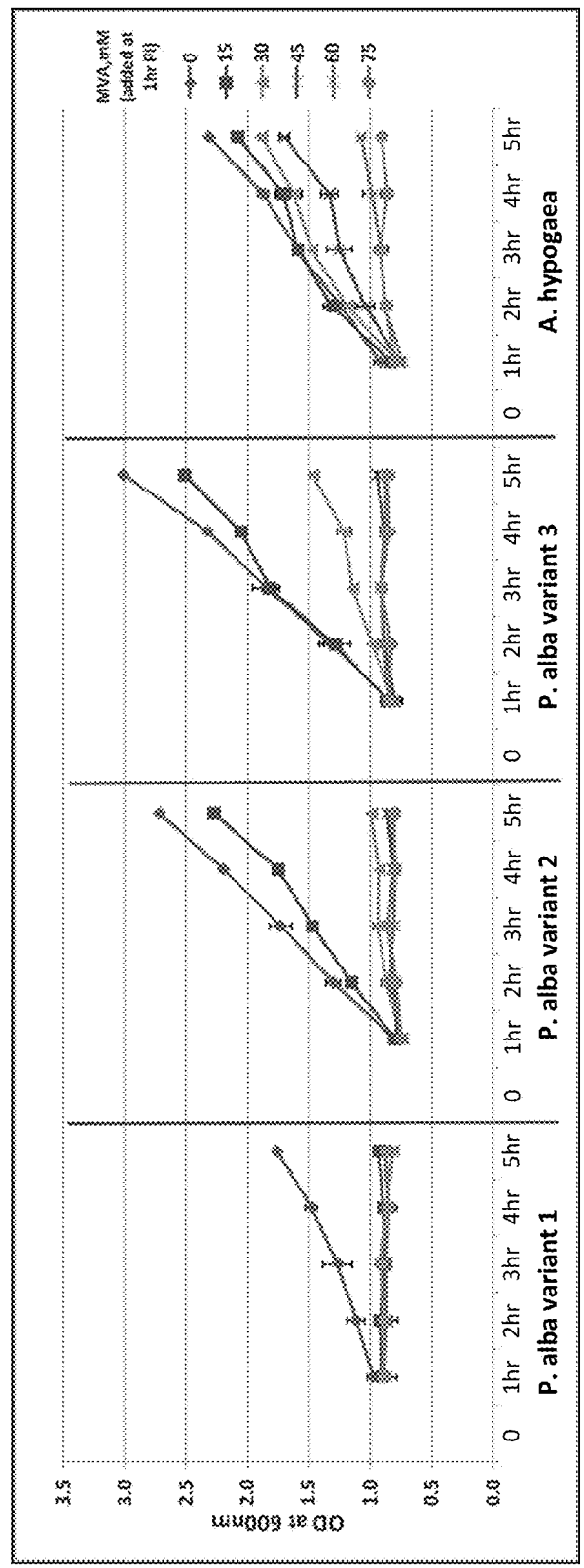
FIG. 13 is a graph showing the relationship between growth and DMAPP concentration in an assay strain. A bacterial strain expressing *A. hypogaea* (DW668) was grown in the presence of 0, 15, 30, 45, 60 or 75 mM mevalonate (MVA) 1 hr after induction with IPTG and growth was measured by assaying optical density (OD) at 600 nm at the start of the assay and at every hour for 5 hrs. Bacterial strains expressing an isoprene synthase from *P. alba* variant 1, *P. alba* variant 2, or *P. alba* variant 3 were used as a positive controls.
Figure 14:
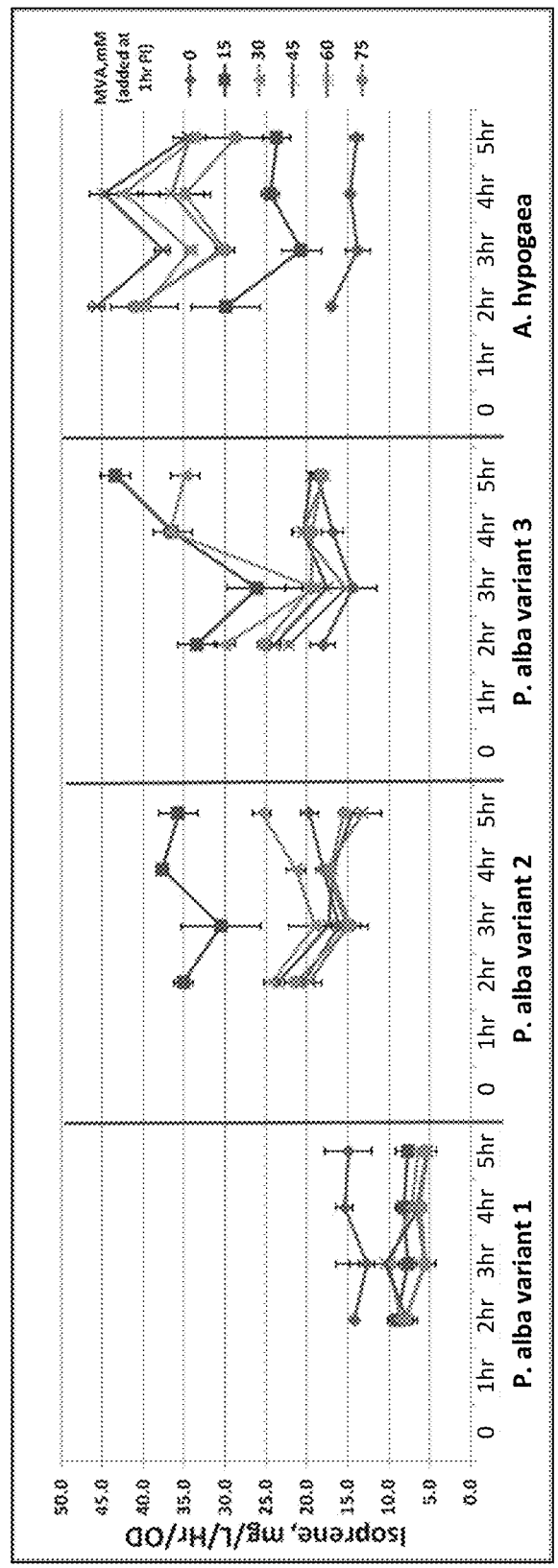
FIG. 14 is a graph showing the relationship between isoprene production and DMAPP concentration in an assay strain. A bacterial strain expressing *A. hypogaea* (DW668) was grown in the presence of 0, 15, 30, 45, 60 or 75 mM mevalonate (MVA) 1 hr after induction with IPTG and isoprene production was measured by GC-FID at the start of the assay and at every hour for 5 hrs. Specific productivity of isoprene synthase was calculated in units of mg isoprene/L/hr/OD. Bacterial strains expressing an isoprene synthase from *P. alba* variant 1, *P. alba* variant 2, or *P. alba* variant 3 were used as a positive controls.

Cell growth and isoprene production in the presence of increasing MVA concentrations was measured over time in cells expressing *A. hypogaea* IspS (strain EWL1043). For *P. alba* variant 1 IspS expressing cells, growth was inhibited at any concentration of MVA tested (FIG. 13; first panel). For *P. alba* variant 2 IspS expressing cells, growth was inhibited when MVA was supplied at concentrations higher than about 15 mM (FIG. 13, second panel). For *P. alba* variant 3 IspS expressing cells, growth was partially inhibited when MVA was supplied at MVA concentrations of at least about 30 mM and full inhibited at concentration of about 45 to 75 mM MVA (FIG. 13; third panel). For *A. hypogaea* IspS expressing cells, growth was partially inhibited at MVA concentrations of about 60 to 75 mM but significant growth was seen at MVA concentrations of about 15-45 mM (FIG. 13; fourth panel). Levels of cell growth corresponded to levels of specific productivity for isoprene, with *A. hypogaea* IspS expressing cells producing significant levels of isoprene as compared to *P. alba* variant1 IspS, *P. alba* variant 2 IspS, and *P. alba* variant 3 IspS (FIG. 14).

Figure 16:
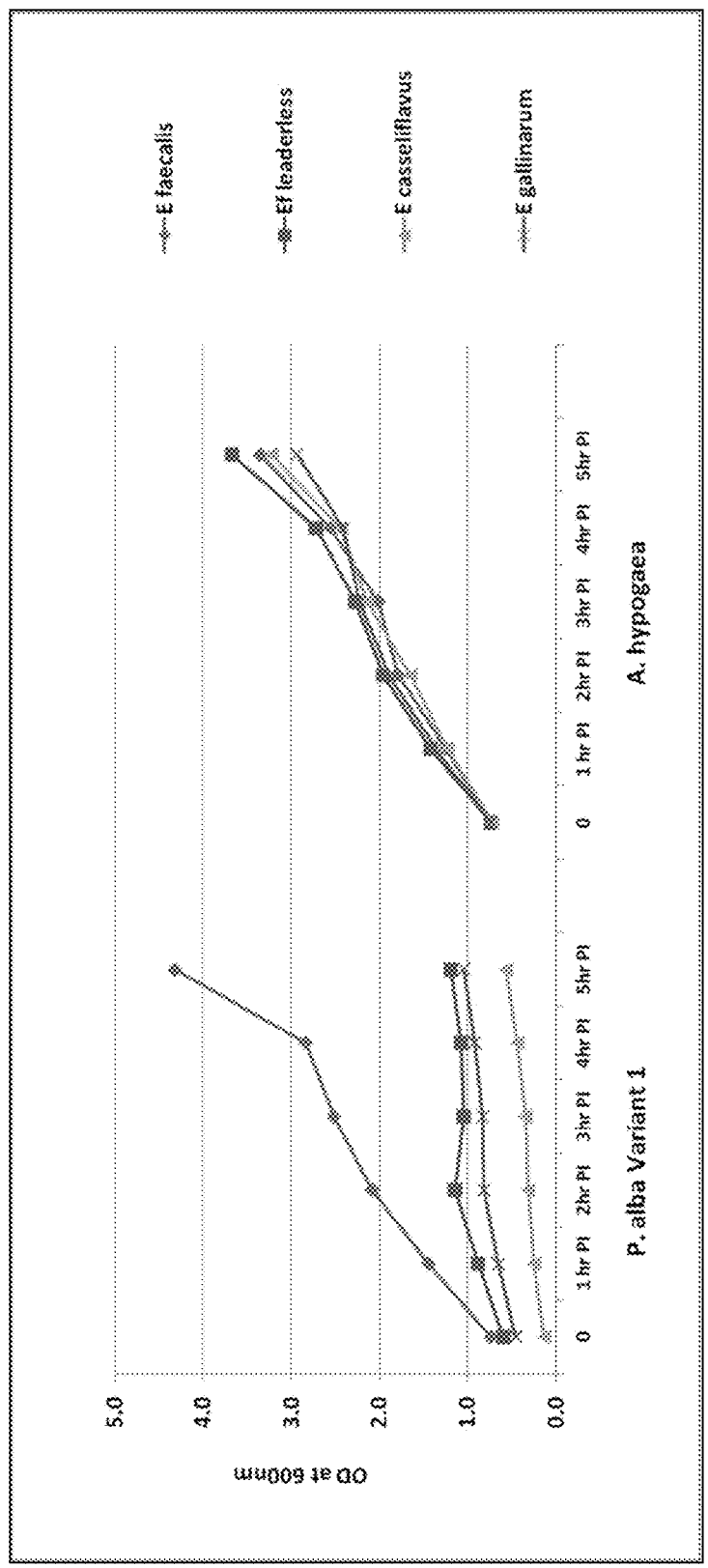
FIG. 16 is a graph showing the growth of a bacterial strain co-expressing a legume isoprene synthase with an upper MVA pathway polypeptides (*E. faecalis*) or upper MVA pathway polypeptides (*E. casseliflavus* and *E. gallinarum*). Growth was measured in bacterial strains co-expressing *A. hypogaea* with an *E. faecalis* upper MVA pathway polypeptides (EWL1043 and EWL1047), *E. casseliflavus* upper MVA pathway polypeptides (EWL1049), or *E. gallinarum* upper MVA pathway polypeptides (EWL1052) after induction with IPTG. Growth was assayed by optical density (OD) at 600 nm at the start of the growth assay and at every hour for 5 hrs. Bacterial strains expressing an isoprene synthase from *P. alba* variant 1 with the different upper MVA pathways were used as a controls.
Figure 17:
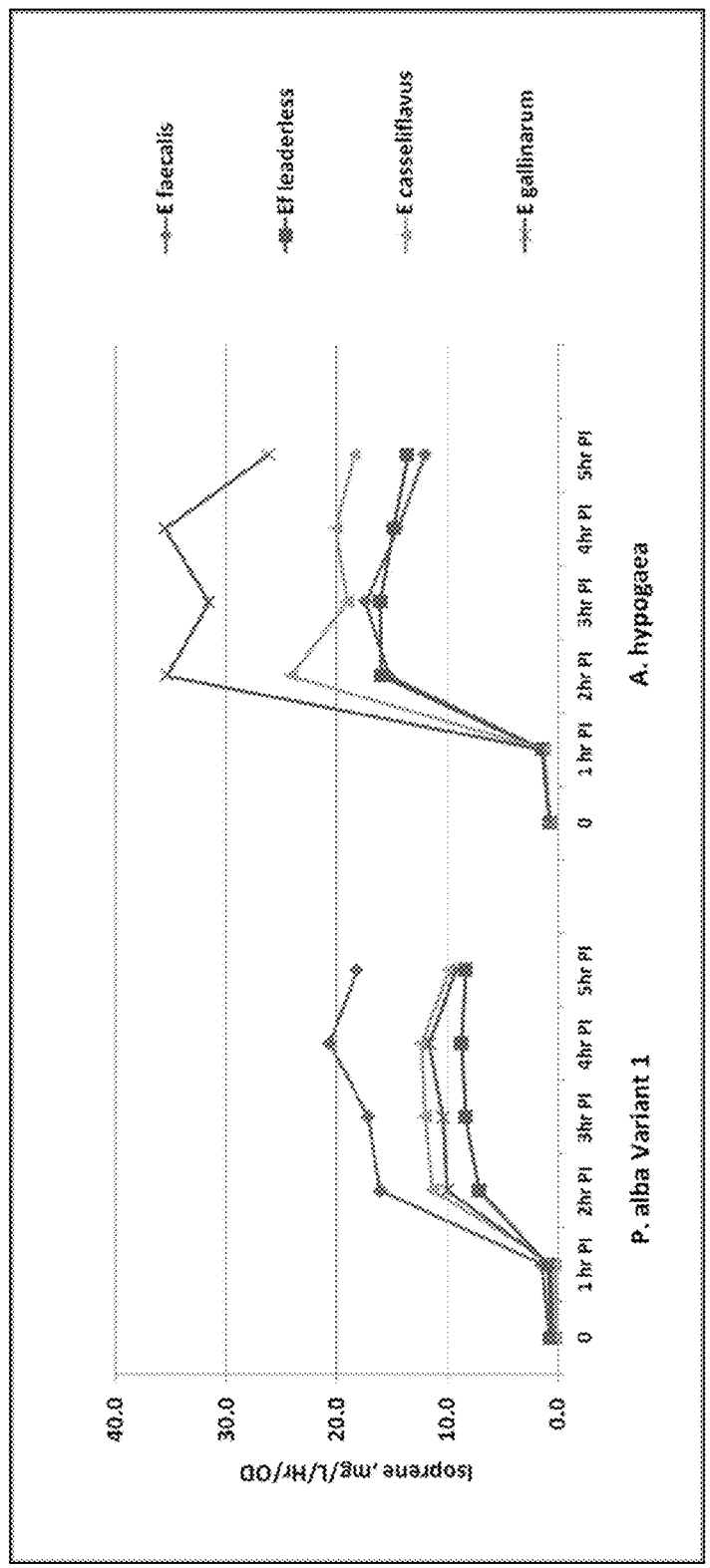
FIG. 17 is a graph showing the isoprene production of a bacterial strain co-expressing a legume isoprene synthase with an upper MVA pathway polypeptides (*E. faecalis*) or upper MVA pathway polypeptides (*E. casseliflavus* and *E. gallinarum*). Isoprene production was measured in bacterial strains co-expressing *A. hypogaea* with an *E. faecalis* upper MVA pathway polypeptides (EWL1043 and EWL1047), *E. casseliflavus* upper MVA pathway polypeptides (EWL1049), or *E. gallinarum* upper MVA pathway polypeptides (EWL1052) after induction with IPTG. Isoprene was measured by GC-FID at the start of the assay and at every hour for 5 hrs. Specific productivity of isoprene synthase was calculated in units of mg isoprene/L/hr/OD. Bacterial strains expressing an isoprene synthase from *P. alba* variant 1 with the different upper MVA pathways were used as a controls.

Cell growth and isoprene production was measured over time in cells co-expressing an *A. hypogaea* IspS or *P. alba* variant 1 IspS, with the *E. faecalis* upper MVA pathway (EWL1043 and EWL1047), the *E. casseliflavus* upper MVA pathway (EWL1049) or the *E. gallinarum* upper MVA pathway (EWL1052). For *P. alba* variant 1 IspS expressing cells, growth was reduced when the *E. casseliflavus* or *E. galli-* narum upper MVA pathway was co-expressed as compared to co-expression with the *E. faecalis* upper MVA pathway (FIG. 16; left panel). For *A. hypogaea* IspS expressing cells, co-expression with the *E. casseliflavus* or *E. gallinarum* upper MVA pathway resulted in comparable growth to cells co-expressing the *E. faecalis* upper MVA pathway (FIG. 16; right panel). Levels of cell growth corresponded to levels of specific productivity for isoprene, with *A. hypogaea* IspS expressing cells producing significant levels of isoprene as compared to *P. alba* variant1 IspS (FIG. 17).

Example 4

Isoprene Production from *E. coli* Expressing Legume Isoprene Synthase, Grown in Fed-Batch Culture at the 15-L Scale Materials and Methods Medium Recipe (Per Liter Fermentation Medium):

K2HPO4 7.5 g, MgSO4.7H2O 2 g, citric acid monohydrate 2 g, ferric ammonium citrate 0.3 g, yeast extract 0.5 g, 50% sulphuric acid 1.6 mL, 1000× Modified Trace Metal Solution 1 ml. All of the components are added together and dissolved in Di H2O. This solution is heat sterilized (123° C. for 20 minutes). The pH was adjusted to 7.0 with ammonium hydroxide (28%) and q.s. to volume. Glucose 10 g, Vitamin Solution 8 mL, and antibiotics are added after sterilization and pH adjustment.

1000× Modified Trace Metal Solution (Per Liter):

Citric Acids.H2O 40 g, MnSO4.H2O 30 g, NaCl 10 g, FeSO4.7H2O 1 g, CoCl2.6H2O 1 g, ZnSO.7H2O 1 g, CuSO4.5H2O 100 mg, H3BO3 100 mg, NaMoO4.2H2O 100 mg. Each component are dissolved one at a time in Di H2O, pH is adjusted to 3.0 with HCl/NaOH, and then the solution is q.s. to volume and filter sterilized with a 0.22 micron filter.

Vitamin Solution (Per Liter):

Thiamine hydrochloride 1.0 g, D-(+)-biotin 1.0 g, nicotinic acid 1.0 g, D-pantothenic acid 4.8 g, pyridoxine hydrochloride 4.0 g. Each component is dissolved one at a time in Di H2O, pH is adjusted to 3.0 with HCl/NaOH, and then the solution is q.s. to volume and filter sterilized with 0.22 micron filter.

Feed Solution (Per Kilogram):

Glucose 0.57 kg, Di H2O 0.38 kg, K2HPO4 7.5 g, and 100% Foamblast 10 g. All components are mixed together and autoclaved. Macro Salt Solution 3.4 mL, 1000× Modified Trace Metal Solution 0.8 ml, and Vitamin Solution 6.7 mL are added after the solution had cooled to 25° C.

Macro Salt Solution (Per Liter):

MgSO4.7H2O 296 g, citric acid monohydrate 296 g, ferric ammonium citrate 49.6 g. All components are dissolved in water, q.s. to volume and filter sterilized with 0.22 micron filter.

Fermentation is performed in a 15-L bioreactor with *E. coli* BL21 cells overexpressing the upper MVA pathway (pCLUpper—MCM82), the lower MVA pathway (PL.2-mKKDyI) and isoprene synthase from *A. hypogaea* (pET24a PT7-A).

This experiment is carried out to monitor isoprene formation from glucose at the desired fermentation pH 7.0 and temperature 34° C. A frozen vial of the *E. coli* strain is thawed and inoculated into a flask with tryptone-yeast extract medium and the appropriate antibiotics. After the inoculum grows to optical density 1.0, measured at 550 nm ($OD_{550}$), 500 mL is used to inoculate a 15-L bioreactor and bring the initial tank volume to 5 L.

The feed solution is fed at an exponential rate until a top feed rate of 6 g/min is reached. After this time, the glucose feed is fed to meet metabolic demands at rates less than or equal to 6 g/min. The total amount of glucose delivered to the bioreactor during the 52 hr fermentation is 6.8 kg. Induction is achieved by adding isopropyl-beta-D-1-thiogalactopyranoside (IPTG). A shot of IPTG is added to the tank to bring the concentration to 100 uM when the cells are at an $OD_{550}$ of 6 and a second shot is added bring the concentration to 100 uM when the cells are at an $OD_{550}$ of 100.

The isoprene level in the off-gas from the bioreactor is determined using an iSCAN (Hamilton Sundstrand) mass spectrometer.

The invention claimed is:

1. A host cell comprising a heterologous polynucleotide sequence encoding a polypeptide from a legume having isoprene synthase activity in operable combination with a promoter, wherein said polypeptide has at least 85% sequence identity to SEQ ID NO: 3 or at least 90% identity to SEQ ID NO: 9, wherein said isoprene synthase has one or more properties selected from the group consisting of a $K_{cat}$ value of at least about 1.3, a $K_m$ value of at least about 2.5, and a $K_i$ value of at least about 13.0, and wherein said isolated polypeptide is not from *P. montana*.

2. The host cell of claim 1, wherein the polynucleotide sequence is contained within a plasmid.

3. The host cell of claim 1, wherein the polynucleotide sequence is integrated into a chromosome of the host cell.

4. The host cell of claim 1, wherein the host cell is selected from the group consisting of gram-positive bacterial cells, gram-negative bacterial cells, filamentous fungal cells, and yeast cells.

5. The host cell of claim 1, wherein the host cell is selected from the group consisting of *Escherichia* sp. (*E. coli*), *Pantoea* sp. (*P. citrea*), *Bacillus* sp. (*B. subtilis*), *Yarrowia* sp. (*Y. lipolytica*), *Trichoderma* (*T. reesei*) and *Saccharomyces* (*S. cerevisiae*).

6. The host cell of claim 1, wherein the host cell is cultured in a medium comprising a carbon source selected from the group consisting of glucose, glycerol, glycerine, dihydroxyacetone, yeast extract, biomass, molasses, sucrose, and oil.

7. The host cell of claim 1, wherein the host cell further comprises one or more heterologous or native nucleic acid(s) encoding one or more mevalonate (MVA) pathway polypeptides.

8. The host cell of claim 7, wherein the host cell further comprises a heterologous nucleic acid encoding a mevalonate (MVA) pathway polypeptide selected from the group consisting of an MVA pathway polypeptide from *Saccharomyces cerevisiae* and *Enterococcus faecalis*.

9. The host of claim 7, further comprising one or more nucleic acids encoding a heterologous or native nucleic acid encoding an isopentenyl diphosphate isomerase (IDI) polypeptide.

10. The host cell of claim 1, wherein the host cell further comprises a heterologous or native nucleic acid encoding an IDI polypeptide and/or a heterologous or native nucleic acid encoding a 1-deoxy-D-xylulose 5-phosphate synthase (DXS) polypeptide, optionally in combination with the native DXP pathway.

11. The host cell of claim 10, wherein the host cell further comprises one or more nucleic acids encoding an IDI polypeptide and the DXS polypeptide.

12. The host cell of claim 10, wherein the host cell comprises one vector encoding the isoprene synthase, the IDI polypeptide, and the DXS polypeptide.

13. The host cell of claim 1, wherein the host cell further comprises one or more nucleic acids encoding an MVA pathway polypeptide and/or a DXS polypeptide.

14. The host cell of claim 13, wherein the host cell further comprises one or more nucleic acids encoding a DXS polypeptide, an IDI polypeptide, or one or more of the rest of the DXP pathway polypeptides, and a MVA pathway polypeptide.

15. The host cell of claim 9 further comprising DXS.

16. A method of producing isoprene, comprising:
(a) culturing the host cell of claim 1 under suitable culture conditions for production of isoprene; and
(b) producing the isoprene.

17. The method of claim 16 further comprising (c) recovering the isoprene.

18. The method of claim 17 further comprising (d) polymerizing isoprene.

* * * * *